United States Patent
Wang et al.

(10) Patent No.: US 11,976,058 B2
(45) Date of Patent: *May 7, 2024

(54) AROMATIC DERIVATIVES, PREPARATION METHODS, AND MEDICAL USES THEREOF

(71) Applicant: Bioardis LLC, San Diego, CA (US)

(72) Inventors: Ding Wang, Beijing (CN); Ning Shao, Beijing (CN); Hongbin Yuan, Shanghai (CN); Frank Kayser, San Francisco, CA (US)

(73) Assignee: BIOARDIS LLC, San Diego, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 17/436,476

(22) PCT Filed: Feb. 19, 2020

(86) PCT No.: PCT/CN2020/075849
§ 371 (c)(1),
(2) Date: Sep. 3, 2021

(87) PCT Pub. No.: WO2020/177534
PCT Pub. Date: Sep. 10, 2020

(65) Prior Publication Data
US 2022/0169634 A1  Jun. 2, 2022

(30) Foreign Application Priority Data

Mar. 5, 2019 (WO) .............. PCT/CN2019/076926

(51) Int. Cl.
C07D 403/04 (2006.01)
A61P 35/00 (2006.01)
C07D 405/04 (2006.01)
C07D 491/052 (2006.01)
C07D 491/10 (2006.01)

(52) U.S. Cl.
CPC ............ *C07D 403/04* (2013.01); *A61P 35/00* (2018.01); *C07D 405/04* (2013.01); *C07D 491/052* (2013.01); *C07D 491/10* (2013.01); *C07B 2200/05* (2013.01)

(58) Field of Classification Search
CPC .. C07D 231/56; C07D 231/54; A61K 31/415; A61K 31/416; A61K 31/4162
See application file for complete search history.

(56) References Cited

U.S. PATENT DOCUMENTS

| | | | |
|---|---|---|---|
| 11,279,697 B2 | 3/2022 | Shao et al. | |
| 2016/0136168 A1 | 5/2016 | Sootome | |
| 2017/0114000 A1 | 4/2017 | Knauf | |
| 2020/0262827 A1 | 8/2020 | Shao et al. | |

FOREIGN PATENT DOCUMENTS

| | | |
|---|---|---|
| CN | 104540809 A | 4/2015 |
| CN | 105658642 A | 6/2016 |
| CN | 105906630 A | 8/2016 |
| CN | 107286130 A | 10/2017 |
| EP | 3029864 A1 | 6/2016 |
| EP | 3680236 A1 | 7/2020 |
| WO | 2012174476 A2 | 12/2012 |
| WO | 2012174476 A3 | 2/2013 |
| WO | 2014011900 A2 | 1/2014 |
| WO | 2014011900 A3 | 2/2014 |
| WO | 2014144737 A1 | 9/2014 |
| WO | 2015008844 A1 | 1/2015 |
| WO | 2015057938 A1 | 4/2015 |
| WO | 2015057963 A1 | 4/2015 |
| WO | 2015059668 A1 | 4/2015 |
| WO | 2015061572 A1 | 4/2015 |
| WO | 2015108992 A1 | 7/2015 |
| WO | 2015197519 A1 | 12/2015 |
| WO | 2016064960 A1 | 4/2016 |
| WO | 2016134294 A1 | 8/2016 |
| WO | 2016134314 A1 | 8/2016 |
| WO | 2016134320 A1 | 8/2016 |
| WO | 2016164703 A1 | 10/2016 |
| WO | 2018113584 A1 | 6/2018 |
| WO | 2019047826 A1 | 3/2019 |
| WO | 2020082651 A1 | 4/2020 |
| WO | 2020082816 A1 | 4/2020 |

OTHER PUBLICATIONS

Acute Leukemia (2016). Merck Manual (Online Edition) 6 pages.
Banker, G.S. et al. (1996). "Prodrugs," in Modern Pharmaceutics, Third Edition, Revised and Expanded, pp. 451 and 596, 3 pages.
Berge, S.M. et al. (Jan. 1977). "Pharmaceuticals Salts," J. Pharmaceutical Sciences 66(1):1-19.
Brown, A.P. et al. (2005). "Cartilage Dysplasia and Tissue Mineralization in the Rat Following Administration of a FGF Receptor Tyrosine Kinase Inhibitor," Toxicol. Pathol. 33:449-455.
Bundgaard, H. (1985). "Design of Prodrugs: Bioreversible Derivatives for Various Functional Groups and Chemical Entities," in Design of Prodrugs, 3 pages.
Cao, L. et al. (2010, e-pub. Jul. 27, 2010). "Genome-Wide Identification of PAX3-FKHR Binding Sites in Rhabdomyosarcoma Reveals Candidate Target Genes Important for Development and Cancer," Cancer Res. 70(16):6497-6508.
Ding, L. et al. (Oct. 23, 2008). "Somatic Mutations Affect key Pathways in Lung Adenocarcinoma," Nature 455(7216):1069-1075, 17 pages.
Fairhurst, R.A. et al. (Jun. 8, 2017). "Approaches to Selective Fibroblast Growth Factor Receptor 4 Inhibition Through Targeting the ATP-Pocket Middle-Hinge Region," Med. Chem. Comm. 8(8):1604-1613.

(Continued)

Primary Examiner — Deepak R Rao
(74) Attorney, Agent, or Firm — Morrison & Foerster LLP

(57) ABSTRACT

The present disclosure relates generally to aromatic derivatives that are inhibitors of FGFR4 and are useful in treating FGFR4-associated diseases or conditions. Compositions containing the compounds of the present disclosure are also provided.

48 Claims, No Drawings

(56) References Cited

OTHER PUBLICATIONS

Gura, T. (1997). "Systems for Identifying New Drugs Are Often Faulty," Science 278(5340):1041-1042, , 5 pages.
Ho, H.K. et al. (2008, e-pub. Oct. 12, 2008). "Fibroblast Growth Factor Receptor 4 Regulates Proliferation, Anti-Apoptosis and Alpha-Fetoprotein Secretion During Hepatocellular Carcinoma Progression and Represents a Potential Target for Therapeutic Intervention," Journal of Hepatology 50:118-127.
Johnson, J. et al. (2001). "Relationships between drug activity in NCI preclinical in vitro and in vivo models and early clinical trials," British Journal of Cancer 84(10): 1424-1431.
Pearce, H.L. et al. (2008). "Chapter 18—Failure Modes In Anticancer Drug Discovery and Development," Cancer Drug Design and Discovery, pp. 424-435, 12 pages.
Remington's Pharmaceutical Sciences, Mack Publishing Company, Philadelphia, PA, 21th ed. (2000) TOC, 4 Pages.
Roidl, A. et al. (2010, e-pub. Nov. 30, 2009). "The FGFR4 Y367C Mutant is a Dominant Oncogene in MDA-MB453 Breast Cancer Cells," Oncogene 29(10):1543-1552.
Sawey, E.T. et al. (Mar. 15, 2011). "Identification of a Therapeutic Strategy Targeting Amplified FGF19 in Liver Cancer by Oncogenomic Screening," Cancer Cell 19:347-358.
Shraga, A. et al. (Jan. 17, 2019, e-pub. Nov. 15, 2018). "Covalent Docking Identifies a Potent and Selective MKK7 Inhibitor," Cell Chemical Biology 26:98-108 and Supplementary, 17 pages.
Silverman, R.B. (1992). "Prodrugs and Drug Delivery Systems," in The Organic Chemistry of Drug Design and Drug Action, pp. 352-399, 51 pages.
Simone, J.V. et al. (1996). "Oncology," Part XIV in Cecil Textbook of Medicine, 20th edition, Bennet, J.C. et al. eds., W.B. Saunders Company, pp. 1004-1010.
Taylor, J.G. et al. (Nov. 2009). "Identification of FGFR4-Activation Mutations in Human Rhabdomyosarcomas That Promote Metastasis in Xenotransplanted Models," J Clin Invest. 119(11):3395-3407.
Tomassi, S. et al. (2017). "Indazole-Based Covalent Inhibitors To Target Drug-Resistant Epidermal Growth Factor Receptor," Journal of Medicinal Chemistry, 60(6):2361-2372.
Vergnes, L. et al. (Jun. 4, 2013). "Diet1 Functions in the FGF15/19 Enterophepatic Signaling Axis to Modulated Bile Acid and Lipid Levels," Cell Metabolism 17(6):916-928, 26 pages.
Wolff, M.E. (1995). "Chapter 9—Some Consideration For Prodrug Design," in Burger's Medicinal Chemistry and Drug Discovery, 5th Edition, vol. 1: Principles and Practice, pp. 975-977, 4 pages.
Wu, X. et al. (Feb. 19, 2010). "FGF19-Induce Hepatocyte Proliferation is Mediated Through FGFR4 Activation," J Biol Chem 285(8):5165-5170.
Zaid, T.M. et al. (2013, e-pub. Jan. 23, 2013). "Identification of FGFR4 as a Potential Therapeutic Target for Advanced-Stage, High-Grade Serous Ovarian Cancer," Clin. Cancer Res. 19(4):809-820.
Extended European Search Report, dated Oct. 10, 2022, for European Patent Application No. 20767365.8, 8 pages.

AROMATIC DERIVATIVES, PREPARATION METHODS, AND MEDICAL USES THEREOF

CROSS REFERENCE TO RELATED APPLICATIONS

[1] This application is a national stage application under 35 U.S.C. § 371 of International Application No. PCT/CN2020/075849, filed internationally on Feb. 19, 2020, which claims the benefit of priority to International Patent Application No. PCT/CN2019/076926, filed internationally on Mar. 5, 2019, the content of which is incorporated herein by reference in its entirety.

FIELD

The present disclosure relates generally to aromatic derivatives that are inhibitors of FGFR4 and are useful in treating FGFR4-associated diseases or conditions. Compositions containing the compounds of the present disclosure are also provided.

BACKGROUND

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Eswarakumar et al. Cytokine & Growth Factor Reviews, 2005; 16:139-49).

FGFR4 regulates proliferation, survival, and alpha-feto-protein secretion during hepatocellular carcinoma (HCC) progression; inhibitors of FGFR4 are therefore promising potential therapeutic agents for this unmet medical need (Ho et al., Journal of Hepatology, 2009, 50: 118-27). HCC afflicts more than 550,000 people worldwide every year and has one of the worst 1-year survival rates of any cancer type. Further evidence of the link between FGFR4 and HCC is shown through the involvement of FGF 19, a member of the fibroblast growth factor (FGF) family, which consists of hormones that regulate glucose, lipid, and energy homeostasis. Increased hepatocyte proliferation and liver tumor formation have been observed in FGF 19 transgenic mice. FGF 19 activates FGFR4, its predominant receptor in the liver, and it is believed that activation of FGFR4 is the mechanism whereby FGF 19 can increase hepatocyte proliferation and induce hepatocellular carcinoma formation (Wu et al., J Biol Chem (2010) 285(8):5165-5170). FGF 19 has been identified as a driver gene in HCC by others as well (Sawey et al., Cancer Cell (2011) 19: 347-358). It is therefore believed that the compounds disclosed herein, which are potent and selective inhibitors of FGFR4, can be used to treat HCC and other liver cancers.

Oncogenome screening has identified an activating fibroblast growth factor receptor 4 (FGFR4) Y367 C mutation in the human breast cancer cell line MDA-MB-453. This mutation was shown to elicit constitutive phosphorylation, leading to an activation of the mitogen-activated protein kinase cascade. Accordingly, it has been suggested that FGFR4 may be a driver of tumor growth in breast cancer (Roidl et al., Oncogene (2010) 29(10): 1543-1552). It is therefore believed that the compounds disclosed herein, which are potent and selective inhibitors of FGFR4, can be used to treat FGFR4 modulated breast cancer.

Molecular changes (e.g., translocations) in genes upstream of FGFR4 can lead to activation/overexpression of FGFR4. For example, a PAX3-FKHR translocation/gene fusion can lead to FGFR4 overexpression. Overexpression of FGFR4 due to this mechanism has been associated with rhabdomyosarcoma (RMS) (Cao et al., Cancer Res (2010) 70(16): 6497-6508).

Mutations in FGFR4 itself (e.g., kinase domain mutations) can lead to over-activation of the protein; this mechanism has been associated with a subpopulation of RMS (Taylor et al., J Clin Invest (2009) 119: 3395-3407). It is therefore believed that the compounds disclosed herein, which are potent and selective inhibitors of FGFR4, can be used to treat FGFR4 modulated RMS and other sarcomas.

Other diseases have been associated with changes in genes upstream of FGFR4 or with mutations in FGFR4 itself. For example, mutations in the kinase domain of FGFR4 lead to over-activation, which has been associated with lung adenocarcinoma (Ding et al., Nature (2008) 455 (7216): 1069-1075). Amplification of FGFR4 has been associated with conditions such as renal cell carcinoma (TCGA provisional data). In addition, silencing FGFR4 and inhibiting ligand-receptor binding significantly decrease ovarian tumor growth, suggesting that inhibitors of FGFR4 could be useful in treating ovarian cancer. (Zaid et al., Clin. Cancer Res. (2013) 809).

Pathogenic elevations of bile acid levels have been linked to variations in FGF19 levels (Vergnes et al., Cell Metabolism (2013) 17, 916-28). Reduction in the level of FGF19 may therefore be of benefit in promoting the synthesis of bile acid and thus in the treatment of hyperlipidemia.

There is still a need for new FGFR4 inhibitors. In this regard, the compounds provided herein address the need.

BRIEF SUMMARY

In one aspect, provided herein is a compound of formula (I):

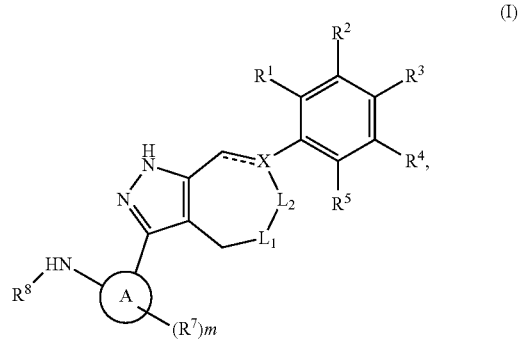

or a stereoisomer, tautomer, or a pharmaceutically acceptable salt of any of the foregoing, wherein $----$, X, $L_1$, $L_2$, A, m, $R^1$, $R^2$, $R^3$, $R^4$, $R^5$, $R^7$, and $R^8$ are as described herein.

In another aspect, provided herein is a composition comprising a compound of formula (I) or any related formula, or a stereoisomer, tautomer or a pharmaceutically acceptable salt of any of the foregoing and a pharmaceutically acceptable carrier or excipient.

In another aspect, provided herein is a kit comprising a compound of formula (I) or any related formula, or a stereoisomer, tautomer or a pharmaceutically acceptable salt of any of the foregoing.

In another aspect, provided herein is a method of treating a disease mediated by FGFR4 in an individual in need thereof, comprising administering to the individual a therapeutically effective amount of a compound of formula (I) or any related formula, or a stereoisomer, tautomer or a pharmaceutically acceptable salt of any of the foregoing. In some embodiments, the compound, or a stereoisomer, tautomer or a pharmaceutically acceptable salt of any of the foregoing, is administered orally. In some embodiments, the disease is cancer. In some embodiments, the disease is liver cancer such as hepatocellular carcinoma, breast cancer, rhabdomyosarcoma, or ovarian cancer. In some embodiments, the disease is hyperlipidemia.

In another aspect, provided herein is a method of inhibition FGFR4, comprising contacting FGFR4 with a compound of formula (I) or any related formula, or a stereoisomer, tautomer or a pharmaceutically acceptable salt of any of the foregoing.

In another aspect, provided herein is a compound of formula (I) or any related formula, or a stereoisomer, tautomer or a pharmaceutically acceptable salt of any of the foregoing, in the manufacture of a medicament for use in therapy.

DETAILED DESCRIPTION

Described herein are compounds, including therapeutic agents, that can inhibit FGFR4. These compounds could be used in the prevention and/or treatment of certain pathological conditions as described herein.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having 1 to 10 carbon atoms (a "$C_{1-10}$ alkyl"), having 6 to 10 carbon atoms (a "$C_{6-10}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_{1-20}$ alkylene"), having 1 to 10 carbon atoms (a "$C_{1-10}$ alkylene"), having 6 to 10 carbon atoms (a "$C_{6-10}$ alkylene"), having 1 to 6 carbon atoms (a "$C_{1-6}$ alkylene"), 1 to 5 carbon atoms (a "$C_{1-5}$ alkylene"), 1 to 4 carbon atoms (a "$C_{1-4}$ alkylene") or 1 to 3 carbon atoms (a "$C_{1-3}$ alkylene"). Examples of alkylene include, but are not limited to, groups such as methylene (—CH$_2$—), ethylene (—CH$_2$CH$_2$—), propylene (—CH$_2$CH$_2$CH$_2$—), isopropylene (—CH$_2$CH(CH$_3$)—), butylene (—CH$_2$(CH$_2$)$_2$CH$_2$—), isobutylene (—CH$_2$CH(CH$_3$)CH$_2$—), pentylene (—CH$_2$(CH$_2$)$_3$CH$_2$—), hexylene (—CH$_2$(CH$_2$)$_4$CH$_2$—), heptylene (—CH$_2$(CH$_2$)$_5$CH$_2$—), octylene (—CH$_2$(CH$_2$)$_6$CH$_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). An alkenyl group may have "cis" or "trans" configurations, or alternatively have "E" or "Z" configurations. Particular alkenyl groups are those having 2 to 20 carbon atoms (a "$C_{2-20}$ alkenyl"), having 6 to 10 carbon atoms (a "$C_{6-10}$ alkenyl"), having 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_{2-20}$ alkenylene"), having 2 to 10 carbon atoms (a "$C_{2-30}$ alkenylene"), having 6 to 10 carbon atoms (a "$C_{6-10}$ alkenylene"), having 2 to 6 carbon atoms (a "$C_{2-6}$ alkenylene"), 2 to 4 carbon atoms (a "$C_{2-4}$ alkenylene") or 2 to 3 carbon atoms (a "$C_{2-3}$ alkenylene"). Examples of alkenylene include, but are not limited to, groups such as ethenylene (or vinylene) (—CH=CH—), propenylene (—CH=CHCH$_2$—), 1,4-but-1-enylene (—CH=CH—CH$_2$CH$_2$—), 1,4-but-2-enylene (—CH$_2$CH=CHCH$_2$—), 1,6-hex-1-enylene (—CH=CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_{2-10}$ means two to ten carbon atoms). Particular alkynyl groups are those having 2 to 20 carbon atoms (a "$C_{2-20}$ alkynyl"), having 6 to 10 carbon atoms (a "$C_{6-10}$ alkynyl"), having 2 to 8 carbon atoms (a "$C_{2-8}$ alkynyl"), having 2 to 6 carbon atoms (a "$C_{2-6}$ alkynyl"), or having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_{2-20}$ alkynylene"), having 2 to 10 carbon atoms (a "$C_{2-10}$ alkynylene"), having 6 to 10 carbon atoms (a "$C_{6-10}$ alkynylene"), having 2 to 6 carbon atoms (a "$C_{2-6}$ alkynylene"), 2 to 4 carbon atoms (a "$C_{2-4}$ alkynylene") or 2 to 3 carbon atoms (a "$C_{2-3}$ alkynylene"). Examples of alkynylene include, but are not limited to, groups such as ethynylene (or acetylenylene) propynylene (—C≡CCH$_2$—), and the like.

"Cycloalkyl" as used herein refers to and includes, unless otherwise stated, cyclic univalent nonaromatic hydrocarbon structures, which may be fully saturated, mono- or polyunsaturated, but which are non-aromatic, having the number of carbon atoms designated (i.e., $C_{3-10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_{3-8}$ cycloalkyl"), having 3 to 6 carbon atoms (a "$C_{3-6}$ cycloalkyl"), or having from 3 to 4 annular carbon atoms (a "$C_{3-4}$ cycloalkyl"). Examples of cycloalkyl include, but are not limited to, cyclopropyl, cyclobutyl, cyclopentyl, cyclohexyl, cycloheptyl, norbornyl, and the like. A cycloalkyl group may be fused with aryl, heteroaryl, or heterocyclyl. In one variation, a cycloalkyl group having more than one ring where at least one ring is aryl, heteroaryl, or heterocyclyl is connected to the parent structure at an atom in the nonaromatic hydrocarbon cyclic group.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_{3-8}$ cycloalkylene"), having 3 to 6 carbon atoms (a "$C_{3-6}$ cycloalkylene"), or having from 3 to 4 annular carbon atoms (a "$C_{3-4}$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_{6-14}$ aryl"). An aryl group may be fused with heteroaryl, cycloalkyl, or heterocyclyl. In one variation, an aryl group having more than one ring where at least one ring is heteroaryl, cycloalkyl, or heterocyclyl is connected to the parent structure at an atom in the aromatic carbocyclic group.

"Arylene" as used herein refers to the same residues as aryl, but having bivalency. Particular arylene groups are those having from 6 to 14 annular carbon atoms (a "$C_{6-14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen, and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen, and sulfur, 5 to 10-membered rings having 1 to 8 annular carbon atoms and 1 to 4 annular heteroatoms independently selected from nitrogen, oxygen, and sulfur, or 5, 6 or 7-membered rings having 1 to 5 annular carbon atoms and 1 to 4 annular heteroatoms independently selected from nitrogen, oxygen, and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen, and sulfur. A heteroaryl group may be fused with aryl, cycloalkyl, or heterocyclyl. In one variation, a heteroaryl group having more than one ring where at least one ring is aryl, cycloalkyl, or heterocyclyl is connected to the parent structure at an atom in the aromatic cyclic group having at least one annular heteroatom. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. In certain embodiments, the nitrogen and/or sulfur atom(s) of the heterocyclic group are optionally oxidized to provide for N-oxide, —S(O)—, or —SO$_2$— moieties. A heterocycle comprising more than one ring may be fused, bridged or spiro, or any combination thereof, but excludes heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur. A heterocyclyl group may be fused with aryl, cycloalkyl, or heteroaryl. In one variation, a heterocyclyl group having more than one ring where at least one ring is aryl, cycloalkyl, or heteroaryl is connected to the parent structure at an atom in the non-aromatic cyclic group having at least one heteroatom.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. A haloalkyl is an alkyl group that is substituted with one or more halogens. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl.

"Carbonyl" refers to the group C=O.

"Acyl" refers to —C(=O)R where R is an aliphatic group, preferably a $C_{1-6}$ moiety. The term "aliphatic" refers to saturated and unsaturated straight chained, branched chained, or cyclic hydrocarbons. Illustrative examples of aliphatic groups include $C_{1-6}$ alkyl, $C_{2-6}$ alkenyl, $C_{2-6}$ alkynyl, or $C_{3-6}$ cycloalkyl.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods of the present disclosure contemplate any one or more of these aspects of treatment.

As used herein, the term "effective amount" intends such amount of a compound described herein which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the present disclosure in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

When a moiety is indicated as substituted by "at least one" substituent, this also encompasses the disclosure of exactly one substituent.

Compounds

In one aspect, provided is a compound of formula (I):

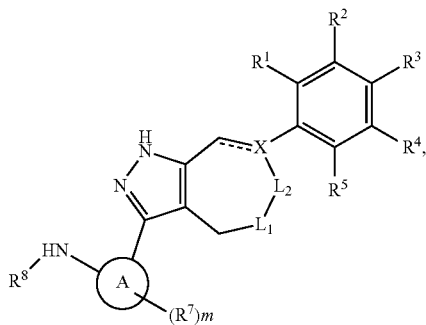

(I)

or a stereoisomer, tautomer, or a pharmaceutically acceptable salt of any of the foregoing, wherein:
- ---- is a single bond or a double bond;
- X is CH or C;
- $L_1$ is —CR'R"—, —O—, or —NR'"—, wherein R' and R" are each independently H, $C_{1-6}$ alkyl, $C_{1-6}$ haloalkyl, or halo, and R'" is H, $C_{1-6}$ alkyl, $C_{1-6}$ haloalkyl, or acyl;
- $L_2$ is a bond or —CH$_2$—;
- A is a $C_{6-14}$ arylene, 5- to 10-membered heteroarylene, $C_{3-8}$ cycloalkylene, or 3- to 10-membered heterocyclylene,
  - provided that when $L_1$ is —CH$_2$— and $L_2$ is a bond, then A is 5- to 10-membered heteroarylene, $C_{3-8}$ cycloalkylene, or 3- to 10-membered heterocyclylene;
- $R^1$, $R^2$, $R^3$, $R^4$, and $R^5$ are each independently H, halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^{11}$R$^{12}$, or $R^1$ and X are taken together with the carbons to which they are attached to form a 4- to 8-membered heterocyclyl;
- m is 0, 1, or 2;
- each $R^7$ is independently halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^a$R$^b$, wherein R$^a$ and R$^b$ are each independently H or $C_{1-6}$ alkyl, wherein the $C_{1-6}$ alkyl, $C_{1-6}$ haloalkyl, $C_{2-6}$ alkenyl, $C_{2-6}$ alkynyl, $C_{3-8}$ cycloalkyl, and —OR$^{13}$ of R$^7$ and the $C_{1-6}$ alkyl of R$^a$ and R$^b$ are each independently optionally substituted by —NR$^c$R$^d$, wherein R$^c$ and R$^d$ are each independently H or $C_{1-6}$ alkyl;
- $R^8$ is —C(O)R$^9$ or —S(O)$_2$R$^9$;
- $R^9$ is $C_{1-6}$ alkyl, $C_{2-6}$ alkenyl, $C_{3-8}$ cycloalkyl, or 3- to 10-membered heterocyclyl, each of which is optionally substituted with $C_{1-6}$ alkyl, halo, —CN, or —C(O)OR$^{9a}$, wherein R$^{9a}$ is $C_{1-6}$ alkyl; and
- $R^{11}$, $R^{12}$ and $R^{13}$ are each independently H, $C_{1-6}$ alkyl, $C_{1-6}$ haloalkyl, $C_{1-6}$ heteroalkyl, $C_{6-14}$ aryl, 5- to 10-membered heteroaryl, $C_{3-8}$ cycloalkyl, or 3- to 10-membered heterocyclyl.

In some embodiments, provided is a compound of formula (I):

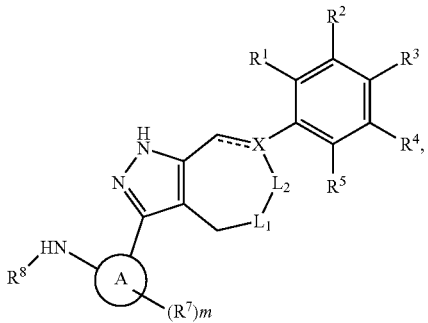

(I)

or a stereoisomer, tautomer, or a pharmaceutically acceptable salt of any of the foregoing, wherein:
- ---- is a single bond or a double bond;
- X is CH or C;
- $L_1$ is —CR'R"—, —O—, or —NR'"—, wherein R' and R" are each independently H, $C_{1-6}$ alkyl, $C_{1-6}$ haloalkyl, or halo, and R'" is H, $C_{1-6}$ alkyl, $C_{1-6}$ haloalkyl, or acyl;
- $L_2$ is a bond or —CH$_2$—;
- A is a $C_{6-14}$ arylene, 5- to 10-membered heteroarylene, $C_{3-8}$ cycloalkylene, or 3- to 10-membered heterocyclylene,
  - provided that when $L_1$, is —CH$_2$— and $L_2$ is a bond, then A is 5- to 10-membered heteroarylene, $C_{3-8}$ cycloalkylene, or 3- to 10-membered heterocyclylene;
- $R^1$, $R^2$, $R^3$, $R^4$, and $R^5$ are each independently H, halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^{11}$R$^{12}$, or $R^1$ and X are taken together with the carbons to which they are attached to form a 4- to 8-membered heterocyclyl;
- m is 0, 1, or 2;
- each $R^7$ is independently halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^a$R$^b$, wherein R$^a$ and R$^b$ are each independently H or $C_{1-6}$ alkyl optionally substituted by —NR$^c$R$^d$, wherein R' and R$^d$ are each independently H or $C_{1-6}$ alkyl;
- $R^8$ is —C(O)R$^9$ or —S(O)$_2$R$^9$;
- $R^9$ is $C_{1-6}$ alkyl, $C_{2-6}$ alkenyl, $C_{3-8}$ cycloalkyl, or 3- to 10-membered heterocyclyl, each of which is optionally substituted with $C_{1-6}$ alkyl, halo, —CN, or —C(O)OR$^{9a}$, wherein R$^{9a}$ is $C_{1-6}$ alkyl; and
- $R^{11}$, $R^{12}$ and $R^{13}$ are each independently H, $C_{1-6}$ alkyl, $C_{1-6}$ haloalkyl, $C_{1-6}$ heteroalkyl, $C_{6-14}$ aryl, 5- to 10-membered heteroaryl, $C_{3-8}$ cycloalkyl, or 3- to 10-membered heterocyclyl.

In some embodiments, the compound of formula (I) is not a compound selected from Table 1X, or a stereoisomer, tautomer, or a pharmaceutically acceptable salt of any of the foregoing.

TABLE 1X

| Compound No. | Name |
|---|---|
| 1x | N-(3-(6-(2,6-dichloro-3,5-dimethoxyphenyl)-4,5,6,7-tetrahydro-1H-indazol-3-yl)-1H-pyrazol-4-yl)acrylamide |
| 2x | N-(3-(6-(2,6-dichloro-3,5-dimethoxyphenyl)-4,5,6,7-tetrahydro-1H-indazol-3-yl)-1-methyl-1H-pyrazol-4-yl)acrylamide |

TABLE 1X-continued

| Compound No. | Name |
|---|---|
| 3x | N-(5-(6-(2,6-dichloro-3,5-dimethoxyphenyl)-4,5,6,7-tetrahydro-1H-indazol-3-yl)-1-methyl-1H-pyrazol-4-yl)acrylamide |
| 4x | N-(5-(6-(2,6-difluoro-3,5-dimethoxyphenyl)-4,5,6,7-tetrahydro-1H-indazol-3-yl)-1-methyl-1H-pyrazol-4-yl)acrylamide |
| 5x | N-(5-(6-(2-fluoro-3,5-dimethoxyphenyl)-4,5,6,7-tetrahydro-1H-indazol-3-yl)-1-methyl-1H-pyrazol-4-yl)acrylamide |
| 6x | N-(5-(6-(2-chloro-6-fluoro-3,5-dimethoxyphenyl)-4,5,6,7-tetrahydro-1H-indazol-3-yl)-1-methyl-1H-pyrazol-4-ypacrylamide |
| 7x | N-(5-(6-(3,5-dimethoxyphenyl)-4,5,6,7-tetrahydro-1H-indazol-3-yl)-1-methyl-1H-pyrazol-4-yl)acrylamide |
| 8x | N-(5-(6-(2-chloro-3,5-dimethoxyphenyl)-4,5,6,7-tetrahydro-1H-indazol-3-yl)-1-methyl-1H-pyrazol-4-yl)acrylamide |

In some embodiments of a compound of formula (I), or a stereoisomer, tautomer, or a pharmaceutically acceptable salt of any of the foregoing, ---- is a single bond. In some embodiments, ---- is a double bond.

In some embodiments of a compound of formula (I), or a stereoisomer, tautomer, or a pharmaceutically acceptable salt of any of the foregoing, X is CH. In some embodiments, X is C. In some embodiments, ---- is a single bond and X is CH. In some embodiments, ---- is a single bond and X is C. In some embodiments, ---- is a double bond and X is C.

In some embodiments of a compound of formula (I), or a stereoisomer, tautomer, or a pharmaceutically acceptable salt of any of the foregoing, $L_2$ is a bond. In some embodiments, $L_2$ is —$CH_2$—.

In some embodiments of a compound of formula (I), or a stereoisomer, tautomer, or a pharmaceutically acceptable salt of any of the foregoing, ---- is a single bond; X is CH; and $L_2$ is a bond. In some embodiments, ---- is a single bond; X is CH; and $L_2$ is —$CH_2$—. In some embodiments, ---- is a double bond; X is C; and $L_2$ is a bond. In some embodiments, ---- is a double bond; X is C; and $L_2$ is —$CH_2$—. In some embodiments, ---- is a sing bond; X is C; and $L_2$ is —$CH_2$—. In some embodiments, ---- is a sing bond; X is C; and $L_2$ is a bond.

In some embodiments, the compound of formula (I) is a compound of formula (II), or a stereoisomer, tautomer, or a pharmaceutically acceptable salt of any of the foregoing,

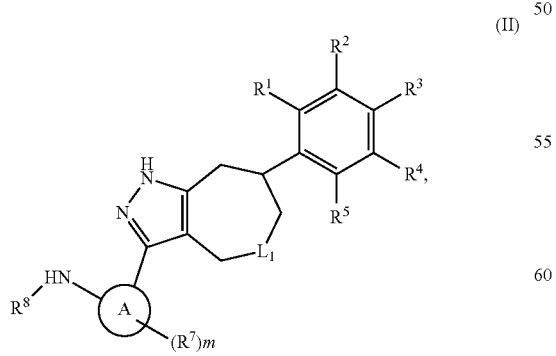

(II)

wherein $L_1$, A, m, $R^1$, $R^2$, $R^3$, $R^4$, $R^5$, $R^7$, and $R^8$ are as defined herein for any embodiment of a compound of formula (I).

In some embodiments, the compound of formula (I) is a compound of formula (III), or a stereoisomer, tautomer, or a pharmaceutically acceptable salt of any of the foregoing,

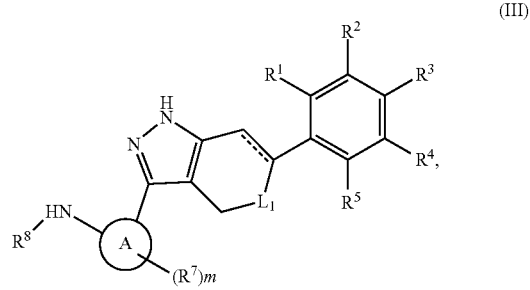

(III)

wherein $L_1$, A, m, $R^1$, $R^2$, $R^3$, $R^4$, $R^5$, $R^7$, and $R^8$ are as defined herein for any embodiment of a compound of formula (I).

In some embodiments of a compound of formula (I) or any related formula such as formula (II) or (III), or a stereoisomer, tautomer, or a pharmaceutically acceptable salt of any of the foregoing, $L_1$ is —CR'R"—. In some embodiments, $L_1$ is —O—. In some embodiments, $L_1$ is —NR'"—. In some embodiments, $L_1$ is —O— or —NR'"—. In some embodiments, $L_1$ is —CR'R"— or —O—.

In some embodiments, the compound of formula (II) is a compound of formula (II-a), or a stereoisomer, tautomer, or a pharmaceutically acceptable salt of any of the foregoing,

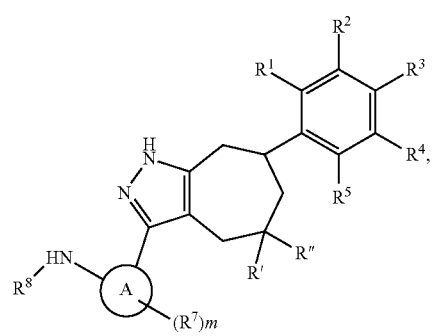

(II-a)

wherein A, m, R', R", $R^2$, $R^3$, $R^4$, $R^5$, $R^7$, and $R^8$ are as defined herein for any embodiment of a compound of formula (I).

In some embodiments, the compound of formula (II) is a compound of formula (II-b), or a stereoisomer, tautomer, or a pharmaceutically acceptable salt of any of the foregoing,

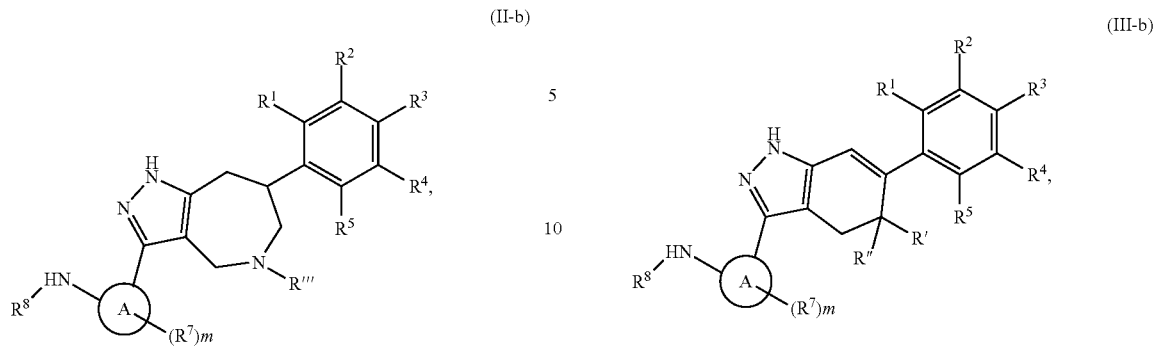

(II-b)

wherein A, m, R''', R$^1$, R$^2$, R$^3$, R$^4$, R$^5$, R$^7$, and R$^8$ are as defined herein for any embodiment of a compound of formula (I).

In some embodiments, the compound of formula (II) is a compound of formula (II-c), or a stereoisomer, tautomer, or a pharmaceutically acceptable salt of any of the foregoing,

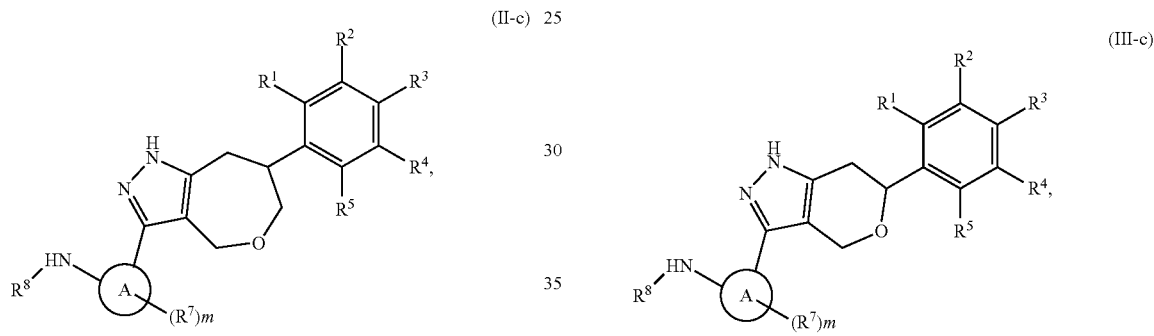

(II-c)

wherein A, m, R$^1$, R$^2$, R$^3$, R$^4$, R$^5$, R$^7$, and R$^8$ are as defined herein for any embodiment of a compound of formula (I).

In some embodiments, the compound of formula (III) is a compound of formula (III-a), or a stereoisomer, tautomer, or a pharmaceutically acceptable salt of any of the foregoing,

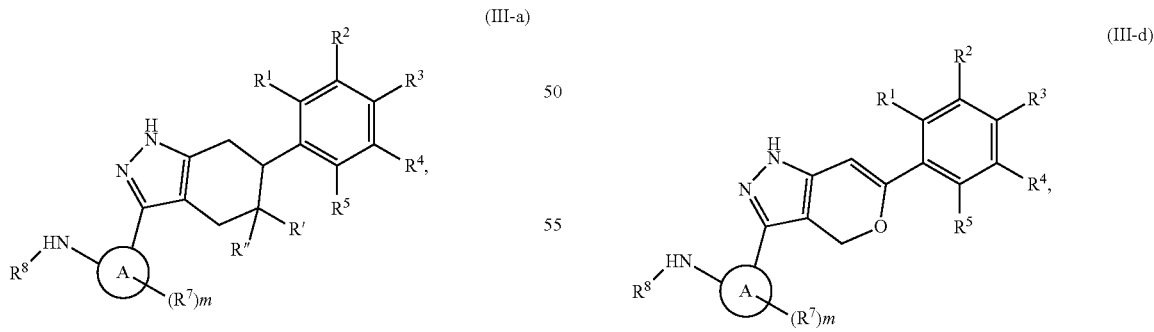

(III-a)

wherein A, m, R', R", R$^2$, R$^3$, R$^4$, R$^5$, R$^7$, and R$^8$ are as defined herein for any embodiment of a compound of formula (I).

In some embodiments, the compound of formula (III) is a compound of formula (III-b), or a stereoisomer, tautomer, or a pharmaceutically acceptable salt of any of the foregoing, (III-b)

wherein A, m, R', R", R$^2$, R$^3$, R$^4$, R$^5$, R$^7$, and R$^8$ are as defined herein for any embodiment of a compound of formula (I).

In some embodiments, the compound of formula (III) is a compound of formula (III-c), or a stereoisomer, tautomer, or a pharmaceutically acceptable salt of any of the foregoing, (III-c)

wherein A, m, R$^1$, R$^2$, R$^3$, R$^4$, R$^5$, R$^7$, and R$^8$ are as defined herein for any embodiment of a compound of formula (I).

In some embodiments, the compound of formula (III) is a compound of formula (III-d), or a stereoisomer, tautomer, or a pharmaceutically acceptable salt of any of the foregoing, (III-d)

wherein A, m, R$^1$, R$^2$, R$^3$, R$^4$, R$^5$, R$^7$, and R$^8$ are as defined herein for any embodiment of a compound of formula (I).

In some embodiments, the compound of formula (III) is a compound of formula (III-e), or a stereoisomer, tautomer, or a pharmaceutically acceptable salt of any of the foregoing,

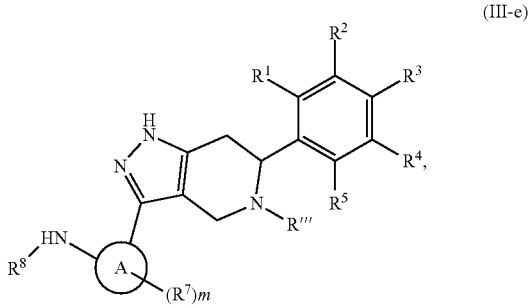

(III-e)

wherein A, m, R''', $R^1$, $R^2$, $R^3$, $R^4$, $R^5$, $R^7$, and $R^8$ are as defined herein for any embodiment of a compound of formula (I).

In some embodiments, the compound of formula (III) is a compound of formula (III-f), or a stereoisomer, tautomer, or a pharmaceutically acceptable salt of any of the foregoing,

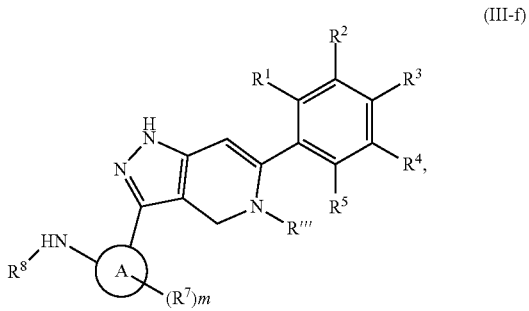

(III-f)

wherein A, m, R''', $R^1$, $R^2$, $R^3$, $R^4$, $R^5$, $R^7$, and $R^8$ are as defined herein for any embodiment of a compound of formula (I).

In some embodiments of a compound of formula (I), or any related formula, such as formula (II) or (III), or a stereoisomer, tautomer, or a pharmaceutically acceptable salt of any of the foregoing, R' is H. In some embodiments, R' is $C_{1-6}$ alkyl such as methyl, ethyl, n-propyl, or isopropyl. In some embodiments, R' is methyl. In some embodiments, R' is $C_{1-6}$ haloalkyl. In some embodiments, R' is halo such as fluoro, chloro, or bromo. In some embodiments, R' is H or $C_{1-6}$ alkyl.

In some embodiments of a compound of formula (I), or any related formula, such as formula (II) or (III), or a stereoisomer, tautomer, or a pharmaceutically acceptable salt of any of the foregoing, R" is H. In some embodiments, R" is $C_{1-6}$ alkyl such as methyl, ethyl, n-propyl, or isopropyl. In some embodiments, R" is methyl. In some embodiments, R" is $C_{1-6}$ haloalkyl. In some embodiments, R" is halo such as fluoro, chloro, or bromo. In some embodiments, R" is $C_{1-6}$ alkyl, $C_{1-6}$ haloalkyl, or halo. In some embodiments, R" is H or $C_{1-6}$ alkyl.

In some embodiments of a compound of formula (I), or any related formula, such as formula (II) or (III), or a stereoisomer, tautomer, or a pharmaceutically acceptable salt of any of the foregoing, R' is H and R" is H. In some embodiments, R' is $C_{1-6}$ alkyl and R" is H. In some embodiments, R' is $C_{1-6}$ alkyl and R" is $C_{1-6}$ alkyl. In some embodiments, R' is $C_{1-6}$ alkyl and R" is halo. In some embodiments, R' is halo and R" is H. In some embodiments, R' is halo and R" is halo. In some embodiments, R' is methyl and R" is H. In some embodiments, R' is H or $C_{1-6}$ alkyl; and R" is H.

In some embodiments of a compound of formula (I), or any related formula, such as formula (II) or (III), or a stereoisomer, tautomer, or a pharmaceutically acceptable salt of any of the foregoing, R''' is H. In some embodiments, R''' is $C_{1-6}$ alkyl such as methyl, ethyl, n-propyl, or isopropyl. In some embodiments, R''' is $C_{1-6}$ haloalkyl. In some embodiments, R''' is acyl. In some embodiments, R''' is —C(=O)R, wherein R is $C_{1-6}$ alkyl, $C_{2-6}$ alkenyl, $C_{2-6}$ alkynyl, or $C_{3-6}$ cycloalkyl. In some embodiments, R''' is —C(=O)R, wherein R is $C_{1-6}$ alkyl such as methyl, ethyl, n-propyl, or isopropyl.

In some embodiments of a compound of formula (I), or any related formula, such as formula (II) or (III), or a stereoisomer, tautomer, or a pharmaceutically acceptable salt of any of the foregoing, $R^1$ is H or halo. In some embodiments, $R^1$ is H. In some embodiments, $R^1$ is $C_{1-6}$ alkyl such as methyl, ethyl, n-propyl, or isopropyl. In some embodiments, $R^1$ is halo. In some embodiments, $R^1$ is fluoro or chloro. In some embodiments, $R^1$ is fluoro. In some embodiments, $R^1$ is —$OR^{13}$ and $R^{13}$ is $C_{1-6}$ alkyl or $C_{1-6}$ haloalkyl. In some embodiments, $R^1$ is —$OR^{13}$ and $R^{13}$ is $C_{1-6}$ alkyl. In some embodiments, $R^1$ is chloro. In some embodiments, $R^1$ and X are taken together with the carbons to which they are attached to form a 4- to 8-membered heterocyclyl. In some embodiments, $R^1$ and X are taken together with the carbons to which they are attached to form a 5-membered heterocyclyl. In some embodiments, the compound of formula (I) is a compound of any one of the formulae (I-1)-(I-4), (II-1)-(II-4), and (III-1)-(III-4), or a stereoisomer, tautomer, or a pharmaceutically acceptable salt of any of the foregoing,

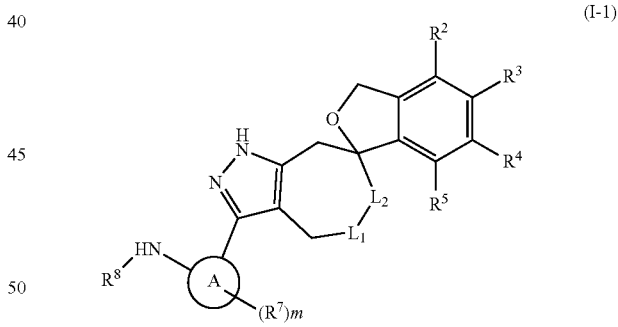

(I-1)

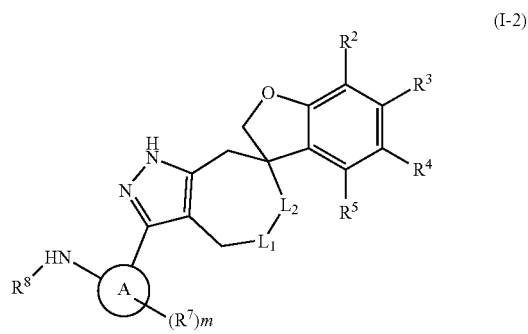

(I-2)

-continued
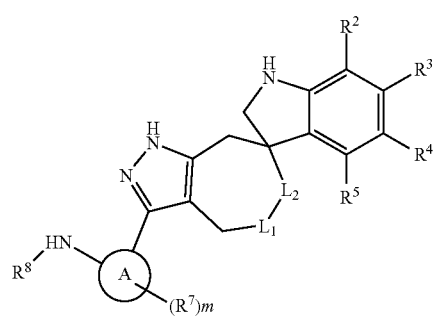
(I-3)
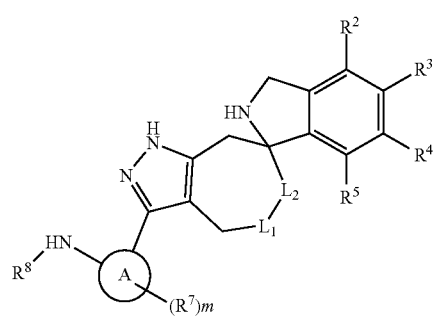
(I-4)
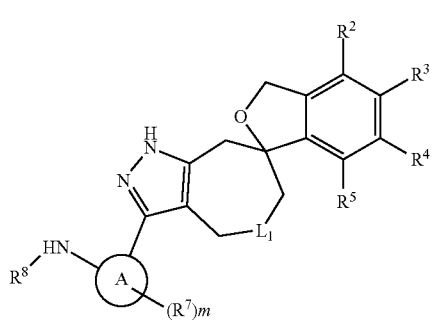
(II-1)
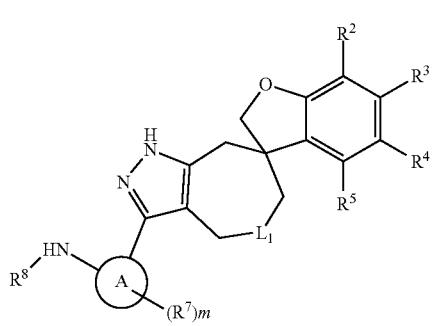
(II-2)
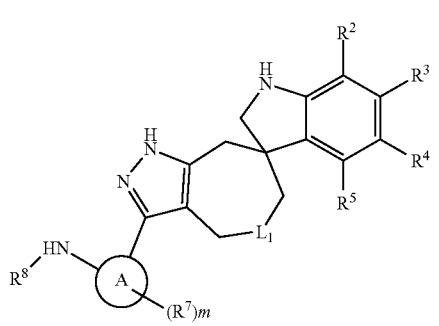
(II-3)
-continued
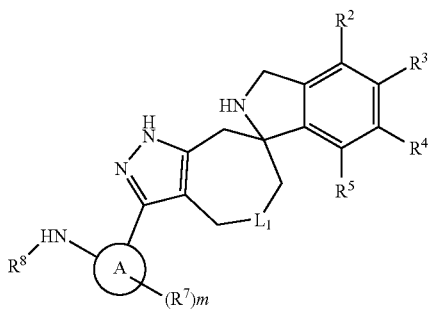
(II-4)
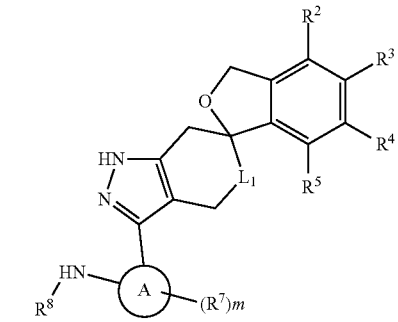
(III-1)
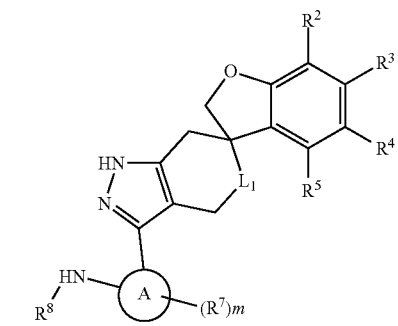
(III-2)
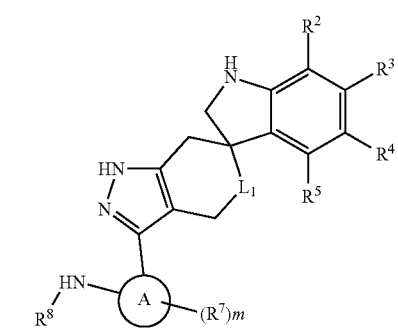
(III-3)
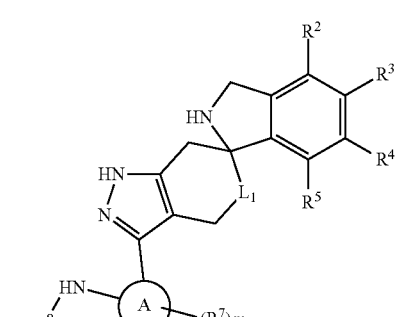
(III-4)

wherein $L_1$, $L_2$, A, m, $R^2$, $R^3$, $R^4$, $R^5$, $R^7$, and $R^8$ are as defined herein for any embodiment of a compound of formula (I).

In some embodiments of a compound of formula (I), or any related formula, such as formula (II) or (III), or a stereoisomer, tautomer, or a pharmaceutically acceptable salt of any of the foregoing, $R^2$ is H. In some embodiments, $R^2$ is $C_{1-6}$ alkyl such as methyl, ethyl, n-propyl, or isopropyl. In some embodiments, $R^2$ is halo. In some embodiments, $R^2$ is —$OR^{13}$ and $R^{13}$ is $C_{1-6}$ alkyl or $C_{1-6}$ haloalkyl. In some embodiments, $R^2$ is —$OR^{13}$ and $R^{13}$ is $C_{1-6}$ alkyl. In some embodiments, $R^2$ is —$OCH_3$ or —$OCD_3$.

In some embodiments of a compound of formula (I), or any related formula, such as formula (II) or (III), or a stereoisomer, tautomer, or a pharmaceutically acceptable salt of any of the foregoing, $R^3$ is H. In some embodiments, $R^3$ is $C_{1-6}$ alkyl such as methyl, ethyl, n-propyl, or isopropyl. In some embodiments, $R^3$ is halo.

In some embodiments of a compound of formula (I), or any related formula, such as formula (II) or (III), or a stereoisomer, tautomer, or a pharmaceutically acceptable salt of any of the foregoing, $R^4$ is H. In some embodiments, $R^4$ is $C_{1-6}$ alkyl such as methyl, ethyl, n-propyl, or isopropyl. In some embodiments, $R^4$ is halo. In some embodiments, $R^4$ is —$OR^{13}$ and $R^{13}$ is $C_{1-6}$ alkyl or $C_{1-6}$ haloalkyl. In some embodiments, $R^4$ is —$OR^{13}$ and $R^{13}$ is $C_{1-6}$ alkyl. In some embodiments, $R^4$ is —$OCH_3$ or —$OCD_3$.

In some embodiments of a compound of formula (I), or any related formula, such as formula (II) or (III), or a stereoisomer, tautomer, or a pharmaceutically acceptable salt of any of the foregoing, $R^5$ is H or halo. In some embodiments, $R^5$ is H. In some embodiments, $R^5$ is $C_{1-6}$ alkyl such as methyl, ethyl, n-propyl, or isopropyl. In some embodiments, $R^5$ is halo. In some embodiments, $R^5$ is fluoro or chloro. In some embodiments, $R^5$ is fluoro. In some embodiments, $R^5$ is chloro. In some embodiments, $R^5$ is —$OR^{13}$ and $R^{13}$ is $C_{1-6}$ alkyl or $C_{1-6}$ haloalkyl. In some embodiments, $R^4$ is —$OR^{13}$ and $R^{13}$ is $C_{1-6}$ alkyl.

In some embodiments of a compound of formula (I), or any related formula, such as formula (II) or (III), or a stereoisomer, tautomer, or a pharmaceutically acceptable salt of any of the foregoing, $R^1$ is H or halo; $R^2$ is —$OR^{13}$, wherein $R^{13}$ is $C_{1-6}$ alkyl; $R^3$ is H; $R^4$ is —$OR^{13}$, wherein $R^{13}$ is $C_{1-6}$ alkyl; and $R^5$ is H or halo. In some embodiments, $R^1$ and X are taken together with the carbons to which they are attached to form a 5-membered heterocyclyl; $R^2$ is —$OR^{13}$, wherein $R^{13}$ is $C_{1-6}$ alkyl; $R^3$ is H; $R^4$ is —$OR^{13}$, wherein $R^{13}$ is $C_{1-6}$ alkyl; and $R^5$ is H or halo. In some embodiments, $R^1$ is H, chloro, or fluoro; $R^2$ is —$OCH_3$ or —$OCD_3$; $R^3$ is H; $R^4$ is —$OCH_3$ or —$OCD_3$; and $R^5$ is H, chloro, or fluoro.

In some embodiments of a compound of formula (I), or any related formula, such as formula (II) or (III), or a stereoisomer, tautomer, or a pharmaceutically acceptable salt of any of the foregoing, ring A is $C_{6-14}$ arylene. In some embodiments, ring A is $C_6$ arylene. In some embodiments, ring A is 1,3-phenylene. In some embodiments, ring A is 1,2-phenylene. In some embodiments, ring A is 1,4-phenylene.

In some embodiments of a compound of formula (I), or any related formula, such as formula (II) or (III), or a stereoisomer, tautomer, or a pharmaceutically acceptable salt of any of the foregoing, ring A is 5- to 10-membered heteroarylene. In some embodiments, ring A is 5- to 6-membered heteroarylene. In some embodiments, ring A is a 6-membered heteroarylene. In some embodiments, ring A is pyridin-2,3-diyl, pyridin-2,4-diyl, pyridin-2,5-diyl, pyridin-2,6-diyl, pyridin-3,4-diyl, pyridin-3,5-diyl, pyrazin-2,3-diyl, pyrazin-2,5-diyl, pyrazin-2,6-diyl, pyridazin-3,4-yl, pyridazin-3,5-yl, pyridazin-3,6-yl, pyridazin-4,5-yl, pyridazin-4,6-yl, primidin-2,4-diyl, primidin-2,5-diyl, primidin-4,5-diyl, primidin-4,6-diyl, triazin-diyl, 1,3,5-triazin-2,4-diyl, 1,2,3-triazin-4,5-diyl, 1,2,3-triazin-4,6-diyl, 1,2,3-triazin-5,6-diyl, 1,2,4-triazin-3,5-diyl, 1,2,4-triazin-3,6-diyl or 1,2,4-triazin-5,6-diyl. In some embodiments, ring A is a 5-membered heteroarylene. In some embodiments, ring A is pyrrol-2,5-diyl, pyrrol-1,2-diyl, pyrrol-3,4-diyl, pyrrol-2,3-diyl, pyrrol-1,3-diyl, pyrrol-1,4-diyl, pyrazol-1,3-diyl, pyrazol-1,4-diyl, pyrazol-1,5-diyl, pyrazol-3,4-diyl, pyrazol-4,5-diyl, pyrazol-3,5-diyl, imidazol-1,2-diyl, imidazol-1,4-diyl, imidazol-1,5-diyl, imidazol-2,4-diyl, imidazol-2,5-diyl, triazol-diyl, tetrazol-diyl, oxazol-2,5-diyl, oxazol-2,4-diyl, thiophen-2,3-diyl, thiophen-2,4-diyl, thiophen-2,5-diyl, thiazol-2,4-diyl, thiazol-2,5-diyl, isoxazol-3,4-diyl, isoxazol-3,5-diyl, isothiazol-3,4-yl, isothiazol-3,5-diyl, furan-2,3-diyl, furan-2,4-diyl or furan-2,5-diyl.

In some embodiments of a compound of formula (I), or any related formula, such as formula (II) or (III), or a stereoisomer, tautomer, or a pharmaceutically acceptable salt of any of the foregoing, ring A is $C_{3-8}$ cycloalkylene. In some embodiments, ring A is $C_{5-6}$ cycloalkylene. In some embodiments, ring A is cycloprop-1,2-diyl, cyclobut-1,2-diyl, cyclobut-1,3-diyl, cyclopent-1,2-diyl, cyclopent-1,3-diyl, cyclohex-1,2-diyl, cyclohex-1,3-diyl, cyclohex-1,4-diyl, cyclohept-1,2-diyl, cyclohept-1,3-diyl, cyclohept-1,4-diyl, cyclooct-1,2-diyl, cyclooct-1,3-diyl, cyclooct-1,4-diyl or cyclooct-1,5-diyl.

In some embodiments of a compound of formula (I), or any related formula, such as formula (II) or (III), or a stereoisomer, tautomer, or a pharmaceutically acceptable salt of any of the foregoing, ring A is 3- to 10-membered heterocyclylene. In some embodiments, ring A is 5- to 6-membered heterocyclylene. In some embodiments, ring A is 5-membered heterocyclylene. In some embodiments, ring A is tetrahydrofuran-2,3-diyl, tetrahydrofuran-2,4-diyl, tetrahydrofuran-2,5-diyl, pyrrolidin-2,5-diyl, pyrrolidin-1,2-diyl, pyrrolidin-3,4-diyl, pyrrolidin-2,3-diyl, pyrrolidin-1,3-diyl, pyrrolidin-1,4-diyl. In some embodiments, ring A is 6-membered heterocyclylene. In some embodiments, ring A is tetrahydro-2H-pyran-2,3-diyl, tetrahydro-2H-pyran-2,4-diyl, tetrahydro-2H-pyran-2,5-diyl, tetrahydro-2H-pyran-2,6-diyl, tetrahydro-2H-pyran-3,4-diyl, tetrahydro-2H-pyran-3,5-diyl, tetrahydro-2H-pyran-3,6-diyl, piperidin-1,2-diyl, piperidin-1,3-diyl, piperidin-1,4-diyl, piperidin-2,3-diyl, piperidin-2,4-diyl, piperidin-2,5-diyl, or piperidin-3,4-diyl.

In some embodiments of a compound of formula (I), or any related formula, such as formula (II) or (III), or a stereoisomer, tautomer, or a pharmaceutically acceptable salt of any of the foregoing, ring A is a $C_6$ arylene, 5- to 6-membered heteroarylene, $C_{5-6}$ cycloalkylene, or 5- to 6-membered heterocyclylene. In some embodiments, ring A is $C_6$ arylene, 5- to 6-membered heteroarylene or 5- to 6-membered heterocyclylene. In some embodiments, ring A is 5- to 6-membered heteroarylene or 5- to 6-membered heterocyclylene. In some embodiments, ring A is

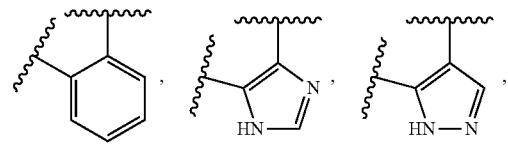

-continued

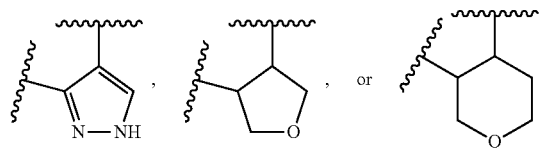

In some embodiments, ring A is

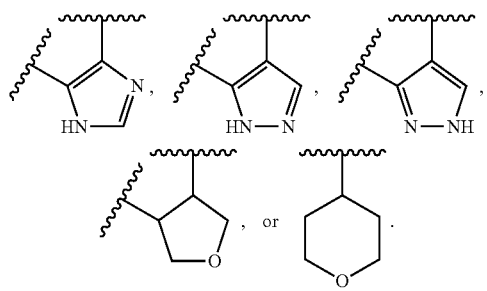

In some embodiments, ring A is

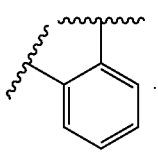 [SMILES: *c1ccccc1*]

In some embodiments, ring A is

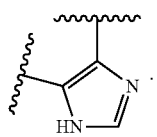

In some embodiments, ring A is

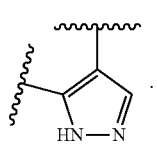

In some embodiments, ring A is

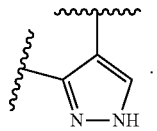

In some embodiments, ring A is

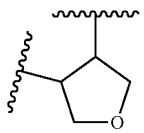

In some embodiments, ring A is

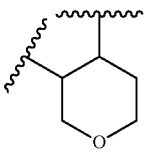

In some embodiments of a compound of formula (I), or any related formula, such as formula (II) or (III), or a stereoisomer, tautomer, or a pharmaceutically acceptable salt of any of the foregoing, m is 0. In some embodiments, m is 1. In some embodiments, m is 2. In some embodiments, m is 0 or 1.

In some embodiments of a compound of formula (I), or any related formula, such as formula (II) or (III), or a stereoisomer, tautomer, or a pharmaceutically acceptable salt of any of the foregoing, each $R^7$ is independently $C_{1-6}$ alkyl or $C_{1-6}$ haloalkyl. In some embodiments, each $R^7$ is independently $C_{1-6}$ alkyl. In some embodiments, each $R^7$ is independently —$CH_3$, —$CH_2CH_3$, —$CH(CH_3)_2$, —$CD_3$, or —$CH_2CF_3$. In some embodiments, each $R^7$ is independently $C_{1-6}$ haloalkyl. In some embodiments, each $R^7$ is independently —$CF_3$ or —$CH_2CF_3$. In some embodiments, m is 1 and $R^7$ is —$CH_3$, —$CH_2CH_3$, —$CH(CH_3)_2$, —$CD_3$, or —$CH_2CF_3$. In some embodiments, each $R^7$ is independently $C_{1-6}$ alkyl or $C_{1-6}$ haloalkyl, wherein the $C_{1-6}$ alkyl and $C_{1-6}$ haloalkyl of $R^7$ are each independently optionally substituted by —$NR^cR^d$. In some embodiments, each $R^7$ is independently —$CH_3$, —$CH_2CH_3$, —$CH(CH_3)_2$, —$CD_3$, —$CH_2CH_2N(CH_3)_2$, or —$CH_2CF_3$.

In some embodiments of a compound of formula (I), or any related formula, such as formula (II) or (III), or a stereoisomer, tautomer, or a pharmaceutically acceptable salt of any of the foregoing, $R^8$ is —$C(O)R^9$. In some embodiments, $R^8$ is —$S(O)_2R^9$. In some embodiments, $R^9$ is $C_{1-6}$ alkyl optionally substituted with $C_{1-6}$ alkyl, halo, —CN, or —$C(O)OR^{9a}$. In some embodiments, $R^9$ is $C_{2-6}$ alkenyl optionally substituted with $C_{1-6}$ alkyl, halo, —CN, or —$C(O)OR^{9a}$. In some embodiments, $R^9$ is $C_{3-8}$ cycloalkyl optionally substituted with $C_{1-6}$ alkyl, halo, —CN, or —$C(O)OR^{9a}$. In some embodiments, $R^9$ is $C_{3-8}$ cycloalkyl which is unsubstituted. In some embodiments, $R^9$ is 3- to 10-membered heterocyclyl optionally substituted with $C_{1-6}$ alkyl, halo, —CN, or —$C(O)OR^{9a}$. In some embodiments, $R^9$ is 3- to 10-membered heterocyclyl which is unsubstituted. In some embodiments, $R^9$ is $C_{1-6}$ alkyl or $C_{2-6}$ alkenyl, each optionally substituted with halo. In some embodiments, $R^9$ is $C_{1-6}$ alkyl optionally substituted with halo. In some embodiments, $R^9$ is $C_{1-6}$ alkyl which is unsubstituted. In some embodiments, $R^9$ is methyl. In some embodiments, $R^9$ is $C_{2-6}$ alkenyl optionally substituted with halo. In some embodiments, $R^9$ is $C_{2-6}$ alkenyl which is unsubstituted. In some embodiments, $R^9$ is $C_{1-6}$ alkyl, $C_{2-6}$ alkenyl, or 3- to 10-membered heterocyclyl, each of which is optionally substituted with halo or —$C(O)OR^{9a}$, wherein $R^{9a}$ is $C_{1-6}$ alkyl. In some embodiments, $R^9$ is —$CH_3$, —$CH_2CH_3$,

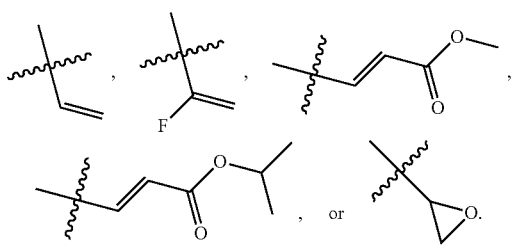

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of formula (I) may be combined with every description, variation, embodiment or aspect of ----, X, $L_1$, $L_2$, A, m, $R^2$, $R^3$, $R^4$, $R^5$, $R^7$, and $R^8$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as formulae (II), (III), (II-a), (II-b), (II-c), (III-b), (III-c), (III-d), (III-e), (III-f), (I-1)-(I-4), (II-1)-(II-4), and (III-1)-(III-4), and are equally described, the same as if each and every description, variation, embodiment or aspect were separately and individually listed for all formulae. For example, in some embodiments of a compound of formula (I) or any related formula where applicable, $L_1$ is —CR'R"— or —O—; R' is H or $C_{1-6}$ alkyl; R" is H; $R^1$ is H or halo, or $R^1$ and X are taken together with the carbons to which they are attached to form a 5-membered heterocyclyl; $R^2$ is —$OR^{13}$, wherein $R^{13}$ is $C_{1-6}$ alkyl; $R^3$ is H; $R^4$ is —$OR^{13}$, wherein $R^{13}$ is $C_{1-6}$ alkyl; $R^5$ is H or halo; ring A is 5- to 6-membered heteroarylene or 5- to 6-membered heterocyclylene; m is 0 or 1; each $R^7$ is independently $C_{1-6}$ alkyl or $C_{1-6}$ haloalkyl; $R^8$ is —C(O)$R^9$; and $R^9$ is $C_{1-6}$ alkyl, $C_{2-6}$ alkenyl, or 3- to 10-membered heterocyclyl, each of which is optionally substituted with halo or —C(O)$OR^{9a}$, wherein $R^{9a}$ is $C_{1-6}$ alkyl. As another example, in some embodiments of a compound of formula (I) or any related formula where applicable, $L_1$ is —CR'R"— or —O—; R' is H or $C_{1-6}$ alkyl; R" is H; $R^1$ is H or halo; $R^2$ is —$OR^{13}$, wherein $R^{13}$ is $C_{1-6}$ alkyl; $R^3$ is H; $R^4$ is —$OR^{13}$, wherein $R^{13}$ is $C_{1-6}$ alkyl; $R^5$ is H or halo; ring A is

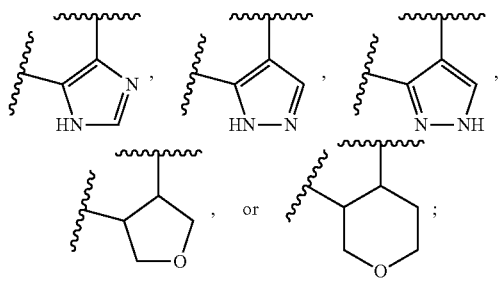

m is 0 or 1; each $R^7$ is independently $C_{1-6}$ alkyl or $C_{1-6}$ haloalkyl; $R^8$ is —C(O)$R^9$; and $R^9$ is $C_{1-6}$ alkyl, $C_{2-6}$ alkenyl, or 3- to 10-membered heterocyclyl, each of which is optionally substituted with halo or —C(O)$OR^{9a}$, wherein $R^{9a}$ is $C_{1-6}$ alkyl.

In some embodiments, provided is a compound selected from compounds in Table 1, or a stereoisomer, tautomer, solvate, prodrug or salt thereof. In some embodiments, provided is a compound selected from compounds in Table 1, or a stereoisomer, tautomer, or a pharmaceutically acceptable salt of any of the foregoing. Although certain compounds described in Table 1 are presented as specific stereoisomers and/or in a non-stereochemical form, it is understood that any or all stereochemical forms, including any enantiomeric or diastereomeric forms, and any tautomers or other forms of any of the compounds of Table 1 are herein described.

TABLE 1

| No. | Structure |
|---|---|
| 1 | 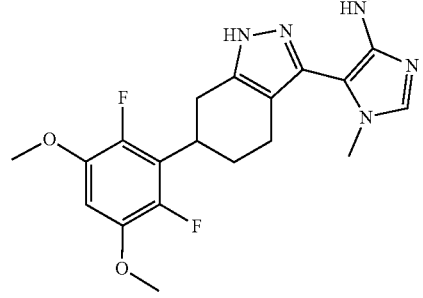 |
| 2 | 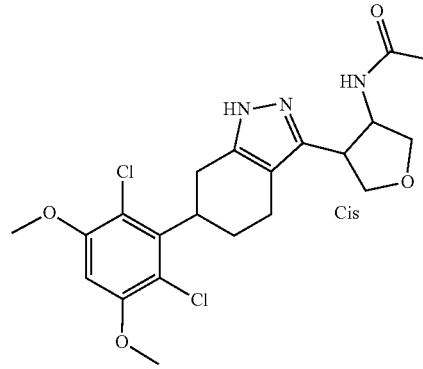 |
| 3 | 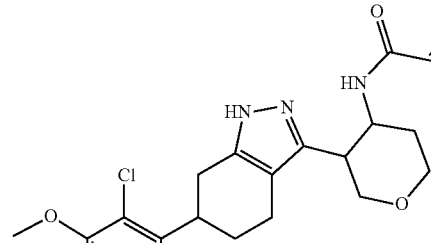 |

TABLE 1-continued
| No. | Structure |
|---|---|
| 4 | 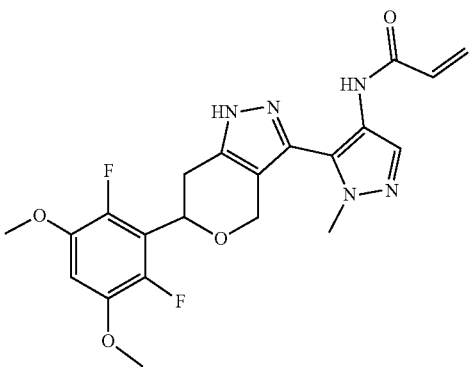 [SMILES: C=CC(=O)Nc1cnn(C)c1-c1n[nH]c2c1COC(c1c(F)c(OC)cc(OC)c1F)C2] |
| 5 | 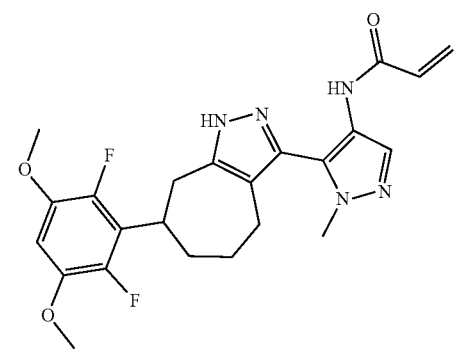 [SMILES: C=CC(=O)Nc1cnn(C)c1-c1n[nH]c2c1CCCC(c1c(F)c(OC)cc(OC)c1F)C2] |
| 6 | 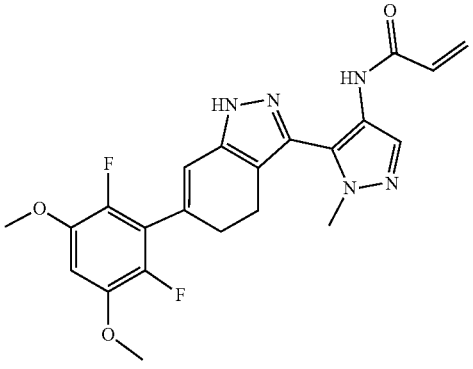 [SMILES: C=CC(=O)Nc1cnn(C)c1-c1n[nH]c2c1CCC(c1c(F)c(OC)cc(OC)c1F)=C2] |
| 7 | 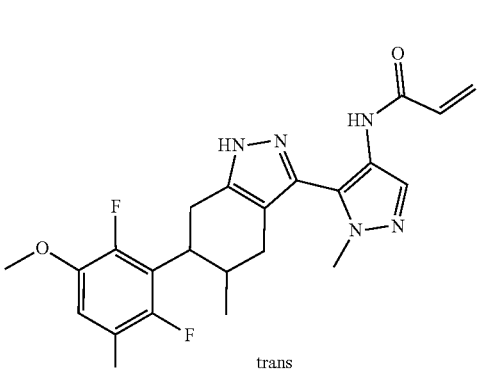 trans |
| 8 | 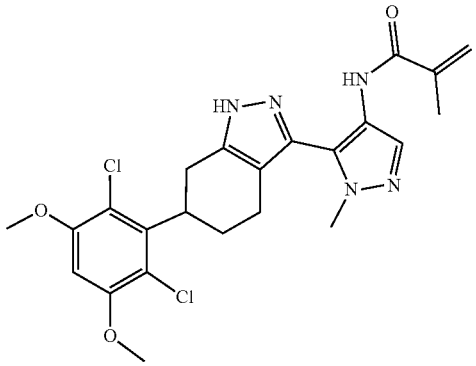 [SMILES: C=C(C)C(=O)Nc1cnn(C)c1-c1n[nH]c2c1CCC(c1c(Cl)c(OC)cc(OC)c1Cl)C2] |
| 9 | 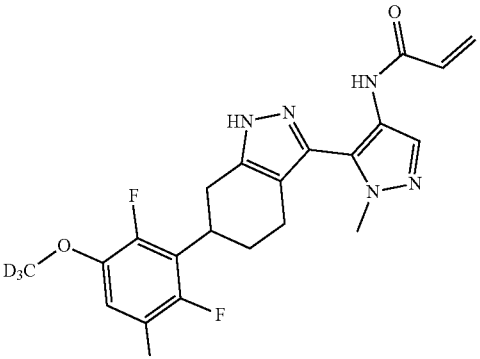 |
| 10 | 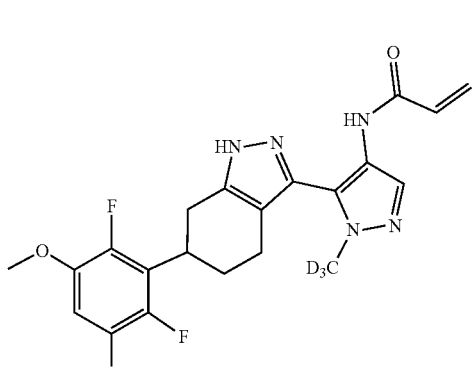 |
| 11 | 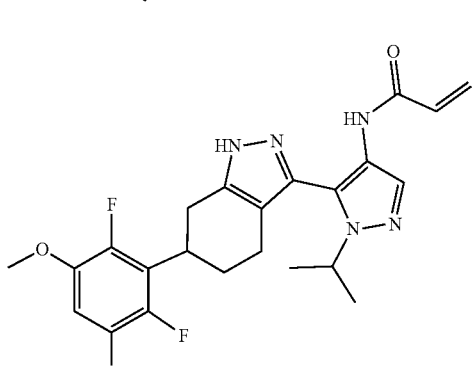 |

TABLE 1-continued
| No. | Structure |
|---|---|
| 12 | 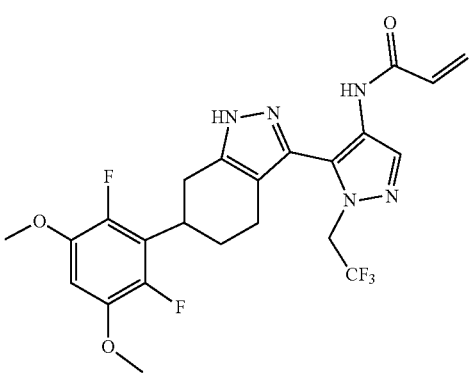 [SMILES: C=CC(=O)Nc1cnn(CC(F)(F)F)c1-c1n[nH]c2c1CCC(c1c(F)c(OC)cc(OC)c1F)C2] |
| 13 | 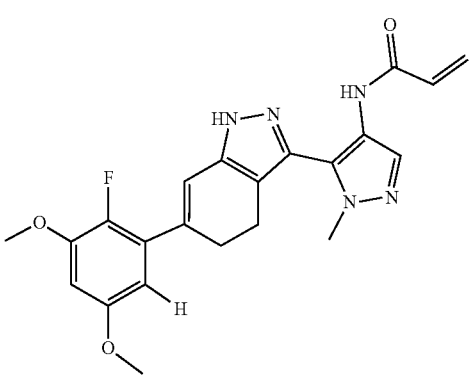 [SMILES: C=CC(=O)Nc1cnn(C)c1-c1n[nH]c2c1CCC(c1cc(OC)cc(OC)c1F)=C2] |
| 14 | 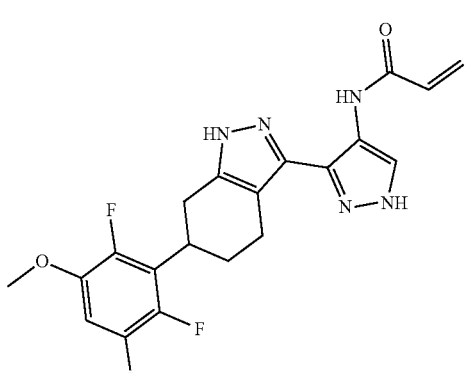 |
| 15 | 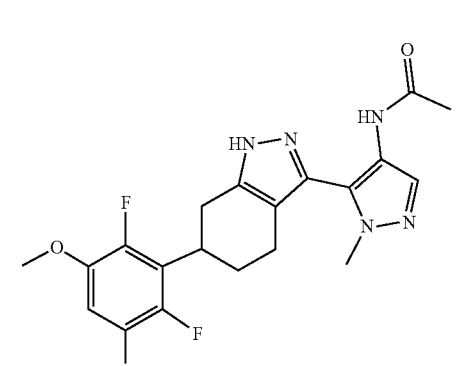 |
| 16 | 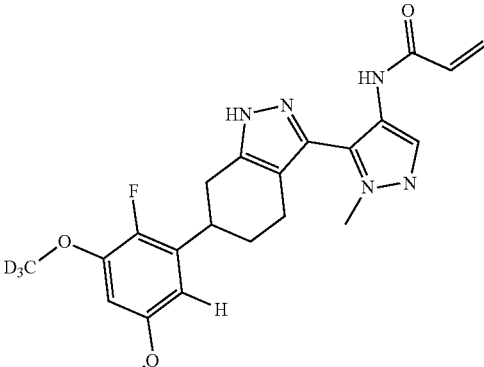 |
| 17 | 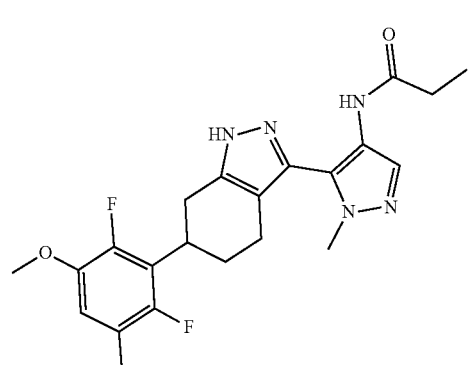 |
| 18 | 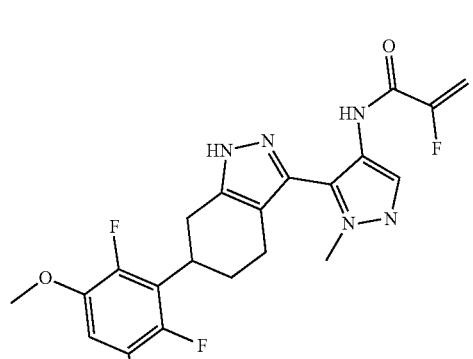 |
| 19 | 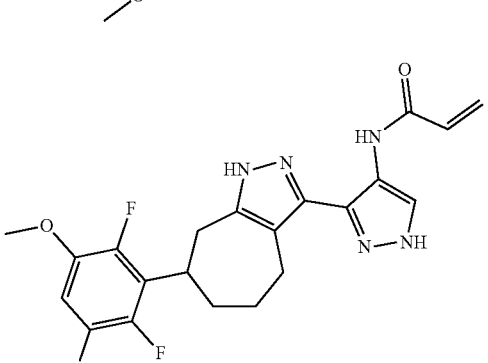 |

TABLE 1-continued

| No. | Structure |
|---|---|
| 20 | 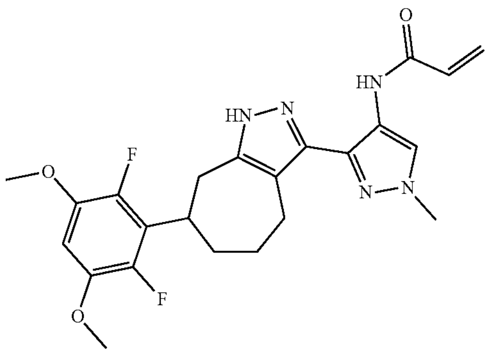 [SMILES: C=CC(=O)Nc1cn(C)nc1-c1n[nH]c2c1CCCC(c1c(F)c(OC)cc(OC)c1F)C2] |
| 21 | 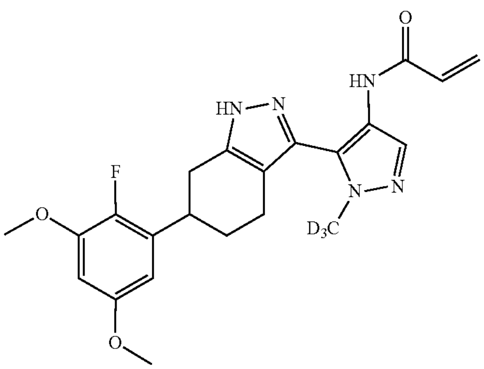 [SMILES: [2H]C([2H])([2H])n1ncc(NC(=O)C=C)c1-c1n[nH]c2c1CCC(c1cc(OC)cc(OC)c1F)C2] |
| 22 | 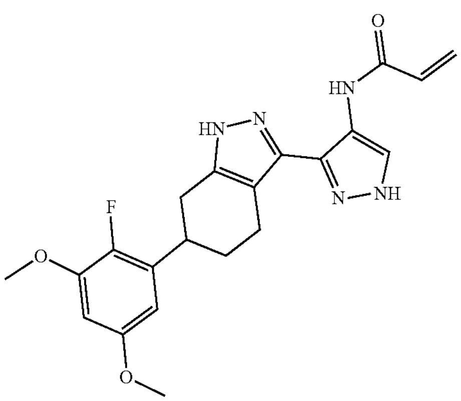 [SMILES: C=CC(=O)Nc1c[nH]nc1-c1n[nH]c2c1CCC(c1cc(OC)cc(OC)c1F)C2] |
| 23 | 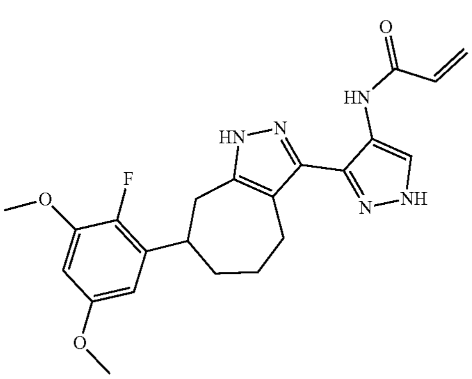 [SMILES: C=CC(=O)Nc1c[nH]nc1-c1n[nH]c2c1CCCC(c1cc(OC)cc(OC)c1F)C2] |
| 24 | |
| 25 | |
| 26 | |
| 27 | |

TABLE 1-continued

| No. | Structure |
|---|---|
| 28 | (structure) |
| 29 | (structure) |
| 30 | (structure) |
| 31 | (structure) |
| 32 | (structure) |
| 34 | (structure) |
| 35 | (structure) |
| 37 | (structure) |
| 38 | (structure) |

TABLE 1-continued

| No. | Structure |
|---|---|
| 39 | (structure) |
| 40 | (structure) |
| 41 | (structure) |
| 42 | (structure) |
| 43 | (structure) |
| 44 | (structure) |
| 45 | (structure) |

Also provided are salts of compounds referred to herein, such as pharmaceutically acceptable salts. The present disclosure also includes any or all of the stereochemical forms, including any enantiomeric or diastereomeric forms, and any tautomers or other forms of the compounds described. Thus, if a particular stereochemical form, such as a specific enantiomeric form or diastereomeric form, is depicted for a given compound, then it is understood that any or all stereochemical forms, including any enantiomeric or diastereomeric forms, and any tautomers or other forms of any of that same compound are herein described. Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The disclosure also intends isotopically-labeled and/or isotopically-enriched forms of compounds described herein.

The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds described herein include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution studies. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances. Isotopically-labeled compounds described herein can generally be prepared by standard methods and techniques known to those skilled in the art or by procedures similar to those described in the accompanying Examples substituting appropriate isotopically-labeled reagents in place of the corresponding non-labeled reagent.

The disclosure also includes any or all metabolites of any of the compounds described. The metabolites may include any chemical species generated by a biotransformation of any of the compounds described, such as intermediates and products of metabolism of the compound, such as would be generated in vivo following administration to a human.

Solvates and/or polymorphs of a compound provided herein or a salt thereof are also contemplated. Solvates contain either stoichiometric or non-stoichiometric amounts of a solvent and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Articles of manufacture comprising a compound described herein, or a salt or solvate thereof, in a suitable container are provided. The container may be a vial, jar, ampoule, preloaded syringe, i.v. bag, and the like.

In some embodiments, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

Pharmaceutical Compositions and Formulations

Pharmaceutical compositions of any of the compounds detailed herein are embraced by this disclosure. Thus, the present disclosure includes pharmaceutical compositions comprising a compound as detailed herein, or a stereoisomer, tautomer, or a pharmaceutically acceptable salt of any of the foregoing, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein, or a stereoisomer, tautomer, or a pharmaceutically acceptable salt of any of the foregoing, may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound detailed herein, or a stereoisomer, tautomer, or a pharmaceutically acceptable salt of any of the foregoing, can be used in the preparation of a formulation, such as a pharmaceutical formulation, by combining the compound or compounds, or a salt thereof, as an active ingredient with a pharmaceutically acceptable carrier. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, PA, 20$^{th}$ ed. (2000), which is incorporated herein by reference.

A compound detailed herein, or a stereoisomer, tautomer, or a pharmaceutically acceptable salt of any of the foregoing, may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound, or a stereoisomer, tautomer, or a pharmaceutically acceptable salt of any of the foregoing, and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use

Compounds and compositions detailed herein, such as a pharmaceutical composition containing a compound of any formula provided herein, or a stereoisomer, tautomer, or a pharmaceutically acceptable salt of any of the foregoing, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound describes herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

Compounds and compositions detailed herein can inhibit the activity of the FGFR4. For example, the compounds of the disclosure can be used to inhibit activity of FGFR4 in a cell or in an individual or patient in need of inhibition of the enzyme by administering an inhibiting amount of a compound of the disclosure to the cell, individual, or patient. In some embodiments, the compounds of the disclosure are selective for the FGFR4 over one or more of FGFR1, FGFR2, and/or FGFR3. In some embodiments, compounds and compositions detailed herein are selective for FGFR4 over FGFR1, FGFR2, and FGFR3. In some embodiments, the selectivity is 2-fold or more, 3-fold or more, 5-fold or more, 10-fold or more, 25-fold or more, 50-fold or more, or 100-fold or more.

Compounds and compositions detailed herein are useful in the treatment of cancer. Examples of cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors). Further examples of cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma. Other cancers treatable with the compounds and compositions detailed herein include tumors of the eye, glioblastoma, melanoma, rhabdosarcoma, lymphosarcoma, and osteosarcoma. Compounds and compositions detailed herein can also be useful in the inhibition of tumor metastasis.

Combinations

In certain aspects, compounds or compositions described herein are administered to an individual for treatment of a disease in combination with one or more additional pharmaceutical agents that can treat the disease. For example, in some embodiments, an effective amount of the compound is administered to an individual for the treatment of cancer in combination with one or more additional anticancer agents.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of Formula (I) or a compound as described herein for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds or compositions described herein for the treatment of cancer include chemotherapeutic agents, targeted cancer therapies, immunotherapies or radiation therapy. Compounds or compositions described herein may be effective in combination with antihormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds or compositions described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds or compositions described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds or compositions described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds or compositions described herein. In some embodiments, the JAK inhibitor is selective for JAK1 over JAK2 and JAK3.

Other suitable agents for use in combination with compounds or compositions described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds or compositions described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds or compositions described herein may also be combined with immunotherapy drugs, including cytokines such as interferon alpha and interleukin 2.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Dosing and Method of Administration

The dose of a compound described herein, or a stereoisomer, tautomer, solvate, prodrug or salt thereof, administered to an individual (such as a human) may vary with the particular compound or salt thereof, the method of administration, and the particular disease, such as type and stage of cancer, being treated. In some embodiments, the amount of the compound, or a stereoisomer, tautomer, solvate, prodrug or salt thereof, is a therapeutically effective amount.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a stereoisomer, tautomer, solvate, prodrug or salt thereof, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more).

Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or a stereoisomer, tautomer, solvate, prodrug or salt thereof. The kits may be used for any one or more of the uses described herein, and, accordingly, may contain instructions for the treatment of any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

Certain representative embodiments are provided below.

Embodiment 1. A compound of formula (I):

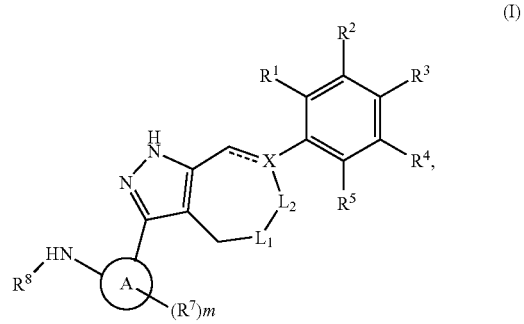

or a stereoisomer, tautomer, or a pharmaceutically acceptable salt of any of the foregoing, wherein:
- - - - is a single bond or a double bond;
X is CH or C;
$L_1$ is —CR'R''—, —O—, or —NR'''—, wherein R' and R'' are each independently H, $C_{1-6}$ alkyl, $C_{1-6}$ haloalkyl, or halo, and R''' is H, $C_{1-6}$ alkyl, $C_{1-6}$ haloalkyl, or acyl;
$L_2$ is a bond or —CH$_2$—;
A is a $C_{6-14}$ arylene, 5- to 10-membered heteroarylene, $C_{3-8}$ cycloalkylene, or 3- to 10-membered heterocyclylene,
provided that when $L_1$ is —CH$_2$— and $L_2$ is a bond, then A is 5- to 10-membered heteroarylene, $C_{3-8}$ cycloalkylene, or 3- to 10-membered heterocyclylene;
$R^1$, $R^2$, $R^3$, $R^4$, and $R^5$ are each independently H, halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^{11}$R$^{12}$, or $R^1$ and X are taken together with the carbons to which they are attached to form a 4- to 8-membered heterocyclyl;
m is 0, 1, or 2;
each $R^7$ is independently halo, —CN, —NO$_2$, $C_{1-6}$ alkyl, $C_{1-6}$ haloalkyl, $C_{2-6}$ alkenyl, $C_{2-6}$ alkynyl, $C_{3-8}$ cycloalkyl, —OR$^{13}$, or —NR$^a$R$^b$, wherein R$^a$ and R$^b$ are each independently H or $C_{1-6}$ alkyl optionally substituted by —NR$^c$R$^d$, wherein R$^c$ and R$^d$ are each independently H or $C_{1-6}$ alkyl;
$R^8$ is —C(O)R$^9$ or —S(O)$_2$R$^9$;
$R^9$ is $C_{1-6}$ alkyl, $C_{2-6}$ alkenyl, $C_{3-8}$ cycloalkyl, or 3- to 10-membered heterocyclyl, each of which is optionally substituted with $C_{1-6}$ alkyl, halo, —CN, or —C(O)OR$^{9a}$, wherein R$^{9a}$ is $C_{1-6}$ alkyl; and
$R^{11}$, $R^{12}$, and $R^{13}$ are each independently H, $C_{1-6}$ alkyl, $C_{1-6}$ haloalkyl, $C_{1-6}$ heteroalkyl, $C_{6-14}$ aryl, 5- to 10-membered heteroaryl, $C_{3-8}$ cycloalkyl, or 3- to 10-membered heterocyclyl;
provided that the compound is not a compound selected from the group consisting of:
N-(3-(6-(2,6-dichloro-3,5-dimethoxyphenyl)-4,5,6,7-tetrahydro-1H-indazol-3-yl)-1H-pyrazol-4-yl)acrylamide,
N-(3-(6-(2,6-dichloro-3,5-dimethoxyphenyl)-4,5,6,7-tetrahydro-1H-indazol-3-yl)-1-methyl-1H-pyrazol-4-yl)acrylamide,
N-(5-(6-(2,6-dichloro-3,5-dimethoxyphenyl)-4,5,6,7-tetrahydro-1H-indazol-3-yl)-1-methyl-1H-pyrazol-4-yl)acrylamide,
N-(5-(6-(2,6-difluoro-3,5-dimethoxyphenyl)-4,5,6,7-tetrahydro-1H-indazol-3-yl)-1-methyl-1H-pyrazol-4-yl)acrylamide,
N-(5-(6-(2-fluoro-3,5-dimethoxyphenyl)-4,5,6,7-tetrahydro-1H-indazol-3-yl)-1-methyl-1H-pyrazol-4-yl)acrylamide,
N-(5-(6-(2-chloro-6-fluoro-3,5-dimethoxyphenyl)-4,5,6,7-tetrahydro-1H-indazol-3-yl)-1-methyl-1H-pyrazol-4-yl)acrylamide,
N-(5-(6-(3,5-dimethoxyphenyl)-4,5,6,7-tetrahydro-1H-indazol-3-yl)-1-methyl-1H-pyrazol-4-yl)acrylamide, and
N-(5-(6-(2-chloro-3,5-dimethoxyphenyl)-4,5,6,7-tetrahydro-1H-indazol-3-yl)-1-methyl-1H-pyrazol-4-yl)acrylamide,
or a stereoisomer, tautomer, or a pharmaceutically acceptable salt of any of the foregoing.

Embodiment 2. The compound of embodiment 1, or a stereoisomer, tautomer, or a pharmaceutically acceptable salt of any of the foregoing, wherein the compound is of formula (II):

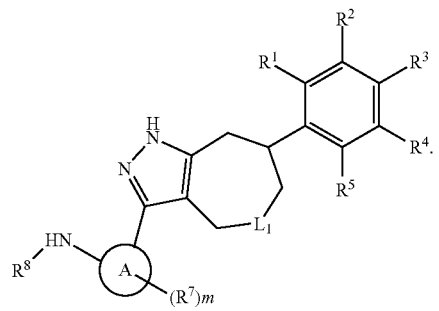

Embodiment 3. The compound of embodiment 1 or 2, or a stereoisomer, tautomer, or a pharmaceutically acceptable salt of any of the foregoing, wherein the compound is of formula (II-a):

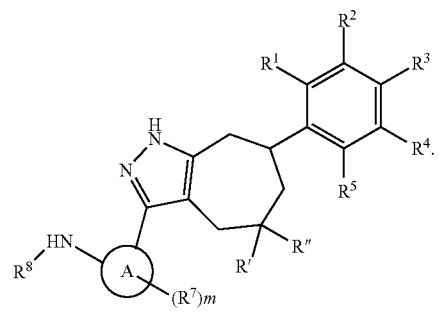

Embodiment 4. The compound of embodiment 1, or a stereoisomer, tautomer, or a pharmaceutically acceptable salt of any of the foregoing, wherein the compound is of formula (III):

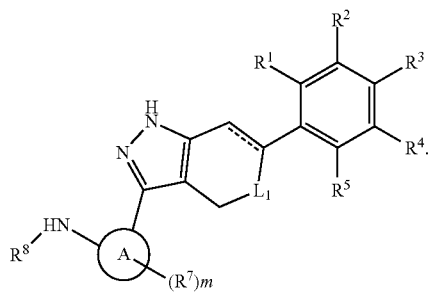

Embodiment 5. The compound of embodiment 1 or 4, or a stereoisomer, tautomer, or a pharmaceutically acceptable salt of any of the foregoing, wherein the compound is of formula (III-a):

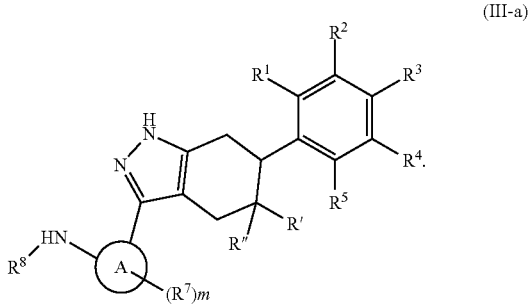

(III-a)

Embodiment 6. The compound of embodiment 1 or 4, or a stereoisomer, tautomer, or a pharmaceutically acceptable salt of any of the foregoing, wherein the compound is of formula (III-b):

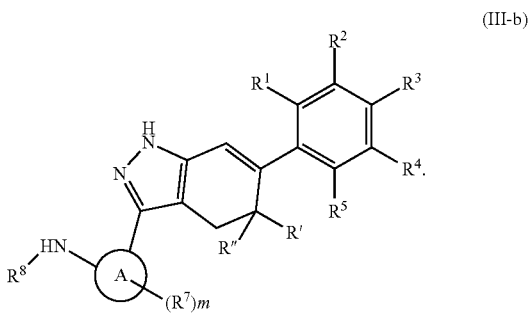

(III-b)

Embodiment 7. The compound of embodiment 1 or 4, or a stereoisomer, tautomer, or a pharmaceutically acceptable salt of any of the foregoing, wherein the compound is of formula (III-c):

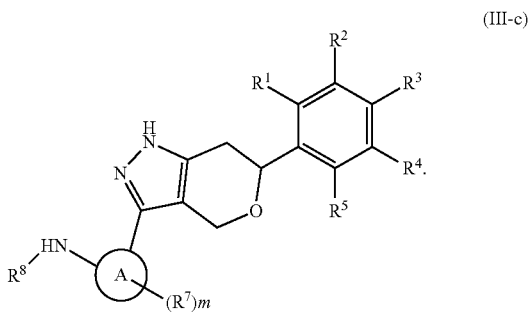

(III-c)

Embodiment 8. The compound of embodiment 1 or 4, or a stereoisomer, tautomer, or a pharmaceutically acceptable salt of any of the foregoing, wherein is a single bond.

Embodiment 9. The compound of embodiment 1 or 4, or a stereoisomer, tautomer, or a pharmaceutically acceptable salt of any of the foregoing, wherein is a double bond.

Embodiment 10. The compound of embodiment 1, or a stereoisomer, tautomer, or a pharmaceutically acceptable salt of any of the foregoing, wherein $L_1$ is —CR'R"—.

Embodiment 11. The compound of embodiment 1, or a stereoisomer, tautomer, or a pharmaceutically acceptable salt of any of the foregoing, wherein $L_1$ is —O— or —NR'''—.

Embodiment 12. The compound of embodiment 1, or a stereoisomer, tautomer, or a pharmaceutically acceptable salt of any of the foregoing, wherein $L_2$ is a bond.

Embodiment 13. The compound of embodiment 1, or a stereoisomer, tautomer, or a pharmaceutically acceptable salt of any of the foregoing, wherein $L_2$ is —CH$_2$—.

Embodiment 14. The compound of any one of embodiments 1-6 and 8-13, or a stereoisomer, tautomer, or a pharmaceutically acceptable salt of any of the foregoing, wherein R' is H.

Embodiment 15. The compound of any one of embodiments 1-6 and 8-13, or a stereoisomer, tautomer, or a pharmaceutically acceptable salt of any of the foregoing, wherein R' is $C_{1-6}$ alkyl.

Embodiment 16. The compound of any one of embodiments 1-6 and 8-13, or a stereoisomer, tautomer, or a pharmaceutically acceptable salt of any of the foregoing, wherein R' is methyl.

Embodiment 17. The compound of any one of embodiments 1-6 and 8-13, or a stereoisomer, tautomer, or a pharmaceutically acceptable salt of any of the foregoing, wherein R" is H.

Embodiment 18. The compound of any one of embodiments 1-6 and 8-13, or a stereoisomer, tautomer, or a pharmaceutically acceptable salt of any of the foregoing, wherein R" is $C_{1-6}$ alkyl, $C_{1-6}$ haloalkyl, or halo.

Embodiment 19. The compound of any one of embodiments 1-18, or a stereoisomer, tautomer, or a pharmaceutically acceptable salt of any of the foregoing, wherein $R^2$ is —OR$^{13}$ and $R^{13}$ is $C_{1-6}$ alkyl.

Embodiment 20. The compound of any one of embodiments 1-18, or a stereoisomer, tautomer, or a pharmaceutically acceptable salt of any of the foregoing, wherein $R^2$ is —OCH$_3$ or —OCD$_3$.

Embodiment 21. The compound of any one of embodiments 1-20, or a stereoisomer, tautomer, or a pharmaceutically acceptable salt of any of the foregoing, wherein $R^3$ is H.

Embodiment 22. The compound of any one of embodiments 1-21, or a stereoisomer, tautomer, or a pharmaceutically acceptable salt of any of the foregoing, wherein $R^4$ is —OR$^{13}$ and $R^{13}$ is $C_{1-6}$ alkyl.

Embodiment 23. The compound of any one of embodiments 1-21, or a stereoisomer, tautomer, or a pharmaceutically acceptable salt of any of the foregoing, wherein $R^4$ is —OCH$_3$ or —OCD$_3$.

Embodiment 24. The compound of any one of embodiments 1-23, or a stereoisomer, tautomer, or a pharmaceutically acceptable salt of any of the foregoing, wherein $R^5$ is H.

Embodiment 25. The compound of any one of embodiments 1-23, or a stereoisomer, tautomer, or a pharmaceutically acceptable salt of any of the foregoing, wherein $R^5$ is halo.

Embodiment 26. The compound of any one of embodiments 1-25, or a stereoisomer, tautomer, or a pharmaceutically acceptable salt of any of the foregoing, wherein $R^1$ is H.

Embodiment 27. The compound of any one of embodiments 1-25, or a stereoisomer, tautomer, or a pharmaceutically acceptable salt of any of the foregoing, wherein $R^1$ is halo.

Embodiment 28. The compound of any one of embodiments 1-25, or a stereoisomer, tautomer, or a pharmaceutically acceptable salt of any of the foregoing, wherein $R^1$ and X are taken together with the carbons to which they are attached to form a 4- to 8-membered heterocyclyl.

Embodiment 29. The compound of any one of embodiments 1-28, or a stereoisomer, tautomer, or a pharmaceutically acceptable salt of any of the foregoing, wherein A is a $C_6$ arylene, 5- to 6-membered heteroarylene, $C_{5-6}$ cycloalkylene, or 5- to 6-membered heterocyclylene.

Embodiment 30. The compound of any one of embodiments 1-29, or a stereoisomer, tautomer, or a pharmaceutically acceptable salt of any of the foregoing, wherein A is

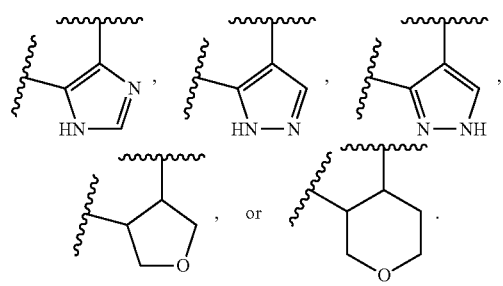

Embodiment 31. The compound of any one of embodiments 1-30, or a stereoisomer, tautomer, or a pharmaceutically acceptable salt of any of the foregoing, wherein m is 0.

Embodiment 32. The compound of any one of embodiments 1-30, or a stereoisomer, tautomer, or a pharmaceutically acceptable salt of any of the foregoing, wherein m is 1.

Embodiment 33. The compound of any one of embodiments 1-30 and 32, or a stereoisomer, tautomer, or a pharmaceutically acceptable salt of any of the foregoing, wherein each $R^7$ is independently $C_{1-6}$ alkyl or $C_{1-6}$ haloalkyl.

Embodiment 34. The compound of any one of embodiments 1-30 and 32, or a stereoisomer, tautomer, or a pharmaceutically acceptable salt of any of the foregoing, wherein each $R^7$ is independently —$CH_3$, —$CH_2CH_3$, —$CH(CH_3)_2$, —$CD_3$, or —$CH_2CF_3$.

Embodiment 35. The compound of any one of embodiments 1-34, or a stereoisomer, tautomer, or a pharmaceutically acceptable salt of any of the foregoing, wherein $R^8$ is —C(O)$R^9$.

Embodiment 36. The compound of any one of embodiments 1-34, or a stereoisomer, tautomer, or a pharmaceutically acceptable salt of any of the foregoing, wherein $R^8$ is —S(O)$_2R^9$.

Embodiment 37. The compound of any one of embodiments 1-36, or a stereoisomer, tautomer, or a pharmaceutically acceptable salt of any of the foregoing, wherein $R^9$ is $C_{1-6}$ alkyl, $C_{2-6}$ alkenyl, or 3- to 10-membered heterocyclyl, each of which is optionally substituted with halo or —C(O)O$R^{9a}$, wherein $R^{9a}$ is $C_{1-6}$ alkyl.

Embodiment 38. The compound of any one of embodiments 1-37, or a stereoisomer, tautomer, or a pharmaceutically acceptable salt of any of the foregoing, wherein $R^9$ is —$CH_3$, —$CH_2CH_3$,

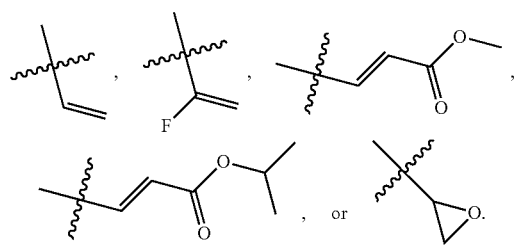

Embodiment 39. A compound selected from the Compound Nos. 1-37 in Table 1, or a stereoisomer, tautomer, or a pharmaceutically acceptable salt of any of the foregoing.

Embodiment 40. A pharmaceutical composition comprising at least one compound according to any one of embodiments 1-39, or a stereoisomer, tautomer or a pharmaceutically acceptable salt of any of the foregoing, and a pharmaceutically acceptable carrier or excipient.

Embodiment 41. A kit comprising at least one compound according to any one of embodiments 1-39, or a stereoisomer, tautomer or a pharmaceutically acceptable salt of any of the foregoing.

Embodiment 42. A method of treating a disease mediated by FGFR4 in an individual in need thereof, comprising administering to the individual a therapeutically effective amount of a compound according to any one of embodiments 1-39, or a stereoisomer, tautomer or a pharmaceutically acceptable salt of any of the foregoing.

Embodiment 43. The method of embodiment 42, wherein the compound is administered orally.

Embodiment 44. The method of embodiment 42, wherein the disease is cancer.

Embodiment 45. A method of inhibiting FGFR4, comprising contacting FGFR4 with a compound according to any one of embodiments 1-39, or a stereoisomer, tautomer or a pharmaceutically acceptable salt of any of the foregoing.

Embodiment 46. Use of a compound of any one of embodiments 1-39, or a stereoisomer, tautomer or a pharmaceutically acceptable salt of any of the foregoing, in the manufacture of a medicament for use in therapy.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High-Performance Liquid Chromatography.

Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Chromatography, recrystallization and other conventional separation procedures may also be used with intermediates or final products where it is desired to obtain a particular isomer of a compound or to otherwise purify a product of a reaction.

EXAMPLES

It is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure. The following examples are intended to illustrate, but not limit, this disclosure.

The following abbreviations may be used herein:
~ about
+ve or pos. ion positive ion
Δ heat
Ac Acetyl
ACN Acetonitrile
$Ac_2O$ acetic anhydride
aq aqueous
AcOH acetic acid
ATP adenosine triphosphate
Bn benzyl
Boc tert-butyloxycarbonyl
BSA bovine serum albumin
Bz benzoyl
Calcd or Calc'd calculated
Conc. concentrated
d day(s) or doublet (NMR)
DCE dichloroethane
DCM dichloromethane
dd Dublet of doublets (NMR)
DEA diethylamine
DIEA or DIPEA diisopropylethylamine
DME 1,2-dimethoxyethane
DMF N,N-dimethylformamide
DMSO dimethyl sulfoxide
EA Ethyl acetate
eq equivalent
ESI electrospray ionization
Et ethyl
$Et_2O$ diethyl ether
$Et_3N$ triethylamine
EtOAc ethyl acetate
EtOH ethyl alcohol
FA formic acid
FRET fluorescence resonance energy transfer
g gram(s)
h hour(s)
HEPES 2-[4-(2-hydroxyethyl)piperazin-1-yl]ethane-sulfonic acid
Hex hexanes
HMPA hexamethylphosphoramide
HPLC high performance liquid chromatography
Hz Hertz
IPA or iPrOH isopropyl alcohol
J Coupling constant (NMR) in Hz
KOAc potassium acetate
LCMS, LC-MS or LC/MS liquid chromatography mass spectrometry
LDA lithium diisopropylamide
LHMDS or LiHMDS lithium hexamethyldisilazide
m Multiplet (NMR)
M molar (mol $L^{-1}$)
Me methyl
MeCN acetonitrile
MeI iodomethane
MeOH methyl alcohol
mg milligram(s)
min minute(s)
mL milliliter(s)
M mole(s)
MS mass spectrometry
MSCl methanesulfonyl chloride
MTBE or MtBE methyl tert-butyl ether
m/z mass-to-charge ratio
NaHMDS sodium hexamethyldisilazide
NaOtBu sodium tert-butoxide
nBuLi n-butyl lithium
NCS N-chloro succinimide
nm Nanometer (wavelength)
NMR nuclear magnetic resonance
P1 Product one; faster eluting isomer
P2 Product two; slower eluting isomer
PCC Pyridinium chlorochromate, CAS Number: 26299-14-9
PE Petroleum ether, CAS Number: 101316-46-5
PBS phosphate buffered saline
PMB para-methoxybenzyl, 4-methoxybenzyl
Pr propyl
prep-TLC preparative thin layer chromatography
ppm parts per million
p-tol para-toluoyl
rac racemic RP-HPLC or RPHPLC reversed phase high performance liquid chromatography
RT or rt or r.t. room temperature
s singlet (NMR)
sat. or sat'd or satd saturated
Selectfluor™ 1-chloromethyl-4-fluoro-1,4-diazoniabicyclo[2.2.2]octane bis(tetrafluoroborate)
SFC Supercritical fluid chromatography
t triplet (NMR)
TBS tert-Butyldimethylsilyl
TBSCl tert-Butyldimethylsilyl chloride
TEA triethylamine
tert or t tertiary
TFA triflouroacetic acid
THF tetrahydrofuran
TLC thin layer chromatography
TMS trimethylsilyl or trimethylsilane
tBuOH tert-butyl alcohol
v/v volume per volume Example S1

Synthesis of N-(5-(6-(2,6-difluoro-3,5-dimethoxyphenyl)-4,5,6,7-tetrahydro-1H-indazol-3-yl)-1-methyl-1H-pyrazol-4-yl)acrylamide

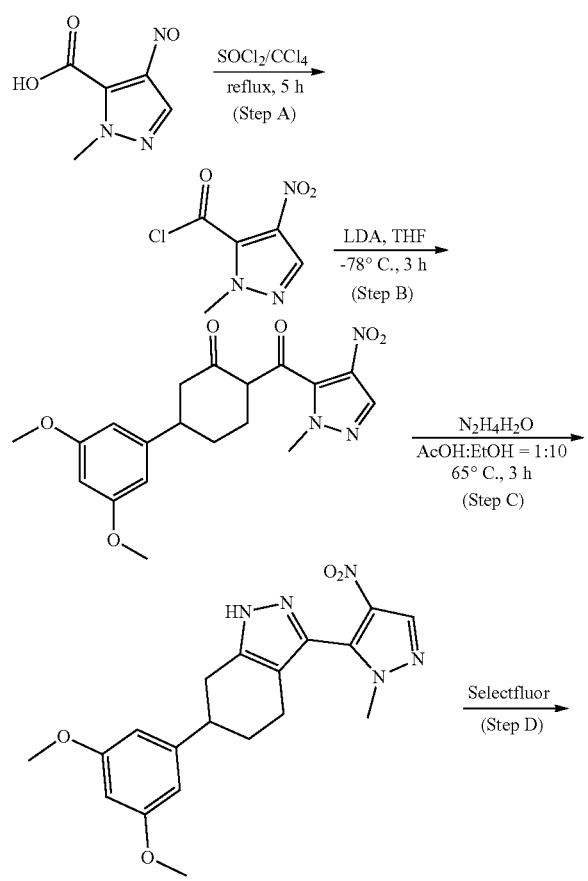

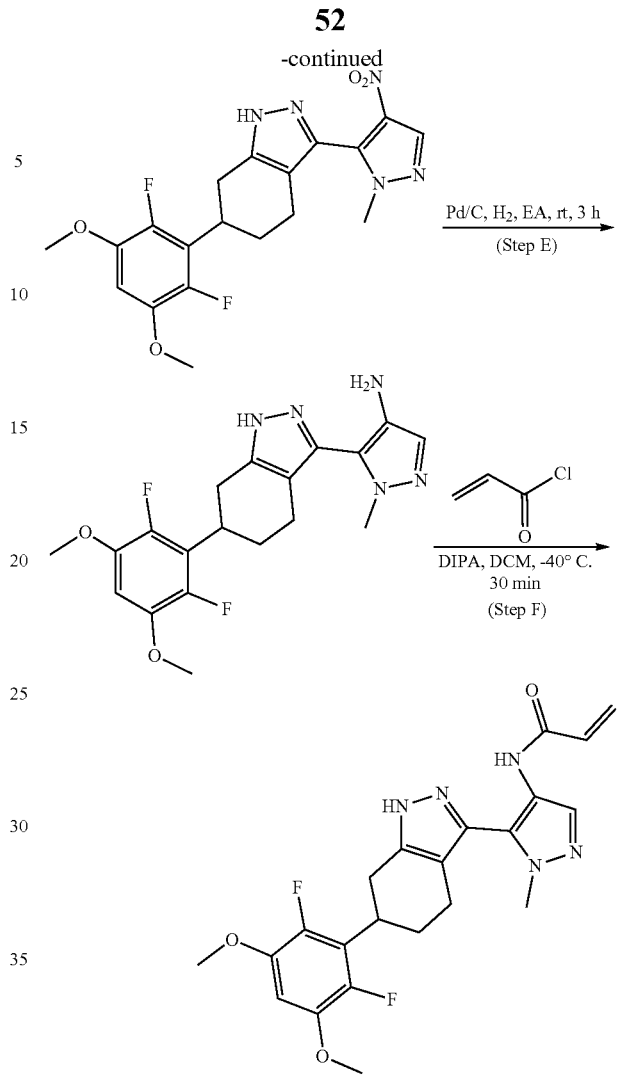

Step A: In a round-bottomed flask was placed 1-methyl-4-nitro-1H-pyrazole-5-carboxylic acid (10 g, 0.06 mol), 100 mL SOCl$_2$ and 2 drops of DMF. The mixture was heated to reflux at 76° C. for 1 h. The solvent was evaporated to give a brown slurry (10.5 g, 95%) which was used in the next step without further purification.

Step B: To a solution of 3-(3,5-dimethoxyphenyl)cyclohexan-1-one (13.0 g, 0.05 mol) in THF (200 mL) was added LDA (180 mL) at −78° C. and the mixture was stirred at −40° C. for 1 h. A solution of 1-methyl-4-nitro-1H-pyrazole-5-carbonylchloride (10.5 g, 0.05 mol) was added dropwise to the above solution at −78° C., then the mixture was warmed to rt. LCMS suggested the reaction was completed. To the mixture, saturated aq. NH$_4$Cl was added. The organic layer was diluted with water (300 mL) and the aqueous layer was further extracted with ethyl acetate (3×50 mL), the combined organic layers were washed with H$_2$O (100 mL), dried over Na$_2$SO$_4$ filtered and the filtrate was concentrated. The crude product (19.0 g, 0.04 mol) was used in the next step without further purification. MS m/z (ESI): 387.7 [M+H$^+$].

Step C: 5-(3,5-Dimethoxyphenyl)-2-(1-methyl-4-nitro-1H-pyrazole-5-carbonyl) cyclohexan-1-one (19.0 g, 0.04 mol) and hydrazine hydrate (5.1 g, 0.1 mol) were added to a mixture of AcOH and EtOH (20 mL AcOH, 180 mL EtOH). The mixture was stirred for 0.5 h at 50° C. Most of the solvent was removed by evaporating under reduced pressure, and the remainder was diluted with EtOAc (40 mL) and washed with H$_2$O (3×50 mL). The organic layer was dried over anhydrous Na$_2$SO$_4$ filtered and the filtrate was concentrated. The crude product was purified by chromatography on silica gel (eluent: PE/EtOAc, gradient elution 5:1 to 1:1) to give 6-(3,5-dimethoxyphenyl)-3-(1-methyl-4-nitro-1H-pyrazol-5-yl)-4,5,6,7-tetrahydro-1H-indazole as a yellow solid (8 g, 42%). MS (ESI) m/z: 384.1 [M+H$^+$].

Step D: A solution of 6-(3,5-dimethoxyphenyl)-3-(1-methyl-4-nitro-1H-pyrazol-5-yl)-4,5,6,7-tetrahydro-1H-indazole (8 g, 0.02 mol) in CH$_3$CN (400 mL) was cooled to 0° C. using an ice bath. 1-Chloromethyl-4-fluoro-1,4-diazoniabicyclo[2.2.2]octane bis(tetrafluoroborate) ("Selectfluor", 14.5 g, 0.04 mol) was added in several portions. The resulting solution was stirred at rt for 2 h. Then the reaction mixture was washed with aq. NaHCO$_3$, dried over sodium sulfate and concentrated. The crude product was purified by chromatography on silica gel and SFC (Chromatography Column: Chiralpak-AD (Daicel Corporation); mobile phase: CO$_2$-EtOH(DEA)) to give 6-(2,6-difluoro-3,5-dimethoxyphenyl)-3-(1-methyl-4-nitro-1H-pyrazol-5-yl)-4,5,6,7-tetrahydro-1H-indazole (400 mg, 5%) as a white solid. MS (ESI) m/z: 420.0 [M+H$^+$].

Step E: A suspension of 6-(2,6-difluoro-3,5-dimethoxyphenyl)-3-(1-methyl-4-nitro-1H-pyrazol-5-yl)-4,5,6,7-tetrahydro-1H-indazole (50 mg, 0.13 mmol), Pd/C (10 mg) in EtOAc (25 mL) was stirred at 50° C. for 5 h under a H$_2$ atmosphere. The Pd/C was filtered off and the filtrate was concentrated. The residue was purified by silica gel chromatography to give 5-(6-(2,6-difluoro-3,5-dimethoxyphenyl)-4,5,6,7-tetrahydro-1H-indazol-3-yl)-1-methyl-1H-pyrazol-4-amine as a brown solid (240 mg, 65%). MS (ESI) m/z: 390.0 [M+H$^+$].

Step F: To a solution of 5-(6-(2,6-difluoro-3,5-dimethoxyphenyl)-4,5,6,7-tetrahydro-1H-indazol-3-yl)-1-methyl-1H-pyrazol-4-amine (240 mg, 0.57 mmol) and DIPEA (200 mg, 0.12 mmol) in DCM (20 mL) was dropwise added acryloyl chloride (52.6 mg, 0.57 mmol) at −40° C., stirred for 15 min. The mixture was concentrated, purified by reversed-phase HPLC (H$_2$O (0.05% NH$_3$·H$_2$O)-ACN (0.05% NH$_3$·H$_2$O), ACN from 10% to 100% over 8 minutes) and SFC (Chromatography Column: Chiralpak-AD (Daicel Corporation); mobile phase: CO$_2$-ETOH(DEA)) to give single enantiomers of the title compound (P1=25 mg; P2=25 mg) as a white solids.

P1: $^1$H NMR (400 MHz, DMSO): δ 12.92 (s, 1H), 9.42 (s, 1H), 7.84 (s, 1H), 6.93 (t, J=8.3 Hz, 1H), 6.53 (dd, J=17.0, 10.2 Hz, 1H), 6.19 (dd, J=17.0, 2.1 Hz, 1H), 5.66 (dd, J=10.2, 2.1 Hz, 1H), 3.86 (s, 6H), 3.76 (s, 3H), 3.43-3.36 (m, 1H), 2.98-2.92 (m, 2H), 2.47-2.38 (m, 1H), 2.13-2.05 (m, 1H), 1.90 (d, J=12.4 Hz, 1H). MS (ESI) m/z: 443.8 [M+H$^+$].
P2: $^1$H NMR (400 MHz, DMSO): δ 12.92 (s, 1H), 9.42 (s, 1H), 7.84 (s, 1H), 6.93 (t, J=8.3 Hz, 1H), 6.53 (dd, J=17.0, 10.2 Hz, 1H), 6.19 (dd, J=17.0, 2.1 Hz, 1H), 5.66 (dd, J=10.2, 2.1 Hz, 1H), 3.86 (s, 6H), 3.76 (s, 3H), 3.43-3.36 (m, 1H), 2.98-2.92 (m, 2H), 2.47-2.38 (m, 1H), 2.13-2.05 (m, 1H), 1H), 1.90 (d, J=12.4 Hz, 1H). MS (ESI) m/z: 443.8 [M+H$^+$.

Example S2

Synthesis of N-(5-(6-(2,6-dichloro-3,5-Dimethoxyphenyl)-4,5,6,7-tetrahydro-1H-indazol-3-yl)-1-methyl-1H-pyrazol-4-yl) Methacrylamide

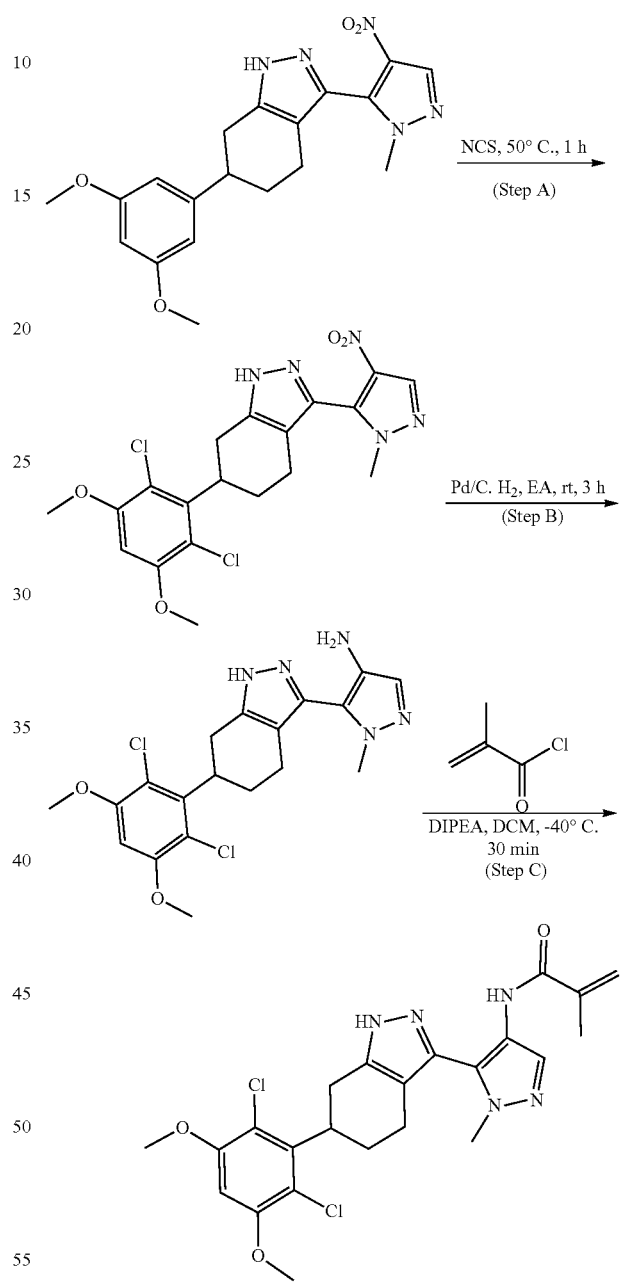

Step A: To a solution of 6-(3,5-dimethoxyphenyl)-3-(1-methyl-4-nitro-1H-pyrazol-5-yl)-4,5,6,7-tetrahydro-1H-indazole (500 mg, 1.11 mol) in AcOH (15 mL) was added NCS (296 mg, 2.22 mol) in several portions. The resulting solution was stirred at 50° C. for 2 h. The solvent was evaporated, the residue was purified by silica gel chromatography (PE:EA, gradient elution 5:1 to 1:1) to give the 6-(2,6-dichloro-3,5-dimethoxyphenyl)-3-(1-methyl-4-nitro-1H-pyrazol-5-yl)-4,5,6,7-tetrahydro-1H-indazole as a white solid (200 mg, 35%). MS (ESI) m/z: 451.9 (M+1).

Step B: A suspension of 6-(2,6-dichloro-3,5-dimethoxyphenyl)-3-(1-methyl-4-nitro-1H-pyrazol-5-yl)-4,5,6,7-tetrahydro-1H-indazole (200 mg, 0.44 mmol) and Pd/C (200 mg) in ethyl acetate (40 mL) was stirred at 50° C. for 12 h under a H₂ atmosphere. The Pd/C was filtered off and the filtrate was concentrated. The residue was purified by silica gel chromatography to give 5-(6-(2,6-dichloro-3,5-dimethoxyphenyl)-4,5,6,7-tetrahydro-1H-indazol-3-yl)-1-methyl-1H-pyrazol-4-amine as a brown solid (90 mg, 52%). MS (ESI) m/z: 422.1 (M+1).

Step C: To a solution of 5-(6-(2,6-dichloro-3,5-dimethoxyphenyl)-4,5,6,7-tetrahydro-1H-indazol-3-yl)-1-methyl-1H-pyrazol-4-amine (90 mg, 0.21 mmol) and DIPEA (90 mg, 0.63 mmol) in DCM (20 mL) was dropwise added methacryloyl chloride (21.8 mg, 0.21 mmol) at −40° C., then the mixture was stirred for 15 min. The mixture was concentrated, purified by reversed-phase HPLC (H₂O (0.05% NH₃·H₂O)-ACN (0.05% NH₃ in H₂O), ACN from 10% to 100% over 8 minutes) and SFC (Chromatography Column: Chiralpak-AD (Daicel Corporation); mobile phase: CO₂-ETOH(DEA)) to give single enantiomers of the title compound (P1=13.4 mg; P2=6.4 mg).

P1: ¹H NMR (400 MHz, DMSO) δ 12.93 (s, 1H), 9.23 (s, 1H), 7.67 (s, 1H), 6.88 (s, 1H), 5.74 (s, 1H), 5.44 (s, 1H), 4.00 (d, J=4.6 Hz, 1H), 3.93 (s, 3H), 3.92 (s, 3H), 3.83 (s, 2H), 3.46-3.33 (m, 2H), 2.75 (d, J=10.7 Hz, 1H), 2.59 (d, J=6.2 Hz, 2H), 1.91 (s, 3H), 1.75 (d, J=10.1 Hz, 1H). MS (ESI) m/z: 490.1 (M+1).

P2: ¹H NMR (400 MHz, DMSO) δ 12.93 (s, 1H), 9.23 (s, 1H), 7.67 (s, 1H), 6.88 (s, 1H), 5.74 (s, 1H), 5.44 (s, 1H), 4.00 (d, J=4.6 Hz, 1H), 3.93 (s, 3H), 3.92 (s, 3H), 3.83 (s, 2H), 3.46-3.33 (m, 2H), 2.75 (d, J=10.7 Hz, 1H), 2.59 (d, J=6.2 Hz, 2H), 1.91 (s, 3H), 1.75 (d, J=10.1 Hz, 1H). MS (ESI) m/z: 490.1 (M+1).

Example S3

Synthesis of N-(5-(6-(2,6-Difluoro-3,5-dimethoxyphenyl)-4,5,6,7-tetrahydro-1H-indazol-3-yl)-1-methyl-1H-imidazol-4-yl) Acrylamide

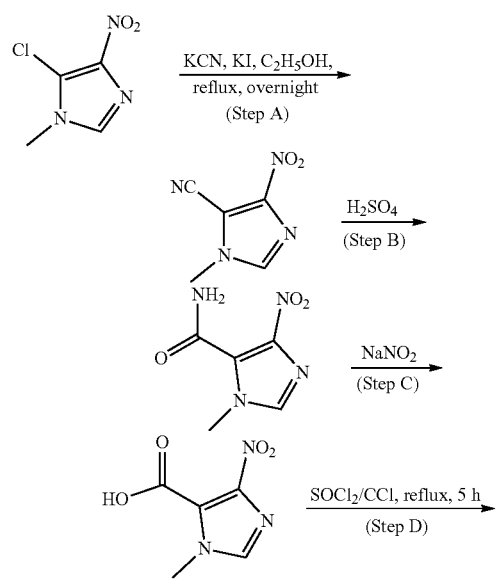

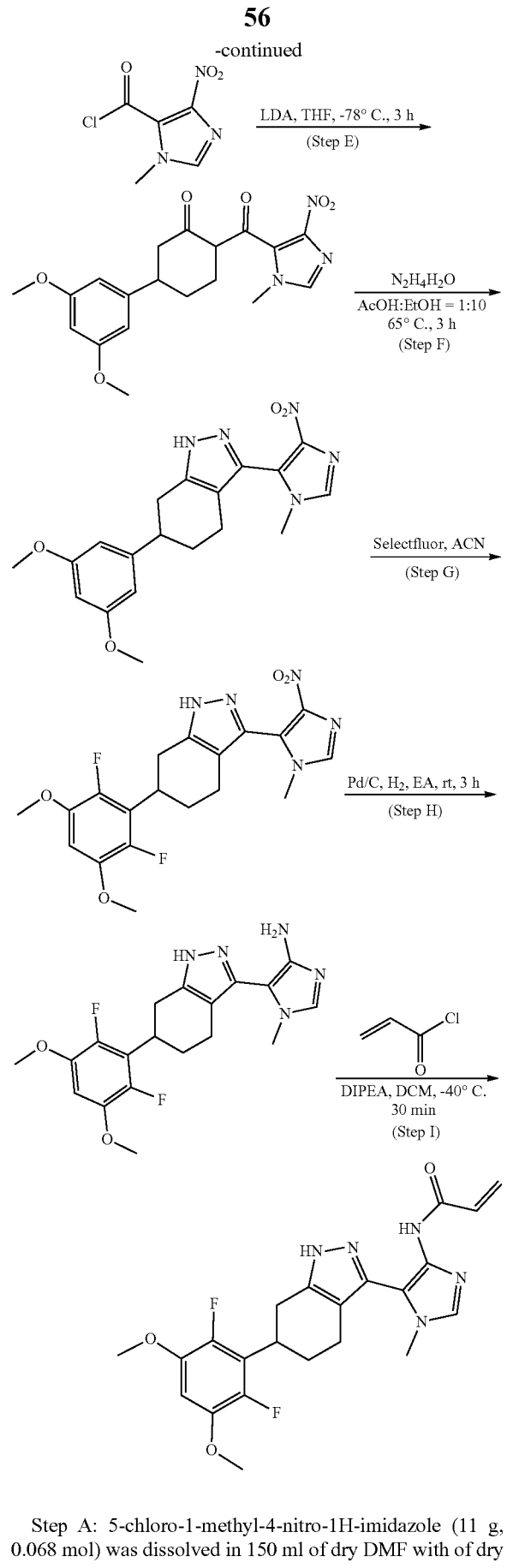

Step A: 5-chloro-1-methyl-4-nitro-1H-imidazole (11 g, 0.068 mol) was dissolved in 150 ml of dry DMF with of dry KI (1.1 g, 6.6 mmol) and placed on a magnetic stirrer in a 2-neck flask equipped with a thermometer. Then dried and finely pulverized potassium cyanide (6 g, 0.092 mol) was added, the reaction mixture was warmed to 40° C. and stirred at this temperature for 3 h with occasional cooling in a cold-water bath, if necessary. Then the mixture was warmed to 50° C. and maintained at this temperature for 4 h with constant stirring. After inorganic residue was filtered off, the solvent was evaporated under reduced pressure, and the crude compound was washed with cold water and filtered off. Recrystallization from water gave 1-methyl-4-nitro-1H-imidazole-5-carbonitrile (3.7 g, 36%). MS (ESI) m/z: 153.1 (M+1).

Step B: 1-methyl-4-nitro-1H-imidazole-5-carbonitrile (3.7 g, 24 mmol) was dissolved in 30 ml of 98% sulfuric acid and heated in a boiling water bath with stirring for 2 h. After cooling, the reaction mixture was poured into 160 g of ice and maintained at rt until melting of the ice to give 1-methyl-4-nitro-1H-imidazole-5-carboxamide, which was used for the next step without further purification. MS (ESI) m/z: 171.1 (M+1).

Step C: 5 g (0.073 mol) of NaNO$_2$ was added in several small portions to crude 1-methyl-4-nitro-1H-imidazole-5-carboxamide over 1 h with constant stirring. The reaction mixture was left overnight, the precipitate was filtered off, washed with water and dried. The resulting crude product was purified by dissolving in 70 ml of a 5% sodium carbonate solution, the insoluble material was filtered off, and the filtrate was acidified with 10% aq. HCl to pH ~2. After filtration, the resulting precipitate was washed with water and dried to get 1-methyl-4-nitro-1H-imidazole-5-carboxylic acid (3 g, 81%) which was confirmed by LCMS. MS (ESI) m/z: 172.1 (M+1).

Step D: In a round-bottomed flask were placed 1-methyl-4-nitro-1H-imidazole-5-carboxylic acid (3 g, 17 mmol), SOCl$_2$ (30 mL) and 2 dropwise DMF. The flask was fitted with a reflux condenser, and the mixture was heated to reflux at 76° C. for 1 h. The SOCl$_2$ was evaporated to get 1-methyl-4-nitro-1H-imidazole-5-carbonyl chloride (2.5 g, 71%) as a brown slurry which was used for the next step without further purification. MS (ESI) m/z: 387.0 (M+ CH$_3$OH).

Step E: To a solution of 3-(3,5-dimethoxyphenyl)cyclohexan-1-one (3.14 g, 13 mmol) in THF (20 mL) was added LDA (8 mL, 16 mmol) at −78° C., then stirred at −40° C. for 1 h. After a solution of 1-methyl-4-nitro-1H-imidazole-5-carbonyl chloride (2.5 g, 13 mmol) was dropwise added to above solution at −78° C. and stirred at rt for 2 h. After monitoring by LCMS suggested the reaction was completed, saturated aq. NH$_4$Cl was added, the THF layer was diluted with water (30 mL) and the aqueous layer was further extracted with EtOAc (3×50 mL). The combined organic layers were washed with H$_2$O (10 mL), dried over Na$_2$SO$_4$, filtered and the filtrate was concentrated. The crude product was purified by chromatography on silica gel, eluting with PE/EtOAc (gradient elution 5:1 to 2:1) to give 5-(3,5-dimethoxyphenyl)-2-(1-methyl-4-nitro-1H-imidazole-5-carbonyl) cyclohexan-1-one (2.5 g, 62%) as a light-yellow liquid. MS (ESI) m/z: 388.0 (M+1).

Step F: 5-(3,5-Dimethoxyphenyl)-2-(1-methyl-4-nitro-1H-imidazole-5-carbonyl) cyclohexan-1-one (2.5 g, 6 mmol) and hydrazine hydrate (1.5 ml) were added to a mixture of AcOH and EtOH (18 mL AcOH:2 mL EtOH). The mixture was stirred at 50° C. for 0.5 h. The solvent was evaporated, and the residue was diluted with EtOAc, then washed with aq. NaHCO$_3$ and the organic layer was dried over anhydrous Na$_2$SO$_4$, filtered and the filtrate was concentrated. The crude product was purified by chromatography on silica gel (PE:EA, gradient elution from 5:1 to 1:1) to give 6-(3,5-Dimethoxyphenyl)-3-(1-methyl-4-nitro-1H-imidazol-5-yl)-4,5,6,7-tetrahydro-1H-indazole as a yellow solid (1.8 g, 71%). MS (ESI) m/z: 384.1 (M+1).

Step G: A suspension of 6-(3,5-dimethoxyphenyl)-3-(1-methyl-4-nitro-1H-imidazol-5-yl)-4,5,6,7-tetrahydro-1H-indazole (1 g, 2.6 mmol) in CH$_3$CN was cooled to 0° C. by ice bath. 1-Chloromethyl-4-fluoro-1,4-diazoniabicyclo[2.2.2]octane bis(tetrafluoroborate) ("Selectfluor", 1.8 g, 5.2 mol) was added sequentially. The resulting solution was stirred at rt for 2 h. Then the reaction mixture was washed with aq. NaHCO$_3$, dried over sodium sulfate, filtered and the filtrate was concentrated. The crude product was purified by chromatography on silica gel to give 6-(2,6-difluoro-3,5-dimethoxyphenyl)-3-(1-methyl-4-nitro-1H-imidazol-5-yl)-4,5,6,7-tetrahydro-1H-indazole (320 mg, 29%) as a white solid. MS (ESI) m/z: 420.0 (M+1).

Step H: A suspension of 6-(2,6-difluoro-3,5-dimethoxyphenyl)-3-(1-methyl-4-nitro-1H-imidazol-5-yl)-4,5,6,7-tetrahydro-1H-indazole (300 mg, 0.7 mmol), Pd/C (100 mg) in EtOAc (25 mL) under H$_2$ atmosphere was stirred for 5 h at 50° C. The Pd/C was filtered, and the filtrate was concentrated. The residue was purified by silica gel chromatography to give 5-(6-(2,6-difluoro-3,5-dimethoxyphenyl)-4,5,6,7-tetrahydro-1H-indazol-3-yl)-1-methyl-1H-imidazol-4-amine (160 mg, 58%) as a brown solid. MS (ESI) m/z: 390.1 (M+1).

Step I: To a solution of 5-(6-(2,6-difluoro-3,5-dimethoxyphenyl)-4,5,6,7-tetrahydro-1H-indazol-3-yl)-1-methyl-1H-imidazol-4-amine (160 mg, 0.4 mmol) and DIPEA (103 mg, 0.08 mol) in DCM (20 mL) was added acryloyl chloride (52 mg, 0.4 mmol) at −40° C., The resulting solution was stirred at rt for 2 h. Then the reaction mixture was washed with NaHCO$_3$, dried over sodium sulfate, filtered and the filtrate was concentrated. The residue was purified by silica gel chromatography and SFC (Chromatography Column: Chiralpak-AD (Daicel Corporation); mobile phase: CO$_2$-EtOH (DEA)) to give single enantiomers of the title compound as a white solid. (P1=2.6 mg; P2=2.8 mg).

P1: $^1$H NMR (400 MHz, DMSO) δ 12.64 (s, 1H), 9.62 (s, 1H), 7.61 (s, 1H), 6.92 (t, J=8.3 Hz, 1H), 6.37 (d, J=10.2 Hz, 1H), 6.12 (dd, J=17.1, 1.8 Hz, 1H), 5.66 (d, J=10.5 Hz, 1H), 3.86 (s, 6H), 3.62 (s, 3H), 3.28 (d, J=9.5 Hz, 1H), 2.87 (d, J=9.7 Hz, 2H), 2.37 (dd, J=28.9, 7.1 Hz, 2H), 1.94 (d, J=53.4 Hz, 2H). MS (ESI) m/z: 444.0 (M+1).

P2: $^1$H NMR (400 MHz, DMSO) δ 12.64 (s, 1H), 9.62 (s, 1H), 7.61 (s, 1H), 6.92 (t, J=8.3 Hz, 1H), 6.37 (d, J=10.2 Hz, 1H), 6.12 (dd, J=17.1, 1.8 Hz, 1H), 5.66 (d, J=10.5 Hz, 1H), 3.86 (s, 6H), 3.62 (s, 3H), 3.28 (d, J=9.5 Hz, 1H), 2.87 (d, J=9.7 Hz, 2H), 2.37 (dd, J=28.9, 7.1 Hz, 2H), 1.94 (d, J=53.4 Hz, 2H). MS (ESI) m/z: 444.0 (M+1).

Example S4

Synthesis of N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide

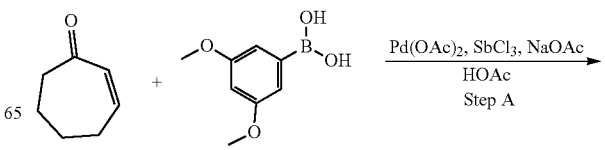

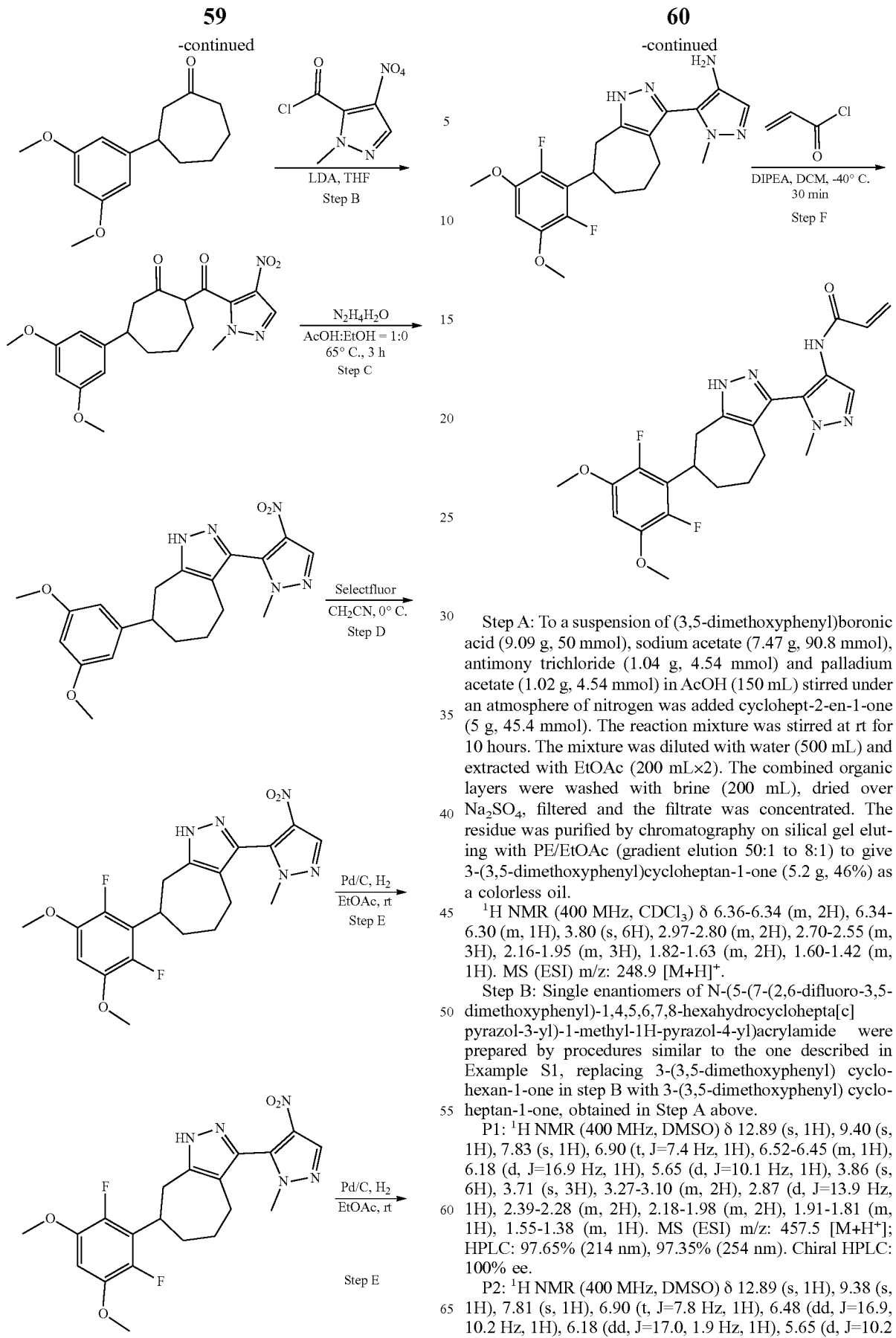

Step A: To a suspension of (3,5-dimethoxyphenyl)boronic acid (9.09 g, 50 mmol), sodium acetate (7.47 g, 90.8 mmol), antimony trichloride (1.04 g, 4.54 mmol) and palladium acetate (1.02 g, 4.54 mmol) in AcOH (150 mL) stirred under an atmosphere of nitrogen was added cyclohept-2-en-1-one (5 g, 45.4 mmol). The reaction mixture was stirred at rt for 10 hours. The mixture was diluted with water (500 mL) and extracted with EtOAc (200 mL×2). The combined organic layers were washed with brine (200 mL), dried over $Na_2SO_4$, filtered and the filtrate was concentrated. The residue was purified by chromatography on silical gel eluting with PE/EtOAc (gradient elution 50:1 to 8:1) to give 3-(3,5-dimethoxyphenyl)cycloheptan-1-one (5.2 g, 46%) as a colorless oil.

$^1$H NMR (400 MHz, $CDCl_3$) δ 6.36-6.34 (m, 2H), 6.34-6.30 (m, 1H), 3.80 (s, 6H), 2.97-2.80 (m, 2H), 2.70-2.55 (m, 3H), 2.16-1.95 (m, 3H), 1.82-1.63 (m, 2H), 1.60-1.42 (m, 1H). MS (ESI) m/z: 248.9 [M+H]$^+$.

Step B: Single enantiomers of N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide were prepared by procedures similar to the one described in Example S1, replacing 3-(3,5-dimethoxyphenyl) cyclohexan-1-one in step B with 3-(3,5-dimethoxyphenyl) cycloheptan-1-one, obtained in Step A above.

P1: $^1$H NMR (400 MHz, DMSO) δ 12.89 (s, 1H), 9.40 (s, 1H), 7.83 (s, 1H), 6.90 (t, J=7.4 Hz, 1H), 6.52-6.45 (m, 1H), 6.18 (d, J=16.9 Hz, 1H), 5.65 (d, J=10.1 Hz, 1H), 3.86 (s, 6H), 3.71 (s, 3H), 3.27-3.10 (m, 2H), 2.87 (d, J=13.9 Hz, 1H), 2.39-2.28 (m, 2H), 2.18-1.98 (m, 2H), 1.91-1.81 (m, 1H), 1.55-1.38 (m, 1H). MS (ESI) m/z: 457.5 [M+H$^+$]; HPLC: 97.65% (214 nm), 97.35% (254 nm). Chiral HPLC: 100% ee.

P2: $^1$H NMR (400 MHz, DMSO) δ 12.89 (s, 1H), 9.38 (s, 1H), 7.81 (s, 1H), 6.90 (t, J=7.8 Hz, 1H), 6.48 (dd, J=16.9, 10.2 Hz, 1H), 6.18 (dd, J=17.0, 1.9 Hz, 1H), 5.65 (d, J=10.2 Hz, 1H), 3.89 (s, 6H), 3.72 (s, 3H), 3.28-3.13 (m, 2H), 2.88

(d, J=13.6 Hz, 1H), 2.38-2.30 (m, 2H), 2.20-1.98 (m, 2H), 1.92-1.79 (m, 1H), 1.54-1.39 (m, 1H). MS (ESI) m/z: 457.5 [M+H]⁺; HPLC: 95.14% (214 nm), 95.50% (254 nm). Chiral HPLC: 100% ee.

Example S5

Synthesis of N-(5-(6-(2,6-difluoro-3,5-dimethoxyphenyl)-4,5-dihydro-1H-indazol-3-yl)-1-methyl-1H-pyrazol-4-yl) acrylamide and N-(5-(6-(2-fluoro-3,5-dimethoxyphenyl)-4,5-dihydro-1H-indazol-3-yl)-1-methyl-1H-pyrazol-4-yl)acrylamide

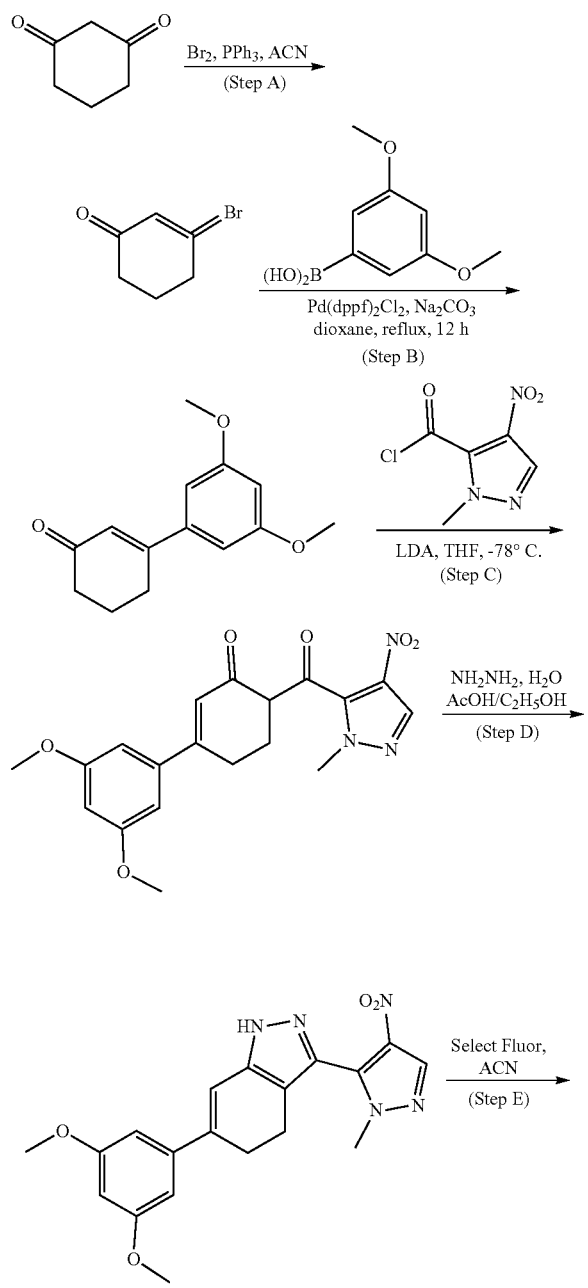

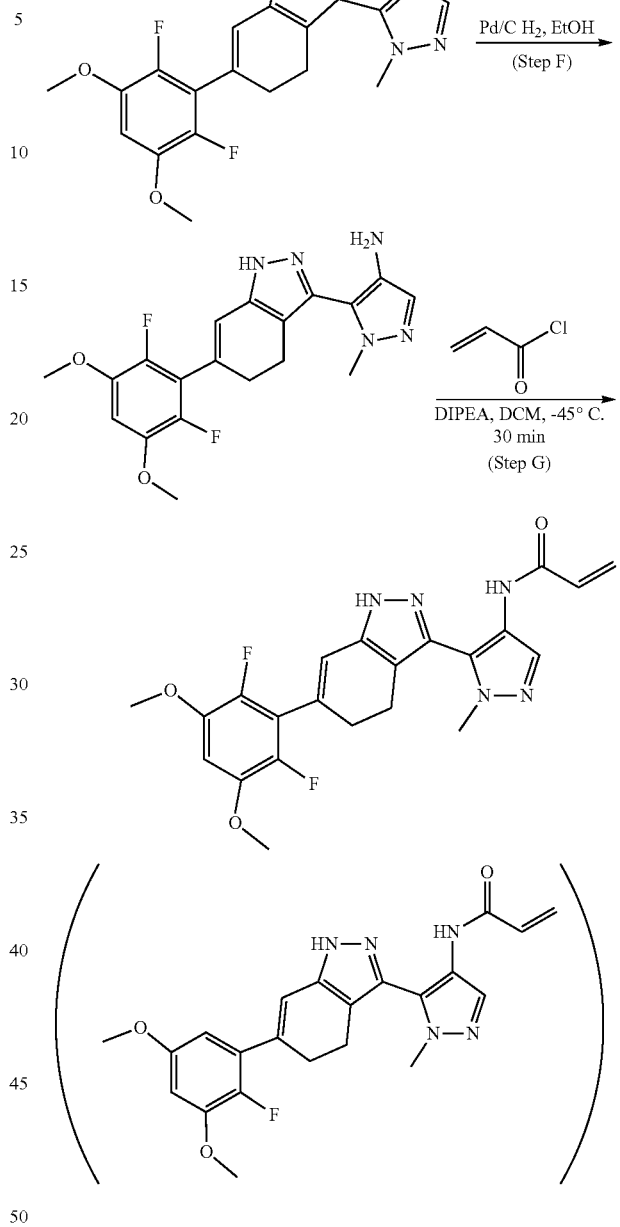

Step A: A magnetically stirred solution of triphenylphosphine (26 g, 99 mmol) in dry acetonitrile (250 mL) maintained at 0° C. was treated, dropwise via addition funnel, with a solution of bromine (16 g, 100 mmol) in dry acetonitrile (100 mL). The resulting mixture was then warmed to 22° C. and after 0.5 h it was treated with triethylamine (10 g, 100 mmol) then cyclohexane-1,3-dione (10 g, 100 mmol) before being stirred at 22° C. for 16 h, then concentrated under reduced pressure. The residue thus obtained was stirred vigorously with diethyl ether (300 mL) and the supernatant liquid decanted. This process was repeated twice more, and the combined organic phases were then diluted with 40-60 petroleum ether (50 mL) to precipitate triphenylphosphine oxide. The ensuing mixture was filtered through a plug of TLC-grade silica gel topped with Celite® (J. T. Baker, Phillipsberg, NJ, diatomaceous earth) and the filtrate was concentrated under reduced pressure to afford 3-bromocyclohex-2-en-1-one (10.5 g, 67%) as a light-yellow oil.

Step B: A solution of (3,5-dimethoxyphenyl) boronic acid (12.6 g, 69 mmol), 3-bromocyclohex-2-en-1-one (10 g, 57 mmol), Pd(dppf)Cl$_2$ (1 g, 1.37 mmol), and Na$_2$CO$_3$ (12 g, 113 mmol) in dioxane (100 ml) under argon was stirred at 100° C. for 12 h. After cooling to rt, the solvent was evaporated under reduced pressure, and the crude product was purified by chromatography on silica gel, eluting with PE/EtOAc (gradient elution 5:1 to 2:1) to get 3',5'-dimethoxy-5,6-dihydro-[1,1'-biphenyl]-3(4H)-one as a yellow liquid compound (5.3 g, 41%). MS (ESI) m/z: 233.1 (M+1).

Step C: To a solution of 3',5'-dimethoxy-5,6-dihydro-[1,1'-biphenyl]-3(4H)-one (3.14 g, 13.5 mmol) in THF (20 mL) was added LDA (8 mL, 16 mmol) at −78° C., then stirred at −40° C. for 1 h. After a solution of 1-methyl-4-nitro-1H-pyrazole-5-carbonyl chloride (2.5 g, 13 mmol) was added dropwise to the above solution at −78° C. and stirring was continued at rt for 2 h. LCMS suggested the reaction was completed. Saturated aq. NH$_4$Cl solution was added and the THF layer was diluted with water (30 mL). The aqueous layer was further extracted with EtOAc (3*50 mL). The combined organic layers were washed with H$_2$O (100 mL), dried over Na$_2$SO$_4$, filtered and the filtrate was concentrated, then used for next step without further purification. MS (ESI) m/z: 386.1 (M+1).

Step D: 3',5'-Dimethoxy-4-(1-methyl-4-nitro-1H-pyrazole-5-carbonyl)-5,6-dihydro-[1,1'-biphenyl]-3(4H)-one (2.17 g, 5.6 mmol) and hydrazine (3 ml) were added to solution of AcOH/EtOH (20 mL, AcOH:EtOH=1:10). The mixture was stirred at 50° C. for 0.5 h. The solvent was evaporated and the residue was diluted with EtOAc, then washed with aq.NaHCO$_3$ and the organic layer was dried over anhydrous Na$_2$SO$_4$, concentrated and the residue was purified by silica gel chromatography and eluting with PE/EtOAc (gradient elution 5:1 to 1:1) to give 6-(3,5-dimethoxyphenyl)-3-(1-methyl-4-nitro-1H-pyrazol-5-yl)-4,5-dihydro-1H-indazole (1.2 g, 30%) as a light yellow solid. MS (ESI) m/z: 381.8 (M+1).

Step E: A suspension of 6-(3,5-dimethoxyphenyl)-3-(1-methyl-4-nitro-1H-pyrazol-5-yl)-4,5,6,7-tetrahydro-1H-indazole (2.5 g, 6 mmol) in CH$_3$CN was cooled to 0° C. with an ice bath. 1-Chloromethyl-4-fluoro-1,4-diazoniabicyclo[2.2.2]octane bis(tetrafluoroborate) ("Selectfluor", 3.5 g, 12 mmol) was added. The resulting solution was stirred at rt for 2 h. Then the reaction mixture was washed with aq. NaHCO$_3$, dried over Na$_2$SO$_4$, filtered and the filtrate was concentrated. The residue was purified by silica gel chromatography to give 6-(2,6-difluoro-3,5-dimethoxyphenyl)-3-(1-methyl-4-nitro-1H-pyrazol-5-yl)-1,4,6,7-tetrahydropyrano[4,3-c] pyrazole, Mass Spectrum (ESI) m/z=421.7 (M+1) and 6-(2-fluoro-3,5-dimethoxyphenyl)-3-(1-methyl-4-nitro-1H-pyrazol-5-yl)-4,5-dihydro-1H-indazole, MS (ESI) m/z: 403.7 (M+1) as a white solid (600 mg, 15%).

Step F: A suspension of 6-(2,6-difluoro-3,5-dimethoxyphenyl)-3-(1-methyl-4-nitro-1H-pyrazol-5-yl)-1,4,6,7-tetrahydropyrano[4,3-c] pyrazole and 6-(2-fluoro-3,5-dimethoxyphenyl)-3-(1-methyl-4-nitro-1H-pyrazol-5-yl)-4,5-dihydro-1H-indazole (600 mg, 1.4 mmol), Pd/C (600 mg) in ethyl acetate (25 mL) was stirred at 50° C. for 5 h under a H$_2$ atmosphere. The Pd/C was filtered off, and the filtrate was concentrated. The residue was purified by silica gel chromatography to give a mixture of 5-(6-(2,6-difluoro-3,5-dimethoxyphenyl)-4,5,6,7-tetrahydro-1H-indazol-3-yl)-1-methyl-1H-pyrazol-4-amine, Mass Spectrum (ESI) m/z=388.1 (M+1) and 5-(6-(2-fluoro-3,5-dimethoxyphenyl)-4,5-dihydro-1H-indazol-3-yl)-1-methyl-1H-pyrazol-4-amine. MS (ESI) m/z: 370.1 (M+1) (350 mg, 65%) as a brown solid.

Step G: To a solution of 5-(6-(2,6-difluoro-3,5-dimethoxyphenyl)-4,5,6,7-tetrahydro-1H-indazol-3-yl)-1-methyl-1H-pyrazol-4-amine and 5-(6-(2-fluoro-3,5-dimethoxyphenyl)-4,5-dihydro-1H-indazol-3-yl)-1-methyl-1H-pyrazol-4-amine (200 mg, 0.52 mmol) and DIPEA (130 mg, 1 mmol) in DCM (20 mL) was dropwise added acryloyl chloride (46 mg) at −40° C., then stirred for 15 min. The mixture was concentrated and purified by reversed-phase HPLC and SFC (Chromatography Column: Chiralpak-AD (Daicel Corporation); mobile phase: CO$_2$-ETOH(DEA)) to give the title compound as white solids (P1=8.3 mg, P2=11.7 mg).

N-(5-(6-(2,6-difluoro-3,5-dimethoxyphenyl)-4,5-dihydro-1H-indazol-3-yl)-1-methyl-1H-pyrazol-4-yl) acrylamide (P1): $^1$H NMR (400 MHz, DMSO) 13.24 (s, 1H), 9.53 (d, J=45.0 Hz, 1H), 7.86 (d, J=37.5 Hz, 1H), 6.99 (s, 1H), 6.69 (d, J=10.1 Hz, 1H), 6.48 (s, 1H), 6.22 (s, 1H), 5.67 (d, J=10.1 Hz, 1H), 3.96-3.67 (m, 9H), 2.65-2.53 (m, 4H). MS (ESI) m/z: 442.1 (M+1).

N-(5-(6-(2-fluoro-3,5-dimethoxyphenyl)-4,5-dihydro-1H-indazol-3-yl)-1-methyl-1H-pyrazol-4-yl)acrylamide (P2): $^1$H NMR (400 MHz, DMSO) δ 13.19 (s, 1H), 9.56 (s, 1H), 7.88 (s, 1H), 6.80 (s, 1H), 6.69 (dd, J=6.7, 2.7 Hz, 1H), 6.57-6.40 (m, 2H), 6.19 (dd, J=17.0, 2.0 Hz, 1H), 5.72-5.62 (m, 1H), 4.01-3.57 (m, 9H), 2.67 (d, J=7.5 Hz, 2H), 2.59 (dd, J=12.2, 4.7 Hz, 2H). MS (ESI) m/z: 424.1 (M+1).

Example S6

Synthesis of N-(5-(6-(2,6-difluoro-3,5-dimethoxyphenyl)-1,4,6,7-tetrahydropyrano[4,3-c] pyrazol-3-yl)-1-methyl-1H-pyrazol-4-yl) Acrylamide

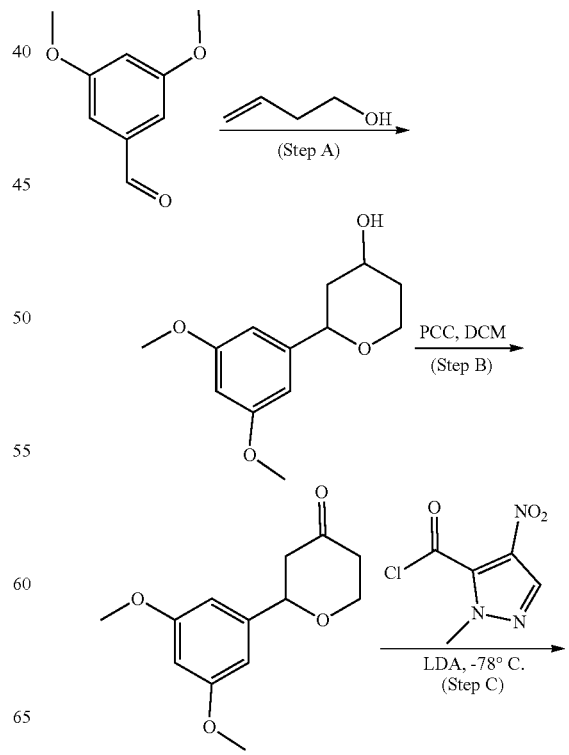

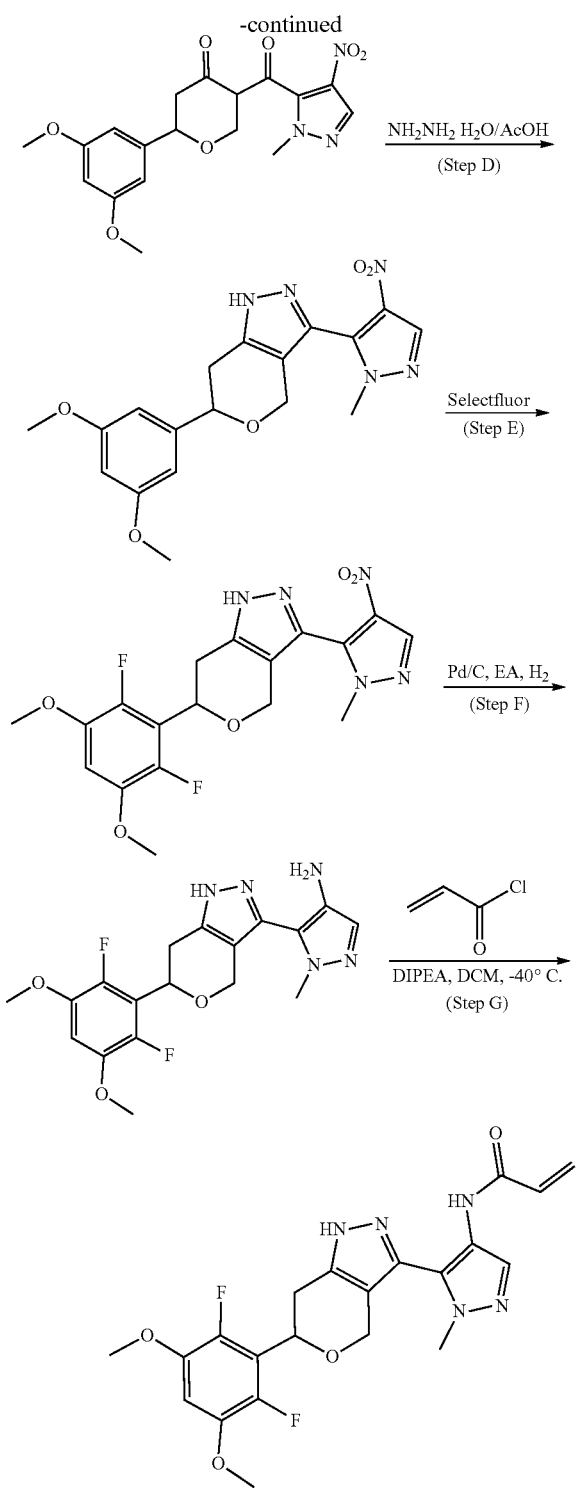

Step A: In a round-bottomed flask were placed 3,5-dimethoxybenzaldehyde (25 g, 150.6 mmol), but-3-en-1-ol (22 g, 301.2 mmol) and phosphomolybdic acid hydrate (136 g, 75 mmol) in water. The flask was fitted with a reflux condenser and the mixture was heated to reflux at 90° C. overnight. The aqueous layer was extracted with EtOAc (3*50 mL) and the combined organic layers were dried and concentrated. The crude was purified by silica gel chromatography to give 2-(3,5-dimethoxyphenyl) tetrahydro-2H-pyran-4-ol (10 g, 35%). MS (ESI) m/z: 239.0 (M+1).

Step B: To a solution of 2-(3,5-dimethoxyphenyl) tetrahydro-2H-pyran-4-ol (10 g, 0.04 mol) in DCM (200 mL) was added PCC (20 g, 0.09) at rt, then stirred for 2 h, the organic layer was extracted with $H_2O$ (3*50 mL), the combined organic layers were dried over $Na_2SO_4$ and concentrated. The crude product was purified by silica gel chromatography and eluting with PE and EtOAc (gradient elution 5:1 to 2:1) to give 2-(3,5-dimethoxyphenyl) tetrahydro-4H-pyran-4-one (5.5 g, 55%) as a light yellow solid. MS (ESI) m/z: 237.0 (M+1).

Step C: To a solution of 2-(3,5-dimethoxyphenyl) tetrahydro-4H-pyran-4-one (5.5 g, 0.02 mol) in THF (200 mL) was added LiHMDS (18 mL) at −78° C., then the mixture was stirred at −40° C. for 1 h. Then a solution of 1-methyl-4-nitro-1H-pyrazole-5-carbonyl chloride (4.75 g, 0.024 mol) in 20 mL of THF was dropwise added to above solution at −78° C. and the mixture was stirred at rt for 2 h. Once LCMS suggested the reaction was complete, it was quenched by saturated aq. $NH_4Cl$ solution. The THF layer was diluted with water (300 mL) and the aqueous layer was further extracted with EtOAc (3×50 mL). The combined organic layers were concentrated to afford 2-(3,5-dimethoxyphenyl)-5-(1-methyl-4-nitro-1H-pyrazole-5-carbonyl) tetrahydro-4H-pyran-4-one (5.2 g, crude) as an oil which was used in the next step without further purification. MS (ESI) m/z: 390.0 (M+1).

Step D: To 2-(3,5-dimethoxyphenyl)-5-(1-methyl-4-nitro-1H-pyrazole-5-carbonyl) tetrahydro-4H-pyran-4-one (5.2 g, crude) and hydrazine hydrate (1.38 g, 13 mmol) was added to a mixture of AcOH and EtOH (2 mL AcOH, 18 mL EtOH). The mixture was stirred for 0.5 h at 50° C. The reaction solution was evaporated and diluted with EtOAc, washed with aq. $NaHCO_3$ and the organic layer was dried over anhydrous $Na_2SO_4$ and concentrated. The crude product was purified by chromatography on silica gel (PE:EA=5:1 to 1:1) to give 6-(3,5-dimethoxyphenyl)-3-(1-methyl-4-nitro-1H-pyrazol-5-yl)-4,5,6,7-tetrahydro-1H-indazole (2.5 g, 71%) as a yellow solid compound. MS (ESI) m/z: 387.0 (M+1).

Step E: To A suspension of 6-(3,5-dimethoxyphenyl)-3-(1-methyl-4-nitro-1H-pyrazol-5-yl)-4,5,6,7-tetrahydro-1H-indazole (2.5 g, 6 mmol) in $CH_3CN$ was cooled to 0° C. using an ice bath. 1-Chloromethyl-4-fluoro-1,4-diazoniabicyclo[2.2.2]octane bis(tetrafluoroborate) ("Selectfluor", 3.5 g, 12 mmol) was added sequentially. The resulting solution was stirred at rt for 2 h. Then the reaction mixture was washed with aq. $NaHCO_3$, dried over $Na_2SO_4$, and the organic solvent was removed under reduced pressure. The residue was purified by silica gel chromatography and SFC to give 6-(2,6-difluoro-3,5-dimethoxyphenyl)-3-(1-methyl-4-nitro-1H-pyrazol-5-yl)-1,4,6,7-tetrahydropyrano[4,3-c]pyrazole as a white solid (600 mg, 15%). MS (ESI) m/z: 421.7 (M+1).

Step F: A suspension of 6-(2,6-difluoro-3,5-dimethoxyphenyl)-3-(1-methyl-4-nitro-1H-pyrazol-5-yl)-1,4,6,7-tetrahydropyrano[4,3-c] pyrazole (600 mg, 1.4 mmol), Pd/C (600 mg) in ethyl acetate (25 mL) was stirred at 50° C. for 5 h under a $H_2$ atmosphere. The Pd/C was filtered, and the filtrate was concentrated. The residue was purified by silica gel chromatography to give 5-(6-(2,6-difluoro-3,5-dimethoxyphenyl)-4,5,6,7-tetrahydro-1H-indazol-3-yl)-1-methyl-1H-pyrazol-4-amine as a brown solid (350 mg, 65%). MS (ESI) m/z: 391.8 (M+1).

Step G: To a solution of 5-(6-(2,6-difluoro-3,5-dimethoxyphenyl)-4,5,6,7-tetrahydro-1H-indazol-3-yl)-1-methyl-1H-pyrazol-4-amine (350 mg, 0.89 mmol) and DIPEA (200 mg, 1.78 mmol) in DCM (20 mL) was dropwise added acryloyl chloride (80.1 mg, 0.89 mmol) at −40° C., then the mixture was stirred for 15 min. The solvent was concentrated, purified by reversed-phase HPLC (H$_2$O (0.05% NH$_3$·H$_2$O)-ACN (0.05% NH$_3$H$_2$O), ACN from 10% to 100% over 8 minutes) and SFC (Chromatography Column: Chiralpak-AD (Daicel Corporation); mobile phase: CO$_2$-ETOH(DEA)) to give single enantiomers of N-(5-(6-(2,6-difluoro-3,5-dimethoxyphenyl)-1,4,6,7-tetrahydropyrano[4,3-c] pyrazol-3-yl)-1-methyl-1H-pyrazol-4-yl) acrylamide (P1=4.94 mg; P2=13.4 mg) as a white solids.

P1 (3.0 min): $^1$H NMR (400 MHz, MeOD) δ 7.92 (s, 1H), 6.92 (t, J=8.1 Hz, 1H), 6.40 (qd, J=17.0, 5.9 Hz, 2H), 5.77 (dd, J=9.9, 2.0 Hz, 1H), 5.14 (dd, J=11.2, 3.5 Hz, 1H), 4.86-4.56 (m, 2H), 3.90 (s, 6H), 3.86 (s, 3H), 3.45-3.35 (m, 1H), 2.96 (dd, J=15.8, 2.9 Hz, 1H). MS (ESI) m/z: 446.1 [M+H$^+$].

P2 (4.7 min): $^1$H NMR (400 MHz, MeOD) δ 7.90 (s, 1H), 6.92 (t, J=8.1 Hz, 1H), 6.40 (qd, J=17.0, 5.9 Hz, 2H), 5.77 (dd, J=9.9, 2.0 Hz, 1H), 5.14 (dd, J=11.2, 3.5 Hz, 1H), 4.86-4.56 (m, 2H), 3.90 (s, 6H), 3.86 (s, 3H), 3.45-3.35 (m, 1H), 2.96 (dd, J=15.8, 2.9 Hz, 1H). MS (ESI) m/z: 446.1 [M+H$^+$].

Example S7

Synthesis of N-(3-((S)-6-(2,6-dichloro-3,5-dimethoxyphenyl)-4,5,6,7-tetrahydro-1H-indazol-3-yl) tetrahydro-2H-pyran-4-yl) Acrylamide

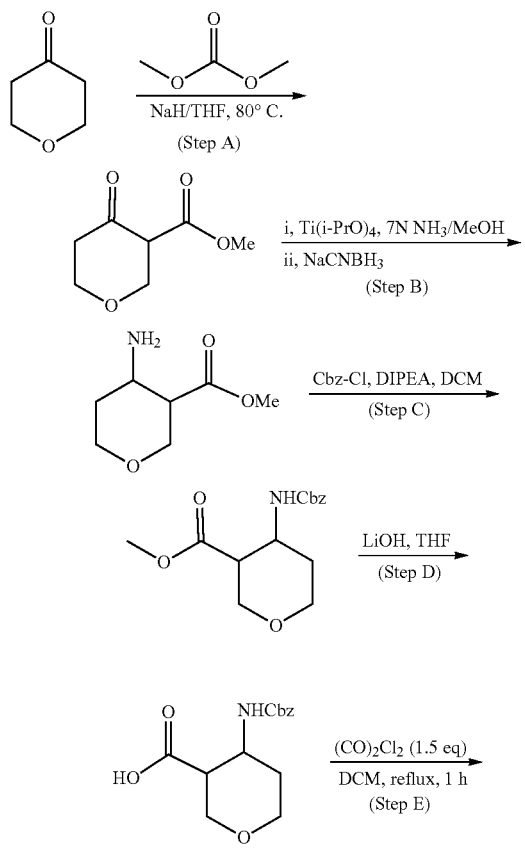

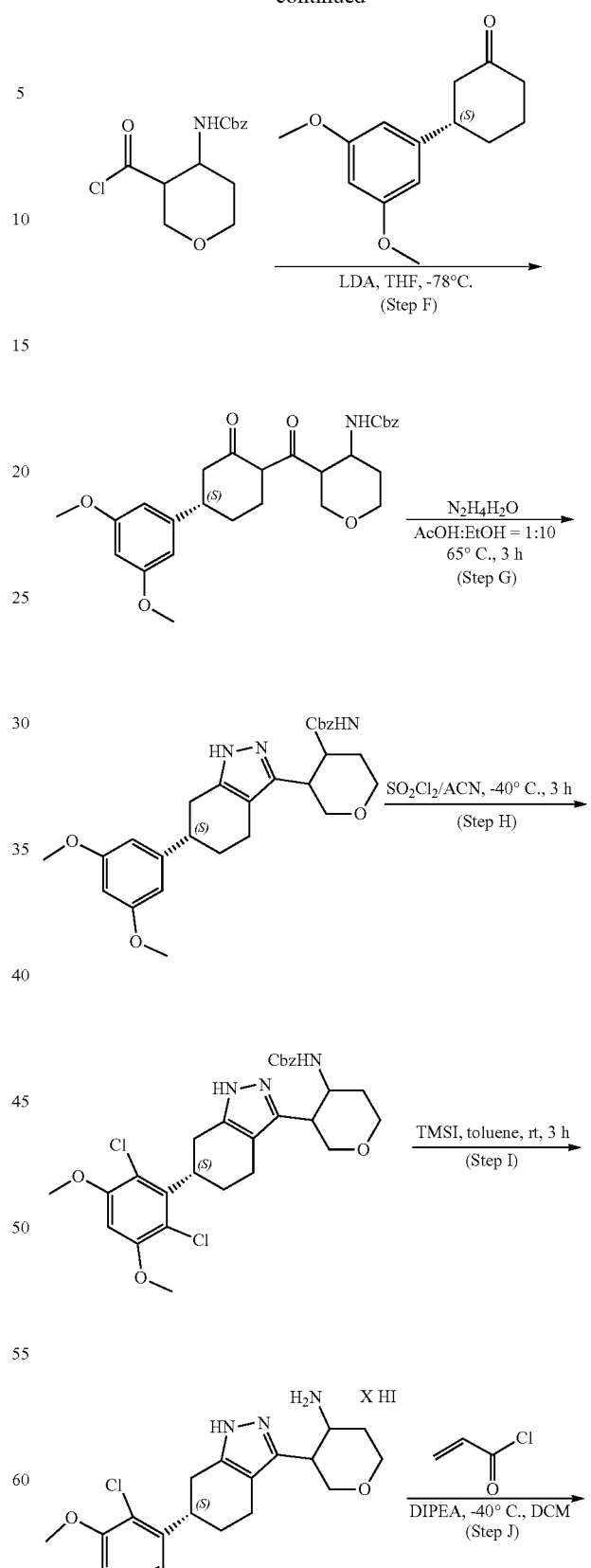

-continued

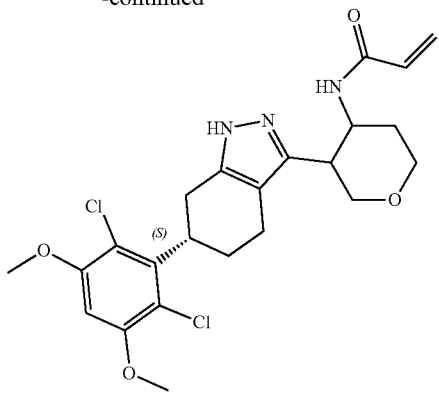

Step A: In a round-bottomed flask were placed sodium hydride (100 g, 1 mol) and THF (1000 ml). The flask was cooled to −20° C. with dry ice/ethanol, tetrahydro-4H-pyran-4-one (100 g, 2.5 mol) and dimethyl carbonate (225 g, 2.5 mol) in THF (300 ml) were slowly added dropwise into the system and the mixture was slowly warmed to 40° C. Then the mixture was quenched with sat' d aq. NH$_4$Cl solution (300 ml) and extracted with ethyl acetate (3×150 ml). The combined organic layers were concentrated to get the crude product which was purified by silica gel column chromatography to give methyl 4-oxotetrahydro-2H-pyran-3-carboxylate (65 g, 48%) as a light yellow oil. MS (ESI) m/z: 157.0 (M+1).

Step B: In a sealed tube were placed methyl 4-oxotetrahydro-2H-pyran-3-carboxylate (20 g, 0.127 mol), tetraisopropyl titanate (72 g, 0.254 mol), ammonia (7M in methanol, 60 ml) and methanol (100 ml). The mixture was heated to 50° C. for 3 h. Then the mixture was dropwise added into the solution of sodium cyanoborohydride in MeOH at 0° C. over 10 minutes. The MeOH was evaporated and the crude was purified by chromatography on silica gel (eluting with PE/EtOAc, gradient elution 30:1 to 20:1) to give methyl 4-aminotetrahydro-2H-pyran-3-carboxylate (12 g, 60%) as a yellow oil. MS (ESI) m/z: 160.0 (M+1).

Step C: In a round-bottomed flask were placed methyl 4-aminotetrahydro-2H-pyran-3-carboxylate (12 g, 0.075 mol) and DIPEA (14.5 g, 0.11 mol), The flask was cooled to 0° C. with the help of an ice water bath and benzyl chloroformate (15.3 g, 0.09 mol) was dropwise added. The mixture was stirred at 0° C. for 2 h. To the mixture, saturated aq. NaHCO$_3$ (60 ml) was added and the DCM layer was separated, the aqueous layer was further extracted with ethyl acetate (3*30 mL), the combined organic layers were dried over Na$_2$SO$_4$, concentrated and purified to give methyl 4-(((benzyloxy) carbonyl) amino) tetrahydro-2H-pyran-3-carboxylate (13.5 g, 61%) as a white oil. MS (ESI) m/z: 294 (M+1).

Step D: In a round-bottomed flask were placed methyl 4-(((benzyloxy) carbonyl) amino) tetrahydro-2H-pyran-3-carboxylate (13.5 g, 0.046 mol), LiOH (2.9 g, 0.069 mol) and THF/MeOH/H$_2$O (30:30:10 ml). The mixture was stirred at rt for 2 h. The solvent was evaporated, and the residue was adjusted to pH=3, extracted with ethyl acetate and the organic solvent was evaporated to get 4-(((benzyloxy) carbonyl) amino) tetrahydro-2H-pyran-3-carboxylic acid (11.1 g, crude) which was used in the next step without further purification. MS (ESI) m/z: 280 (M+1).

Step E: In a round-bottom flask were placed 4-(((benzyloxy) carbonyl) amino) tetrahydro-2H-pyran-3-carboxylic acid (2 g, 0.072 mol) and DCM (50 ml). Oxalyl chloride (1.1 g, 0.086 mol) was added dropwise in the mixture at 0° C., then 2 drops DMF were added and stirring was continued for 2 h. The DCM was evaporated to get benzyl (3-(chlorocarbonyl) tetrahydro-2H-pyran-4-yl) carbamate as a yellow slurry (2 g, crude) which was used in the next step without further purification. MS (ESI) m/z: 294 (M+1).

Step F: To a solution of 3-(3,5-dimethoxyphenyl) cyclohexan-1-one (1.3 g, 0.006 mol) in THF (30 mL) was added LDA (3.5 mL) at −78° C., then stirred at −40° C. for 1 h. Then a solution of benzyl (3-(chlorocarbonyl) tetrahydro-2H-pyran-4-yl) carbamate (2 g, 0.007 mol) was dropwise added to the above solution at −78° C. which was subsequently warmed to rt. LCMS suggested the reaction was completed. To the mixture, saturated aq. NH$_4$Cl solution was added, the THF layer was diluted with water (30 mL) and the aqueous layer was further extracted with ethyl acetate (3*10 mL), the combined organic layers were washed with H$_2$O (10 mL), dried over Na$_2$SO$_4$ and concentrated. The crude benzyl (3-((4S)-4-(3,5-dimethoxyphenyl)-2-oxocyclohexane-1-carbonyl) tetrahydro-2H-pyran-4-yl) carbamate (3.0 g) was used in the next step without further purification. MS (ESI) m/z: 496 (M+1).

Step G: Benzyl (3-((4S)-4-(3,5-dimethoxyphenyl)-2-oxocyclohexane-1-carbonyl) tetrahydro-2H-pyran-4-yl) carbamate (3 g, 0.06 mol) and hydrazine hydrate (0.76 g, 0.015 mol) were added to solution of AcOH/EtOH (20 mL, AcOH/EtOH=1:10). The mixture was stirred at 50° C. for 0.5 h. The reaction solution was evaporated, diluted with brine and extracted with EtOAc (20 mL). The organic layer was dried over anhydrous Na$_2$SO$_4$, filtered and the filtrate was concentrated to give benzyl (3-((S)-6-(3,5-dimethoxyphenyl)-4,5,6,7-tetrahydro-1H-indazol-3-yl) tetrahydro-2H-pyran-4-yl) carbamate (0.9 g, 30%) as a yellow solid. MS (ESI) m/z: 492 (M+1).

Step H: A suspension of benzyl (3-((S)-6-(3,5-dimethoxyphenyl)-4,5,6,7-tetrahydro-1H-indazol-3-yl) tetrahydro-2H-pyran-4-yl) carbamate (0.45 g, 0.91 mmol) in CH$_3$CN (30 ml) was cooled to −40° C. using a dry ice ethanol bath. Chlorosulfonyl chloride (0.22 g, 1.638 mmol) was added slowly. The resulting solution was stirred at −40° C. for 2 h. Then the reaction mixture was washed with aq. NaHCO$_3$, dried over sodium sulfate, filtered and the filtrate was concentrated. The residue was purified by silica gel column chromatography to get benzyl(3-((S)-6-(2,6-dichloro-3,5-dimethoxyphenyl)-4,5,6,7-tetrahydro-1H-indazol-3-yl) tetrahydro-2H-pyran-4-yl) carbamate (380 mg, 50%) as a yellow solid. MS (ESI) m/z: 561 (M+1).

Step I: In a round-bottomed flask benzyl(3-((S)-6-(2,6-dichloro-3,5-dimethoxyphenyl)-4,5,6,7-tetrahydro-1H-indazol-3-yl) tetrahydro-2H-pyran-4-yl) carbamate (380 mg, 0.38 mmol), trimethylsilyl iodide (410 mg, 2.04 mmol) and DCM (40 mL) were combined at 0° C. After 1 h the mixture was evaporated to get 3-((S)-6-(2,6-dichloro-3,5-dimethoxyphenyl)-4,5,6,7-tetrahydro-1H-indazol-3-yl) tetrahydro-2H-pyran-4-amine (280 mg, 87%) which was used in the next step without further purification. MS (ESI) m/z: 427 (M+1).

Step J: To a solution of 3-((S)-6-(2,6-dichloro-3,5-dimethoxyphenyl)-4,5,6,7-tetrahydro-1H-indazol-3-yl) tetrahydro-2H-pyran-4-amine (280 mg, 0.6 mmol) and DIPEA (350 mg, 2.72 mmol) in DCM (20 mL) was added acryloyl chloride (50 mg, 0.6 mmol) at −40° C., then stirred for 15 min. The mixture was concentrated, the residue was purified by reversed-phase HPLC (H$_2$O (0.05% TFA)-ACN (0.05% TFA) ACN from 10% to 100% over hold 1 min) and SFC (Chromatography Column: Chiralpak-AD (Daicel Corporation); mobile phase: CO₂-ETOH(DEA)) to get single enantiomers of N-(3((S)-6-(2,6-dichloro-3,5-dimethoxyphenyl)-4,5,6,7-tetrahydro-1H-indazol-3-yl) tetrahydro-2H-pyran-4-yl) acrylamide (P1=14 mg; P2=30 mg) as a white solids.

P1: $^1$H NMR (300 MHz, DMSO) δ 12.03 (s, 1H), 7.95 (s, 1H), 6.83 (s, 1H), 6.16-5.90 (m, 2H), 5.49 (d, J=8.7 Hz, 1H), 4.20 (d, J=9.1 Hz, 1H), 3.89 (s, 7H), 3.78 (d, J=11.3 Hz, 2H), 3.51-3.38 (m, 2H), 3.23 (s, 1H), 2.98-2.66 (m, 2H), 2.56 (s, 2H), 2.41 (s, 1H), 1.85 (d, J=10.8 Hz, 1H), 1.71 (d, J=10.2 Hz, 1H), 1.51 (s, 1H). MS (ESI) m/z: 481 (M+1).

P2: $^1$H NMR (300 MHz, DMSO) δ 12.03 (s, 1H), 7.96 (s, 1H), 6.83 (s, 1H), 6.05 (dt, J=35.0, 13.3 Hz, 2H), 5.50 (d, J=9.3 Hz, 1H), 4.15 (s, 1H), 3.89 (s, 7H), 3.85-3.73 (m, 2H), 3.52-3.41 (m, 2H), 3.30-3.16 (m, 1H), 2.92-2.61 (m, 2H), 2.56 (s, 2H), 2.41 (s, 1H), 1.77 (dd, J=32.6, 10.7 Hz, 2H), 1.53 (d, J=9.2 Hz, 1H). MS (ESI) m/z: 481 (M+1).

Example S8

Synthesis of N-(5-(6-(2,6-difluoro-3,5-bis(methoxy-d₃) phenyl)-4,5,6,7-tetrahydro-1H-indazol-3-yl)-1-methyl-1H-pyrazol-4-yl) acrylamide and N-(5-(6-(2-fluoro-3,5-bis(methoxy-d3) phenyl)-4,5,6,7-tetrahydro-1H-indazol-3-yl)-1-methyl-1H-pyrazol-4-yl) Acrylamide

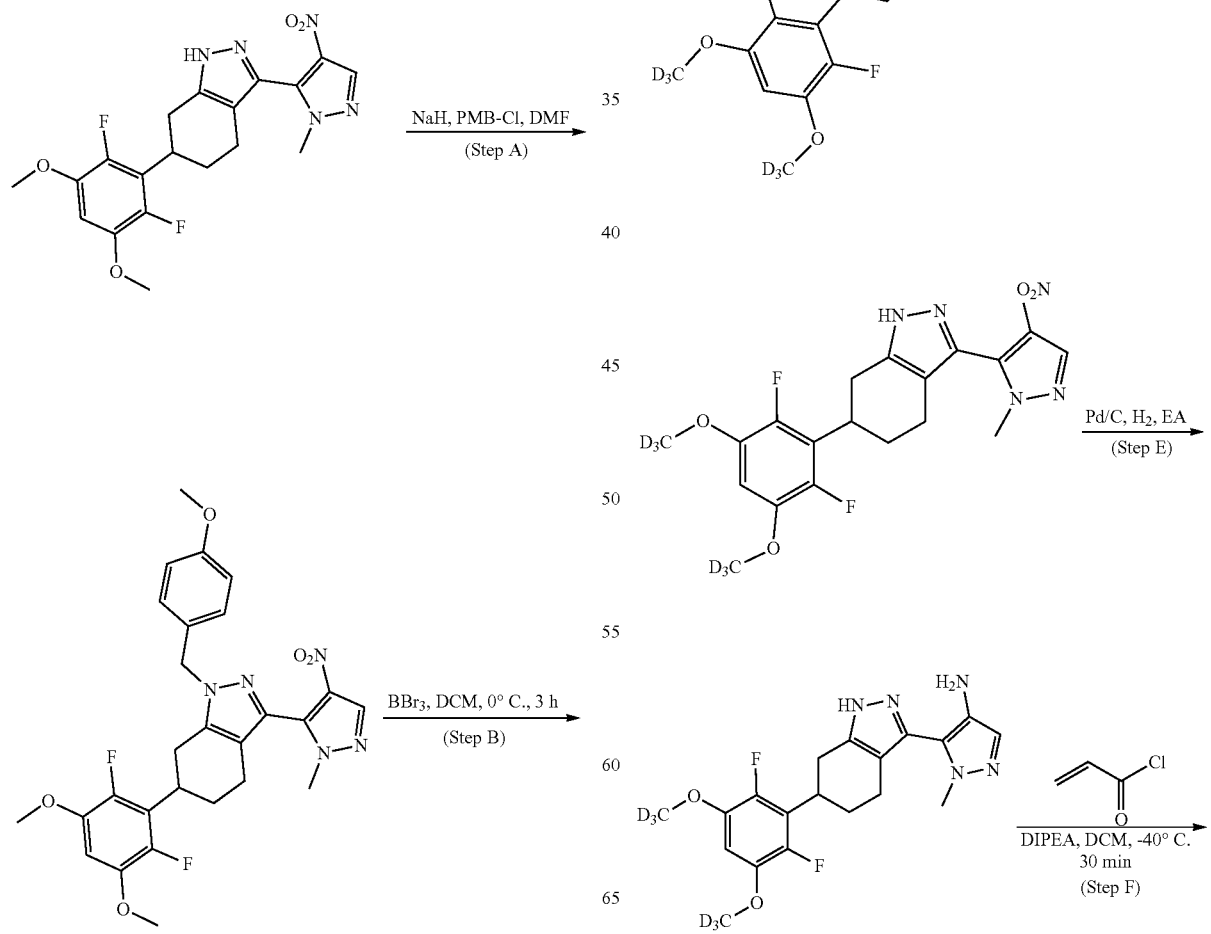

-continued

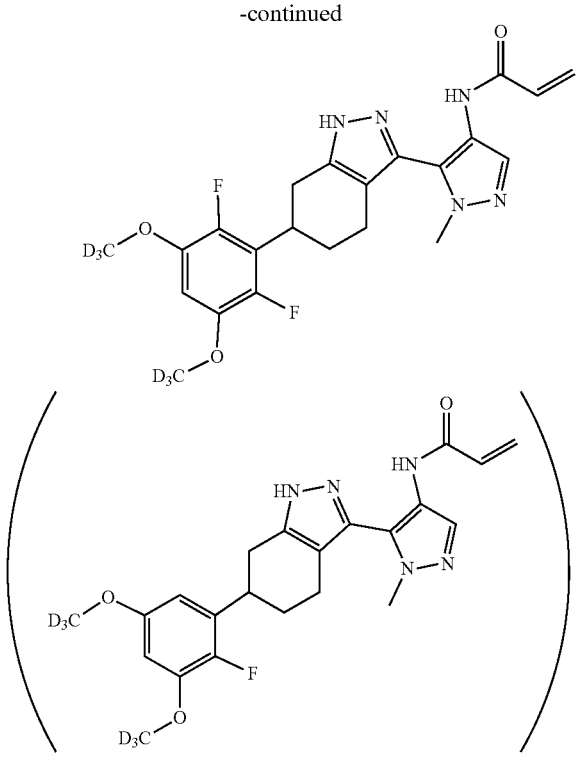

Step A: To a mixture of 6-(2,6-difluoro-3,5-dimethoxyphenyl)-3-(1-methyl-4-nitro-1H-pyrazol-5-yl)-4,5,6,7-tetrahydro-1H-indazole and 6-(2-fluoro-3,5-dimethoxyphenyl)-3-(1-methyl-4-nitro-1H-pyrazol-5-yl)-4,5,6,7-tetrahydro-1H-indazole and 6-(2-fluoro-3,5-dimethoxyphenyl)-3-(1-methyl-4-nitro-1H-pyrazol-5-yl)-4,5,6,7-tetrahydro-1H-indazole (3.2 g, 7.6 mmol) in DMF (20 mL) was added NaH (458 mg, 11 mmol) at 0° C., then stirred at 0° C. for 0.5 h, After a solution of 1-(chloromethyl)-4-methoxybenzene (1.79 g, 11 mmol) was added to above solution and stirred at rt for 12 h. LCMS suggested the reaction was completed. To the mixture, saturated aq. NH$_4$Cl solution (10 ml) was added, the DMF layer was diluted with water (30 mL), and the aqueous layer was further extracted with EtOAc (3*50 mL). The combined organic layers were washed with H$_2$O (10 mL), dried over Na$_2$SO$_4$, filtered and the filtrate was concentrated. The residue was purified by chromatography on silica gel eluting with PE/EtOAc (gradient elution 5:1 to 2:1) to get a mixture of 6-(2,6-difluoro-3,5-dimethoxyphenyl)-1-(4-methoxybenzyl)-3-(1-methyl-4-nitro-1H-pyrazol-5-yl)-4,5,6,7-tetrahydro-1H-indazole. MS (ESI) m/z: 540.1 (M+1) and 6-(2-fluoro-3,5-dimethoxyphenyl)-1-(4-methoxybenzyl)-3-(1-methyl-4-nitro-1H-pyrazol-5-yl)-4,5,6,7-tetrahydro-1H-indazole, MS (ESI) m/z: 522.1 (M+1) (3.6 g, 88%) as a yellow liquid.

Step B: A 250-mL, three-neck, round-bottomed flask, containing a magnetic stirring bar was equipped with a low-temperature thermometer. A mixture of 6-(2,6-difluoro-3,5-dimethoxyphenyl)-1-(4-methoxybenzyl)-3-(1-methyl-4-nitro-1H-pyrazol-5-yl)-4,5,6,7-tetrahydro-1H-indazole and 6-(2-fluoro-3,5-dimethoxyphenyl)-1-(4-methoxybenzyl)-3-(1-methyl-4-nitro-1H-pyrazol-5-yl)-4,5,6,7-tetrahydro-1H-indazole (3.5 g, 7 mmol) in DCM (50 ml) under nitrogen was cooled to 0° C., then BBr$_3$ (10 ml) was added into the solution dropwise over a period of 10 min. The mixture was stirred for 1 h, then warmed to rt. The reaction was quenched with CH$_3$OH and concentrated. The residue was purified by silica gel column chromatography (PE/EA=5:1, v/v) to get a mixture of 4,6-difluoro-5-(1-(4-hydroxybenzyl)-3-(1-methyl-4-nitro-1H-pyrazol-5-yl)-4,5,6,7-tetrahydro-1H-indazol-6-yl) benzene-1,3-diol, Mass Spectrum (ESI) m/z=498.0 (M+1) and 4-fluoro-5-(1-(4-hydroxybenzyl)-3-(1-methyl-4-nitro-1H-pyrazol-5-yl)-4,5,6,7-tetrahydro-1H-indazol-6-yl)benzene-1,3-diol as a yellow solid (1.5 g, 47%). MS (ESI) m/z: 480.1 (M+1).

Step C: A sealed tube was charged with 4,6-difluoro-5-(1-(4-hydroxybenzyl)-3-(1-methyl-4-nitro-1H-pyrazol-5-yl)-4,5,6,7-tetrahydro-1H-indazol-6-yl) benzene-1,3-diol and 4-fluoro-5-(1-(4-hydroxybenzyl)-3-(1-methyl-4-nitro-1H-pyrazol-5-yl)-4,5,6,7-tetrahydro-1H-indazol-6-yl)benzene-1,3-diol (1.3 g, 2.6 mmol), CD$_3$I (1.3 g, 9 mmol), K$_2$CO$_3$ (1.5 g, 11 mmol), and ACN (50 ml). The reaction mixture was stirred at 50° C. for 12 hrs, then cooled to rt. The mixture was filtered through Celite® (J. T. Baker, Phillipsberg, NJ, diatomaceous earth) and the filtrate was concentrated to get the crude product. The product was purified by chromatography on silica gel to get the 6-(2,6-difluoro-3,5-bis(methoxy-d$_3$) phenyl)-1-(4-(methoxy-d$_3$) benzyl)-3-(1-methyl-4-nitro-1H-pyrazol-5-yl)-4,5,6,7-tetrahydro-1H-indazole, Mass Spectrum (ESI) m/z=549.2 (M+1) and 6-(2-fluoro-3,5-bis(methoxy-d$_3$)phenyl)-1-(4-(methoxy-d$_3$)benzyl)-3-(1-methyl-4-nitro-1H-pyrazol-5-yl)-4,5,6,7-tetrahydro-1H-indazole as a white solid (1.1 g, 77%). MS (ESI) m/z: 531.2 (M+1).

Step D: A round-bottom flask was changed with the mixture of 6-(2,6-difluoro-3,5-bis(methoxy-d3) phenyl)-1-(4-(methoxy-d3) benzyl)-3-(1-methyl-4-nitro-1H-pyrazol-5-yl)-4,5,6,7-tetrahydro-1H-indazole and 6-(2-fluoro-3,5-bis(methoxy-d3)phenyl)-1-(4-(methoxy-d3)benzyl)-3-(1-methyl-4-nitro-1H-pyrazol-5-yl)-4,5,6,7-tetrahydro-1H-indazole (900 mg, 1.6 mmol) and trifluoroacetic acid (10 ml), The reaction mixture was heated to reflux overnight. The reaction was quenched with a saturated aq. NaHCO$_3$ solution. Then the mixture was extracted with EtOAc (3×50 mL). The combined extracts were washed with water and brine, dried over sodium sulfate and concentrated. Purified by silica gel column chromatography (PE/EA=2:1, v/v) to get a mixture of 6-(2,6-difluoro-3,5-bis(methoxy-d3) phenyl)-3-(1-methyl-4-nitro-1H-pyrazol-5-yl)-4,5,6,7-tetrahydro-1H-indazole, MS (ESI) m/z: 425.8 (M+1) and 6-(2-fluoro-3,5-bis(methoxy-d3)phenyl)-3-(1-methyl-4-nitro-1H-pyrazol-5-yl)-4,5,6,7-tetrahydro-1H-indazole, (700 mg, 99%) as a white solid. MS (ESI) m/z: 408.2 (M+1).

Step E: A suspension of 6-(2,6-difluoro-3,5-bis(methoxy-d3) phenyl)-3-(1-methyl-4-nitro-1H-pyrazol-5-yl)-4,5,6,7-tetrahydro-1H-indazole and 6-(2-fluoro-3,5-bis(methoxy-d3)phenyl)-3-(1-methyl-4-nitro-1H-pyrazol-5-yl)-4,5,6,7-tetrahydro-1H-indazole (650 mg, 1.53 mmol), Pd/C (300 mg) in EtOAc (25 mL) was stirred at 50° C. for 5 h under a H$_2$ atmosphere. The Pd/C was filtered off, and the filtrate was concentrated. The residue was purified by silica gel chromatography to give a mixture of 5-(6-(2,6-difluoro-3,5-bis(methoxy-d$_3$) phenyl)-4,5,6,7-tetrahydro-1H-indazol-3-yl)-1-methyl-1H-pyrazol-4-amine, MS (ESI) m/z: 396.1 (M+1) and 5-(6-(2-fluoro-3,5-bis(methoxy-d3)phenyl)-4,5,6,7-tetrahydro-1H-indazol-3-yl)-1-methyl-1H-pyrazol-4-amine (350 mg, 58%) as a brown solid. MS (ESI) m/z: 378.1 (M+1).

Step F: To a solution of 5-(6-(2,6-difluoro-3,5-bis (methoxy-d$_3$) phenyl)-4,5,6,7-tetrahydro-1H-indazol-3-yl)-1-methyl-1H-pyrazol-4-amine (300 mg, 0.76 mmol) and DIPEA (196 mg, 1.52 mmol) in DCM (20 mL) was added acryloyl chloride (68 mg, 0.75 mmol) dropwise at −40° C.

The mixture was stirred for 15 min, then concentrated and purified by reversed-phase HPLC and SFC (Chromatography Column: Chiralpak-AD (Daicel Corporation); mobile phase: $CO_2$-ETOH(DEA)) to give single enantiomers of N-(5-(6-(2,6-difluoro-3,5-bis(methoxy-$d_3$) phenyl)-4,5,6,7-tetrahydro-1H-indazol-3-yl)-1-methyl-1H-pyrazol-4-yl) acrylamide (P1=7 mg; P2=9.2 mg).

P1: $^1$H NMR (400 MHz, MeOD) δ 7.96 (s, 1H), 6.81 (s, 1H), 6.39 (dd, J=24.6, 6.0 Hz, 2H), 5.75 (dd, J=10.0, 2.0 Hz, 1H), 3.83 (s, 3H), 3.55 (t, J=22.6 Hz, 1H), 3.11 (dd, J=25.4, 9.5 Hz, 1H), 2.96 (dd, J=16.0, 5.4 Hz, 1H), 2.54 (s, 2H), 2.23 (dd, J=19.3, 11.9 Hz, 1H), 2.00 (dd, J=27.8, 15.6 Hz, 1H). MS (ESI) m/z: 450.1 (M+1).

P2: $^1$H NMR (400 MHz, MeOD) δ 7.96 (s, 1H), 6.81 (s, 1H), 6.39 (dd, J=24.6, 6.0 Hz, 2H), 5.75 (dd, J=10.0, 2.0 Hz, 1H), 3.83 (s, 3H), 3.55 (t, J=22.6 Hz, 1H), 3.11 (dd, J=25.4, 9.5 Hz, 1H), 2.96 (dd, J=16.0, 5.4 Hz, 1H), 2.54 (s, 2H), 2.23 (dd, J=19.3, 11.9 Hz, 1H), 2.00 (dd, J=27.8, 15.6 Hz, 1H). MS (ESI) m/z: 450.1 (M+1).

Further elution yielded single enantiomers of N-(5-(6-(2-fluoro-3,5-bis(methoxy-d3) phenyl)-4,5,6,7-tetrahydro-1H-indazol-3-yl)-1-methyl-1H-pyrazol-4-yl) acrylamide (P3=7.9 mg; P4=6.1 mg).

P3: $^1$H NMR (400 MHz, MeOD) δ 7.94 (s, 1H), 6.56 (dd, J=6.9, 2.9 Hz, 1H), 6.47-6.38 (m, 2H), 6.35 (d, J=2.0 Hz, 1H), 5.74 (dd, J=9.9, 2.0 Hz, 1H), 3.82 (s, 3H), 3.45-3.35 (m, 1H), 3.03 (dd, J=16.0, 5.3 Hz, 1H), 2.84 (dd, J=16.0, 11.1 Hz, 1H), 2.54 (d, J=15.7 Hz, 2H), 2.03 (s, 2H). MS (ESI) m/z: 432.1 [M+1].

P4: $^1$H NMR (400 MHz, MeOD) δ 7.94 (s, 1H), 6.56 (dd, J=6.9, 2.9 Hz, 1H), 6.47-6.38 (m, 2H), 6.35 (d, J=2.0 Hz, 1H), 5.74 (dd, J=9.9, 2.0 Hz, 1H), 3.82 (s, 3H), 3.45-3.35 (m, 1H), 3.03 (dd, J=16.0, 5.3 Hz, 1H), 2.84 (dd, J=16.0, 11.1 Hz, 1H), 2.54 (d, J=15.7 Hz, 2H), 2.03 (s, 2H). MS (ESI) m/z: 432.1 [M+1].

Example S9

Synthesis of N-(5-(7'-fluoro-4',6'-dimethoxy-1,4,5,7-tetrahydro-3'H-spiro[indazole-6,1'-isobenzofuran]-3-yl)-1-methyl-1H-pyrazol-4-yl)acrylamide

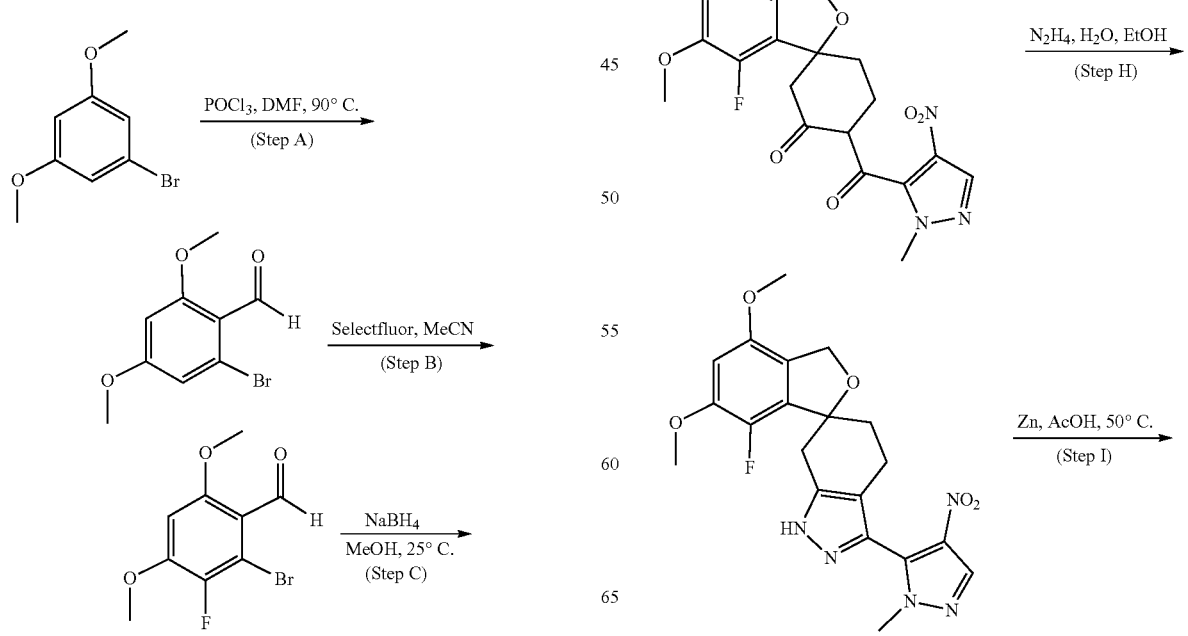

-continued

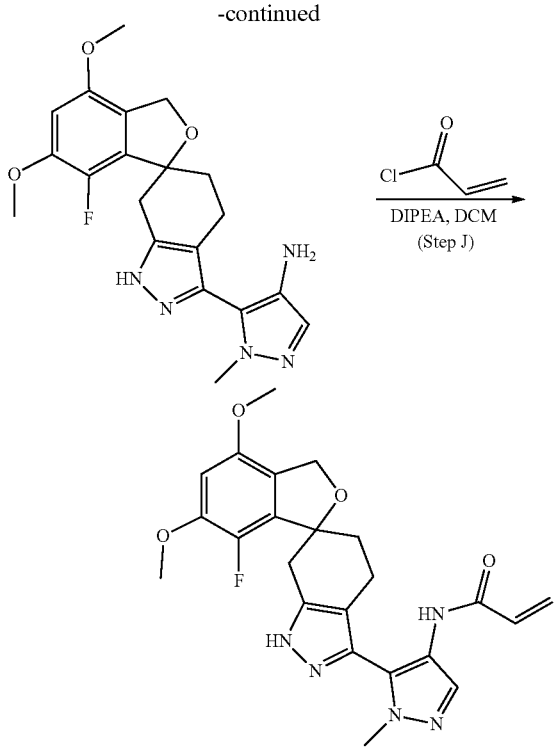

Step A: To a solution of 1-bromo-3,5-dimethoxybenzene (10.0 g, 46.1 mmol) in DMF was added POCl$_3$ (21.2 g, 138.3 mmol) at 0° C. The reaction mixture was stirred at 0° C. for 1 h then warmed to 90° C. for another 2 h. The reaction mixture was poured into ice water (150 mL) and extracted with ethyl acetate (200 mL×4). The combined organic layers were washed with brine (300 mL×2), dried over anhydrous Na$_2$SO$_4$ and then filtered. The filtrate was concentrated to give 2-bromo-4,6-dimethoxybenzaldehyde (8.0 g, 32.64 mmol, 70.8%) as a white solid, which was used directly in the next step without further purification. $^1$H NMR (400 MHz, CDCl$_3$) δ 10.31 (s, 1H), 6.78 (s, 1H), 6.44 (s, 1H), 3.89 (s, 3H), 3.87 (s, 3H). MS (ESI) m/z: 245.0 [M+H]$^+$.

Step B: To a solution of 1-chloromethyl-4-fluoro-1,4-diazoniabicyclo[2.2.2]octanebis(tetrafluoroborate) (65.05 g, 183.6 mmol) in CH$_3$CN (300 mL) and water (30 mL) was added 2-bromo-4,6-dimethoxybenzaldehyde (30 g, 122.4 mmol). The reaction mixture was stirred at 50° C. for 16 h. The reaction was quenched with water (500 mL) and extracted with ethyl acetate (200 mL×3). The combined organic phase was washed with brine (500 mL×3), dried over anhydrous Na$_2$SO$_4$ and then filtered. The filtrate was concentrated under reduced pressure. The residue was purified by silica gel chromatography (PE/EtOAc=3:1) to give 2-bromo-3-fluoro-4,6-dimethoxybenzaldehyde (11.9 g, 1.52 mmol, 36.95%) as a white solid. $^1$H NMR (400 MHz, CDCl$_3$) δ 10.31 (s, 1H), 6.55-6.49 (m, 1H), 3.99 (s, 3H), 3.94 (s, 3H). $^{19}$F NMR (400 MHz, CDCl$_3$) δ 135.30. MS (ESI) m/z: 263.0 [M+H]$^+$.

Step C: To a solution of 2-bromo-4,6-dimethoxybenzaldehyde (12 g, 45.6 mmol) in THF (150 mL) was added sodium borohydride (3.45 g, 91.2 mmol). The reaction mixture was stirred at 25° C. for 16 h. The reaction was quenched with water (300 mL) and extracted with ethyl acetate (50 mL×3). The combined organic layers were washed with brine (200 mL×3), dried over anhydrous Na$_2$SO$_4$ and filtered. The filtrate was concentrated under reduced pressure to give (2-bromo-4,6-dimethoxyphenyl)methanol (9.85 g, 37.16 mmol, 81.49%) as a white solid. $^1$H NMR (400 MHz, CDCl$_3$) δ 6.52 (d, J=8.0 Hz, 1H), 4.82 (s, 2H), 3.92 (s, 3H), 3.87 (s, 3H). MS (ESI) m/z: 247.0 [M-17+H]t Step D: To a solution of (2-bromo-3-fluoro-4,6-dimethoxyphenyl)methanol (9.85 g, 37.1 mmol) and 1H-imidazole (3.6 g, 51.94 mmol) in DMF (150 mL) was added tert-butyl(chloro)dimethylsilane (7.8 g, 51.94 mmol) at 0° C. The reaction mixture was stirred at 25° C. for 16 h. The reaction was quenched with water (500 mL) and then extracted with ethyl acetate (200 mL×3). The combined organic layers were washed with brine (500 mL×3), dried over anhydrous Na$_2$SO$_4$ and filtered. The filtrate was concentrated under reduced pressure. The residue was purified by silica gel chromatography (PE/EtOAc=20:1) to give [(2-bromo-3-fluoro-4,6-dimethoxyphenyl)methoxy](tert-butyl)dimethylsilane (11.4 g, 30.05 mmol, 81%) as a white solid. $^1$H NMR (400 MHz, CDCl$_3$) δ 6.51 (s, 1H), 4.79 (s, 2H), 3.81 (s, 3H), 3.74 (s, 3H), 0.82 (s, 9H), 0.10 (s, 6H).

Step E: To a solution of [(2-bromo-3-fluoro-4,6-dimethoxyphenyl)methoxy](tert-butyl)dimethylsilane (1.0 g, 2.64 mmol) in THF (10 mL) was added n-Butyllithium (2.4 M in THF) (1.2 mL, 2.9 mmol) at −78° C. The reaction mixture was stirred at −78° C. for 30 minutes, and then 1,4-dioxaspiro[4.5]decan-7-one (453 mg, 2.9 mmol) was added. The mixture was stirred at −78° C. for another 2.5 h. The reaction was quenched with aq. NH$_4$Cl (20 mL) and extracted with ethyl acetate (10 mL×3). The combined organic layers were washed with brine (10 mL×3), dried over anhydrous Na$_2$SO$_4$, and filtered. The filtrate was concentrated under reduced pressure. The residue was purified by prep-TLC (PE/EtOAc=2:1) to give 7-(2-{[(tert-butyldimethylsilyl)oxy]methyl}-6-fluoro-3,5-dimethoxyphenyl)-1,4-dioxaspiro[4.5]decan-7-ol (110 mg, 9%) as a white solid. $^1$H NMR (400 MHz, CDCl$_3$) δ 6.44 (s, 1H), 5.17 (m, 2H), 4.06-3.89 (m, 4H), 3.85 (s, 3H), 3.78 (s, 3H), 2.53-2.50 (m, 1H), 2.20 (m, 1H), 2.09 (m, 1H), 2.01 (m, 1H), 1.89-1.69 (m, 3H), 1.48-1.39 (m, 1H), 0.85 (s, 9H), −0.01 (s, 6H).

Step F: To a solution of 7-(2-{[(tert-butyldimethylsilyl)oxy]methyl}-6-fluoro-3,5-dimethoxyphenyl)-1,4-dioxaspiro[4.5]decan-7-ol (800 mg, 1.75 mmol) in DCM (10 mL) was added trifluoroacetic acid (998 mg, 8.8 mmol). The reaction mixture was stirred at 25° C. for 3 h. The reaction was quenched with aq. NaHCO$_3$ (20 mL) and extracted with DCM (20 mL×3). The combined organic layers were washed with brine (20 mL×3), dried over anhydrous Na$_2$SO$_4$ and then filtered. The filtrate was concentrated under reduced pressure. The residue was purified by prep-TLC (PE/EtOAc=2:1) to give 7-fluoro-4,6-dimethoxy-3H-spiro[2-benzofuran-1,1'-cyclohexane]-5'-one (110 mg, 22.3%) as a colorless oil. $^1$H NMR (400 MHz, CDCl$_3$) δ 6.45 (s, 1H), 4.98 (m, 2H), 3.91 (s, 3H), 3.82 (s, 3H), 2.99-2.96 (m, 1H), 2.58 (m, 1H), 2.46 (m, 1H), 2.44-2.36 (m, 1H), 2.29 (m, 1H), 2.23-2.08 (m, 1H), 2.04-1.93 (m, 2H). MS (ESI) m/z: 281.2 [M+H]$^+$.

Step G: To a solution of 7-fluoro-4,6-dimethoxy-3H-spiro[2-benzofuran-1,1'-cyclohexane]- (110 mg, 0.393 mmol) in THF (3 mL) was added diisopropyl(lithio)amine (51 mg, 0.4716 mmol) at −78° C. The reaction mixture was stirred at −78° C. for 0.5 h. To the above mixture was added a solution of 2-methyl-4-nitropyrazole-3-carbonyl chloride (90 mg, 0.47 mmol) in THF (1 mL). The mixture was stirred at −78° C. for another 2.5 h. The reaction was quenched with aq. NH$_4$Cl solution (10 mL) and extracted with ethyl acetate (10 mL×3). The combined organic layers were washed with brine (10 mL×3), dried over anhydrous Na$_2$SO$_4$, and filtered.

The filtrate was concentrated under reduced pressure. The residue was purified by prep-TLC (PE/EtOAc=2:1) to 7'-fluoro-4',6'-dimethoxy-3-(1-methyl-4-nitro-1H-pyrazol-5-yl)-1,4,5,7-tetrahydro-3'H-spiro[indazole-6,1'-isobenzofuran] give (47 mg, yield: 27.9%) as a white solid. $^1$H NMR (400 MHz, CDCl$_3$) δ 8.08 (s, 1H), 6.46 (s, 1H), 5.00 (m, 2H), 3.91 (s, 3H), 3.90 (s, 3H), 3.81 (s, 3H), 3.16 (m, 1H), 2.53 (m, 3H), 2.27-2.08 (m, 2H), 1.92 (m, 1H). MS (ESI) m/z: 433.2 [M+H]$^+$.

Step H: To a solution of 7-fluoro-4,6-dimethoxy-4'-[(2-methyl-4-nitropyrazol-3-yl)carbonyl]-3H-spiro[2-benzofuran-1,1'-cyclohexane]-5'-one (80 mg, 0.1849 mmol) in EtOH (5 mL) was added hydrazine hydrate (90 mg, 1.85 mmol). The reaction mixture was stirred at 85° C. for 16 h. The reaction was quenched with H$_2$O (10 mL) and extracted with ethyl acetate (10 mL×3). The combined organic layers were washed with brine (10 mL×3), dried over anhydrous Na$_2$SO$_4$ and filtered. The filtrate was concentrated under reduced pressure. The residue was purified by prep-TLC (PE/EtOAc=1:1) to give 7'-fluoro-4',6'-dimethoxy-3-(1-methyl-4-nitro-1H-pyrazol-5-yl)-1,4,5,7-tetrahydro-3'H-spiro[indazole-6,1'-isobenzofuran] (15 mg, 16%) as a white solid. $^1$H NMR (400 MHz, CDCl$_3$) δ 8.20 (s, 1H), 6.48 (s, 1H), 5.05 (m, 2H), 3.93 (s, 3H), 3.88 (s, 3H), 3.83 (s, 3H), 3.35 (d, J=16.5 Hz, 1H), 3.03 (d, J=16.5 Hz, 1H), 2.83-2.68 (m, 1H), 2.48 (m, 1H), 2.29 (m, 1H), 2.06 (m, 1H). MS (ESI) m/z: 430.2 [M+H]$^+$.

Step I: To a solution of 7-fluoro-4,6-dimethoxy-3'-(2-methyl-4-nitropyrazol-3-yl)-1',4',5',7'-tetrahydro-3H-spiro[2-benzofuran-1,6'-indazole] (15 mg, 0.034 mmol) in AcOH (2 mL) was added Zn powder (11.4 mg, 0.17 mmol). The reaction mixture was stirred at 50° C. for 6 h. The reaction was quenched with aq. NaHCO$_3$ (20 mL) and then extracted with ethyl acetate (10 mL×3). The combined organic layers were washed with brine (10 mL×3), dried over anhydrous Na$_2$SO$_4$ and filtered. The filtrate was concentrated to give 5-(7'-fluoro-4',6'-dimethoxy-1,4,5,7-tetrahydro-3'H-spiro[indazole-6,1'-isobenzofuran]-3-yl)-1-methyl-1H-pyrazol-4-amine (9 mg, 59%) as a white solid, which was used directly in the next step without further purification. MS (ESI) m/z: 400.2 [M+H]$^+$.

Step J: To a solution of 5-{7-fluoro-4,6-dimethoxy-1',4',5',7'-tetrahydro-3H-spiro[2-benzofuran-1,6'-indazole]-3'-yl}-1-methylpyrazol-4-amine (9 mg, 0.023 mmol) and N-ethyl-N-isopropylpropan-2-amine (5.95 mg, 0.046 mmol) in DCM (2 mL) was added prop-2-enoyl chloride (2.5 mg, 0.0276 mmol). The reaction mixture was stirred at 25° C. for 3 h. The reaction was quenched with H$_2$O (5 mL) and then extracted with ethyl acetate (5 mL×3). The combined organic layers were washed with brine (5 mL×3), dried over anhydrous Na$_2$SO$_4$ and filtered. The filtrate was concentrated under reduced pressure. The residues was purified by Preparative HPLC (Chromatographic column: Kromasil-C18, 100×21.2 mm, 5um, Mobile Phase: CH$_3$CN—H$_2$O (0.1% FA) Gradient: 35-45% in 6 minutes; flow rate: 25 mL/min) to give N-(5-(7'-fluoro-4',6'-dimethoxy-1,4,5,7-tetrahydro-3'H-spiro[indazole-6,1'-isobenzofuran]-3-yl)-1-methyl-1H-pyrazol-4-yl)acrylamide (1.1 mg, 10.5% yield) as a white solid.

$^1$H NMR (400 MHz, CD$_3$OD) δ 8.50 (s, 1H), 7.99 (s, 1H), 6.70-6.69 (m, 1H), 6.44 (m, 1H), 6.32 (m, 1H), 5.72 (m, 1H), 5.01 (s, 2H), 3.91 (s, 3H), 3.85 (s, 3H), 3.80 (s, 3H), 3.25 (s, 1H), 3.02-2.99 (m, 1H), 2.79-2.63 (m, 1H), 2.48 (m, 1H), 2.27 (m, 1H), 2.13-2.00 (m, 1H). MS (ESI) m/z: 454.2 [M+H]$^+$.

Example S10

Synthesis of N-(4-(6-(2,6-dichloro-3,5-dimethoxyphenyl)-4,5,6,7-tetrahydro-1H-indazol-3-yl) tetrahydrofuran-3-yl) Acrylamide

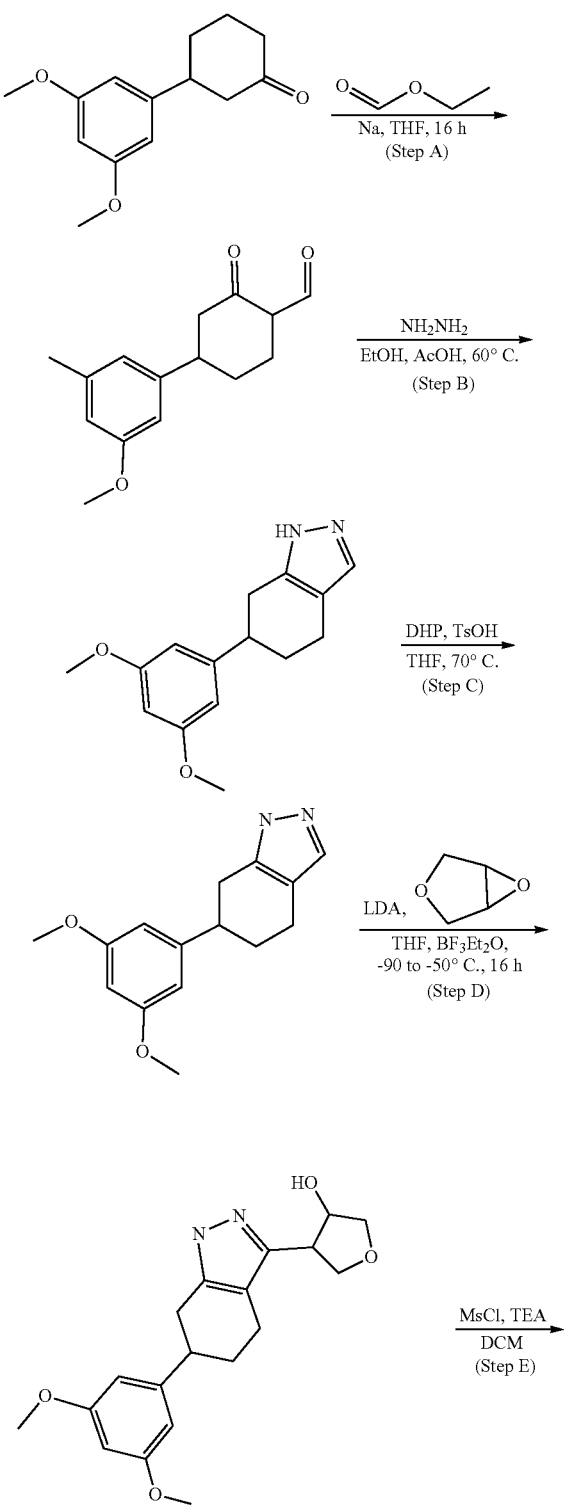

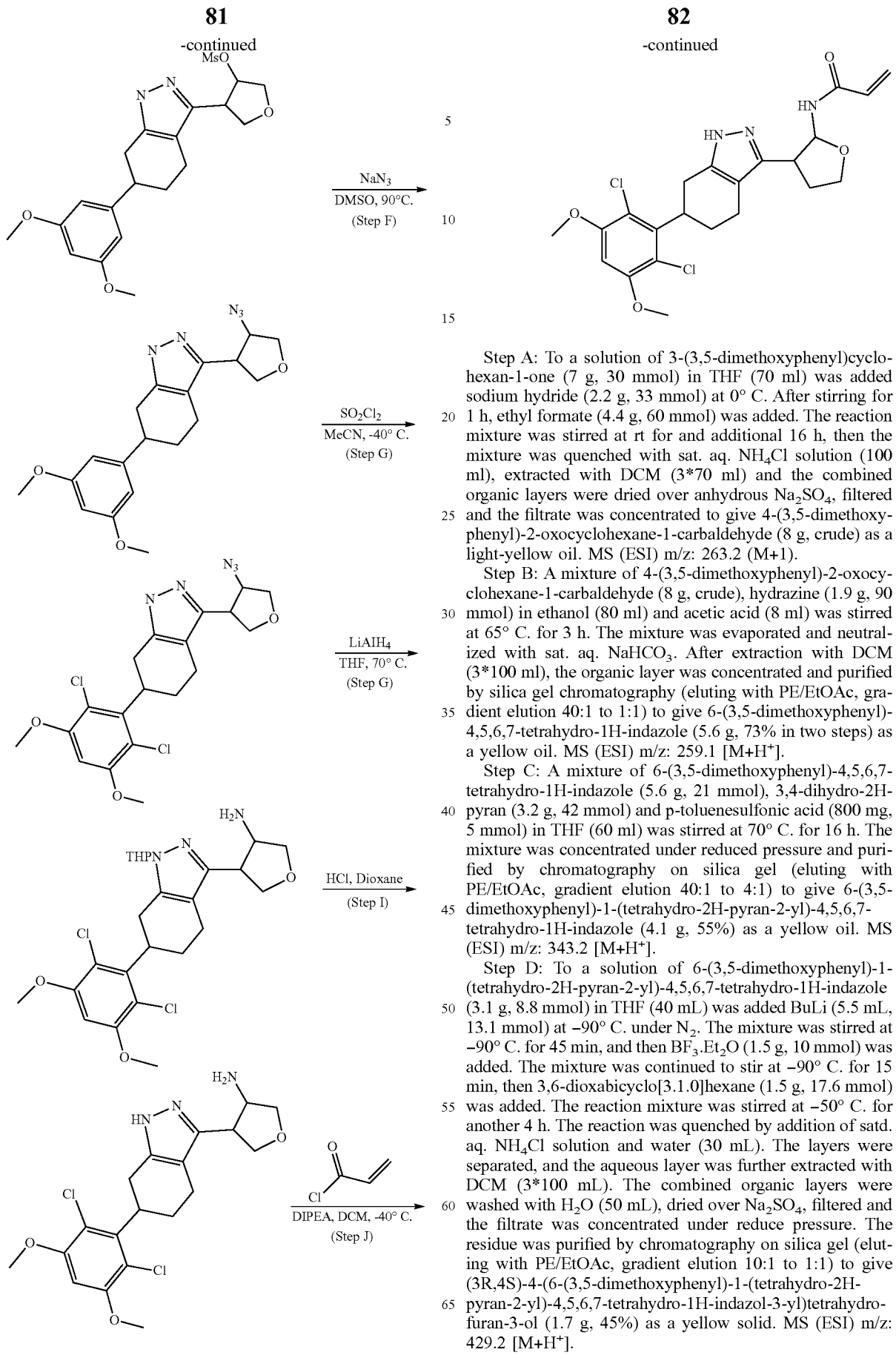

Step A: To a solution of 3-(3,5-dimethoxyphenyl)cyclohexan-1-one (7 g, 30 mmol) in THF (70 ml) was added sodium hydride (2.2 g, 33 mmol) at 0° C. After stirring for 1 h, ethyl formate (4.4 g, 60 mmol) was added. The reaction mixture was stirred at rt for and additional 16 h, then the mixture was quenched with sat. aq. NH$_4$Cl solution (100 ml), extracted with DCM (3*70 ml) and the combined organic layers were dried over anhydrous Na$_2$SO$_4$, filtered and the filtrate was concentrated to give 4-(3,5-dimethoxyphenyl)-2-oxocyclohexane-1-carbaldehyde (8 g, crude) as a light-yellow oil. MS (ESI) m/z: 263.2 (M+1).

Step B: A mixture of 4-(3,5-dimethoxyphenyl)-2-oxocyclohexane-1-carbaldehyde (8 g, crude), hydrazine (1.9 g, 90 mmol) in ethanol (80 ml) and acetic acid (8 ml) was stirred at 65° C. for 3 h. The mixture was evaporated and neutralized with sat. aq. NaHCO$_3$. After extraction with DCM (3*100 ml), the organic layer was concentrated and purified by silica gel chromatography (eluting with PE/EtOAc, gradient elution 40:1 to 1:1) to give 6-(3,5-dimethoxyphenyl)-4,5,6,7-tetrahydro-1H-indazole (5.6 g, 73% in two steps) as a yellow oil. MS (ESI) m/z: 259.1 [M+H$^+$].

Step C: A mixture of 6-(3,5-dimethoxyphenyl)-4,5,6,7-tetrahydro-1H-indazole (5.6 g, 21 mmol), 3,4-dihydro-2H-pyran (3.2 g, 42 mmol) and p-toluenesulfonic acid (800 mg, 5 mmol) in THF (60 ml) was stirred at 70° C. for 16 h. The mixture was concentrated under reduced pressure and purified by chromatography on silica gel (eluting with PE/EtOAc, gradient elution 40:1 to 4:1) to give 6-(3,5-dimethoxyphenyl)-1-(tetrahydro-2H-pyran-2-yl)-4,5,6,7-tetrahydro-1H-indazole (4.1 g, 55%) as a yellow oil. MS (ESI) m/z: 343.2 [M+H$^+$].

Step D: To a solution of 6-(3,5-dimethoxyphenyl)-1-(tetrahydro-2H-pyran-2-yl)-4,5,6,7-tetrahydro-1H-indazole (3.1 g, 8.8 mmol) in THF (40 mL) was added BuLi (5.5 mL, 13.1 mmol) at −90° C. under N$_2$. The mixture was stirred at −90° C. for 45 min, and then BF$_3$.Et$_2$O (1.5 g, 10 mmol) was added. The mixture was continued to stir at −90° C. for 15 min, then 3,6-dioxabicyclo[3.1.0]hexane (1.5 g, 17.6 mmol) was added. The reaction mixture was stirred at −50° C. for another 4 h. The reaction was quenched by addition of satd. aq. NH$_4$Cl solution and water (30 mL). The layers were separated, and the aqueous layer was further extracted with DCM (3*100 mL). The combined organic layers were washed with H$_2$O (50 mL), dried over Na$_2$SO$_4$, filtered and the filtrate was concentrated under reduce pressure. The residue was purified by chromatography on silica gel (eluting with PE/EtOAc, gradient elution 10:1 to 1:1) to give (3R,4S)-4-(6-(3,5-dimethoxyphenyl)-1-(tetrahydro-2H-pyran-2-yl)-4,5,6,7-tetrahydro-1H-indazol-3-yl)tetrahydrofuran-3-ol (1.7 g, 45%) as a yellow solid. MS (ESI) m/z: 429.2 [M+H$^+$].

Step E: In a round-bottom flask were placed (3R,4S)-4-(6-(3,5-dimethoxyphenyl)-1-(tetrahydro-2H-pyran-2-yl)-4,5,6,7-tetrahydro-1H-indazol-3-yl)tetrahydrofuran-3-ol (1.5 g, 3.5 mmol) and DCM (20 ml). Methanesulfonyl chloride (1.2 g, 1.5 mmol) was added dropwise to the reaction mixture at 0° C. and stirring was continued for 5 h. The DCM was evaporated to get (3R,4S)-4-(6-(3,5-dimethoxyphenyl)-1-(tetrahydro-2H-pyran-2-yl)-4,5,6,7-tetrahydro-1H-indazol-3-yl)tetrahydrofuran-3-yl methanesulfonate (1.5 g, crude) as a yellow oil which was used in the next step without further purification. MS (ESI) m/z: 507.1 [M+H$^+$].

Step F: A mixture of (3R,4S)-4-(6-(3,5-dimethoxyphenyl)-1-(tetrahydro-2H-pyran-2-yl)-4,5,6,7-tetrahydro-1H-indazol-3-yl)tetrahydrofuran-3-yl methanesulfonate (1.5 g, 3 mmol), sodium azide (780 mg, 12 mmol) in DMF (15 mL) was stirred at 90° C. for 36 h. The mixture was diluted with water (30 mL) and the aqueous layer was further extracted with DCM (3*50 mL). The combined organic layers were washed with H$_2$O (4*20 mL) and dried over Na$_2$SO$_4$. The organic layer was concentrated under reduced pressure and purified by silica gel chromatography (eluting with PE/EtOAc, gradient elution 10:1 to 1:1) to give 3-((3S,4S)-4-azidotetrahydrofuran-3-yl)-6-(2,6-dichloro-3,5-dimethoxyphenyl)-1-(tetrahydro-2H-pyran-2-yl)-4,5,6,7-tetrahydro-1H-indazole (770 mg, 49% in two steps) as a yellow solid. MS (ESI) m/z: 454.2 [M+H$^+$].

Step G: To a solution of 3-((3S,4S)-4-azidotetrahydrofuran-3-yl)-6-(2,6-dichloro-3,5-dimethoxyphenyl)-1-(tetrahydro-2H-pyran-2-yl)-4,5,6,7-tetrahydro-1H-indazole (770 mg, 1.7 mmol) in MeCN (10 ml) was added SO$_2$Cl$_2$ (620 mg, 4.6 mmol) at −40° C. The mixture was stirred at rt for 0.5 h. The mixture was diluted with DCM (20 ml) and neutralized with sat. aq. NaHCO$_3$. After extraction with DCM (3*20 ml), the organic layers were concentrated and purified by silica gel chromatography (eluting with PE/EtOAc, gradient elution 20:1 to 2:1) to give (3S,4S)-4-(6-(2,6-dichloro-3,5-dimethoxyphenyl)-1-(tetrahydro-2H-pyran-2-yl)-4,5,6,7-tetrahydro-1H-indazol-3-yl)tetrahydrofuran-3-amine (460 mg, 38.8%) as a yellow oil. MS (ESI) m/z: 521.6 [M+1].

Step H: To a solution of LiAlH$_4$ (360 mg, 9.5 mmol) in THF (40 ml) was added (3S,4S)-4-(6-(2,6-dichloro-3,5-dimethoxyphenyl)-1-(tetrahydro-2H-pyran-2-yl)-4,5,6,7-tetrahydro-1H-indazol-3-yl)tetrahydrofuran-3-amine (360 mg, 0.7 mmol) at 70° C. The mixture was stirred at 70° C. for 5 min. The reaction was quenched by water (0.4 ml) at 0° C. and concentrated under reduce pressure. The crude product was purified by chromatography on silica gel (eluting with DCM/methanol, gradient elution 10:0 to 40:1) to give (3S,4S)-4-(6-(2,6-dichloro-3,5-dimethoxyphenyl)-4,5,6,7-tetrahydro-1H-indazol-3-yl)tetrahydrofuran-3-amine (220 g, 62%) as a yellow solid. MS (ESI) m/z: 495.8 [M+1].

Step I: A mixture of (3S,4S)-4-(6-(2,6-dichloro-3,5-dimethoxyphenyl)-4,5,6,7-tetrahydro-1H-indazol-3-yl)tetrahydrofuran-3-amine (220 mg, 0.44 mmol) in HCl/dioxane (6 ml) was stirred at rt for 16 h. the mixture was evaporated to get N-((3S,4S)-4-(6-(2,6-dichloro-3,5-dimethoxyphenyl)-4,5,6,7-tetrahydro-1H-indazol-3-yl)tetrahydrofuran-3-yl)acrylamide (160 mg, crude) which was used in the next step without further purification. MS (ESI) m/z: 412.0 [M+1].

Step J: To a solution of N-((3S,4S)-4-(6-(2,6-dichloro-3,5-dimethoxyphenyl)-4,5,6,7-tetrahydro-1H-indazol-3-yl)tetrahydrofuran-3-yl)acrylamide (160 mg, 0.38 mmol) and DIPEA (223 mg, 1.72 mmol) in DCM (20 mL) was added acryloyl chloride (15 mg, 0.19 mmol) at −40° C., then stirring was continued for 15 min. The mixture was concentrated, and the residue was purified by reversed-phase HPLC (H$_2$O (0.05% TFA)-ACN (0.05% TFA) ACN from 10% to 100% over hold 1 min) and SFC (Chromatography Column: Chiralpak-AD (Daicel Corporation); mobile phase: CO$_2$-ETOH(DEA)) to give N-((3R,4R)-4-((R)-6-(2,6-dichloro-3,5-dimethoxyphenyl)-4,5,6,7-tetrahydro-1H-indazol-3-yl)tetrahydrofuran-3-yl)acrylamide (P1, 6.8 mg), N-((3S,4S)-4-((R)-6-(2,6-dichloro-3,5-dimethoxyphenyl)-4,5,6,7-tetrahydro-1H-indazol-3-yl)tetrahydrofuran-3-yl)acrylamide (P2, 3.4 mg), N-((3S,4S)-4-((S)-6-(2,6-dichloro-3,5-dimethoxyphenyl)-4,5,6,7-tetrahydro-1H-indazol-3-yl)tetrahydrofuran-3-yl)acrylamide (P3, 4.4 mg), and N-((3R,4R)-4-((S)-6-(2,6-dichloro-3,5-dimethoxyphenyl)-4,5,6,7-tetrahydro-1H-indazol-3-yl)tetrahydrofuran-3-yl)acrylamide (P4, 6.8 mg).

P1: $^1$H NMR (400 MHz, MeOD) δ 6.76 (s, 1H), 6.16-6.10 (m, 2H), 5.60 (dd, J=7.9, 4.2 Hz, 1H), 4.90-4.83 (m, 1H), 4.24-4.13 (m, 3H), 4.06-4.01 (m, 1H), 3.94-3.93 (m, 6H), 3.86-3.71 (m, 2H), 3.46-3.39 (m, 1H), 2.81-2.61 (m, 3H), 2.50-2.46 (m, 1H), 1.86-1.74 (m, 1H). MS (ESI) m/z: 465.8 [M+1].

P2: $^1$H NMR (400 MHz, MeOD) δ 6.74 (s, 1H), 6.16-6.07 (m, 2H), 5.58 (dd, J=8.1, 3.9 Hz, 1H), 4.87-4.78 (m, 1H), 4.31-4.08 (m, 3H), 4.06-3.96 (m, 1H), 3.92-3.90 (m, 6H), 3.82-3.70 (m, 2H), 3.47-3.35 (m, 1H), 2.75-2.58 (m, 3H), 2.52-2.43 (m, 1H), 1.80-1.77 (m, 1H). MS (ESI) m/z: 465.8 [M+1]

P3: $^1$H NMR (400 MHz, MeOD) δ 6.74 (s, 1H), 6.20-6.03 (m, 2H), 5.58 (dd, J=8.1, 3.9 Hz, 1H), 4.88-4.79 (m, 1H), 4.30-4.07 (m, 3H), 4.07-3.96 (m, 1H), 3.92-3.91 (m, 6H), 3.85-3.70 (m, 2H), 3.51-3.36 (m, 1H), 2.79-2.56 (m, 3H), 2.51-2.44 (m, 1H), 1.80-1.77 (m, 1H). MS (ESI) m/z: 465.7 [M+1].

P4: $^1$H NMR (400 MHz, MeOD) δ 6.74 (s, 1H), 6.15-6.03 (m, 2H), 5.58 (dd, J=7.9, 4.2 Hz, 1H), 4.86-4.78 (m, 2H), 4.28-4.09 (m, 3H), 4.06-3.98 (m, 1H), 3.92-3.91 (m, 6H), 3.81-3.70 (m, 2H), 3.46-3.34 (m, 1H), 2.77-2.58 (m, 3H), 2.47-2.44 (m, 1H), 1.84-1.73 (m, 1H). MS (ESI) m/z: 465.6 [M+1].

Example S11

Synthesis of N-(5-(7-(2,6-difluoro-3,5-dimethoxyphenyl)-1,4,5,6,7,8-hexahydrocyclohepta[c]pyrazol-3-yl)-1H-pyrazol-4-yl)acrylamide and N-(5-(7-(2-fluoro-3,5-dimethoxyphenyl)-1,4,5,6,7,8-hexahydrocyclohepta[c]pyrazol-3-yl)-1H-pyrazol-4-yl)acrylamide

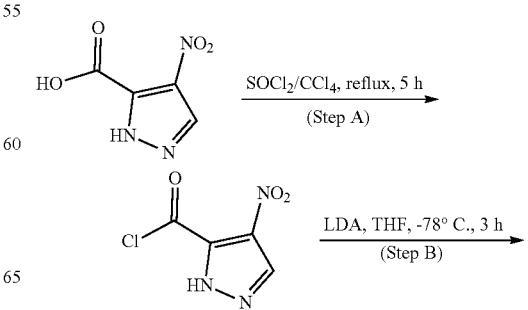

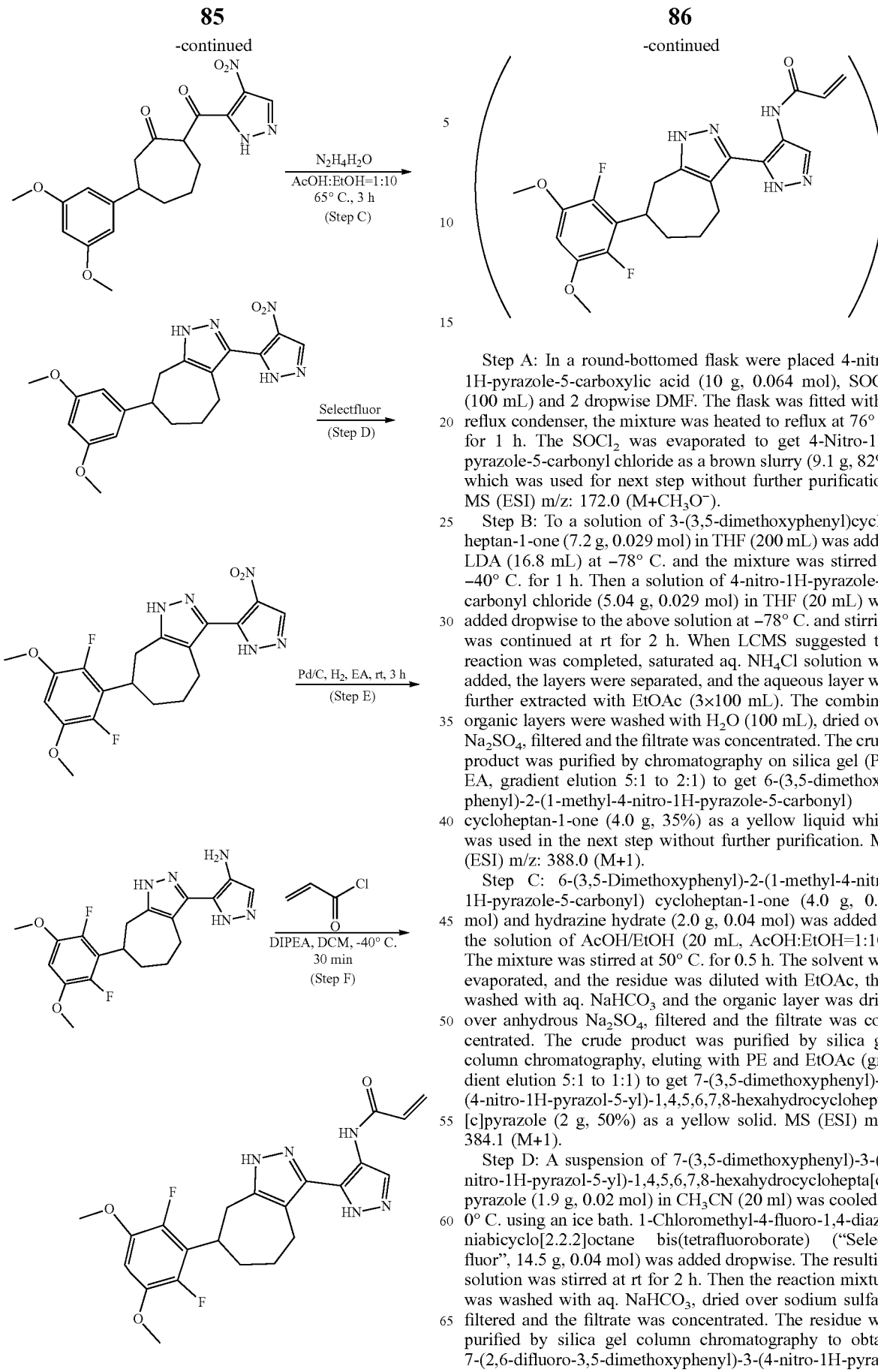

Step A: In a round-bottomed flask were placed 4-nitro-1H-pyrazole-5-carboxylic acid (10 g, 0.064 mol), SOCl₂ (100 mL) and 2 dropwise DMF. The flask was fitted with a reflux condenser, the mixture was heated to reflux at 76° C. for 1 h. The SOCl₂ was evaporated to get 4-Nitro-1H-pyrazole-5-carbonyl chloride as a brown slurry (9.1 g, 82%) which was used for next step without further purification. MS (ESI) m/z: 172.0 (M+CH₃O⁻).

Step B: To a solution of 3-(3,5-dimethoxyphenyl)cycloheptan-1-one (7.2 g, 0.029 mol) in THF (200 mL) was added LDA (16.8 mL) at −78° C. and the mixture was stirred at −40° C. for 1 h. Then a solution of 4-nitro-1H-pyrazole-5-carbonyl chloride (5.04 g, 0.029 mol) in THF (20 mL) was added dropwise to the above solution at −78° C. and stirring was continued at rt for 2 h. When LCMS suggested the reaction was completed, saturated aq. NH₄Cl solution was added, the layers were separated, and the aqueous layer was further extracted with EtOAc (3×100 mL). The combined organic layers were washed with H₂O (100 mL), dried over Na₂SO₄, filtered and the filtrate was concentrated. The crude product was purified by chromatography on silica gel (PE: EA, gradient elution 5:1 to 2:1) to get 6-(3,5-dimethoxyphenyl)-2-(1-methyl-4-nitro-1H-pyrazole-5-carbonyl) cycloheptan-1-one (4.0 g, 35%) as a yellow liquid which was used in the next step without further purification. MS (ESI) m/z: 388.0 (M+1).

Step C: 6-(3,5-Dimethoxyphenyl)-2-(1-methyl-4-nitro-1H-pyrazole-5-carbonyl) cycloheptan-1-one (4.0 g, 0.01 mol) and hydrazine hydrate (2.0 g, 0.04 mol) was added to the solution of AcOH/EtOH (20 mL, AcOH:EtOH=1:10). The mixture was stirred at 50° C. for 0.5 h. The solvent was evaporated, and the residue was diluted with EtOAc, then washed with aq. NaHCO₃ and the organic layer was dried over anhydrous Na₂SO₄, filtered and the filtrate was concentrated. The crude product was purified by silica gel column chromatography, eluting with PE and EtOAc (gradient elution 5:1 to 1:1) to get 7-(3,5-dimethoxyphenyl)-3-(4-nitro-1H-pyrazol-5-yl)-1,4,5,6,7,8-hexahydrocyclohepta[c]pyrazole (2 g, 50%) as a yellow solid. MS (ESI) m/z: 384.1 (M+1).

Step D: A suspension of 7-(3,5-dimethoxyphenyl)-3-(4-nitro-1H-pyrazol-5-yl)-1,4,5,6,7,8-hexahydrocyclohepta[c]pyrazole (1.9 g, 0.02 mol) in CH₃CN (20 ml) was cooled to 0° C. using an ice bath. 1-Chloromethyl-4-fluoro-1,4-diazoniabicyclo[2.2.2]octane bis(tetrafluoroborate) ("Selectfluor", 14.5 g, 0.04 mol) was added dropwise. The resulting solution was stirred at rt for 2 h. Then the reaction mixture was washed with aq. NaHCO₃, dried over sodium sulfate, filtered and the filtrate was concentrated. The residue was purified by silica gel column chromatography to obtain 7-(2,6-difluoro-3,5-dimethoxyphenyl)-3-(4-nitro-1H-pyrazol-5-yl)-1,4,5,6,7,8-hexahydrocyclohepta[c]pyrazole, Mass Spectrum (ESI) m/z=420.0 (M+1) and 7-(2-fluoro-3, 5-dimethoxyphenyl)-3-(4-nitro-1H-pyrazol-5-yl)-1,4,5,6,7, 8-hexahydrocyclohepta[c]pyrazole (0.7 g, 35%). MS (ESI) m/z: 402.0 (M+1).

Step E: A mixture of 7-(2,6-difluoro-3,5-dimethoxyphenyl)-3-(4-nitro-1H-pyrazol-5-yl)-1,4,5,6,7,8-hexahydrocyclohepta[c]pyrazole and 7-(2-fluoro-3,5-dimethoxyphenyl)-3-(4-nitro-1H-pyrazol-5-yl)-1,4,5,6,7,8-hexahydrocyclohepta[c]pyrazole (600 mg, 1.54 mmol) and Pd/C (300 mg) in ethyl acetate (25 mL) was stirred at 50° C. for 5 h under a H$_2$ atmosphere. The Pd/C was filtered off, and the filtrate was concentrated. The residue was purified by silica gel column chromatography to obtain the mixture of 5-(7-(2,6-difluoro-3,5-dimethoxyphenyl)-1,4,5,6,7,8-hexahydrocyclohepta [c] pyrazol-3-yl)-1H-pyrazol-4-amine, MS (ESI) m/z: 390.2 (M+1) and 5-(7-(2-fluoro-3,5-dimethoxyphenyl)-1,4,5,6,7,8-hexahydrocyclohepta[c]pyrazol-3-yl)-1H-pyrazol-4-amine (400 mg, 72%) as a solid. MS (ESI) m/z: 372.2 (M+1).

Step F: To a solution of 5-(7-(2,6-difluoro-3,5-dimethoxyphenyl)-1,4,5,6,7,8-hexahydrocyclohepta[c]pyrazol-3-yl)-1H-pyrazol-4-amine and 5-(7-(2-fluoro-3,5-dimethoxyphenyl)-1,4,5,6,7,8-hexahydrocyclohepta[c]pyrazol-3-yl)-1H-pyrazol-4-amine (300 mg, 0.77 mmol) and DIPEA (300 mg, 2.3 mmol) in DCM (20 mL) was dropwise added acryloyl chloride (68 mg, 0.76 mmol) at −40° C., then the mixture was stirred for 15 min. The mixture was concentrated and the residue was purified by SFC (Chromatography Column: Chiralpak-AD (Daicel Corporation); mobile phase: CO$_2$-EtOH (DEA)) to give N-(5-(7-(2,6-difluoro-3,5-dimethoxyphenyl)-1,4,5,6,7,8-hexahydrocyclohepta[c]pyrazol-3-yl)-1H-pyrazol-4-yl)acrylamide as single enantiomers (P1, 7.36 min, 13.5 mg); (P2, 10.0 min, 18.4 mg).

P1: $^1$H NMR (400 MHz, DMSO) δ 12.71 (s, 2H), 10.07 (s, 1H), 8.20 (s, 1H), 6.91 (t, J=8.2 Hz, 1H), 6.41 (d, J=11.1 Hz, 1H), 6.20 (d, J=17.0 Hz, 1H), 5.74 (d, J=10.0 Hz, 1H), 3.86 (s, 6H), 3.64 (d, J=29.8 Hz, 1H), 3.19 (dt, J=22.8, 11.6 Hz, 2H), 2.87 (d, J=14.7 Hz, 1H), 2.33-1.78 (m, 4H), 1.45 (d, J=12.3 Hz, 1H). MS (ESI) m/z: 444.1 [M+H$^+$].

P2: $^1$H NMR (400 MHz, DMSO) δ 12.71 (s, 2H), 10.07 (s, 1H), 8.20 (s, 1H), 6.91 (t, J=8.2 Hz, 1H), 6.41 (d, J=11.1 Hz, 1H), 6.20 (d, J=17.0 Hz, 1H), 5.74 (d, J=10.0 Hz, 1H), 3.86 (s, 6H), 3.64 (d, J=29.8 Hz, 1H), 3.19 (dt, J=22.8, 11.6 Hz, 2H), 2.87 (d, J=14.7 Hz, 1H), 2.33-1.78 (m, 4H), 1.45 (d, J=12.3 Hz, 1H). MS (ESI) m/z: 444.1 [M+H$^+$].

Further elution yielded single enantiomers of N-(5-(7-(2-fluoro-3,5-dimethoxyphenyl)-1,4,5,6,7,8-hexahydrocyclohepta[c]pyrazol-3-yl)-1H-pyrazol-4-yl)acrylamide (P3, 8.8 min, 4 mg); (P4, 12.7 min, 4.9 mg).

P3: $^1$H NMR (400 MHz, MeOD) δ 8.26 (s, 1H), 6.53 (d, J=6.4 Hz, 1H), 6.44 (t, J=13.3 Hz, 2H), 6.34 (d, J=16.8 Hz, 1H), 5.78 (d, J=9.7 Hz, 1H), 3.87 (d, J=10.0 Hz, 3H), 3.79 (s, 3H), 3.48 (t, J=45.0 Hz, 1H), 3.11 (d, J=9.6 Hz, 2H), 3.00 (t, J=10.2 Hz, 1H), 2.61 (s, 1H), 2.23-1.94 (m, 3H), 1.58 (d, J=12.2 Hz, 1H). MS (ESI) m/z: 426.1 [M+H$^+$].

P4: $^1$H NMR (400 MHz, MeOD) δ 8.26 (s, 1H), 6.53 (d, J=6.4 Hz, 1H), 6.44 (t, J=13.3 Hz, 2H), 6.34 (d, J=16.8 Hz, 1H), 5.78 (d, J=9.7 Hz, 1H), 3.87 (d, J=10.0 Hz, 3H), 3.79 (s, 3H), 3.48 (t, J=45.0 Hz, 1H), 3.11 (d, J=9.6 Hz, 2H), 3.00 (t, J=10.2 Hz, 1H), 2.61 (s, 1H), 2.23-1.94 (m, 3H), 1.58 (d, J=12.2 Hz, 1H). MS (ESI) m/z: 426.1 [M+H$^+$].

Example S12

Synthesis of N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide and N-(3-(7-(2-fluoro-3,5-dimethoxyphenyl)-1,4,5,6,7,8-hexahydrocyclohepta[c]pyrazol-3-yl)-1-methyl-1H-pyrazol-4-yl) Acrylamide

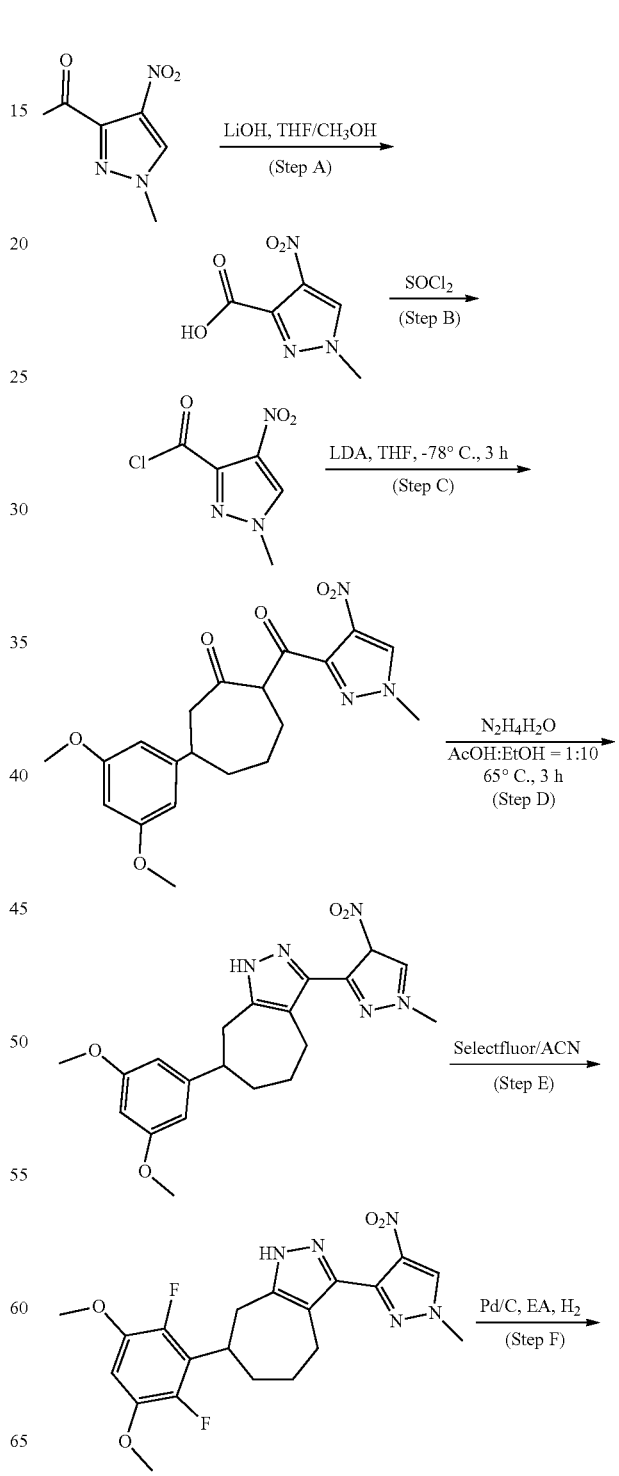

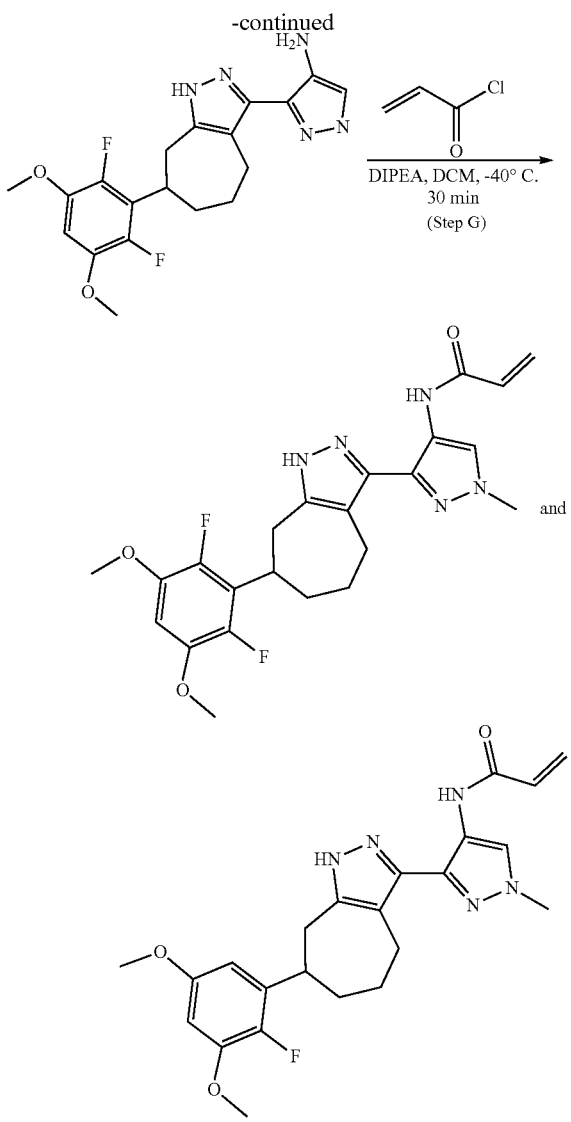

Step A: A mixture of methyl 1-methyl-4-nitro-1H-pyrazole-3-carboxylate (10 g, 0.05 mol) and LiOH (2.4 g, 0.1 mol) in THF (90 ml)/CH$_3$OH (10 ml) was stirred at rt for 1 h. The solvent was evaporated, and the residue was diluted with H$_2$O, adjusted to pH=3 with 2N aq. hydrochloric acid., extracted with ethyl acetate (3*20 ml), and the organic phase was evaporated to give 1-methyl-4-nitro-1H-pyrazole-3-carboxylic acid (8 g, 87%) which was used in the next step without further purification. MS (ESI) m/z: 172.0 (M+1)

Step B: In a round-bottomed flask was placed 1-methyl-4-nitro-1H-pyrazole-3-carboxylic acid (4 g, 0.02 mol), SOCl$_2$ (80 mL) and 2 drops of DMF. The solution was heated to reflux at 76° C. for 1 h. The solvent was evaporated to get 1-methyl-4-nitro-1H-pyrazole-3-carbonyl chloride as a brown slurry (10.5 g, 95%), which was used in the next step without further purification.

Step C: To a solution of 3-(3,5-dimethoxyphenyl) cycloheptan-1-one (4.0 g, 16 mmol) in THF (200 mL) was added LDA (8 mL, 16 mmol, 2M) at −78° C., then the mixture was stirred at −40° C. for 1 h. Subsequently a solution of 1-methyl-4-nitro-1H-pyrazole-3-carbonyl chloride (3 g, 15 mmol) in THF was dropwise added to the above solution at −78° C., then warmed to rt. When LCMS suggested the reaction was completed it was quenched by addition of saturated aq. NH$_4$Cl solution. Water was added (300 mL), the layers were separated, and the aqueous layer was further extracted with ethyl acetate (3*50 mL). The combined organic layers were washed with H$_2$O (100 mL), dried over Na$_2$SO$_4$ filtered and the filtrate was concentrated. The crude 6-(3,5-dimethoxyphenyl)-2-(1-methyl-4-nitro-1H-pyrazole-3-carbonyl) cycloheptan-1-one (4.0 g, crude) was used in the next step without further purification. MS (ESI) m/z: 402.1 [M+H$^+$].

Step D: 6-(3,5-Dimethoxyphenyl)-2-(1-methyl-4-nitro-1H-pyrazole-3-carbonyl) cycloheptan-1-one (4.0 g, 9 mmol) and hydrazine hydrate (0.9 g, 1.8 mmol) were combined in a mixture of AcOH and EtOH (5 mL, AcOH, 45 mL EtOH). The mixture was stirred at 50° C. for 0.5 h. The solvent was evaporated, the residue was diluted with EtOAc and washed with H$_2$O. The organic layer was dried over anhydrous Na$_2$SO$_4$ filtered and the filtrate was concentrated. The crude product was purified by chromatography on silica gel eluting with PE:EtOAc (gradient elution 5:1 to 1:1) to give 7-(3,5-Dimethoxyphenyl)-3-(1-methyl-4-nitro-1H-pyrazol-3-yl)-1,4,5,6,7,8-hexahydrocyclohepta [c]pyrazole (2 g, 55%) as a yellow solid. MS (ESI) m/z: 397.9 [M+H$^+$].

Step E: A solution of 7-(3,5-dimethoxyphenyl)-3-(1-methyl-4-nitro-1H-pyrazol-3-yl)-1,4,5,6,7,8-hexahydrocyclohepta[c]pyrazole (2 g, 5 mmol) in CH$_3$CN (400 mL) was cooled to 0° C. using an ice bath. 1-Chloromethyl-4-fluoro-1,4-diazoniabicyclo[2.2.2]octane bis(tetrafluoroborate) ("Selectfluor", 2.5 g, 10 mmol) was added in several portions. The resulting solution was stirred at rt for 2 h. Then the reaction mixture was washed with aq. NaHCO$_3$, dried over sodium sulfate, filtered and the filtrate was evaporated. The residue was purified by silica gel chromatography to give a mixture of 7-(2,6-difluoro-3,5-dimethoxyphenyl)-3-(1-methyl-4-nitro-1H-pyrazol-3-yl)-1,4,5,6,7,8-hexahydrocyclohepta[c]pyrazole, MS (ESI) m/z: 434.1 (M+1) and 7-(2-fluoro-3,5-dimethoxyphenyl)-3-(1-methyl-4-nitro-1H-pyrazol-3-yl)-1,4,5,6,7,8-hexahydrocyclohepta[c]pyrazole, MS (ESI) m/z: 416.1 (M+1) as a white solid (900 mg, 30%).

Step F: A mixture of 7-(2,6-difluoro-3,5-dimethoxyphenyl)-3-(1-methyl-4-nitro-1H-pyrazol-3-yl)-1,4,5,6,7,8-hexahydrocyclohepta[c]pyrazole and 7-(2-fluoro-3,5-dimethoxyphenyl)-3-(1-methyl-4-nitro-1H-pyrazol-3-yl)-1,4,5,6,7,8-hexahydrocyclohepta[c]pyrazole (900 mg, 2 mmol), and Pd/C (900 mg) in ethyl acetate (40 mL) was stirred under a H$_2$ atmosphere for 8 h at rt. The Pd/C was filtered off and the filtrate was concentrated. The residue was purified by silica gel chromatography to give 3-(7-(2,6-difluoro-3,5-dimethoxyphenyl)-1,4,5,6,7,8-hexahydrocyclohepta[c]pyrazol-3-yl)-1-methyl-1H-pyrazol-4-amine, MS (ESI) m/z: 403.9 (M+1) and 3-(7-(2-fluoro-3,5-dimethoxyphenyl)-1,4,5,6,7,8-hexahydrocyclohepta[c]pyrazol-3-yl)-1-methyl-1H-pyrazol-4-amine, MS (ESI) m/z: 385.9 (M+1) as a solid (500 mg, 65%).

Step G: To a mixture of 3-(7-(2,6-difluoro-3,5-dimethoxyphenyl)-1,4,5,6,7,8-hexahydrocyclohepta[c]pyrazol-3-yl)-1-methyl-1H-pyrazol-4-amine and 3-(7-(2-fluoro-3,5-dimethoxyphenyl)-1,4,5,6,7,8-hexahydrocyclohepta[c]pyrazol-3-yl)-1-methyl-1H-pyrazol-4-amine (200 mg, 0.49 mmol) and DIPEA (190 mg, 1.47 mmol) in DCM (20 mL) was added acryloyl chloride (40.0 mg, 0.44 mmol) at −40° C. and the mixture was stirred for 15 min. The solvent was removed and the residue was purified by reversed-phase HPLC followed by additional purification by SFC (Chromatography Column: Chiralpak-AD (Daicel Corporation); mobile phase: CO$_2$-ETOH(DEA)) to give single enantiomers of N-(3-(7-(2-fluoro-3,5-dimethoxyphenyl)-1,4,5,6,7,8- hexahydrocyclohepta[c]pyrazol-3-yl)-1-methyl-1H-pyrazol-4-yl) acrylamide (P3, 6.6 min, 3.5 mg); (P4, 8.6 min, 4.8 mg).

P3: ¹H NMR (400 MHz, DMSO) δ 12.70 (s, 1H), 10.10 (s, 1H), 8.22 (s, 1H), 6.59 (d, J=5.8 Hz, 1H), 6.50 (s, 1H), 6.37 (d, J=10.1 Hz, 1H), 6.20 (d, J=16.9 Hz, 1H), 5.75 (d, J=9.6 Hz, 1H), 3.87 (s, 3H), 3.82 (s, 3H), 3.75 (s, 3H), 3.59 (d, J=15.3 Hz, 1H), 3.07 (d, J=13.4 Hz, 1H), 2.99 (d, J=10.0 Hz, 1H), 2.86 (d, J=14.2 Hz, 1H), 2.19-1.82 (m, 4H), 1.44 (d, J=12.0 Hz, 1H). MS (ESI) m/z: 439.9 (M+1).

P4: ¹H NMR (400 MHz, DMSO) δ 12.71 (s, 1H), 10.10 (s, 1H), 8.22 (s, 1H), 6.59 (d, J=5.8 Hz, 1H), 6.50 (s, 1H), 6.37 (d, J=10.1 Hz, 1H), 6.20 (d, J=16.9 Hz, 1H), 5.75 (d, J=9.6 Hz, 1H), 3.87 (s, 3H), 3.82 (s, 3H), 3.75 (s, 3H), 3.59 (d, J=15.3 Hz, 1H), 3.07 (d, J=13.4 Hz, 1H), 2.99 (d, J=10.0 Hz, 1H), 2.86 (d, J=14.2 Hz, 1H), 2.19-1.82 (m, 4H), 1.44 (d, J=12.0 Hz, 1H). MS (ESI) m/z: 439.9 (M+1).

Further elution yielded N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide as single enantiomers (P1, 9.43 min, 4.6 mg); (P2, 12.95 min, 4.7 mg).

P1: ¹H NMR (400 MHz, DMSO) δ 12.70 (s, 1H), 10.08 (s, 1H), 8.22 (s, 1H), 6.91 (s, 1H), 6.50-6.29 (m, 1H), 6.20 (d, J=17.1 Hz, 1H), 5.75 (d, J=9.2 Hz, 1H), 3.86 (s, 6H), 3.59 (d, J=14.8 Hz, 1H), 3.33 (s, 3H), 3.23 (d, J=14.2 Hz, 1H), 3.11 (s, 1H), 2.89 (s, 1H), 2.52 (s, 1H), 2.16 (d, J=11.8 Hz, 1H), 2.04 (s, 2H), 1.44 (d, J=12.1 Hz, 1H). MS (ESI) m/z: 457.8 [M+H⁺].

P2: ¹H NMR (400 MHz, DMSO) δ 12.70 (s, 1H), 10.08 (s, 1H), 8.22 (s, 1H), 6.91 (s, 1H), 6.47-6.34 (m, 1H), 6.20 (d, J=16.8 Hz, 1H), 5.75 (d, J=8.8 Hz, 1H), 3.86 (s, 9H), 3.74 (s, 1H), 3.58 (s, 1H), 3.23 (d, J=13.4 Hz, 1H), 3.11 (t, J=10.9 Hz, 1H), 2.87 (d, J=15.3 Hz, 1H), 2.16 (d, J=10.9 Hz, 1H), 2.12-1.84 (m, 3H), 1.44 (d, J=12.1 Hz, 1H). MS (ESI) m/z: 457.8 [M+H⁺].

Example S13

Synthesis of N-((3R,4R)-4-((S)-6-(2,6-difluoro-3,5-dimethoxyphenyl)-4,5,6,7-tetrahydro-1H-indazol-3-yl) tetrahydrofuran-3-yl)acrylamide, N-(((3S,4S)-4-((S)-6-(2,6-difluoro-3,5-dimethoxyphenyl)-4,5,6,7-tetrahydro-1H-indazol-3-yl) tetrahydrofuran-3-yl) acrylamide, N-((3R,4R)-4-((S)-6-(2-fluoro-3,5-dimethoxyphenyl)-4,5,6,7-tetrahydro-1H-indazol-3-yl) tetrahydrofuran-3-yl)acrylamide, and N-((3S,4S)-4-((S)-6-(2-fluoro-3,5-dimethoxyphenyl)-4,5,6,7-tetrahydro-1H-indazol-3-yl) tetrahydrofuran-3-yl) acrylamide

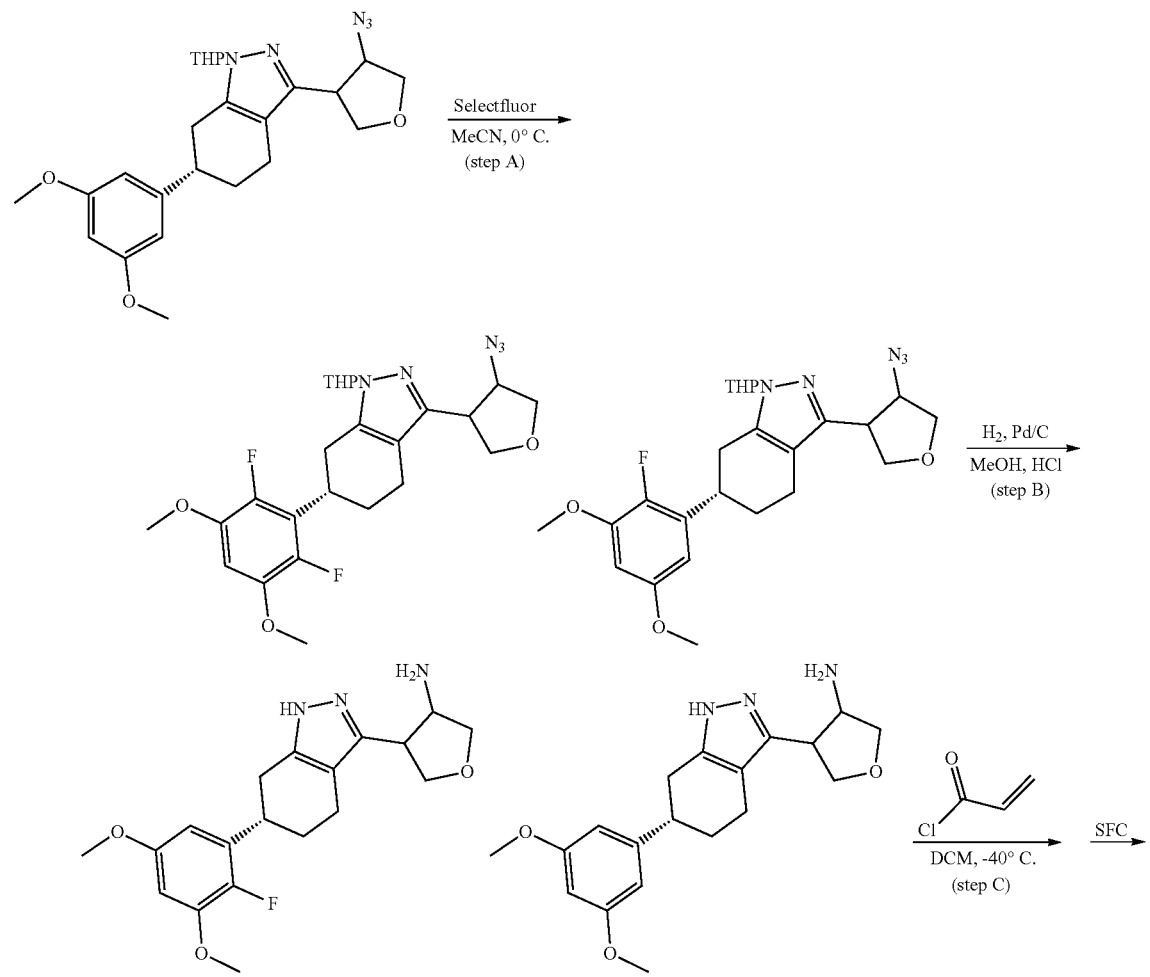

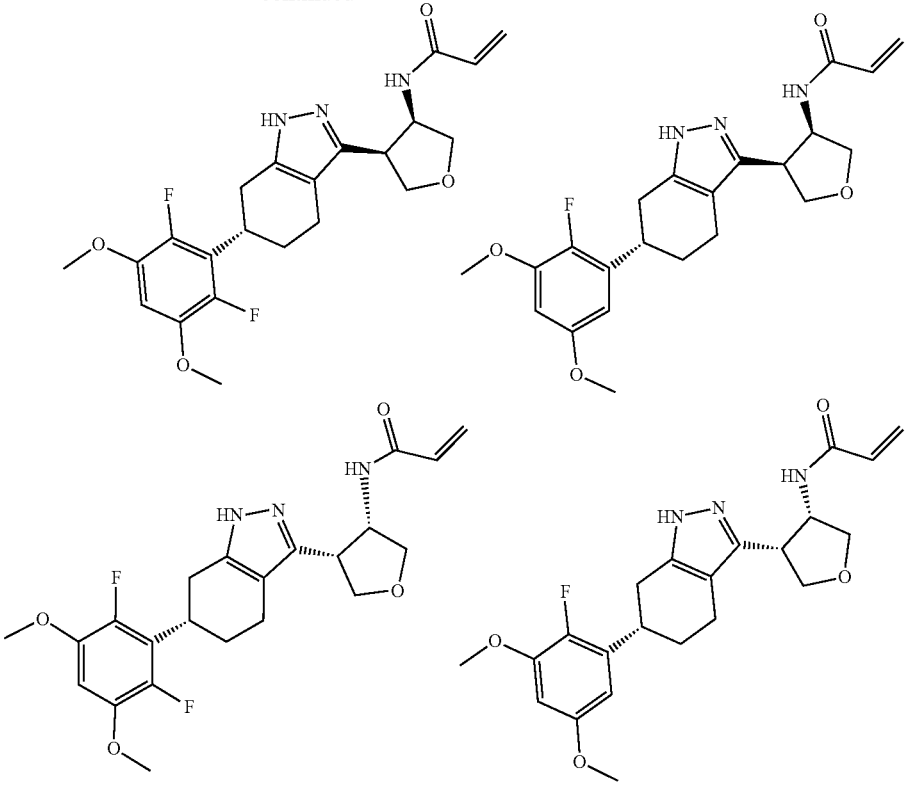

Step A: (6S)-3-(4-azidotetrahydrofuran-3-yl)-6-(3,5-dimethoxyphenyl)-1-(tetrahydro-2H-pyran-2-yl)-4,5,6,7-tetrahydro-1H-indazole (1.5 g, 3.3 mmol) was dissolved in MeCN (15 mL) and cooled to 0° C. 1-Chloromethyl-4-fluoro-1,4-diazoniabicyclo[2.2.2]octane bis(tetrafluoroborate) ("Selectfluor", 2.3 g, 6.6 mmol) was dissolved in MeCN (10 mL) and added into the first solution dropwise. The mixture was stirred at r.t overnight and then concentrated under reduced pressure. The residue was dissolved in ethyl acetate (35 mL) and water (45 mL) was added. The mixture was extracted with ethyl acetate (25 mL×2) and the combined organics were dried over anhydrous $Na_2SO_4$, filtered and the filtrate was concentrated under reduced pressure. The crude product was purified by silica gel column chromatography (PE:EA, gradient elution 10:1-4:1) to give a mixture of (6S)-3-(4-azidotetrahydrofuran-3-yl)-6-(2,6-difluoro-3,5-dimethoxyphenyl)-1-(tetrahydro-2H-pyran-2-yl)-4,5,6,7-tetrahydro-1H-indazole and (6S)-3-(4-azidotetrahydrofuran-3-yl)-6-(2-fluoro-3,5-dimethoxyphenyl)-1-(tetrahydro-2H-pyran-2-yl)-4,5,6,7-tetrahydro-1H-indazole as a light yellow solid (660 mg, mixture). MS (ESI) m/z: 489.9, 471.8 [M+1].

Step B: The mixture of (6S)-3-(4-azidotetrahydrofuran-3-yl)-6-(2,6-difluoro-3,5-dimethoxyphenyl)-1-(tetrahydro-2H-pyran-2-yl)-4,5,6,7-tetrahydro-1H-indazole and (6S)-3-(4-azidotetrahydrofuran-3-yl)-6-(2-fluoro-3,5-dimethoxyphenyl)-1-(tetrahydro-2H-pyran-2-yl)-4,5,6,7-tetrahydro-1H-indazole (660 mg, crude) was dissolved in MeOH (15 ml). Pd/C (150 mg) and conc. aq. HCl (0.1 ml) were added. The mixture was stirred under $H_2$ at rt for 12 h and then filtered through Celite® (J. T. Baker, Phillipsberg, NJ, diatomaceous earth). The filtrate was concentrated under vacuum to give the crude product, which was purified by preparative TLC (DCM:MeOH=20:1) to give the mixture of 4-((S)-6-(2,6-difluoro-3,5-dimethoxyphenyl)-4,5,6,7-tetrahydro-1H-indazol-3-yl)tetrahydrofuran-3-amine and 4-((S)-6-(2-fluoro-3,5-dimethoxyphenyl)-4,5,6,7-tetrahydro-1H-indazol-3-yl)tetrahydrofuran-3-amine (70 mg, crude) as a yellow solid. MS (ESI) m/z: 362.2, 380.2 [M+1].

Step C: To a solution of 4-((S)-6-(2,6-difluoro-3,5-dimethoxyphenyl)-4,5,6,7-tetrahydro-1H-indazol-3-yl)tetrahydrofuran-3-amine and 4-((S)-6-(2-fluoro-3,5-dimethoxyphenyl)-4,5,6,7-tetrahydro-1H-indazol-3-yl) tetrahydrofuran-3-amine (70 mg, crude) and TEA (46 mg, 0.46 mmol) in DCM (10 mL) was added acryloyl chloride (11 mg, 0.12 mmol) at −40° C., then stirred for 15 min. The mixture was concentrated, the residue was purified by reversed-phase HPLC ($H_2O$ (0.05% TFA)-ACN (0.05% TFA) ACN from 10% to 100% over hold 1 min) and SFC (Chromatography Column: Chiralpak-AD (Daicel Corporation); mobile phase: $CO_2$-ETOH(DEA)) to give N-((3R,4R)-4-((S)-6-(2,6-difluoro-3,5-dimethoxyphenyl)-4,5,6,7-tetrahydro-1H-indazol-3-yl) tetrahydrofuran-3-yl)acrylamide (P1, 6.4 mg), N-((3S,4S)-4-((S)-6-(2,6-difluoro-3,5-dimethoxyphenyl)-4,5,6,7-tetrahydro-1H-indazol-3-yl) tetrahydrofuran-3-yl)acrylamide (P2, 11.8 mg), N-((3R,4R)-4-((S)-6-(2-fluoro-3,5-dimethoxyphenyl)-4,5,6,7-tetrahydro-1H-indazol-3-yl) tetrahydrofuran-3-yl)acrylamide (P3, 1.8 mg), and N-((3S,4S)-4-((S)-6-(2-fluoro-3,5-dimethoxyphenyl)-4,5,6,7-tetrahydro-1H-indazol-3-yl) tetrahydrofuran-3-yl)acrylamide (P4, 5.3 mg) as a white solids.

P1: $^1$H NMR (400 MHz, MeOD) δ 6.79-6.74 (m, 1H), 6.17-6.10 (m, 2H), 5.60-5.57 (m, 1H), 4.84-4.73 (m, 1H), 4.23-4.11 (m, 3H), 3.86 (s, 6H), 3.81-3.68 (m, 2H), 3.41-3.34 (m, 1H), 3.00-2.85 (m, 1H), 2.81-2.60 (m, 2H), 2.60-2.47 (m, 1H), 2.27-2.06 (m, 1H), 1.99-1.90 (m, 1H). MS (ESI) m/z: 434.1 [M+1].

P2: $^1$H NMR (400 MHz, MeOD) δ 6.79-6.74 (m, 1H), 6.17-6.05 (m, 2H), 5.59 (dd, J=7.9, 4.2 Hz, 1H), 4.84-4.77 (m, 1H), 4.27-4.10 (m, 3H), 3.89-3.69 (m, 8H), 3.41-3.31 (m, 1H), 2.98-2.87 (m, 1H), 2.81-2.62 (m, 2H), 2.58-2.43 (m, 1H), 2.23-2.09 (m, 1H), 2.00-2.85 (m, 1H). MS (ESI) m/z: 434.2 [M+1].

P3: $^1$H NMR (400 MHz, MeOD) δ 6.53-6.50 (m, 1H), 6.36-6.35 (m, 1H), 6.16-6.10 (m, 2H), 5.60-5.57 (m, 1H), 4.86-4.74 (m, 1H), 4.27-4.10 (m, 3H), 3.85-3.68 (m, 8H), 3.30-3.14 (m, 1H), 2.87-2.81 (m, 1H), 2.76-2.48 (m, 3H), 2.06-1.83 (m, 2H). MS (ESI) m/z: 415.9 [M+1].

P4: $^1$H NMR (400 MHz, MeOD) δ 1H NMR (400 MHz, MeOD) δ 6.53-6.50 (m, 1H), 6.39-6.31 (m, 1H), 6.18-6.06 (m, 2H), 5.58 (dd, J=7.9, 4.1 Hz, 1H), 4.85-4.76 (m, 1H), 4.26-4.09 (m, 3H), 3.92-3.66 (m, 8H), 3.86-3.70 (m, 1H), 2.88-2.83 (m, 1H), 2.71-2.64 (m, 2H), 2.58-2.46 (m, 1H), 2.03-1.83 (m, 2H). MS (ESI) m/z: 416.1 [M+1].

Example S14

Synthesis of (R)—N-(5-(6-(2,6-difluoro-3,5-dimethoxyphenyl)-4,5,6,7-tetrahydro-1H-indazol-3-yl)-1-ethyl-1H-pyrazol-4-yl) acrylamide, (S)—N-(5-(6-(2,6-difluoro-3,5-dimethoxyphenyl)-4,5,6,7-tetrahydro-1H-indazol-3-yl)-1-ethyl-1H-pyrazol-4-yl) acrylamide, and (R)—N-(1-ethyl-5-(6-(2-fluoro-3,5-dimethoxyphenyl)-4,5,6,7-tetrahydro-1H-indazol-3-yl)-1H-pyrazol-4-yl) Acrylamide

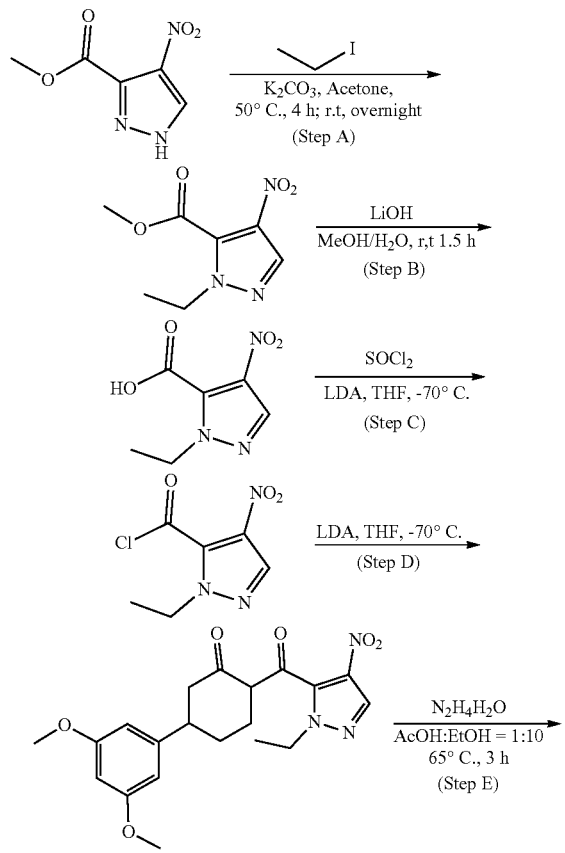

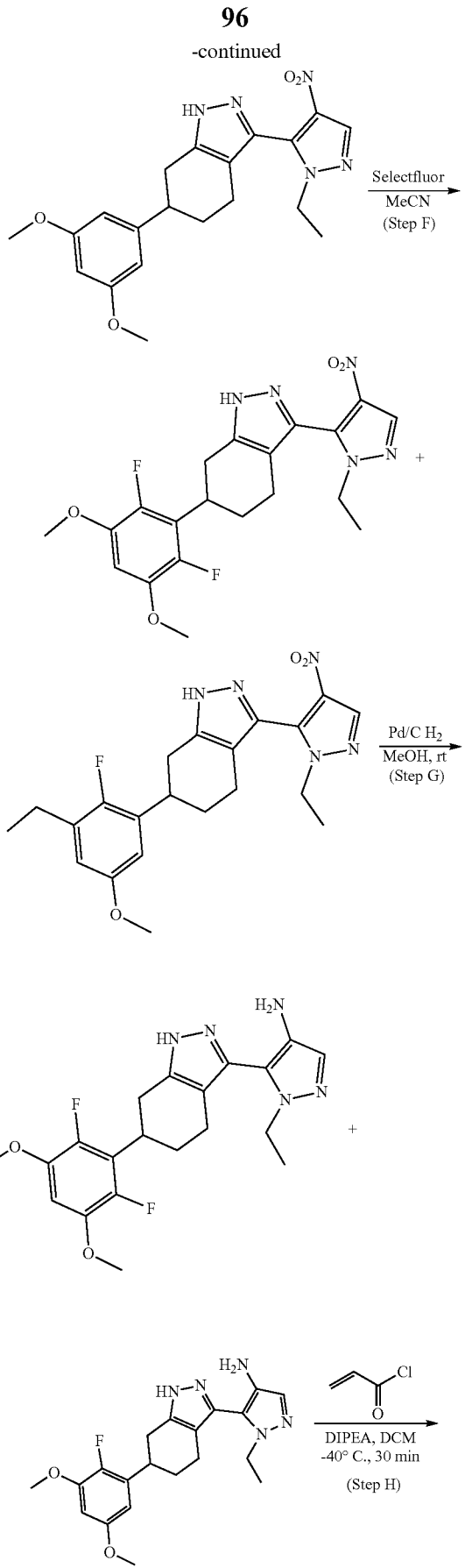

-continued

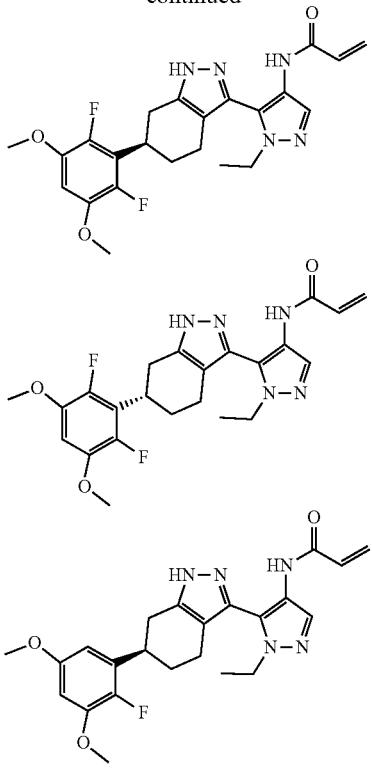

Step A: A mixture of methyl 4-nitro-1H-pyrazole-3-carboxylate (15 g, 87.7 mmol), iodoethane (16406 mg, 105.19 mmol) and potassium carbonate (24.6 g, 175.32 mmol) in acetone (150 ml) was stirred at 50° C. for 4 h. After stirring at rt overnight the mixture was filtered, and the filtrate was concentrated under reduced pressure. The residue was purified by silica gel column chromatography (PE:EtOAc=20: 1-5:1) to give methyl 2-ethyl-4-nitropyrazole-3-carboxylate (5900 mg, 33.8%) as a light-yellow oil. MS (ESI) m/z: 200.1 [M+H]$^+$.

$^1$H NMR (400 MHz, CDCl$_3$) δ 8.03 (s, 1H), 4.32 (d, J=7.3 Hz, 2H), 4.03 (s, 3H), 1.50 (t, J=7.3 Hz, 3H).

Step B: To a stirred solution of methyl 2-ethyl-4-nitropyrazole-3-carboxylate (5900 mg, 29.62 mmol) in MeOH (136 ml), a solution of lithium hydroxide (3546.7 mg, 148.1 mmol) in 34 ml of water was added. The reaction mixture was stirred at rt for 1.5 h. The reaction mixture was concentrated under reduced pressure, then adjusted to pH ~4-5 with 2N aq. hydrochloric acid. The mixture was stirred at rt for 15 min, then concentrated under vacuum to give a white solid. EtOAc (100 ml) was added, the suspension was sonicated for 15 min, filtered and the filter cake was washed with EtOAc. The filtrate was concentrated under vacuum to give 2-ethyl-4-nitropyrazole-3-carboxylic acid (5200 mg, 94.83%) as a white solid. MS (ESI) m/z: 186.1 [M+H]$^+$. $^1$H NMR (400 MHz, DMSO) δ 7.97 (s, 1H), 4.06 (d, J=7.2 Hz, 2H), 1.31 (t, J=7.2 Hz, 3H).

Step C: 2-ethyl-4-nitropyrazole-3-carboxylic acid (5200 mg, 28.09 mmol) was dissolved in SOCl$_2$ (30 mL), followed by DMF (1 mL). The resulting mixture was stirred under reflux for 3 h. The mixture was concentrated under vacuum to give 2-ethyl-4-nitropyrazole-3-carbonyl chloride (5800 mg) as a white oil. MS (ESI) m/z: 200.2 (methyl ester) [M+H]$^+$.

Step D: LDA (24 mL, 2 M in THF) was added dropwise into a solution of 3-(3,5-dimethoxyphenyl) cyclohexan-1-one (5600 mg, 23.6 mmol) in THF (30 mL) at −70° C. under N$_2$ protection. The mixture was stirred at −70° C. for 1.5 h, then warmed to −40° C. 2-Ethyl-4-nitropyrazole-3-carbonyl chloride (5400 mg, 26.3 mmol) in THF (30 mL) was added dropwise at −40° C., then the resulting mixture was allowed to warm to rt. The reaction mixture was stirred at rt overnight and then quenched with saturated aq. NH$_4$Cl solution, washed with brine, dried over Na$_2$SO$_4$, filtered and the filtrate was concentrated under vacuum to give crude 5-(3, 5-dimethoxyphenyl)-2-(1-ethyl-4-nitro-1H-pyrazole-5-carbonyl) cyclohexan-1-one (8300 mg) as a brown oil. MS (ESI) m/z: 402.2 [M+H]$^+$.

Step E: To a solution of 5-(3,5-dimethoxyphenyl)-2-[(2-ethyl-4-nitropyrazol-3-yl)carbonyl]cyclohexan-1-one (8300 mg, crude) in EtOH:AcOH=44:4.4 (mL) was added hydrazine hydrate (10 mL, 80%), the mixture was stirred at 65° C. for 3 h and then the mixture was cooled to r.t. and concentrated under reduced pressure. The residue was purified by chromatography on silica gel, eluting with PE:EtOAc=10: 1-2:1, to give 6-(3,5-dimethoxyphenyl)-3-(2-ethyl-4-nitropyrazol-3-yl)-4,5,6,7-tetrahydro-1H-indazole (3000 mg) as a yellow solid.

$^1$H NMR (400 MHz, CDCl$_3$) δ 8.20 (s, 1H), 6.40 (dd, J=17.6, 2.1 Hz, 3H), 4.14 (dd, J=14.2, 7.1 Hz, 2H), 3.80 (d, J=4.2 Hz, 6H), 3.07 (d, J=14.6 Hz, 2H), 2.88-2.81 (m, 1H), 2.48 (t, J=14.0 Hz, 2H), 2.12 (d, J=13.2 Hz, 1H), 1.91 (s, 1H), 1.40 (t, J=7.1 Hz, 3H). MS (ESI) m/z: 398.2 [M+H]$^+$.

Step F: 6-(3,5-dimethoxyphenyl)-3-(2-ethyl-4-nitropyrazol-3-yl)-4,5,6,7-tetrahydro-1H-indazole (3000 mg, 7.55 mmol) was dissolved in MeCN (30 mL) and the solution was cooled to 0° C. 1-Chloromethyl-4-fluoro-1,4-diazoniabicyclo[2.2.2]octane bis(tetrafluoroborate) ("Selectfluor", 5350 mg, 15.1 mmol) was dissolved in MeCN (150 mL) and added to the first solution dropwise. The mixture was stirred at r.t overnight and then concentrated under reduced pressure. The residue was dissolved in ethyl acetate (35 mL). Water (45 mL) was added into the solution. The mixture was extracted with ethyl acetate (25 mL×2), the combined organics were dried over anhydrous Na$_2$SO$_4$, filtered and the filtrate was concentrated under reduced pressure. The crude product was purified by silica gel column chromatography (PE:EtOAc=10:1-2:1) to give the mixture of 6-(2,6-difluoro-3,5-dimethoxyphenyl)-3-(1-ethyl-4-nitro-1H-pyrazol-5-yl)-4,5,6,7-tetrahydro-1H-indazole, MS (ESI) m/z: 434.2 [M+H]$^+$, and 3-(1-ethyl-4-nitro-1H-pyrazol-5-yl)-6-(2-fluoro-3,5-dimethoxyphenyl)-4,5,6,7-tetrahydro-1H-indazole as a light yellow solid (840 mg, mixture). MS (ESI) m/z: 416.2 [M+H]$^+$.

Step G: The mixture of 6-(2,6-difluoro-3,5-dimethoxyphenyl)-3-(1-ethyl-4-nitro-1H-pyrazol-5-yl)-4,5,6,7-tetrahydro-1H-indazole and 3-(1-ethyl-4-nitro-1H-pyrazol-5-yl)-6-(2-fluoro-3,5-dimethoxyphenyl)-4,5,6,7-tetrahydro-1H-indazole (840 mg, crude) was dissolved in MeOH (15 ml). Pd/C (90 mg) was added. The mixture was stirred under an H$_2$ atmosphere at rt for 24 h and then filtered through Celite® (J. T. Baker, Phillipsberg, NJ, diatomaceous earth). The filtrate was concentrated under reduced pressure to give the crude product, which was purified by preparative TLC (DCM:MeOH=15:1) to give the mixture of 1-ethyl-5-(6-(2-fluoro-3,5-dimethoxyphenyl)-4,5,6,7-tetrahydro-1H-indazol-3-yl)-1H-pyrazol-4-amine and 5-(6-(2,6-difluoro-3,5-dimethoxyphenyl)-4,5,6,7-tetrahydro-1H-indazol-3-yl)-1-ethyl-1H-pyrazol-4-amine (400 mg, crude) as a brown solid. MS (ESI) m/z: 404.2, 386.3 [M+H]$^+$.

Step H: To a solution of 5-[6-(2,6-difluoro-3,5-dimethoxyphenyl)-4,5,6,7-tetrahydro-1H-indazol-3-yl]-1-ethylpyrazol-4-amine (400 mg, 0.99 mmol) in DCM (10 mL), DIPEA (383.85 mg, 2.97 mmol) was added. The reaction mixture was cooled to −40° C., then a solution of acryloyl chloride (89.6 mg, 0.99 mmol) in DCM (2 mL) was added dropwise. The reaction mixture was stirred at −40° C. for 30 min. Water (15 mL) and DCM (30 mL) was added into the reaction mixture. The organics were washed with brine (15 mL) and concentrated under reduced pressure. The obtained residue was purified by preparative TLC (DCM:MeOH=20:1) to give racemic product (310 mg, crude) as a brown solid, which was separated by SFC to give (R)—N-(5-(6-(2,6-difluoro-3,5-dimethoxyphenyl)-4,5,6,7-tetrahydro-1H-indazol-3-yl)-1-ethyl-1H-pyrazol-4-yl) acrylamide (P1, 64.5 mg, white solid) and (S)—N-(5-(6-(2,6-difluoro-3,5-dimethoxyphenyl)-4,5,6,7-tetrahydro-1H-indazol-3-yl)-1-ethyl-1H-pyrazol-4-yl) acrylamide (P2, 72.4 mg, white solid), as well as (R)—N-(1-ethyl-5-(6-(2-fluoro-3,5-dimethoxyphenyl)-4,5,6,7-tetrahydro-1H-indazol-3-yl)-1H-pyrazol-4-yl) acrylamide (P3, 29.6 mg, white solid).

P1: $^1$H NMR (400 MHz, CDCl$_3$) δ 8.06 (s, 2H), 6.57 (t, J=8.0 Hz, 1H), 6.41 (d, J=16.5 Hz, 1H), 6.33-6.24 (m, 1H), 5.72 (d, J=9.8 Hz, 1H), 4.05 (d, J=6.6 Hz, 2H), 3.89 (s, 6H), 3.52 (s, 1H), 3.17-3.08 (m, 1H), 2.97 (d, J=11.9 Hz, 1H), 2.57 (d, J=4.6 Hz, 2H), 2.25 (s, 1H), 2.09-2.05 (m, 1H), 1.37 (t, J=7.0 Hz, 3H). MS (ESI) m/z: 458.2 [M+H$^+$].

P2: $^1$H NMR (400 MHz, CDCl$_3$) δ 8.09 (s, 1H), 7.93 (s, 1H), 6.56 (d, J=8.0 Hz, 1H), 6.41 (d, J=16.9 Hz, 1H), 6.26 (d, J=6.6 Hz, 1H), 5.72 (d, J=10.0 Hz, 1H), 4.08 (d, J=4.7 Hz, 2H), 3.89 (s, 6H), 3.53 (s, 1H), 3.12 (d, J=12.1 Hz, 1H), 3.01-2.95 (m, 1H), 2.58 (d, J=4.8 Hz, 2H), 2.25 (s, 1H), 2.05 (d, J=12.7 Hz, 1H), 1.39 (t, J=7.2 Hz, 3H). MS (ESI) m/z: 458.2 [M+H$^+$].

P3: $^1$H NMR (400 MHz, CDCl$_3$) δ 8.11 (s, 1H), 7.89 (s, 1H), 6.47-6.37 (m, 2H), 6.32-6.21 (m, 2H), 5.72 (d, J=10.1 Hz, 1H), 4.07 (d, J=7.1 Hz, 2H), 3.89 (s, 3H), 3.77 (s, 3H), 3.42 (s, 1H), 3.08 (s, 1H), 2.81 (d, J=16.1 Hz, 1H), 2.58 (s, 2H), 2.10 (s, 1H), 1.95 (s, 1H), 1.38 (t, J=7.2 Hz, 3H). MS (ESI) m/z: 440.2 [M+H]$^+$.

Example S15

Synthesis of N-(3-(6-(2,6-difluoro-3,5-dimethoxyphenyl)-4,5,6,7-tetrahydro-1H-indazol-3-yl)-1H-pyrazol-4-yl)acrylamide and N-(3-(6-(2-fluoro-3,5-dimethoxyphenyl)-4,5,6,7-tetrahydro-1H-indazol-3-yl)-1H-pyrazol-4-yl)acrylamide

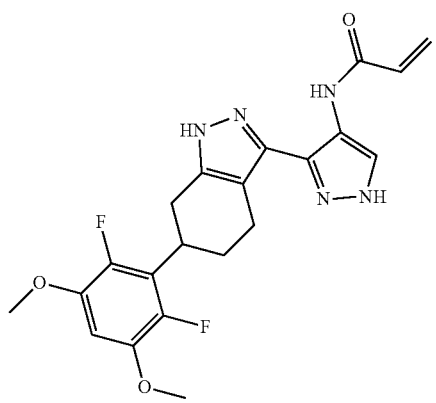

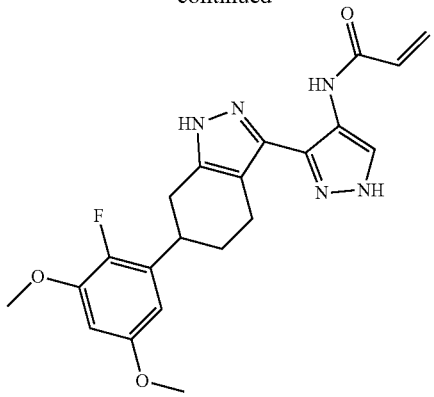

N-(3-(6-(2,6-difluoro-3,5-dimethoxyphenyl)-4,5,6,7-tetrahydro-1H-indazol-3-yl)-1H-pyrazol-4-yl)acrylamide and N-(3-(6-(2-fluoro-3,5-dimethoxyphenyl)-4,5,6,7-tetrahydro-1H-indazol-3-yl)-1H-pyrazol-4-yl)acrylamide were prepared by procedures similar to the one described in Example S14, omitting step A and using methyl 4-nitro-1H-pyrazole-3-carboxylate in Step B.

Enantiomer 1 of N-(3-(6-(2,6-difluoro-3,5-dimethoxyphenyl)-4,5,6,7-tetrahydro-1H-indazol-3-yl)-1H-pyrazol-4-yl)acrylamide (P1): $^1$H NMR (400 MHz, MeOD): δ 8.26 (s, 1H), 6.81 (t, J=7.8 Hz, 1H), 6.43 (dt, J=39.9, 13.6 Hz, 2H), 5.81 (d, J=10.0 Hz, 1H), 3.89 (s, 6H), 3.50 (s, 1H), 3.16-3.02 (m, 2H), 2.91 (d, J=11.9 Hz, 1H), 2.78 (s, 1H), 2.29 (d, J=12.3 Hz, 1H), 2.05 (d, J=11.4 Hz, 1H). MS (ESI) m/z: 430 [M+1].

Enantiomer 2 of N-(3-(6-(2,6-difluoro-3,5-dimethoxyphenyl)-4,5,6,7-tetrahydro-1H-indazol-3-yl)-1H-pyrazol-4-yl)acrylamide (P2): $^1$H NMR (400 MHz, MeOD): δ 8.26 (s, 1H), 6.81 (t, J=7.8 Hz, 1H), 6.47 (dd, J=16.7, 10.1 Hz, 1H), 6.35 (d, J=17.2 Hz, 1H), 5.81 (d, J=10.1 Hz, 1H), 3.89 (s, 6H), 3.50 (s, 1H), 3.17-3.02 (m, 2H), 2.92 (d, J=13.7 Hz, 1H), 2.78 (s, 1H), 2.29 (d, J=10.8 Hz, 1H), 2.05 (d, J=10.3 Hz, 1H). MS (ESI) m/z: 430 [M+1].

Enantiomer 1 of N-(3-(6-(2-fluoro-3,5-dimethoxyphenyl)-4,5,6,7-tetrahydro-1H-indazol-3-yl)-1H-pyrazol-4-yl)acrylamide (P3): $^1$H NMR (400 MHz, MeOD): δ 8.26 (s, 1H), 6.56 (dd, J=6.9, 2.8 Hz, 1H), 6.50-6.42 (m, 2H), 6.35 (dd, J=17.0, 1.6 Hz, 1H), 5.81 (d, J=10.1 Hz, 1H), 3.87 (s, 3H), 3.78 (s, 3H), 3.36 (s, 1H), 3.00 (dd, J=15.8, 4.9 Hz, 2H), 2.83 (dd, J=15.5, 10.7 Hz, 2H), 2.04 (dd, J=14.0, 8.9 Hz, 2H). MS (ESI) m/z: 412 [M+1].

Enantiomer 2 of N-(3-(6-(2-fluoro-3,5-dimethoxyphenyl)-4,5,6,7-tetrahydro-1H-indazol-3-yl)-1H-pyrazol-4-yl)acrylamide (P4): $^1$H NMR (400 MHz, MeOD): δ 8.24 (s, 0H), 6.56 (dd, J=6.9, 2.8 Hz, 0H), 6.50-6.42 (m, 1H), 6.37 (d, J=1.6 Hz, 0H), 5.81 (dd, J=10.1, 1.6 Hz, 0H), 3.87 (s, 1H), 3.78 (s, 3H), 3.35 (s, 0H), 3.00 (dd, J=15.9, 4.9 Hz, 1H), 2.85 (d, J=11.3 Hz, 1H), 2.10-2.00 (m, 1H). MS (ESI) m/z: 412 [M+1].

Example S16

Synthesis of N-(5-(6-(2,6-difluoro-3,5-dimethoxyphenyl)-4,5,6,7-tetrahydro-1H-indazol-3-yl)-1-(methyl-d3)-1H-pyrazol-4-yl)acrylamide and N-(5-(6-(2-fluoro-3,5-dimethoxyphenyl)-4,5,6,7-tetrahydro-1H-indazol-3-yl)-1-(methyl-d3)-1H-pyrazol-4-yl)acrylamide

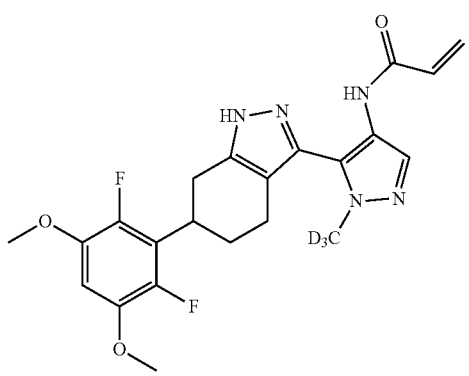

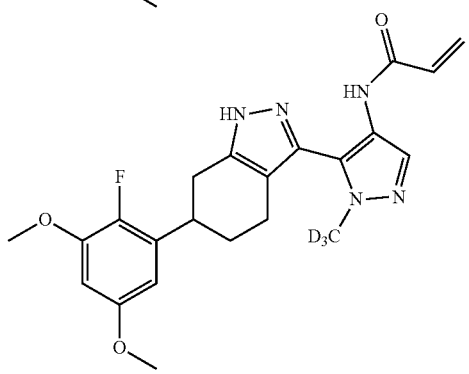

N-(5-(6-(2,6-difluoro-3,5-dimethoxyphenyl)-4,5,6,7-tetrahydro-1H-indazol-3-yl)-1-(methyl-d3)-1H-pyrazol-4-yl)acrylamide and N-(5-(6-(2-fluoro-3,5-dimethoxyphenyl)-4,5,6,7-tetrahydro-1H-indazol-3-yl)-1-(methyl-d3)-1H-pyrazol-4-yl)acrylamide were prepared by procedures similar to the one described in Example S14, replacing iodoethane in step A with iodomethane-d3.

Enantiomer 1 of N-(5-(6-(2,6-difluoro-3,5-dimethoxyphenyl)-4,5,6,7-tetrahydro-1H-indazol-3-yl)-1-(methyl-d3)-1H-pyrazol-4-yl)acrylamide (P1): $^1$H NMR (400 MHz, DMSO): δ 12.92 (s, 1H), 9.44 (s, 1H), 7.85 (s, 1H), 6.93 (t, J=8.2 Hz, 1H), 6.52 (dd, J=17.0, 10.2 Hz, 1H), 6.19 (dd, J=17.0, 2.0 Hz, 1H), 5.66 (dd, J=10.2, 1.9 Hz, 1H), 3.86 (s, 6H), 3.39 (s, 1H), 2.93 (d, J=10.9 Hz, 2H), 2.40 (s, 2H), 2.11 (d, J=9.7 Hz, 1H), 1.91 (s, 1H). MS (ESI) m/z: 447 [M+H$^+$].

Enantiomer 2 of N-(5-(6-(2,6-difluoro-3,5-dimethoxyphenyl)-4,5,6,7-tetrahydro-1H-indazol-3-yl)-1-(methyl-d3)-1H-pyrazol-4-yl)acrylamide (P2): $^1$H NMR (400 MHz, DMSO): δ 12.93 (d, J=5.0 Hz, 1H), 9.42 (d, J=4.1 Hz, 1H), 7.84 (d, J=0.9 Hz, 1H), 6.93 (dd, J=12.3, 4.1 Hz, 1H), 6.57-6.48 (m, 1H), 6.23-6.15 (m, 1H), 5.65 (t, J=7.9 Hz, 1H), 3.91-3.82 (m, 6H), 3.40 (d, J=8.4 Hz, 1H), 2.98-2.88 (m, 2H), 2.42-2.32 (m, 2H), 2.07 (d, J=5.8 Hz, 1H), 1.91 (d, J=3.4 Hz, 1H). MS (ESI) m/z: 447 [M+H$^+$].

Enantiomer 1 of N-(5-(6-(2-fluoro-3,5-dimethoxyphenyl)-4,5,6,7-tetrahydro-1H-indazol-3-yl)-1-(methyl-d3)-1H-pyrazol-4-yl)acrylamide (P3): $^1$H NMR (400 MHz, DMSO): δ 12.90 (s, 1H), 9.43 (s, 1H), 7.82 (s, 1H), 6.61 (dd, J=7.0, 2.8 Hz, 1H), 6.55-6.46 (m, 2H), 6.18 (dd, J=17.0, 2.1 Hz, 1H), 5.66 (dd, J=10.2, 2.1 Hz, 1H), 3.82 (s, 3H), 3.74 (s, 3H), 3.27 (d, J=5.3 Hz, 1H), 2.90 (dd, J=15.7, 5.2 Hz, 1H), 2.84-2.73 (m, 1H), 2.36 (d, J=19.3 Hz, 2H), 1.89 (s, 2H). MS (ESI) m/z: 429 [M+H$^+$].

Enantiomer 2 of N-(5-(6-(2-fluoro-3,5-dimethoxyphenyl)-4,5,6,7-tetrahydro-1H-indazol-3-yl)-1-(methyl-d3)-1H-pyrazol-4-yl)acrylamide (P4): $^1$H NMR (400 MHz, DMSO): δ 12.90 (s, 1H), 9.43 (s, 1H), 7.82 (s, 1H), 6.61 (dd, J=7.0, 2.8 Hz, 1H), 6.55-6.46 (m, 2H), 6.18 (dd, J=17.0, 2.1 Hz, 1H), 5.66 (dd, J=10.2, 2.1 Hz, 1H), 3.82 (s, 3H), 3.74 (s, 3H), 3.27 (d, J=5.3 Hz, 1H), 2.90 (dd, J=15.7, 5.2 Hz, 1H), 2.84-2.73 (m, 1H), 2.36 (d, J=19.3 Hz, 2H), 1.89 (s, 2H). MS (ESI) m/z: 429 [M+H$^+$].

Example S17

Synthesis of N-(5-(6-(2,6-difluoro-3,5-dimethoxyphenyl)-4,5,6,7-tetrahydro-1H-indazol-3-yl)-1-isopropyl-1H-pyrazol-4-yl)acrylamide

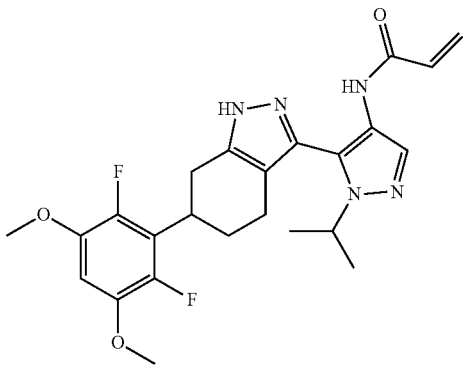 [SMILES: C=CC(=O)Nc1cnn(C(C)C)c1-c1n[nH]c2c1CCC(c1c(F)c(OC)cc(OC)c1F)C2]

N-(5-(6-(2,6-difluoro-3,5-dimethoxyphenyl)-4,5,6,7-tetrahydro-1H-indazol-3-yl)-1-isopropyl-1H-pyrazol-4-yl)acrylamide was prepared by procedures similar to the ones described in Example S14, replacing iodoethane in step A with 2-iodopropane.

Enantiomer 1 of N-(5-(6-(2,6-difluoro-3,5-dimethoxyphenyl)-4,5,6,7-tetrahydro-1H-indazol-3-yl)-1-isopropyl-1H-pyrazol-4-yl)acrylamide (P1): $^1$H NMR (400 MHz, MeOD) δ 8.04 (s, 1H), 6.82 (s, 1H), 6.42 (d, J=10.0 Hz, 1H), 6.35 (d, J=1.9 Hz, 1H), 5.73 (dd, J=10.0, 1.9 Hz, 1H), 4.57 (s, 1H), 3.89 (s, 6H), 3.60-3.48 (m, 1H), 3.19-3.05 (m, 1H), 2.96 (dd, J=15.9, 5.5 Hz, 1H), 2.52 (s, 2H), 2.32-2.18 (m, 1H), 2.02 (t, J=13.1 Hz, 1H), 1.48 (d, J=6.7 Hz, 3H), 1.40 (d, J=6.6 Hz, 3H). MS (ESI) m/z: 472 [M+H$^+$].

Enantiomer 2 of N-(5-(6-(2,6-difluoro-3,5-dimethoxyphenyl)-4,5,6,7-tetrahydro-1H-indazol-3-yl)-1-isopropyl-1H-pyrazol-4-yl)acrylamide (P2): $^1$H NMR (400 MHz, MeOD) δ 8.04 (s, 1H), 6.82 (s, 1H), 6.42 (d, J=10.0 Hz, 1H), 6.35 (d, J=1.9 Hz, 1H), 5.73 (dd, J=10.0, 1.9 Hz, 1H), 4.57 (s, 1H), 3.89 (s, 6H), 3.60-3.48 (m, 1H), 3.19-3.05 (m, 1H), 2.96 (dd, J=15.9, 5.5 Hz, 1H), 2.52 (s, 2H), 2.32-2.18 (m, 1H), 2.02 (t, J=13.1 Hz, 1H), 1.48 (d, J=6.7 Hz, 3H), 1.40 (d, J=6.6 Hz, 3H). MS (ESI) m/z: 472 [M+H$^+$].

Example S18

Synthesis of N-(5-(6-(2,6-difluoro-3,5-dimethoxyphenyl)-4,5,6,7-tetrahydro-1H-indazol-3-yl)-1-(2,2,2-trifluoroethyl)-1H-pyrazol-4-yl)acrylamide

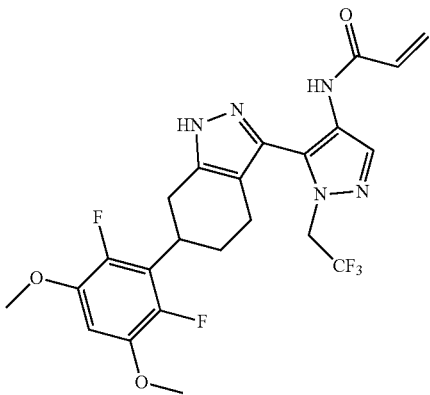 [SMILES: C=CC(=O)Nc1cnn(CC(F)(F)F)c1-c1n[nH]c2c1CCC(c1c(F)c(OC)cc(OC)c1F)C2]

N-(5-(6-(2,6-difluoro-3,5-dimethoxyphenyl)-4,5,6,7-tetrahydro-1H-indazol-3-yl)-1-(2,2,2-trifluoroethyl)-1H-pyrazol-4-yl)acrylamide was prepared by procedures similar to the ones described in Example S14, replacing iodoethane in step A with 2,2,2-trifluoroethyl trifluoromethanesulfonate.

Enantiomer 1 of N-(5-(6-(2,6-difluoro-3,5-dimethoxyphenyl)-4,5,6,7-tetrahydro-1H-indazol-3-yl)-1-(2,2,2-trifluoroethyl)-1H-pyrazol-4-yl)acrylamide (P1): $^1$H NMR (400 MHz, DMSO) δ 13.02 (s, 1H), 9.60 (s, 1H), 8.01 (s, 1H), 6.93 (t, J=7.9 Hz, 1H), 6.56-6.49 (m, 1H), 6.22 (d, J=16.7 Hz, 1H), 5.69 (d, J=10.1 Hz, 1H), 5.20-5.50 (m, 2H), 3.86 (s, 6H), 3.42-3.35 (m, 1H), 2.96-2.85 (m, 2H), 2.45-2.37 (m, 1H), 2.35-2.28 (m, 1H), 2.15-2.03 (m, 1H), 1.95-1.85 (m, 1H). MS (ESI) m/z: 511.6 [M+H$^+$].

Enantiomer 2 of N-(5-(6-(2,6-difluoro-3,5-dimethoxyphenyl)-4,5,6,7-tetrahydro-1H-indazol-3-yl)-1-(2,2,2-trifluoroethyl)-1H-pyrazol-4-yl)acrylamide (P2): $^1$H NMR (400 MHz, DMSO) δ 13.02 (s, 1H), 9.60 (s, 1H), 8.01 (s, 1H), 6.93 (t, J=8.1 Hz, 1H), 6.56-6.46 (m, 1H), 6.25-6.15 (m, 1H), 5.69 (d, J=10.1 Hz, 1H), 5.25-5.20 (m, 2H), 3.86 (s, 6H), 3.45-3.35 (m, 1H), 2.96-2.85 (m, 2H), 2.45-2.37 (m, 1H), 2.11-2.05 (m, 1H), 1.93-1.85 (m, 1H). MS (ESI) m/z: 511.6 [M+H$^+$].

Example S19

Synthesis of N-(5-(6-(2,6-difluoro-3,5-dimethoxyphenyl)-4,5,6,7-tetrahydro-1H-indazol-3-yl)-1-methyl-1H-pyrazol-4-yl)acetamide

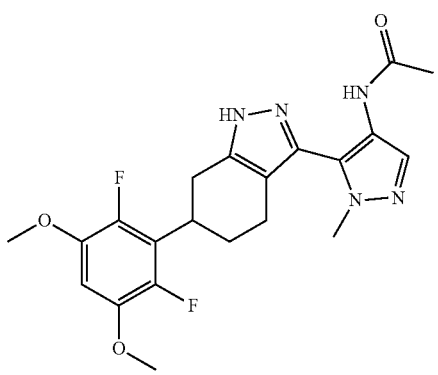 [SMILES: COc1cc(OC)c(F)c(C2CCc3c(-c4c(NC(C)=O)cnn4C)n[nH]c3C2)c1F]

N-(5-(6-(2,6-difluoro-3,5-dimethoxyphenyl)-4,5,6,7-tetrahydro-1H-indazol-3-yl)-1-methyl-1H-pyrazol-4-yl)acetamide was prepared by procedures similar to the ones described in Example 51, replacing acryloyl chloride in step F with acetyl chloride.

Enantiomer 1 of N-(5-(6-(2,6-difluoro-3,5-dimethoxyphenyl)-4,5,6,7-tetrahydro-1H-indazol-3-yl)-1-methyl-1H-pyrazol-4-yl)acetamide (P1): $^1$H NMR (400 MHz, DMSO) δ: 12.87 (s, 1H), 9.16 (s, 1H), 7.72 (s, 1H), 6.93 (t, J=8.3 Hz, 1H), 3.86 (s, 6H), 3.73 (s, 3H), 3.41 (dd, J=17.3, 10.6 Hz, 1H), 3.33 (s, 4H), 2.99-2.83 (m, 1H), 2.41 (d, J=12.1 Hz, 1H), 2.18-2.04 (m, 1H), 1.96 (s, 4H). MS (ESI) m/z: 432.1 [M+1].

Enantiomer 2 of N-(5-(6-(2,6-difluoro-3,5-dimethoxyphenyl)-4,5,6,7-tetrahydro-1H-indazol-3-yl)-1-methyl-1H-pyrazol-4-yl)acetamide (P2): $^1$H NMR (400 MHz, DMSO) δ: 12.88 (s, 1H), 9.17 (s, 1H), 7.72 (s, 1H), 6.93 (t, J=8.3 Hz, 1H), 3.86 (s, 6H), 3.73 (s, 3H), 3.41 (dd, J=17.4, 10.7 Hz, 1H), 3.47-3.25 (m, 1H), 2.92 (d, J=10.7 Hz, 2H), 2.41 (d, J=12.4 Hz, 1H), 2.10 (t, J=8.7 Hz, 1H), 1.97 (s, 4H). MS (ESI) m/z: 432.1 [M+1].

Example S20

Synthesis of N-(5-(6-(2,6-difluoro-3,5-dimethoxyphenyl)-4,5,6,7-tetrahydro-1H-indazol-3-yl)-1-methyl-1H-pyrazol-4-yl)propionamide

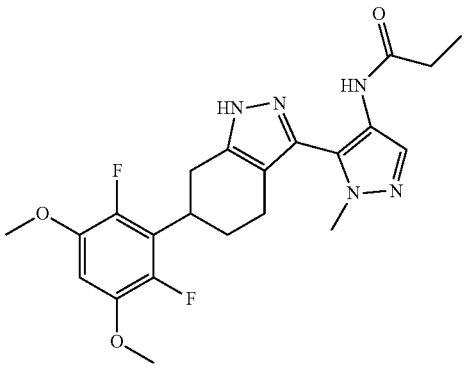 [SMILES: CCC(=O)Nc1cnn(C)c1-c1n[nH]c2c1CCC(c1c(F)c(OC)cc(OC)c1F)C2]

N-(5-(6-(2,6-difluoro-3,5-dimethoxyphenyl)-4,5,6,7-tetrahydro-1H-indazol-3-yl)-1-methyl-1H-pyrazol-4-yl)propionamide was prepared by procedures similar to the ones described in Example S1, replacing acryloyl chloride in step F with propionyl chloride.

Enantiomer 1 of N-(5-(6-(2,6-difluoro-3,5-dimethoxyphenyl)-4,5,6,7-tetrahydro-1H-indazol-3-yl)-1-methyl-1H-pyrazol-4-yl)propionamide (P1): $^1$H NMR (400 MHz, DMSO) δ 12.88 (s, 1H), 9.09 (s, 1H), 7.72 (s, 1H), 6.93 (t, J=8.3 Hz, 1H), 3.86 (s, 6H), 3.74 (s, 3H), 3.40 (dd, J=18.0, 11.4 Hz, 1H), 2.92 (d, J=10.5 Hz, 2H), 2.52 (s, 1H), 2.41 (d, J=12.3 Hz, 1H), 2.26 (q, J=7.5 Hz, 2H), 2.11 (d, J=10.9 Hz, 1H), 1.92 (d, J=12.4 Hz, 1H), 1.02 (t, J=7.6 Hz, 3H). MS (ESI) m/z: 445.8 [M+H$^+$].

Enantiomer 2 of N-(5-(6-(2,6-difluoro-3,5-dimethoxyphenyl)-4,5,6,7-tetrahydro-1H-indazol-3-yl)-1-methyl-1H-pyrazol-4-yl)propionamide (P2): $^1$H NMR (400 MHz, DMSO) δ 12.88 (s, 1H), 9.09 (s, 1H), 7.72 (s, 1H), 6.93 (t, J=8.3 Hz, 1H), 3.86 (s, 6H), 3.74 (s, 3H), 3.40 (dd, J=18.0, 11.4 Hz, 1H), 2.92 (d, J=10.5 Hz, 2H), 2.52 (s, 1H), 2.41 (d, J=12.3 Hz, 1H), 2.26 (q, J=7.5 Hz, 2H), 2.11 (d, J=10.9 Hz, 1H), 1.92 (d, J=12.4 Hz, 1H), 1.02 (t, J=7.6 Hz, 3H). MS (ESI) m/z: 445.8 [M+H⁺].

Example S21

N-(5-(6-(2,6-difluoro-3,5-dimethoxyphenyl)-4,5,6,7-tetrahydro-1H-indazol-3-yl)-1-methyl-1H-pyrazol-4-yl)-2-fluoroacrylamide

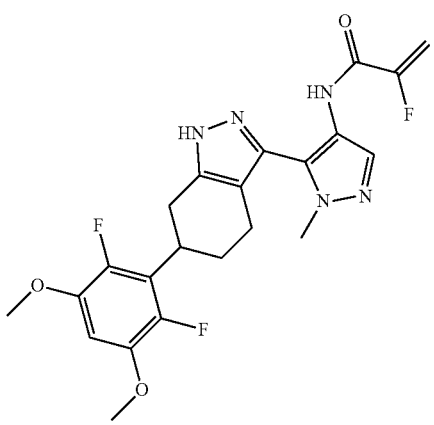 [SMILES: C=C(F)C(=O)Nc1cnn(C)c1-c1n[nH]c2c1CCC(c1c(F)c(OC)cc(OC)c1F)C2]

(5-(6-(2,6-difluoro-3,5-dimethoxyphenyl)-4,5,6,7-tetrahydro-1H-indazol-3-yl)-1-methyl-1H-pyrazol-4-yl)-2-fluoroacrylamide was prepared by procedures similar to the ones described in Example S1, replacing acryloyl chloride in step F with 2-fluoroacryloyl chloride.

Enantiomer 1 of (5-(6-(2,6-difluoro-3,5-dimethoxyphenyl)-4,5,6,7-tetrahydro-1H-indazol-3-yl)-1-methyl-1H-pyrazol-4-yl)-2-fluoroacrylamide (P1): ¹H NMR (400 MHz, DMSO): δ 12.98 (s, 1H), 9.73 (s, 1H), 7.70 (s, 1H), 6.94 (d, J=8.2 Hz, 1H), 5.64 (d, J=44.6 Hz, 1H), 5.39-5.34 (m, 1H), 3.86 (s, 6H), 3.83 (s, 3H), 3.36 (s, 1H), 2.93 (d, J=8.4 Hz, 2H), 2.49-2.46 (m, 2H), 2.08 (s, 1H), 1.92 (d, J=11.9 Hz, 1H). MS (ESI) m/z: 462.4 [M+H⁺].

Enantiomer 2 of (5-(6-(2,6-difluoro-3,5-dimethoxyphenyl)-4,5,6,7-tetrahydro-1H-indazol-3-yl)-1-methyl-1H-pyrazol-4-yl)-2-fluoroacrylamide (P2): ¹H NMR (400 MHz, DMSO): δ 12.98 (s, 1H), 9.74 (s, 1H), 7.71 (s, 1H), 6.94 (d, J=8.3 Hz, 1H), 5.71-5.58 (m, 1H), 5.39-5.34 (m, 1H), 3.86 (s, 6H), 3.82 (s, 3H), 3.39 (s, 1H), 2.93 (d, J=8.7 Hz, 2H), 2.49-2.46 (m, 2H), 2.08 (s, 1H), 1.92 (d, J=10.3 Hz, 1H). MS (ESI) m/z: 462.4 [M+H⁺].

Example S22

Synthesis of methyl (S,E)-4-((5-(6-(2,6-difluoro-3,5-dimethoxyphenyl)-4,5,6,7-tetrahydro-1H-indazol-3-yl)-1-methyl-1H-pyrazol-4-yl)amino)-4-oxobut-2-enoate

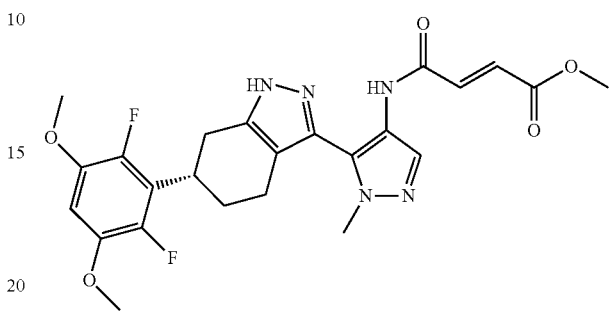

Methyl (S,E)-4-((5-(6-(2,6-difluoro-3,5-dimethoxyphenyl)-4,5,6,7-tetrahydro-1H-indazol-3-yl)-1-methyl-1H-pyrazol-4-yl)amino)-4-oxobut-2-enoate was prepared by procedures similar to the ones described in Example S1, replacing acryloyl chloride in step F with (E)-4-methoxy-4-oxobut-2-enoic acid.

¹H NMR (400 MHz, CDCl₃) δ 8.44 (s, 1H), 8.23 (s, 1H), 6.98 (dd, J=44.4, 15.3 Hz, 2H), 6.60 (t, J=8.0 Hz, 1H), 3.95-3.87 (m, 9H), 3.83 (s, 3H), 3.58 (s, 1H), 3.15 (d, J=11.8 Hz, 1H), 3.00 (dd, J=16.0, 5.3 Hz, 1H), 2.66 (s, 2H), 2.25 (d, J=36.4 Hz, 1H), 2.17-2.03 (m, 1H). MS (ESI) m/z: 503.1 [M+H⁺].

Example S23

Synthesis of isopropyl (S,E)-4-((5-(6-(2,6-difluoro-3,5-dimethoxyphenyl)-4,5,6,7-tetrahydro-1H-indazol-3-yl)-1-methyl-1H-pyrazol-4-yl)amino)-4-oxobut-2-enoate

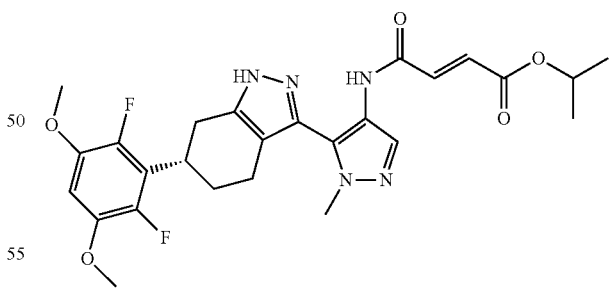

Isopropyl (S,E)-4-((5-(6-(2,6-difluoro-3,5-dimethoxyphenyl)-4,5,6,7-tetrahydro-1H-indazol-3-yl)-1-methyl-1H-pyrazol-4-yl)amino)-4-oxobut-2-enoate was prepared by procedures similar to the ones described in Example S1, replacing acryloyl chloride in step F with (E)-4-isopropoxy-4-oxobut-2-enoic acid.

¹H NMR (400 MHz, CDCl₃) δ 8.33 (s, 1H), 8.25 (s, 1H), 6.99 (d, J=15.3 Hz, 1H), 6.88 (d, J=15.3 Hz, 1H), 6.60 (t, J=8.0 Hz, 1H), 5.31-5.03 (m, 1H), 3.91 (s, 9H), 3.58 (s, 1H), 3.15 (d, J=11.9 Hz, 1H), 3.01 (d, J=5.2 Hz, 1H), 2.66 (s, 2H), 2.28 (s, 1H), 2.10 (s, 1H), 1.31 (d, J=6.2 Hz, 6H). MS (ESI) m/z: 530.1 [M+H⁺].

Example S24

Synthesis of N-(5-((S)-6-(2,6-difluoro-3,5-dimethoxyphenyl)-4,5,6,7-tetrahydro-1H-indazol-3-yl)-1-methyl-1H-pyrazol-4-yl)oxirane-2-carboxamide

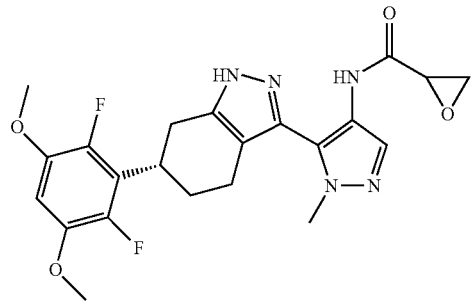 [SMILES: COc1cc(OC)c(F)c([C@H]2CCc3c(-c4c(NC(=O)C5CO5)cnn4C)n[nH]c3C2)c1F]

N-(5-((S)-6-(2,6-difluoro-3,5-dimethoxyphenyl)-4,5,6,7-tetrahydro-1H-indazol-3-yl)-1-methyl-1H-pyrazol-4-yl)oxirane-2-carboxamide was prepared by procedures similar to the ones described in Example S1, replacing acryloyl chloride in step F with oxirane-2-carboxylic acid.

¹H NMR (400 MHz, CDCl₃) δ 8.29 (d, J=35.1 Hz, 1H), 8.11 (d, J=1.0 Hz, 1H), 6.60 (t, J=8.0 Hz, 1H), 3.92 (s, 6H), 3.89 (d, J=0.7 Hz, 3H), 3.63-3.53 (m, 2H), 3.21-3.10 (m, 1H), 3.06 (d, J=7.4 Hz, 1H), 3.02-2.84 (m, 2H), 2.68-2.60 (m, 2H), 2.30 (s, 1H), 2.12-2.02 (m, 1H). MS (ESI) m/z: 460.0 [M+H⁺].

Example S25

Synthesis of (R)—N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide

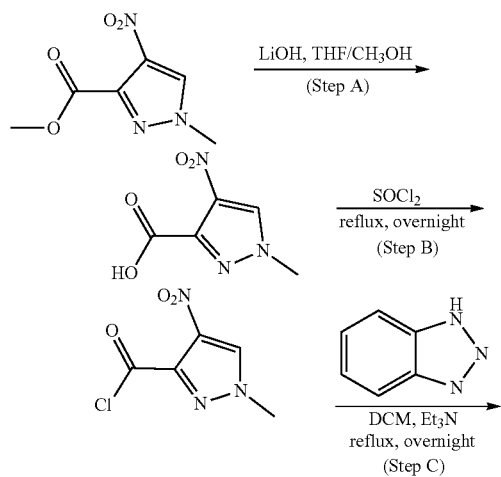

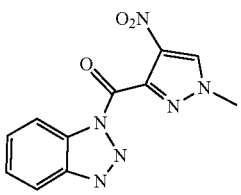

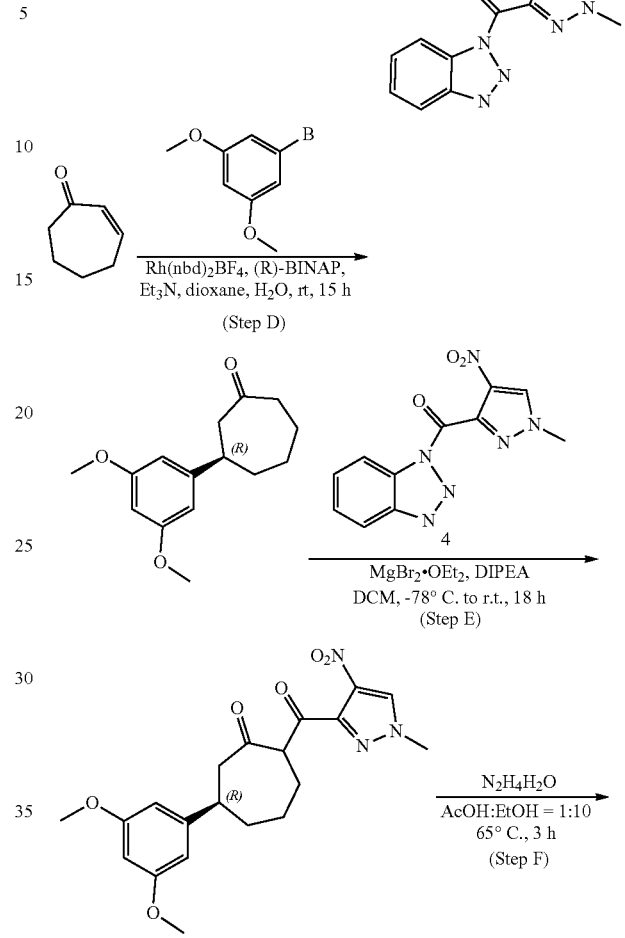

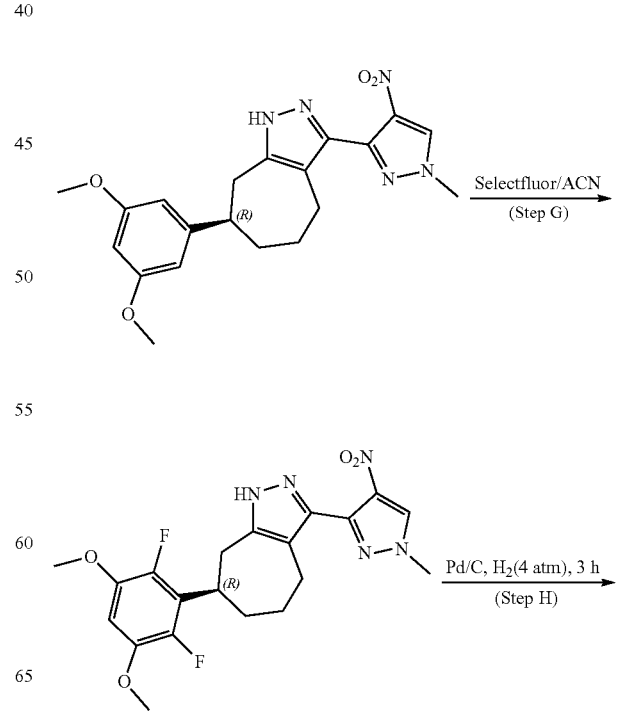

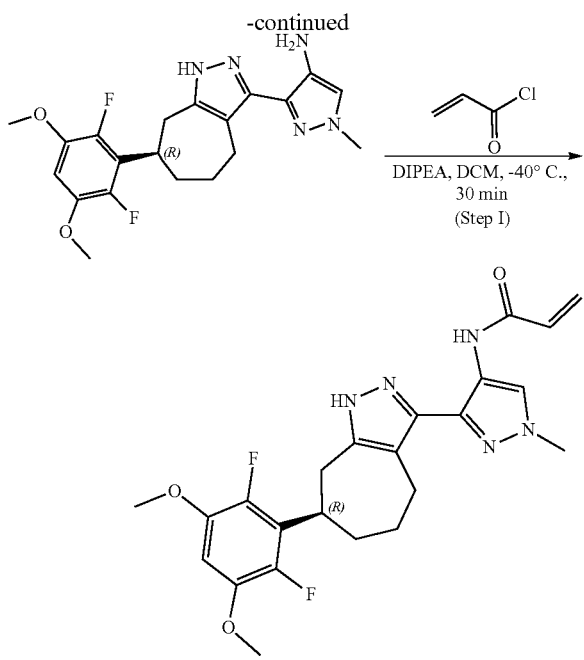

Step A: A mixture of methyl 1-methyl-4-nitro-1H-pyrazole-3-carboxylate (100 g, 0.5 mol), LiOH (24 g, 1.0 mol) in THF (900 ml)/CH₃OH (100 ml) was stirred at rt for 1 h. The solvent was evaporated and the residue was diluted with H₂O, adjusted to pH=3, extracted with ethyl acetate (3*200 ml) and the combined organic layers were evaporated to give 1-methyl-4-nitro-1H-pyrazole-3-carboxylic acid (80 g, 87%) which was used in the next step without further purification. MS (ESI) m/z: 172.0 [M+H]⁺

Step B: In a round-bottomed flask were placed 1-methyl-4-nitro-1H-pyrazole-3-carboxylic acid (50 g, 3.18 mol), 200 mL SOCl₂ and 0.5 ml DMF. The flask was fitted with a reflux condenser, and the mixture was refluxed at 76° C. for 1 h. The SOCl₂ was evaporated and the residue was washed with DCM to get 1-methyl-4-nitro-1H-pyrazole-3-carbonyl chloride as a light yellow solid (50 g, 90%) which was used in the next step without further purification.

Step C: Et₃N (4.24 g, 42 mmol, 1.2 eq) was added dropwise to a stirred solution of 1H-1,2,3-benzotriazole (5.0 g, 42 mmol, 1.2 eq) in anhydrous CH₂Cl₂ (120 mL) at rt, followed by slow addition (over a period of 10 min) of 1-methyl-4-nitro-1H-pyrazole-3-carbonyl chloride (9.34 g, 49.28 mmol, 1.4 eq) (Argon atmosphere). Then the solution was warmed to 40° C. and stirred for 3 h, then evaporated to give (1H-benzo[d][1,2,3]triazol-1-yl)(1-methyl-4-nitro-1H-pyrazol-3-yl)methanone as a light yellow powder (used in the next step without purification). MS (ESI) m/z: 272.9 [M+H]⁺

Step D: To a solution of (3,5-dimethoxyphenyl) boronic acid (125 g, 1.13 mol) in dioxane (1800 ml) was added Rh(nbd)₂BF₄ (6.35 g, 0.017 mol) and (R)-BINAP (12.7 g, 0.020 mol). The mixture was stirred at rt for 5 h. Then Et₃N (114.6 g, 1.13 mol), cyclohept-2-en-1-one (268.5 g, 1.47 mol) and 60 ml water was added in the mixture. The flask was evacuated and purged with nitrogen. The mixture was stirred for 12 h at 30° C. Once LCMS suggested the reaction was completed, the mixture was washed with brine, dried over sodium sulfate, the solvent was evaporated, and the residue was purified by silica gel chromatography (PE/EA, gradient elution, 5:1 to 2:1) to give (R)-3-(3,5-dimethoxyphenyl) cycloheptan-1-one as a light-yellow oil (250 g, 89%). MS (ESI) m/z: 249.0 [M+H]⁺

Step E: (1H-benzo[d][1,2,3]triazol-1-yl)(1-methyl-4-nitro-1H-pyrazol-3-yl)methanone was dissolved in CH₂Cl₂ (750 mL) and the mixture was cooled to −78° C. using a dry ice-ethanol bath. MgBr₂.OEt₂ (113.5 g, 0.44 mol, 2.5 eq) was added to the solution, followed by (R)-3-(3,5-dimethoxyphenyl) cycloheptan-1-one (43.6 g, 0.176 mol, 1.0 eq) in 250 mL CH₂Cl₂, then the mixture was stirred at −78° C. for 30 min. DIEA (68.2 g, 0.528 mol, 3.0 eq) was added dropwise to the solution. The mixture was stirred for another 3 h while let warm to rt. Aqueous sat. NH₄Cl solution (200 mL) was then added and stirring was continued for 5 min. The aqueous layer was extracted with CH₂Cl₂ (5×500 mL). The combined extracts were washed with brine, dried over anhydrous Na₂SO₄ and the solvent was removed under reduced pressure to give the crude product (70 g, crude) which was used in the next step without further purification. MS (ESI) m/z: 402.1 [M+H]⁺

Step F: (6R)-6-(3,5-dimethoxyphenyl)-2-(1-methyl-4-nitro-1H-pyrazole-3-carbonyl)-cycloheptan-1-one (70 g, 0.17 mol) and hydrazine hydrate (21.5 g, 0.43 mmol) were added to a mixture of EtOH (550 mL) and AcOH (55 mL). The mixture was stirred at 60° C. for 0.5 h. After LCMS showed that the reaction was complete, the reaction mixture was evaporated at 70° C. The crude product was purified by silica gel column chromatography (DCM, 0-2.5% MeOH) to obtain (R)-7-(3,5-dimethoxyphenyl)-3-(1-methyl-4-nitro-1H-pyrazol-3-yl)-1,4,5,6,7,8-hexahydrocyclohepta[c]pyrazole (55 g, 75% over two steps) as a yellow solid. MS (ESI) m/z: 397.9 [M+H]⁺

Step G: A solution of 7-(3,5-dimethoxyphenyl)-3-(1-methyl-4-nitro-1H-pyrazol-3-yl)-1,4,5,6,7,8-hexahydrocyclohepta[c]pyrazole (20 g, 0.05 mmol) in CH₃CN (4 L) was cooled to 0° C. using an ice bath. Selectfluor (25 g, 0.10 mol) was added in several portions. The resulting solution was stirred at rt for 2 h. Then the reaction mixture was washed with aq. NaHCO₃, dried over sodium sulfate, filtered and the filtrate was concentrated. The residue was purified by silica gel chromatography (DCM, 0-2.5% MeOH) to give a mixture of (R)-7-(2,6-difluoro-3,5-dimethoxyphenyl)-3-(1-methyl-4-nitro-1H-pyrazol-3-yl)-1,4,5,6,7,8-hexahydrocyclohepta[c]pyrazole, MS (ESI) m/z: 434.1 [M+H]⁺ and (R)-7-(2-fluoro-3,5-dimethoxyphenyl)-3-(1-methyl-4-nitro-1H-pyrazol-3-yl)-1,4,5,6,7,8-hexahydrocyclohepta[c]pyrazole, MS (ESI) m/z: 416.1 [M+H]⁺ as a white solid (9 g, 30%).

Step H: A suspension of (R)-7-(2,6-difluoro-3,5-dimethoxyphenyl)-3-(1-methyl-4-nitro-1H-pyrazol-3-yl)-1,4,5,6,7,8-hexahydrocyclohepta[c]pyrazole (5 g, 10.4 mmol, mixture with (R)-7-(2-fluoro-3,5-dimethoxyphenyl)-3-(1-methyl-4-nitro-1H-pyrazol-3-yl)-1,4,5,6,7,8-hexahydrocyclohepta[c]pyrazole), Pd/C (1.5 g) in MeOH/Ethyl acetate (50/5 ml) was stirred at 40° C. overnight under a H₂ atmosphere. The Pd/C was filtered off and the filtrate was concentrated. The residue was purified by silica gel chromatography (DCM, 0-3% MeOH) to give (R)-3-(7-(2,6-difluoro-3,5-dimethoxyphenyl)-1,4,5,6,7,8-hexahydrocyclohepta[c] pyrazol-3-yl)-1H-pyrazol-4-amine (1.9 g, mixture with (R)-3-(7-(2-fluoro-3,5-dimethoxyphenyl)-1,4,5,6,7,8-hexahydrocyclohepta[c] pyrazol-3-yl)-1H-pyrazol-4-amine) as a brown solid. MS (ESI) m/z: 390 [M+H]⁺

Step I: To a mixture of (R)-3-(7-(2,6-difluoro-3,5-dimethoxyphenyl)-1,4,5,6,7,8-hexahydrocyclohepta[c] pyrazol-3-yl)-1H-pyrazol-4-amine (1.9 g, mixture with (R)-3-(7-(2-fluoro-3,5-dimethoxyphenyl)-1,4,5,6,7,8-hexahydrocyclohepta[c] pyrazol-3-yl)-1H-pyrazol-4-amine, 4.65 mmol) and DIPEA (1.8 g, 14.0 mmol) in DCM (200 mL) was added acryloyl chloride (380 mg, 4.2 mmol) at −40° C., and the mixture was stirred for 15 min. The solvent was removed and the residue was purified by reversed-phase HPLC followed by additional purification by SFC (Chromatography Column: Chiralpak-AD (Daicel Corporation); mobile phase: CO$_2$-ETOH(DEA)) to give (R)—N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide (43 mg) as a white solid.

$^1$H NMR (400 MHz, DMSO) δ 12.70 (s, 1H), 10.08 (s, 1H), 8.22 (s, 1H), 6.91 (s, 1H), 6.47-6.34 (m, 1H), 6.20 (d, J=16.8 Hz, 1H), 5.75 (d, J=8.8 Hz, 1H), 3.86 (s, 9H), 3.74 (s, 1H), 3.58 (s, 1H), 3.23 (d, J=13.4 Hz, 1H), 3.11 (t, J=10.9 Hz, 1H), 2.87 (d, J=15.3 Hz, 1H), 2.16 (d, J=10.9 Hz, 1H), 2.12-1.84 (m, 3H), 1.44 (d, J=12.1 Hz, 1H). MS (ESI) m/z: 457.8 [M+H]$^+$

Example S26

Synthesis of (S)—N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide

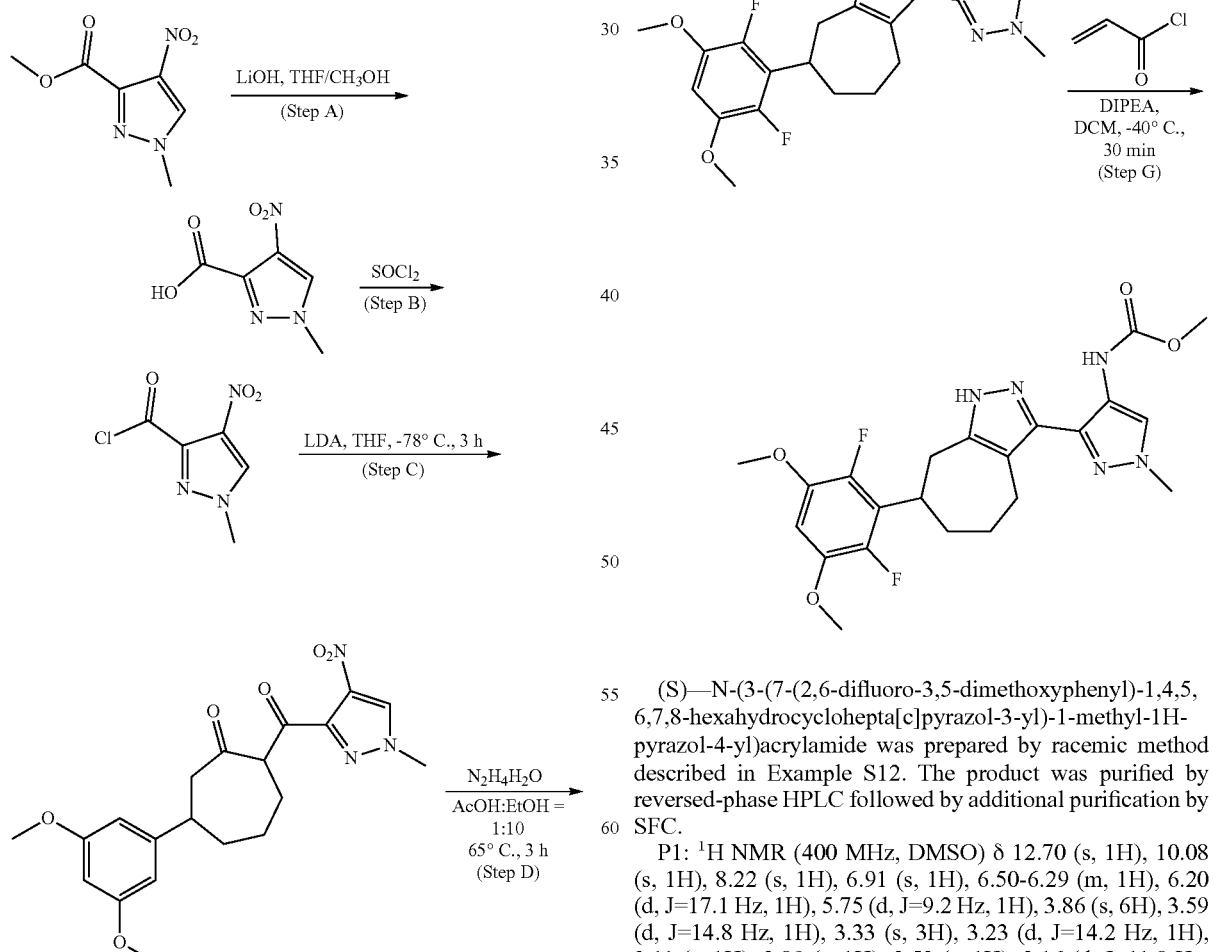

(S)—N-(3-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide was prepared by racemic method described in Example S12. The product was purified by reversed-phase HPLC followed by additional purification by SFC.

P1: $^1$H NMR (400 MHz, DMSO) δ 12.70 (s, 1H), 10.08 (s, 1H), 8.22 (s, 1H), 6.91 (s, 1H), 6.50-6.29 (m, 1H), 6.20 (d, J=17.1 Hz, 1H), 5.75 (d, J=9.2 Hz, 1H), 3.86 (s, 6H), 3.59 (d, J=14.8 Hz, 1H), 3.33 (s, 3H), 3.23 (d, J=14.2 Hz, 1H), 3.11 (s, 1H), 2.89 (s, 1H), 2.52 (s, 1H), 2.16 (d, J=11.8 Hz, 1H), 2.04 (s, 2H), 1.44 (d, J=12.1 Hz, 1H). MS (ESI) m/z: 457.8 [M+H]$^+$

Example S27

Synthesis of (R)—N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide

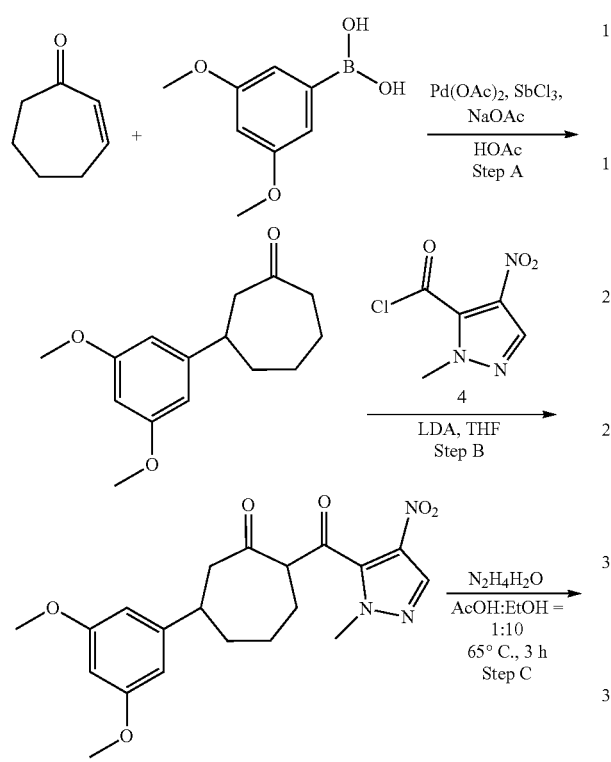

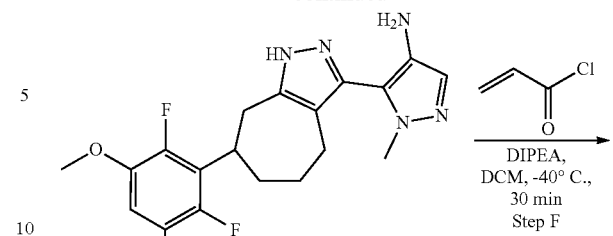

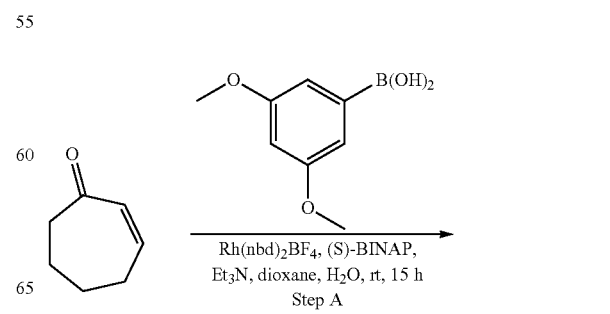

(R)—N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide was prepared by racemic method described in Example S4. The product was purified by reversed-phase HPLC followed by additional purification by SFC.

P1: $^1$H NMR (400 MHz, DMSO) δ 12.89 (s, 1H), 9.40 (s, 1H), 7.83 (s, 1H), 6.90 (t, J=7.4 Hz, 1H), 6.52-6.45 (m, 1H), 6.18 (d, J=16.9 Hz, 1H), 5.65 (d, J=10.1 Hz, 1H), 3.86 (s, 6H), 3.71 (s, 3H), 3.27-3.10 (m, 2H), 2.87 (d, J=13.9 Hz, 1H), 2.39-2.28 (m, 2H), 2.18-1.98 (m, 2H), 1.91-1.81 (m, 1H), 1.55-1.38 (m, 1H). MS (ESI) m/z: 457.5 [M+H$^+$]

Example S28

Synthesis of (S)—N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide

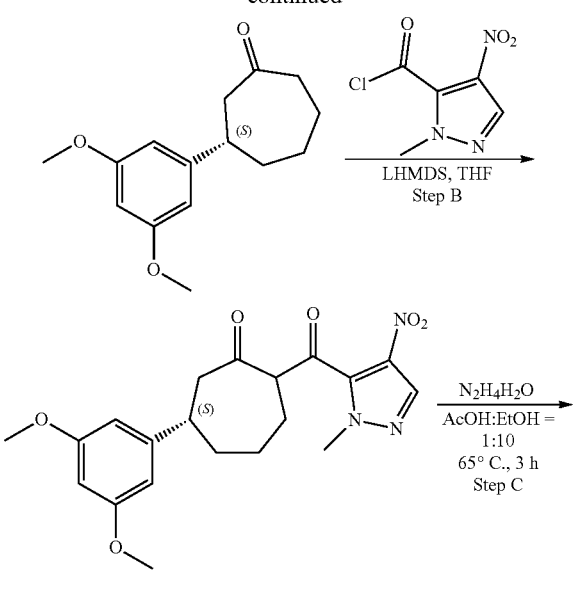
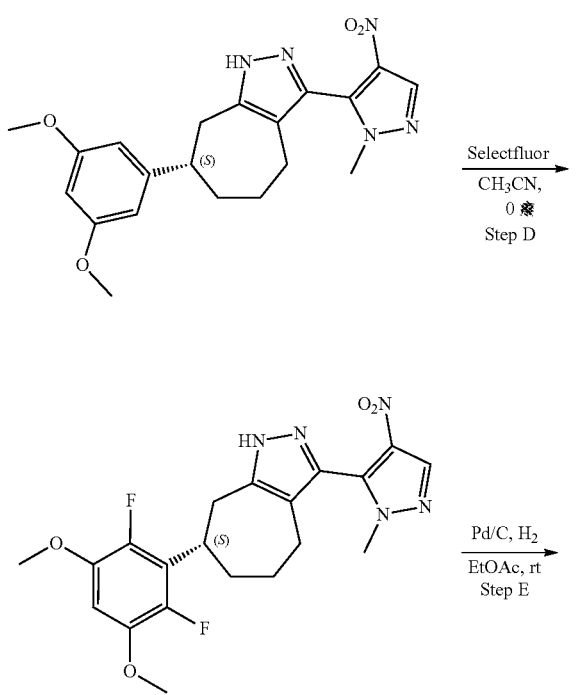
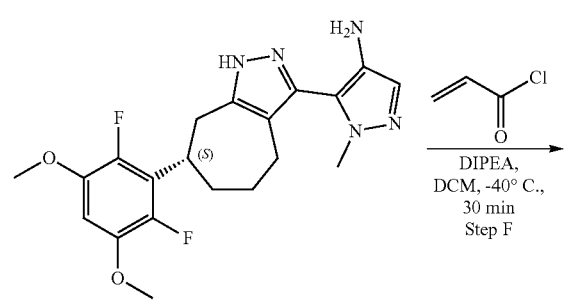

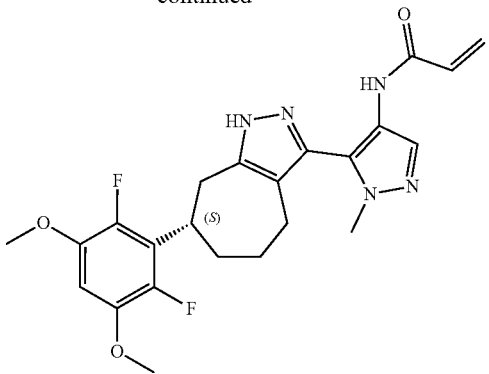

Step A: To a solution of (3,5-dimethoxyphenyl) boronic acid (125 g, 1.13 mol) in dioxane (1800 ml) was added Rh(nbd)$_2$BF$_4$ (6.35 g, 0.017 mol) and (S)-BINAP (12.7 g, 0.020 mol). The mixture was stirred for 5 h at rt. Then Et$_3$N (114.6 g, 1.13 mol), cyclohept-2-en-1-one (268.5 g, 1.47 mol) and 60 ml water was added. The flask was evacuated and purged with nitrogen. The mixture was stirred for 12 h at 30° C. Once LCMS suggested the reaction was completed, the mixture was washed with brine, dried over sodium sulfate, filtered and the filtrate was concentrated and purified by silica gel chromatography to give (S)-3-(3,5-dimethoxyphenyl) cycloheptan-1-one as a light-yellow oil (250 g, 89%). MS (ESI) m/z: 249.0 [M+H]$^+$ Step B: To a solution of (S)-3-(3,5-dimethoxyphenyl) cycloheptan-1-one (51.4 g, 0.21 mol, 1.0 eq) in THF (1.0 L) was added LHMDS (0.22 L, 1.1 eq) at −78° C. in a liquid nitrogen-ethyl acetate bath (the addition lasts for 50 minutes), then the mixture was slowly warmed to −40° C. and stirred for 1 h. 1-methyl-4-nitro-1H-pyrazole-5-carbonyl chloride (43.6 g, 0.23 mol, 1.1 eq) was added separately to the above solution at −78° C. (the addition lasts for 30 minutes), the mixture was stirred for another 30 min, then warmed to rt slowly (keeping in a liquid nitrogen-ethyl acetate bath), after stirring was continued at rt for another 2 h. The mixture was quenched by addition of saturated aq. NH$_4$Cl solution. The THF layer was separated and the aqueous layer was further extracted with ethyl acetate (2*500 mL). The combined extracts were washed with brine, dried over anhydrous Na$_2$SO$_4$, filtered and the filtrate was concentrated under reduced pressure get a solid (60 g, crude) which was used in the next step without further purification. MS (ESI) m/z: 402.1 [M+H]$^+$ Step C: (6S)-6-(3,5-dimethoxyphenyl)-2-(4-nitro-1H-pyrazole-3-carbonyl)cycloheptan-1-one (60 g, 0.15 mol, 1.0 eq) and hydrazine hydrate (22.5 g, 0.45 mol, 3.0 eq) was added to a mixture of acetic acid and EtOH (1200 mL, acetic acid/EtOH=1:10). The mixture was stirred at 50° C. for 3 h. The reaction solution was evaporated and diluted with sat. aq. NaCl, extracted with EA (400 mL) and the organic layer was dried over anhydrous Na$_2$SO$_4$, and concentrated to give (S)-7-(3,5-dimethoxyphenyl)-3-(1-methyl-4-nitro-1H-pyrazol-5-yl)-1,4,5,6,7,8-hexahydrocyclohepta[c]pyrazole (33 g, 40% over two steps of step B and C) as a light yellow solid. MS (ESI) m/z: 397.9 [M+H]$^+$ Step D-F: (S)—N-(5-(7-(2,6-difluoro-3,5-dimethoxyphenyl)-1,4,5,6,7,8-hexahydrocyclohepta[c]pyrazol-3-yl)-1-methyl-1H-pyrazol-4-yl)acrylamide was prepared by procedures similar to the one described in (R)—N-(3-(7-(2,6-difluoro-3,5-dimethoxyphenyl)-1,4,5,6,7,8-hexahydrocyclohepta[c]pyrazol-3-yl)-1-methyl-1H- pyrazol-4-yl)acrylamide. The product was purified by reversed-phase HPLC followed by additional purification by SFC.

¹H NMR (400 MHz, DMSO) δ 12.89 (s, 1H), 9.38 (s, 1H), 7.81 (s, 1H), 6.90 (t, J=7.8 Hz, 1H), 6.48 (dd, J=16.9, 10.2 Hz, 1H), 6.18 (dd, J=17.0, 1.9 Hz, 1H), 5.65 (d, J=10.2 Hz, 1H), 3.89 (s, 6H), 3.72 (s, 3H), 3.28-3.13 (m, 2H), 2.88 (d, J=13.6 Hz, 1H), 2.38-2.30 (m, 2H), 2.20-1.98 (m, 2H), 1.92-1.79 (m, 1H), 1.54-1.39 (m, 1H). MS (ESI) m/z: 457.5 [M+H]⁺

Example S29

Synthesis of (R)—N-(5-(7-(2,6-difluoro-3,5-dimethoxyphenyl)-1,4,5,6,7,8-hexahydrocyclohepta[c]pyrazol-3-yl)-1H-pyrazol-4-yl)acrylamide

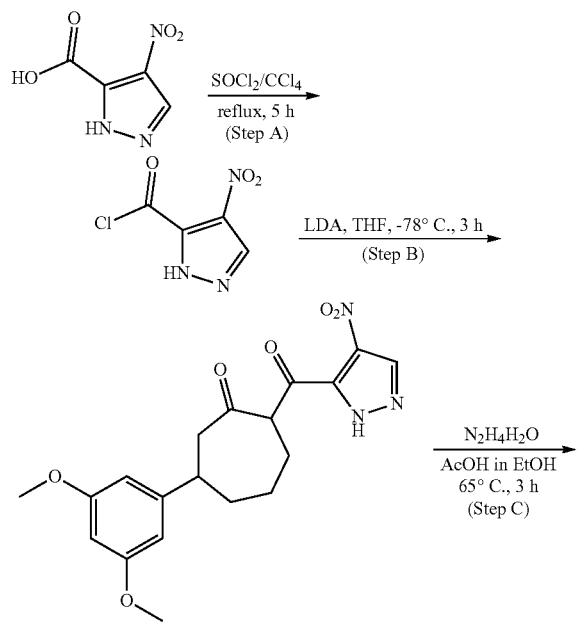

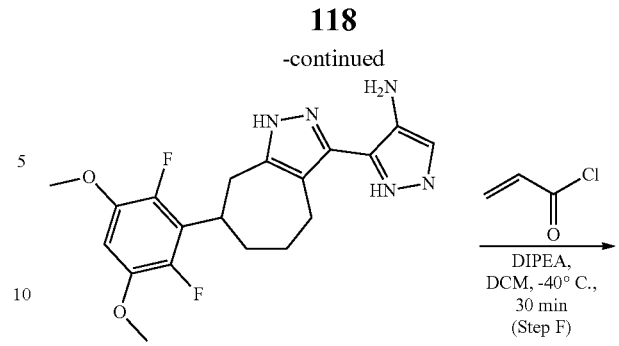

(R)—N-(5-(7-(2,6-difluoro-3,5-dimethoxyphenyl)-1,4,5,6,7,8-hexahydrocyclohepta[c]pyrazol-3-yl)-1H-pyrazol-4-yl)acrylamide was prepared by the method described for Example S11. The product was purified by reversed-phase HPLC followed by additional purification by SFC.

P2: ¹H NMR (400 MHz, DMSO) δ 12.71 (s, 2H), 10.07 (s, 1H), 8.20 (s, 1H), 6.91 (t, J=8.2 Hz, 1H), 6.41 (d, J=11.1 Hz, 1H), 6.20 (d, J=17.0 Hz, 1H), 5.74 (d, J=10.0 Hz, 1H), 3.86 (s, 6H), 3.64 (d, J=29.8 Hz, 1H), 3.19 (dt, J=22.8, 11.6 Hz, 2H), 2.87 (d, J=14.7 Hz, 1H), 2.33-1.78 (m, 4H), 1.45 (d, J=12.3 Hz, 1H). MS (ESI) m/z: 444.1 [M+H]⁺

Example S30

Synthesis of (S)—N-(5-(7-(2,6-difluoro-3,5-dimethoxyphenyl)-1,4,5,6,7,8-hexahydrocyclohepta[c]pyrazol-3-yl)-1H-pyrazol-4-yl)acrylamide

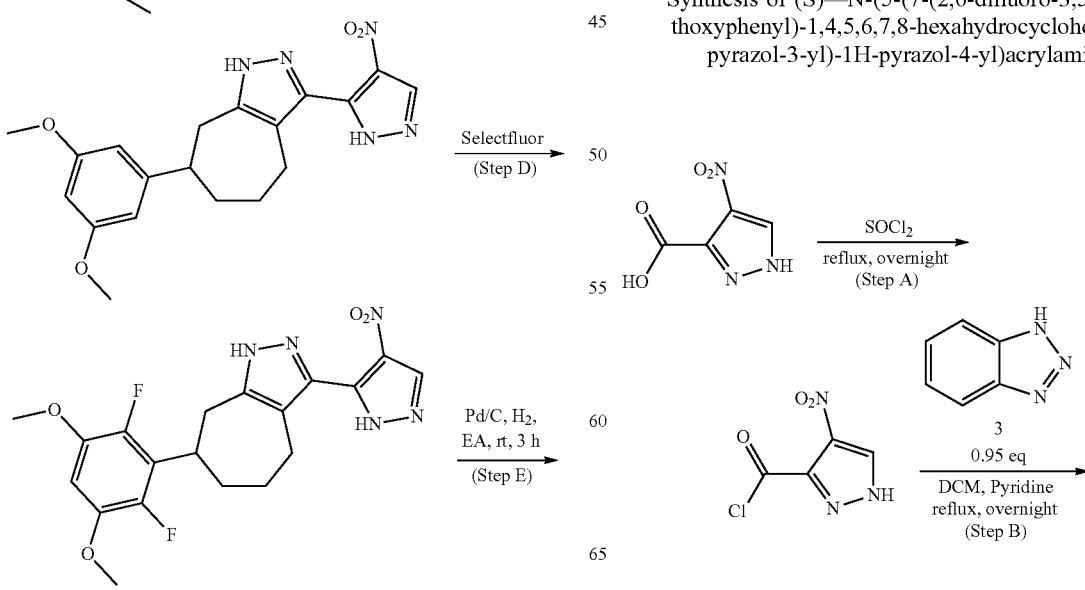

-continued

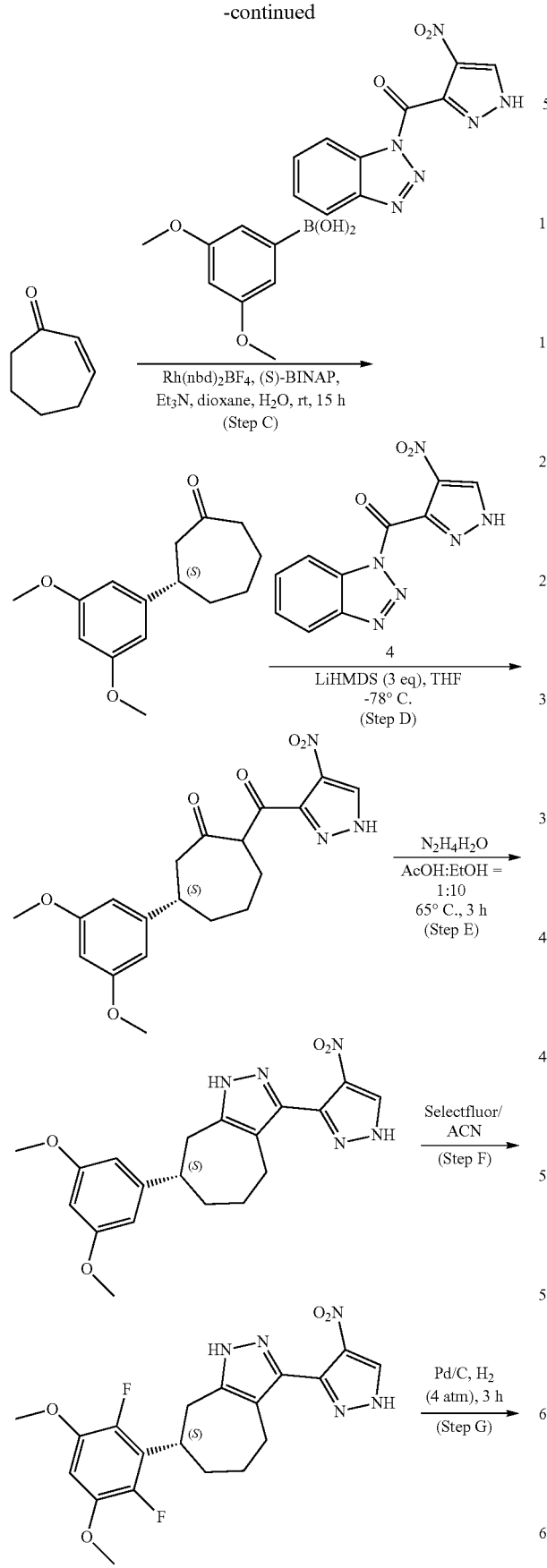

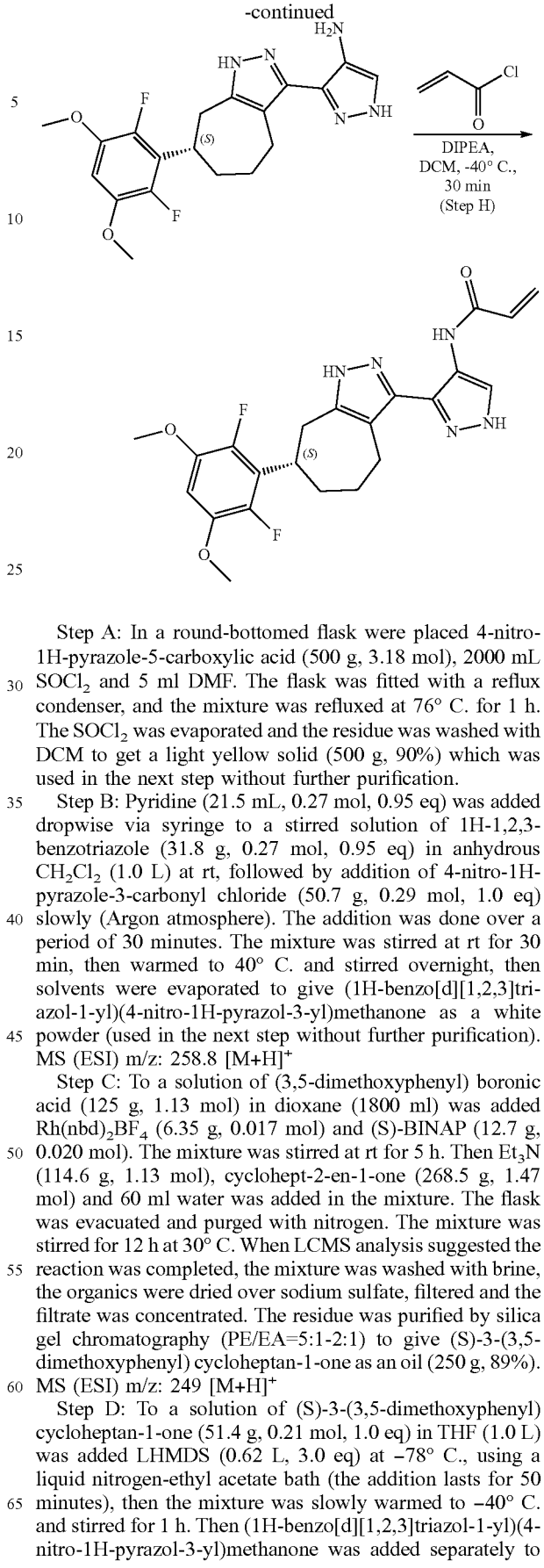

Step A: In a round-bottomed flask were placed 4-nitro-1H-pyrazole-5-carboxylic acid (500 g, 3.18 mol), 2000 mL SOCl₂ and 5 ml DMF. The flask was fitted with a reflux condenser, and the mixture was refluxed at 76° C. for 1 h. The SOCl₂ was evaporated and the residue was washed with DCM to get a light yellow solid (500 g, 90%) which was used in the next step without further purification.

Step B: Pyridine (21.5 mL, 0.27 mol, 0.95 eq) was added dropwise via syringe to a stirred solution of 1H-1,2,3-benzotriazole (31.8 g, 0.27 mol, 0.95 eq) in anhydrous CH₂Cl₂ (1.0 L) at rt, followed by addition of 4-nitro-1H-pyrazole-3-carbonyl chloride (50.7 g, 0.29 mol, 1.0 eq) slowly (Argon atmosphere). The addition was done over a period of 30 minutes. The mixture was stirred at rt for 30 min, then warmed to 40° C. and stirred overnight, then solvents were evaporated to give (1H-benzo[d][1,2,3]triazol-1-yl)(4-nitro-1H-pyrazol-3-yl)methanone as a white powder (used in the next step without further purification). MS (ESI) m/z: 258.8 [M+H]⁺

Step C: To a solution of (3,5-dimethoxyphenyl) boronic acid (125 g, 1.13 mol) in dioxane (1800 ml) was added Rh(nbd)₂BF₄ (6.35 g, 0.017 mol) and (S)-BINAP (12.7 g, 0.020 mol). The mixture was stirred at rt for 5 h. Then Et₃N (114.6 g, 1.13 mol), cyclohept-2-en-1-one (268.5 g, 1.47 mol) and 60 ml water was added in the mixture. The flask was evacuated and purged with nitrogen. The mixture was stirred for 12 h at 30° C. When LCMS analysis suggested the reaction was completed, the mixture was washed with brine, the organics were dried over sodium sulfate, filtered and the filtrate was concentrated. The residue was purified by silica gel chromatography (PE/EA=5:1-2:1) to give (S)-3-(3,5-dimethoxyphenyl) cycloheptan-1-one as an oil (250 g, 89%). MS (ESI) m/z: 249 [M+H]⁺

Step D: To a solution of (S)-3-(3,5-dimethoxyphenyl) cycloheptan-1-one (51.4 g, 0.21 mol, 1.0 eq) in THF (1.0 L) was added LHMDS (0.62 L, 3.0 eq) at −78° C., using a liquid nitrogen-ethyl acetate bath (the addition lasts for 50 minutes), then the mixture was slowly warmed to −40° C. and stirred for 1 h. Then (1H-benzo[d][1,2,3]triazol-1-yl)(4-nitro-1H-pyrazol-3-yl)methanone was added separately to the above solution at −78° C. (the addition lasts for 30 minutes), the mixture was stirred for another 30 min, then warmed to rt slowly (keeping in a liquid nitrogen-ethyl acetate bath). Stirring was continued at rt for another 2 h. The mixture was quenched with sat. aq. NH₄Cl solution. The organic layer was separated, and the aqueous layer was further extracted with EA (2*500 mL). The combined organic extracts were washed with brine, dried over anhydrous Na₂SO₄, filtered and the filtrate was concentrated under reduced pressure get a solid (60 g, crude) which was used in the next step without further purification. MS (ESI) m/z: 387.8 [M+H]⁺

Step E: (6 S)-6-(3,5-dimethoxyphenyl)-2-(4-nitro-1H-pyrazole-3-carbonyl)cycloheptan-1-one (60 g, 0.15 mol, 1.0 eq) and hydrazine hydrate (22.5 g, 0.45 mol, 3.0 eq) were dissolved in a mixture of acetic acid/EtOH (1200 mL, acetic acid/EtOH=1:10). The mixture was stirred at 50° C. for 3 h. The reaction solution was evaporated and diluted with saturated aq. NaCl, extracted with EA (400 mL), and the combined organic layers were dried over anhydrous Na₂SO₄ and concentrated to give (S)-7-(3,5-dimethoxyphenyl)-3-(4-nitro-1H-pyrazol-3-yl)-1,4,5,6,7,8-hexahydro-cyclohepta[c]pyrazol (53 g, 70% for two steps of step D and E) as a light yellow solid. MS (ESI) m/z: 383.9 [M+H]

Step F: A suspension of (S)-7-(3,5-dimethoxyphenyl)-3-(4-nitro-1H-pyrazol-3-yl)-1,4,5,6,7,8-hexahydro-cyclohepta[c]pyrazol (40 g, 104.3 mmol) in CH₃CN (3000 ml) was cooled to 4° C. using an ice bath. Selectfluor (73.8 g, 208.6 mmol) was added. The resulting solution was stirred at 4° C. for 2 h. The reaction mixture was washed with aq. NaHCO₃, dried over sodium sulfate, filtered and the filtrate was concentrated to give the title compound (50 g, crude) as a yellow solid. MS (ESI) m/z: 420 [M+H]⁺

Step G: A suspension of (S)-7-(2,6-difluoro-3,5-dimethoxyphenyl)-3-(4-nitro-1H-pyrazol-3-yl)-1,4,5,6,7,8-hexahydrocyclohepta[c]pyrazole (50 g, 104.3 mmol), Pd/C (15 g) in MeOH/Ethyl acetate (500/50 ml) was stirred at 40° C. overnight under a H₂ atmosphere. The Pd/C was filtered off through a pad of Celite® (J. T. Baker, Phillipsberg, NJ, diatomaceous earth) and the filtrate was concentrated. The residue was purified by silica gel chromatography (DCM, 0-2.5% MeOH) to give (S)-3-(7-(2,6-difluoro-3,5-dimethoxyphenyl)-1,4,5,6,7,8-hexahydrocyclohepta[c] pyrazol-3-yl)-1H-pyrazol-4-amine (19 g, mixture with (S)-3-(7-(2-fluoro-3,5-dimethoxyphenyl)-1,4,5,6,7,8-hexahydrocyclohepta[c] pyrazol-3-yl)-1H-pyrazol-4-amine) as a brown solid. MS (ESI) m/z: 390 [M+H]⁺

Step H: To a solution of (S)-3-(7-(2,6-difluoro-3,5-dimethoxyphenyl)-1,4,5,6,7,8-hexahydrocyclohepta[c] pyrazol-3-yl)-1H-pyrazol-4-amine (19 g, 48.8 mmol) and DIPEA (12.3 g, 122 mmol) in DCM (100 mL) acryloyl chloride (3.9 g, 43.92 mmol) was added dropwise at −40° C. The resulting mixture was stirred for 15 min. The mixture was concentrated, purified by reversed-phase HPLC and SFC to get (S)—N-(3-(7-(2,6-difluoro-3,5-dimethoxyphenyl)-1,4,5,6,7,8-hexahydrocyclohepta[c]pyrazol-3-yl)-1H-pyrazol-4-yl) acrylamide (P=2.4 g) as a white solid.

P: ¹H NMR (400 MHz, DMSO) δ 12.71 (s, 2H), 10.07 (s, 1H), 8.20 (s, 1H), 6.91 (t, J=8.2 Hz, 1H), 6.41 (d, J=11.1 Hz, 1H), 6.20 (d, J=17.0 Hz, 1H), 5.74 (d, J=10.0 Hz, 1H), 3.86 (s, 6H), 3.64 (d, J=29.8 Hz, 1H), 3.19 (dt, J=22.8, 11.6 Hz, 2H), 2.87 (d, J=14.7 Hz, 1H), 2.33-1.78 (m, 4H), 1.45 (d, J=12.3 Hz, 1H). MS (ESI) m/z: 444.1 [M+H]⁺

Example S31

Synthesis of (S)—N-(3-(7-(2,6-difluoro-3,5-dimethoxyphenyl)-1,4,5,6,7,8-hexahydrocyclohepta[c]pyrazol-3-yl)-1-(2-(dimethylamino)ethyl)-1H-pyrazol-4-yl)acrylamide

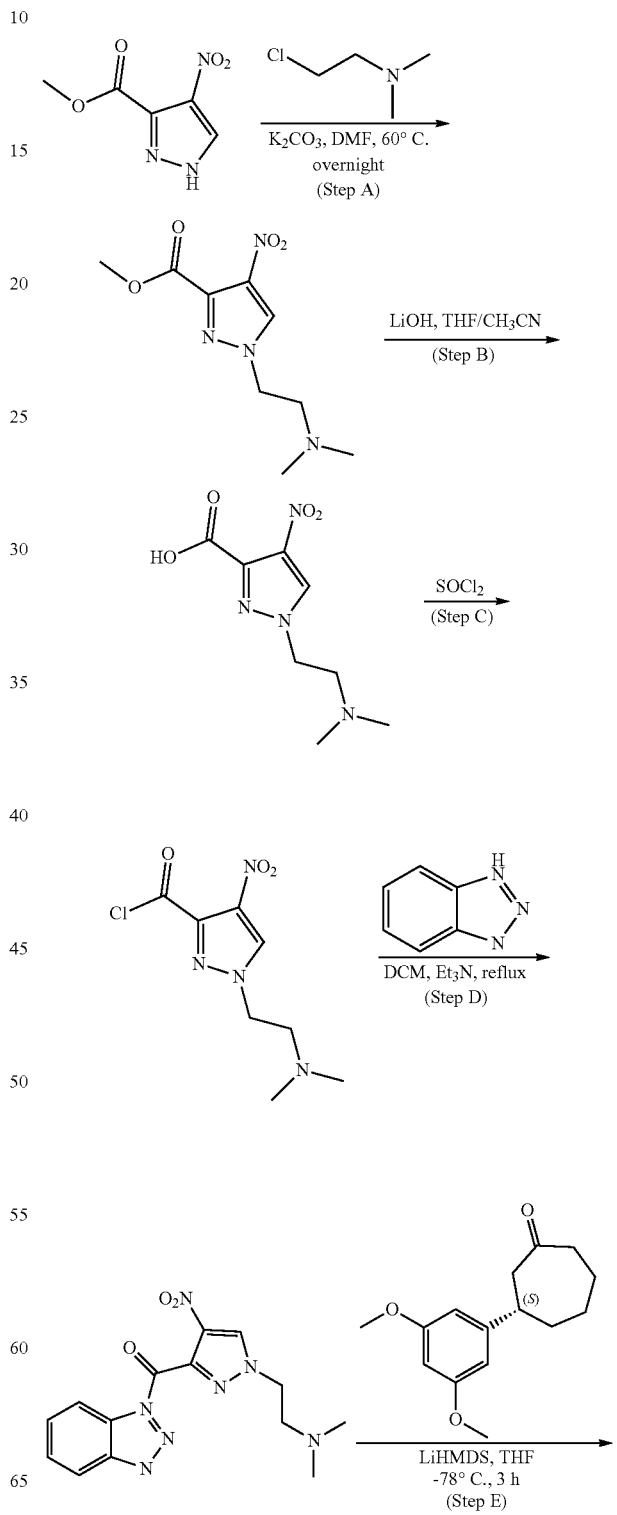

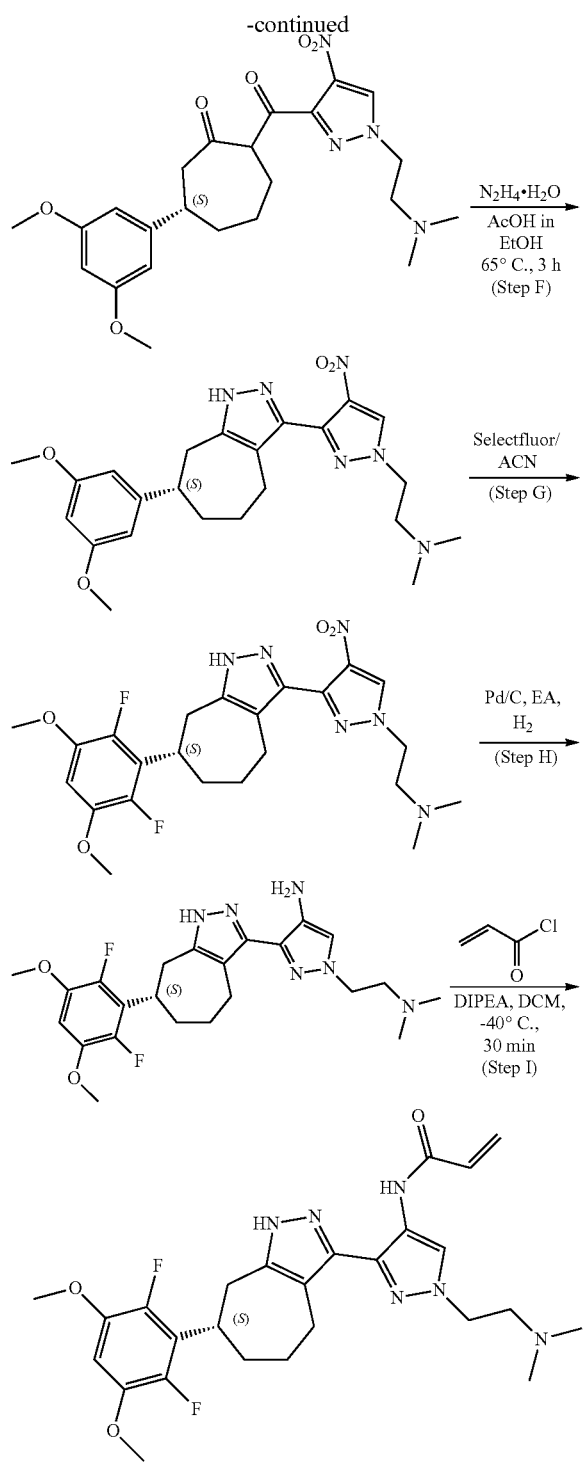

Step A: To a solution of methyl 4-nitro-1H-pyrazole-3-carboxylate (140 g, 0.82 mol, 1.0 eq) in 1000 mL DMF was added 2-chloro-N,N-dimethylethan-1-amine (92 g, 0.9 mol, 1.1 eq) and K₂CO₃ (226 g, 1.64 mol, 2.0 eq). The reaction was allowed to stir at 60° C. for 14 h. Then the mixture was concentrated under reduced pressure. The residue was dissolved in ethyl acetate (1 L), washed with brine, dried over Na₂SO₄ and filtered. The filtrate was concentrated and the residue was purified by silica gel column chromatography (PE/EtOAc=20:1-1:1) to give methyl 1-(2-(dimethylamino) ethyl)-4-nitro-1H-pyrazole-3-carboxylate (77 g, 35%) as a light-yellow oil. MS (ESI) m/z: 242.9 [M+H]⁺.

Step B: a mixture of methyl methyl 1-(2-(dimethylamino) ethyl)-4-nitro-1H-pyrazole-3-carboxylate (77 g, 0.32 mol), LiOH (26.7 g, 0.64 mol) in THF (250 ml)/CH₃OH (250 ml)/H₂O (100 ml) was stirred at rt for 2 h. The solvent was evaporated and the residue was diluted with H₂O, adjusted pH=6, concentrated and filtered to give 1-(2-(dimethyl- amino)ethyl)-4-nitro-1H-pyrazole-3-carboxylic acid (55 g, 72%) which was used in the next step without further purification. MS (ESI) m/z: 172.0 [M+H]⁺

Step C: In a round-bottomed flask were placed 1-(2- (dimethylamino)ethyl)-4-nitro-1H-pyrazole-3-carboxylic acid (71 g, 0.29 mol), 300 mL SOCl₂ and 5 ml DMF. The flask was fitted with a reflux condenser, and the mixture was refluxed at 76° C. for 2 h. The SOCl₂ was evaporated and the reside was washed with DCM to get 1-(2-(dimethylamino) ethyl)-4-nitro-1H-pyrazole-3-carbonyl chloride as light yel- low solid (90 g, 89%) which was used in the next step without further purification.

Step D: Triethylamine (15.1 mL, 0.27 mol, 0.95 eq) was added dropwise via syringe to a stirred solution of 1H-1,2, 3-benzotriazole (31.8 g, 0.19 mol, 0.95 eq) in anhydrous CH₂Cl₂ (1.0 L) at rt, followed by addition of 1-(2-(dimeth- ylamino)ethyl)-4-nitro-1H-pyrazole-3-carbonyl chloride (50 g, 0.20 mol, 1.0 eq) slowly over a period of 30 minutes. The solution was stirred at rt for 30 min, then warmed to 40° C. and stirred for 6 h, then evaporated to give (1H-benzo[d] [1,2,3]triazol-1-yl)(1-(2-(dimethylamino)ethyl)-4-nitro-1H- pyrazol-3-yl)methanone as a white powder (used in the next step without purification). MS (ESI) m/z: 329.8 [M+H]⁺

Steps E-I: (S)—N-(3-(7-(2,6-difluoro-3,5-dimethoxyphe- nyl)-1,4,5,6,7,8-hexahydrocyclohepta[c]pyrazol-3-yl)-1-(2- (dimethylamino)ethyl)-1H-pyrazol-4-yl)acrylamide was prepared by procedures similar to the one described in Example S30 for (S)—N-(3-(7-(2,6-difluoro-3,5-dime- thoxyphenyl)-1,4,5,6,7,8-hexahydrocyclohepta[c] pyrazol- 3-yl)-1H-pyrazol-4-yl) acrylamide, replacing (1H-benzo[d] [1,2,3]triazol-1-yl)(4-nitro-1H-pyrazol-3-yl)methanone in step E with (1H-benzo[d][1,2,3]triazol-1-yl)(1-(2-(dimeth- ylamino)ethyl)-4-nitro-1H-pyrazol-3-yl)methanone, obtained in Step D above. The product was purified by reversed-phase HPLC followed by additional purification by SFC.

¹H NMR (400 MHz, DMSO) δ 12.67 (s, 1H), 10.02 (s, 1H), 8.25 (s, 1H), 7.74-7.64 (m, 1H), 6.91 (t, J=8.3 Hz, 1H), 6.41 (dd, J=16.7, 9.9 Hz, 1H), 6.19 (dd, J=17.0, 1.7 Hz, 1H), 5.74 (d, J=11.0 Hz, 1H), 4.22 (td, J=6.4, 3.6 Hz, 2H), 3.86 (s, 6H), 3.28-3.08 (m, 3H), 2.86 (d, J=14.6 Hz, 1H), 2.66 (t, J=6.4 Hz, 2H), 2.18 (s, 6H), 2.02 (dd, J=18.1, 12.6 Hz, 2H), 1.50-1.34 (m, 2H). MS (ESI) m/z: 514.7 [M+H]⁺

Example S32

Synthesis of (R)—N-(3-(7-(2,6-difluoro-3,5-dime- thoxyphenyl)-1,4,5,6,7,8-hexahydrocyclohepta[c] pyrazol-3-yl)-1-(2-(dimethylamino)ethyl)-1H-pyra- zol-4-yl)acrylamide

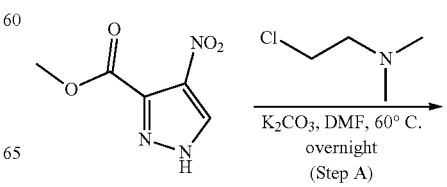

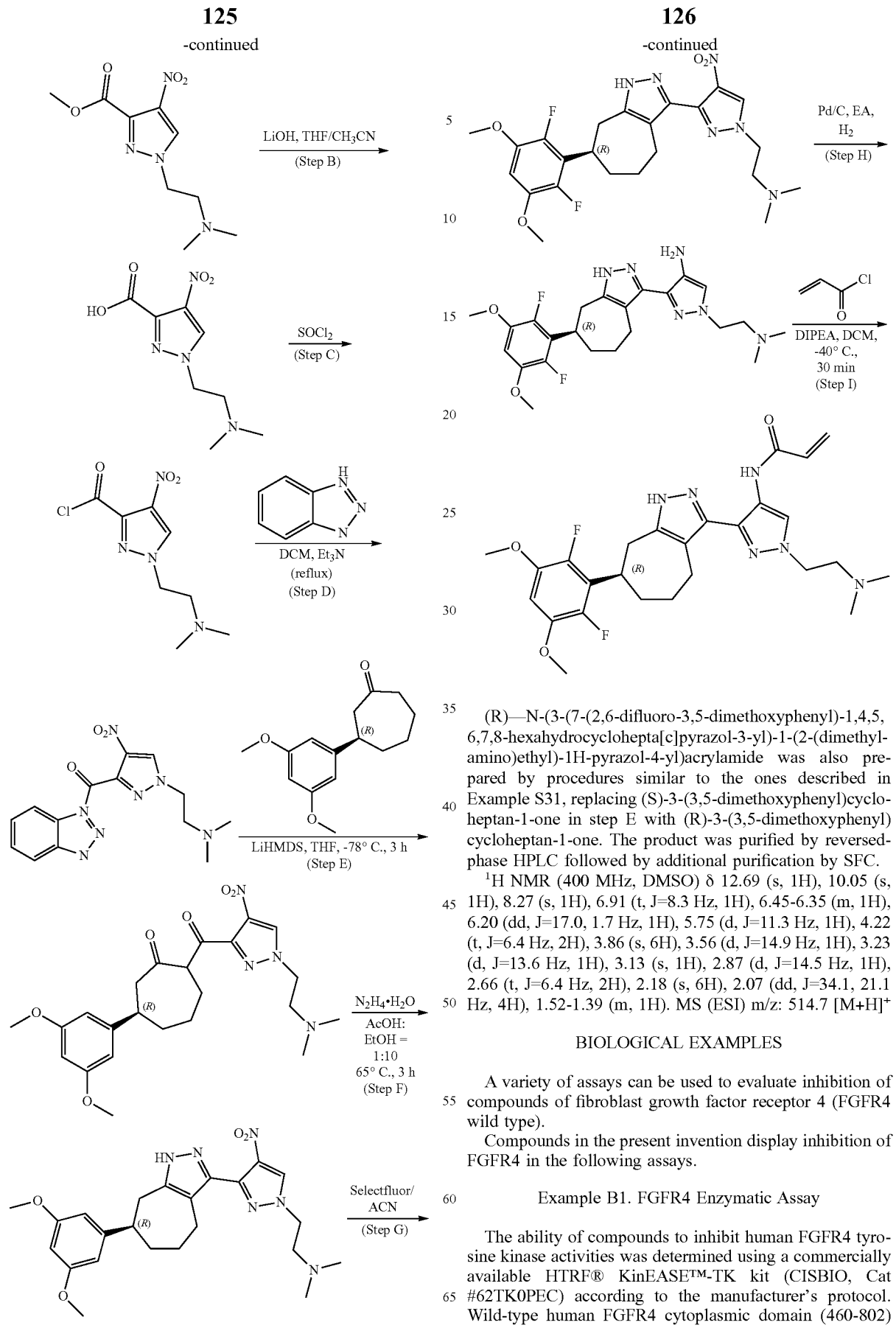

(R)—N-(3-(7-(2,6-difluoro-3,5-dimethoxyphenyl)-1,4,5,6,7,8-hexahydrocyclohepta[c]pyrazol-3-yl)-1-(2-(dimethylamino)ethyl)-1H-pyrazol-4-yl)acrylamide was also prepared by procedures similar to the ones described in Example S31, replacing (S)-3-(3,5-dimethoxyphenyl)cycloheptan-1-one in step E with (R)-3-(3,5-dimethoxyphenyl)cycloheptan-1-one. The product was purified by reversed-phase HPLC followed by additional purification by SFC.

$^1$H NMR (400 MHz, DMSO) δ 12.69 (s, 1H), 10.05 (s, 1H), 8.27 (s, 1H), 6.91 (t, J=8.3 Hz, 1H), 6.45-6.35 (m, 1H), 6.20 (dd, J=17.0, 1.7 Hz, 1H), 5.75 (d, J=11.3 Hz, 1H), 4.22 (t, J=6.4 Hz, 2H), 3.86 (s, 6H), 3.56 (d, J=14.9 Hz, 1H), 3.23 (d, J=13.6 Hz, 1H), 3.13 (s, 1H), 2.87 (d, J=14.5 Hz, 1H), 2.66 (t, J=6.4 Hz, 2H), 2.18 (s, 6H), 2.07 (dd, J=34.1, 21.1 Hz, 4H), 1.52-1.39 (m, 1H). MS (ESI) m/z: 514.7 [M+H]$^+$

BIOLOGICAL EXAMPLES

A variety of assays can be used to evaluate inhibition of compounds of fibroblast growth factor receptor 4 (FGFR4 wild type).

Compounds in the present invention display inhibition of FGFR4 in the following assays.

Example B1. FGFR4 Enzymatic Assay

The ability of compounds to inhibit human FGFR4 tyrosine kinase activities was determined using a commercially available HTRF® KinEASE™-TK kit (CISBIO, Cat #62TK0PEC) according to the manufacturer's protocol. Wild-type human FGFR4 cytoplasmic domain (460-802) with N-terminal GST-tag was purchased from Carna Biosciences (Carna, Cat #08-136) and used in the kinase enzymatic assay. This assay, run in a 384-well plate format, is a generic method for measuring tyrosine kinase activities using one substrate and a universal detection system. It involves two steps: (1) Enzymatic step: the biotin labeled TK Substrate is incubated with the kinase and then ATP is added to start the enzymatic reaction; during this step, FGFR4 will phosphorylate the TK Substrate-biotin. (2) Detection step: The TK-Antibody labeled with $Eu^{3+}$-Cryptate can recognize the phosphorylated TK Substrate-biotin. When the streptavidin-XL665 conjugate binds the biotin, a FRET signal will be detected. Briefly, human FGFR4 (0.25 µg/ml) in the enzymatic buffer solutions (250 mM HEPES, pH7.0, 0.1% $NaN_3$, 0.05% BSA, 0.5 mM Orthovanadate) were mixed with various concentrations of the test compound (dissolved in 100% DMSO). These solutions were incubated for 60 min at 25° C., and subsequently a mixture of substrate peptide and ATP was added with the final peptide and ATP concentrations at 0.3 µM and 200 µM respectively. The final reaction mixture of enzyme-substrate-ATP-compound was incubated for 40 min at 37° C. Meanwhile the detection mixture containing the TK-antibody and Streptavidin-XL665 diluted in the detection buffer (50 mM HEPES, pH7.0, with additives) was prepared, and added to the reaction mixture at final concentrations of 25 nM and 18.5 nM respectively. After incubation for 60 min at 25° C., the FRET signal of the final solution was measured at 665 nm and 612 nm emissions on a TECAN Spark 10M instrument (TECAN). The percent (%) inhibition at each concentration of a compound was calculated relative to the FRET signal in the Max and Min control wells contained within each assay plate. The Max control wells contained enzyme and substrate as 0% inhibition, and the Min control wells only contained substrate without enzyme as 100% inhibition. The concentrations and percent inhibition values for a test compound are plotted and the concentration of the compound required to achieve 50% inhibition ($IC_{50}$) was determined with a four-parameter logistic dose response equation. Dose-response curves were generated using Prism (GraphPad Software, La Jolla, CA, US) to calculate $IC_{50}$ values for each compound tested. Some examples are shown in Table 2 below.

TABLE 2

| Compound | Potency | Compound | Potency |
|---|---|---|---|
| S1-P1 | A | S1-P2 | A |
| S2-P1 | C | S2-P2 | C |
| S3-P1 | C | S3-P2 | B |
| S4-P1 | A | S4-P2 | A |
| S5-P1 | B | S5-P2 | B |
| S6-P1 | C | S6-P2 | B |
| S7-P1 | C | S7-P2 | C |
| S8-P1 | A | S8-P2 | A |
| S8-P3 | B | S8-P4 | B |
| S9 | B | S10-P1 | C |
| S10-P2 | C | S10-P3 | C |
| S10-P4 | C | S11-P1 | A |
| S11-P2 | A | S11-P3 | A |
| S11-P4 | A | S12-P1 | A |
| S12-P2 | A | S12-P3 | B |
| S12-P4 | A | S13-P1 | C |
| S13-P2 | C | S13-P3 | C |
| S13-P4 | C | S14-P1 | B |
| S14-P2 | A | S14-P3 | C |
| S15-P1 | A | S15-P2 | A |
| S15-P3 | B | S15-P4 | B |
| S16-P1 | A | S16-P2 | A |
| S16-P3 | B | S16-P4 | B |
| S17-P1 | B | S17-P2 | B |

TABLE 2-continued

| Compound | Potency | Compound | Potency |
|---|---|---|---|
| S18-P1 | C | S18-P2 | C |
| S19-P1 | C | S19-P2 | C |
| S20-P1 | C | S20-P2 | C |
| S21-P1 | C | S21-P2 | C |
| S22 | C | S23 | C |
| S24 | C | S31 | A |
| S32 | A | | |

In the table "A" means an $IC_{50}$ of <10 nM, "B" means an $IC_{50}$ of 10-100 nM and "C" means an $IC_{50}$ of >100 nM.

Example B2. Hep3B Cell Culture

Hepatocellular carcinoma cell line Hep3B (ATCC, Cat #HB-8064) were cultured at 37° C., 5% $CO_2$ in ATCC-formulated Eagle's Minimum Essential Medium supplemented with 10% fetal bovine serum; 1% Penicillin-Streptomycin.

Example B3. Cell-Based FGFR4 Proliferation Assay

Cell line: Hepatocellular carcinoma cell line Hep3B (ATCC, Cat #HB-8064).

In this assay, Hep3B cells are seeded in 384-well microplates, and after exposure to experimental compounds for two days, CellTiter-Glo® Luminescent Cell Viability Assay kit (Promega, Cat #G7572) are used to determine the number of viable cells in the culture based on quantitation of the ATP present, which signals the presence of metabolically active cells. Luminescent signal is proportional to the amount of ATP present. The amount of ATP is directly proportional to the number of cells present in the culture, allowing drug-induced effects on cell proliferation to be measured.

Hep3B cells were plated at a density of $4 \times 10^4$/ml cells in a 384-well black/clear microplate with 20 µL per well of MEM Medium (Gibco Cat. #11095-080) supplemented with 10% fetal bovine serum; 1% Penicillin-Streptomycin, and cultured overnight at 37° C., 5% $CO_2$. Various concentrations of the test compound (dissolved in 100% DMSO) were added to the wells of the cell plate. The cells were incubated with the test compound for 3 days at 37° C., 5% $CO_2$. 5 µL of CellTiter-Glo® Reagent was added to each well of the cell plate. The cell plate was incubated for 5 min at 25° C. on a plate shaker (IKA MTS 2/4) at 300 rpm. Luminescence signals were read on a TECAN Spark 10M instrument (TECAN). Percent (%) inhibition of the compound is calculated according to the formula below:

% inhibition=100−100*(Luminescence value−Min)/(Max−Min)

where Max controls are wells without the test compound; Min controls are wells without Hep3B cells. The concentrations and percent inhibition values for a test compound were plotted and the concentration of the compound required to achieve 50% inhibition ($IC_{50}$) is determined with a four-parameter logistic dose response equation. Dose-response curves were generated using Prism (GraphPad Software, La Jolla, CA, US) to calculate $IC_{50}$ values for each compound tested. Some examples are shown in Table 3 below.

TABLE 3

| Compound | Potency | Compound | Potency |
| --- | --- | --- | --- |
| S1-P1 | B | S1-P2 | B |
| S3-P1 | C | S3-P2 | C |
| S4-P1 | A | S4-P2 | A |
| S5-P1 | B | S5-P2 | C |
| S6-P1 | C | S6-P2 | C |
| S8-P1 | B | S8-P2 | B |
| S8-P3 | C | S8-P4 | C |
| S9 | C | S11-P1 | A |
| S11-P2 | A | S11-P3 | B |
| S11-P4 | A | S12-P1 | B |
| S12-P2 | A | S12-P3 | B |
| S12-P4 | A | S14-P1 | C |
| S14-P2 | B | S15-P1 | A |
| S15-P2 | A | S15-P3 | B |
| S15-P4 | B | S16-P1 | B |
| S16-P2 | B | S16-P3 | C |
| S16-P4 | C | S17-P1 | C |
| S17-P2 | B | S31 | B |
| S32 | A | | |

In the table "A" means an $IC_{50}$ of <10 nM, "B" means an $IC_{50}$ of 10-100 nM and "C" means an $IC_{50}$ of >100 nM.

Example B4. FGFR4 pMAPK AlphaLISA SureFire Ultra Assay

Cell line: Hepatocellular carcinoma cell line Hep3B (ATCC, Cat #HB-8064).

In normal liver, circulating FGF19 drives liver cell proliferation and regulates bile acid production. However aberrant expression of FGF19 in the liver drives HCC tumorigenesis, upregulates MAPK phosphorylation in FGF19-amplified malignant liver cells. AlphaScreen SureFire technology allows the detection of phosphorylated proteins in cellular lysates in a highly sensitive, quantitative assay. In these assays, sandwich antibody complexes, which are only formed in the presence of analyte, are captured by AlphaScreen Donor and Acceptor beads, bringing them into close proximity. The excitation of the Donor bead provokes the release of singlet oxygen molecules that triggers a cascade of energy transfer in the Acceptor beads, resulting in the emission of light at 520-620 nm.

Hep3B cells were plated at a density of $1 \times 10^4$/ml cells in a 96-well plate (Corning #3599), with 100 uL per well of MEM Medium (Gibco Cat #11095-080) supplemented with 10% fetal bovine serum; 1% Penicillin-Streptomycin, and cultured overnight at 37° C., 5% $CO_2$. Starve Hep3B cells in serum-free medium (SFM) supplemented with 0.2% BSA and incubate the cells again overnight at 37° C., 5% $CO_2$. Various concentrations of the test compound (prepared in 2x SFM) were added to the wells of the cell plate and then incubated for 1 hour at 37° C., 5% $CO_2$. 50 μL of FGF19 in SFM was added to each well of the cell plate with a final FGF19 concentration of 100 ng/ml, and cells treated with FGF19 were stimulated for 4 hours at 37° C., 5% $CO_2$. 5 μL of freshly prepared Donor Mix and Acceptor Mix were sequentially added to the cell plate, each followed with 1 hour of incubation at 25° C., 5% $CO_2$. Read the cell plate on an Alpha Technology-compatible plate reader at 570 nm AlphaScreen, using standard AlphaLISA settings.

The percent (%) inhibition=((ZPE−Alpha-Signal)/ (ZPE−HPE))*100% where the meanings of HPE and ZPE are as provided below.

HPE: Hundred Percent Effect, negative control well without FGF19 nor compound. Final concentration of DMSO is 0.1%.

ZPE: Zero Percent Effect, positive control well without compound. Final concentration of FGF19 is 100 ng/mL, DMSO is 0.1%.

The concentrations and percent inhibition values for a test compound were plotted and the concentration of the compound required to achieve 50% inhibition ($IC_{50}$) was determined with a four-parameter logistic dose response equation. Dose-response curves were generated using Prism (GraphPad Software, La Jolla, CA, US) to calculate $IC_{50}$ values for each compound tested. Some examples are shown in Table 4 below.

TABLE 4

| Compound | Potency | Compound | Potency |
| --- | --- | --- | --- |
| S1-P1 | A | S1-P2 | A |
| S3-P2 | C | S4-P1 | A |
| S4-P2 | A | S5-P1 | A |
| S5-P2 | B | S6-P2 | B |
| S8-P1 | A | S8-P2 | A |
| S8-P3 | B | S8-P4 | B |
| S9 | C | S11-P1 | A |
| S11-P2 | A | S11-P3 | A |
| S11-P4 | A | S12-P1 | A |
| S12-P2 | A | S12-P3 | A |
| S12-P4 | A | S14-P1 | B |
| S14-P2 | A | S15-P1 | A |
| S15-P2 | A | S15-P3 | A |
| S15-P4 | A | S16-P1 | A |
| S16-P1 | A | S16-P3 | B |
| S16-P4 | B | S17-P1 | B |
| S17-P2 | A | | |

In the table "A" means an $IC_{50}$ of <10 nM, "B" means an $IC_{50}$ of 10-100 nM and "C" means an $IC_{50}$ of >100 nM.

All references throughout, such as publications, patents, patent applications and published patent applications, are incorporated herein by reference in their entireties.

The invention claimed is:

1. A compound of formula (I):

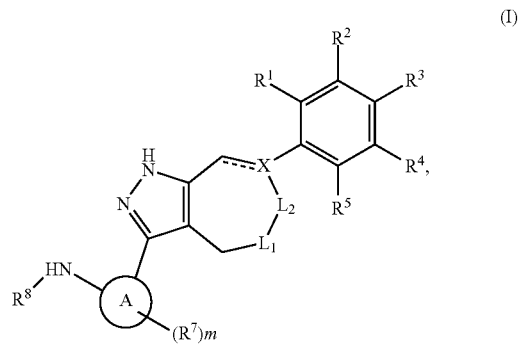

or a stereoisomer, tautomer, or a pharmaceutically acceptable salt of any of the foregoing, wherein:

⸗ is a single bond or a double bond;

X is CH or C;

$L_1$ is —CR'R"—, —O—, or —NR'"—, wherein R' and R" are each independently H, $C_{1-6}$ alkyl, $C_{1-6}$ haloalkyl, or halo, and R'" is H, $C_{1-6}$ alkyl, $C_{1-6}$ haloalkyl, or acyl;

$L_2$ is a bond or —$CH_2$—;

A is a $C_{6-14}$ arylene, 5- to 10-membered heteroarylene, $C_{3-8}$ cycloalkylene, or 3- to 10-membered heterocyclylene, provided that when L₁ is —CH₂— and L₂ is a bond, then A is 5- to 10-membered heteroarylene, $C_{3-8}$ cycloalkylene, or 3- to 10-membered heterocyclylene;

$R^1$, $R^2$, $R^3$, $R^4$, and $R^5$ are each independently H, halo, —CN, —NO₂, $C_{1-6}$ alkyl, $C_{1-6}$ haloalkyl, $C_{2-6}$ alkenyl, $C_{2-6}$ alkynyl, $C_{3-8}$ cycloalkyl, —OR¹³, or —NR¹¹R¹², or $R^1$ and X are taken together with the carbons to which they are attached to form a 4- to 8-membered heterocyclyl;

m is 0, 1, or 2;

each $R^7$ is independently halo, —CN, —NO₂, $C_{1-6}$ alkyl, $C_{1-6}$ haloalkyl, $C_{2-6}$ alkenyl, $C_{2-6}$ alkynyl, $C_{3-8}$ cycloalkyl, —OR¹³, or —NR$^a$R$^b$, wherein R$^a$ and R$^b$ are each independently H or $C_{1-6}$ alkyl, wherein the $C_{1-6}$ alkyl, $C_{1-6}$ haloalkyl, $C_{2-6}$ alkenyl, $C_{2-6}$ alkynl, $C_{3-8}$ cycloalkyl, and —OR¹³ of $R^7$ and the $C_{1-6}$ alkyl of R$^a$ and R$^b$ are each independently optionally substituted by —NR$^c$R$^d$, wherein R$^c$ and R$^d$ are each independently H or $C_{1-6}$ alkyl;

$R^8$ is —C(O)R⁹ or —S(O)₂R⁹;

$R^9$ is $C_{1-6}$ alkyl, $C_{2-6}$ alkenyl, $C_{3-8}$ cycloalkyl, or 3- to 10-membered heterocyclyl, each of which is optionally substituted with $C_{1-6}$ alkyl, halo, —CN, or —C(O)OR$^{9a}$, wherein R$^{9a}$ is $C_{1-6}$ alkyl; and $R^{11}$, $R^{12}$, and $R^{13}$ are each independently H, $C_{1-6}$ alkyl, $C_{1-6}$ haloalkyl, $C_{1-6}$ heteroalkyl, $C_{6-14}$ aryl, 5- to 10-membered heteroaryl, $C_{3-8}$ cycloalkyl, or 3- to 10-membered heterocyclyl;

provided that the compound is not a compound selected from the group consisting of:

N-(3-(6-(2,6-dichloro-3,5-dimethoxyphenyl)-4,5,6,7-tetrahydro-1H-indazol-3-yl)-1H-pyrazol-4-yl)acrylamide, N-(3-(6-(2,6-dichloro-3,5-dimethoxyphenyl)-4,5,6,7-tetrahydro-1H-indazol-3-yl)-1-methyl-1H-pyrazol-4-yl)acrylamide, N-(5-(6-(2,6-dichloro-3,5-dimethoxyphenyl)-4,5,6,7-tetrahydro-1H-indazol-3-yl)-1-methyl-1H-pyrazol-4-yl)acrylamide, N-(5-(6-(2,6-difluoro-3,5-dimethoxyphenyl)-4,5,6,7-tetrahydro-1H-indazol-3-yl)-1-methyl-1H-pyrazol-4-yl)acrylamide, N-(5-(6-(2-fluoro-3,5-dimethoxyphenyl)-4,5,6,7-tetrahydro-1H-indazol-3-yl)-1-methyl-1H-pyrazol-4-yl)acrylamide, N-(5-(6-(2-chloro-6-fluoro-3,5-dimethoxyphenyl)-4,5,6,7-tetrahydro-1H-indazol-3-yl)-1-methyl-1H-pyrazol-4-yl)acrylamide, N-(5-(6-(3,5-dimethoxyphenyl)-4,5,6,7-tetrahydro-1H-indazol-3-yl)-1-methyl-1H-pyrazol-4-yl)acrylamide, and N-(5-(6-(2-chloro-3,5-dimethoxyphenyl)-4,5,6,7-tetrahydro-1H-indazol-3-yl)-1-methyl-1H-pyrazol-4-yl)acrylamide, or a stereoisomer, tautomer, or a pharmaceutically acceptable salt of any of the foregoing.

2. A compound of formula (II):

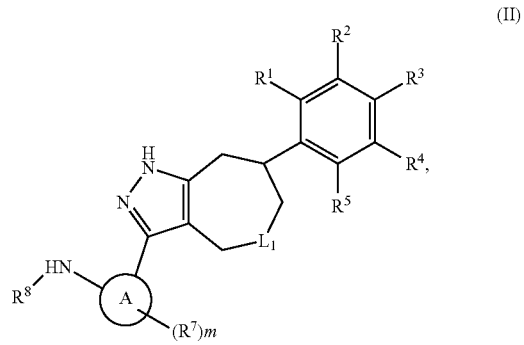

(II)

or a stereoisomer, tautomer, or a pharmaceutically acceptable salt of any of the foregoing, wherein:

⎓⎓⎓ is a single bond or a double bond;

$L_1$ is —CR'R"—, —O—, or —NR"'—, wherein R' and R" are each independently H, $C_{1-6}$ alkyl, $C_{1-6}$ haloalkyl, or halo, and R'" is H, $C_{1-6}$ alkyl, $C_{1-6}$ haloalkyl, or acyl;

A is a $C_{6-14}$ arylene, 5- to 10-membered heteroarylene, $C_{3-8}$ cycloalkylene, or 3- to 10-membered heterocyclylene, $R^1$, $R^2$, $R^3$, $R^4$, and $R^5$ are each independently H, halo, —CN, —NO₂, $C_{1-6}$ alkyl, $C_{1-6}$ haloalkyl, $C_{2-6}$ alkenyl, $C_{2-6}$ alkynyl, $C_{3-8}$ cycloalkyl, —OR¹³, or —NR¹¹R¹², m is 0, 1, or 2;

each $R^7$ is independently halo, —CN, —NO₂, $C_{1-6}$ alkyl, $C_{1-6}$ haloalkyl, $C_{2-6}$ alkenyl, $C_{2-6}$ alkynyl, $C_{3-8}$ cycloalkyl, —OR¹³, or —NR$^a$R$^b$, wherein R$^a$ and R$^b$ are each independently H or $C_{1-6}$ alkyl, wherein the $C_{1-6}$ alkyl, $C_{1-6}$ haloalkyl, $C_{2-6}$ alkenyl, $C_{2-6}$ alkynyl, $C_{3-8}$ cycloalkyl, and —OR¹³ of $R^7$ and the $C_{1-6}$ alkyl of R$^a$ and R$^b$ are each independently optionally substituted by —NR$^c$R$^d$, wherein R$^c$ and R$^d$ are each independently H or $C_{1-6}$ alkyl;

$R^8$ is —C(O)R⁹ or —S(O)₂R⁹;

$R^9$ is $C_{1-6}$ alkyl, $C_{2-6}$ alkenyl, $C_{3-8}$ cycloalkyl, or 3- to 10-membered heterocyclyl, each of which is optionally substituted with $C_{1-6}$ alkyl, halo, —CN, or —C(O)OR$^{9a}$, wherein R$^{9a}$ is $C_{1-6}$ alkyl; and $R^{11}$, $R^{12}$ and $R^{13}$ are each independently H, $C_{1-6}$ alkyl, $C_{1-6}$ haloalkyl, $C_{1-6}$ heteroalkyl, $C_{6-14}$ aryl, 5- to 10-membered heteroaryl, $C_{3-8}$ cycloalkyl, or 3- to 10-membered heterocyclyl.

3. The compound of claim 2, or a stereoisomer, tautomer, or a pharmaceutically acceptable salt of any of the foregoing, wherein the compound is of formula (II-a):

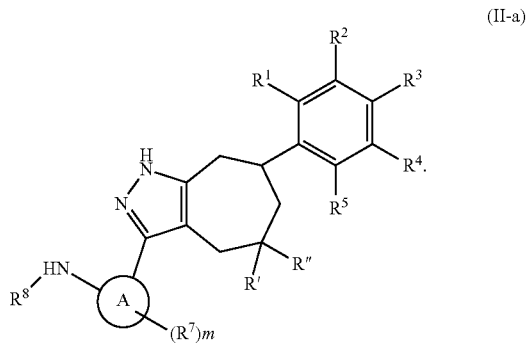

(II-a)

4. The compound of claim 1, or a stereoisomer, tautomer, or a pharmaceutically acceptable salt of any of the foregoing, wherein the compound is of formula (III):

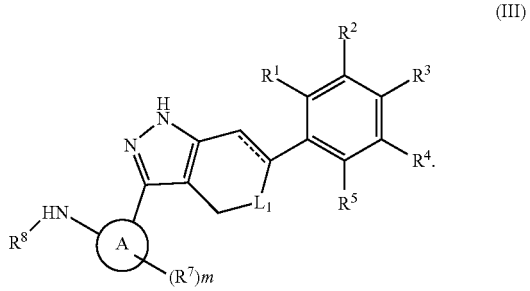

(III)

5. The compound of claim 1, or a stereoisomer, tautomer, or a pharmaceutically acceptable salt of any of the foregoing, wherein the compound is of formula (III-a):

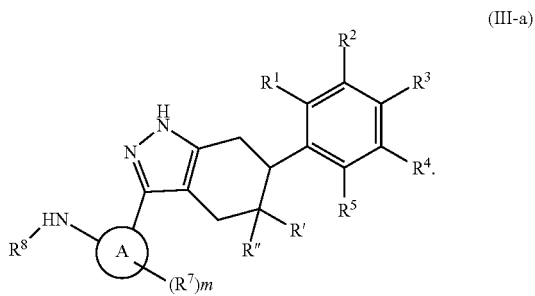

(III-a)

6. The compound of claim 1, or a stereoisomer, tautomer, or a pharmaceutically acceptable salt of any of the foregoing, wherein the compound is of formula (III-b):

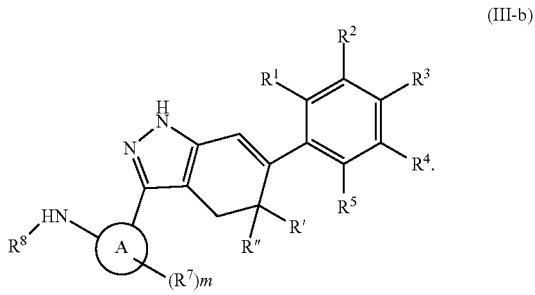

(III-b)

7. The compound of claim 1, or a stereoisomer, tautomer, or a pharmaceutically acceptable salt of any of the foregoing, wherein the compound is of formula (III-c):

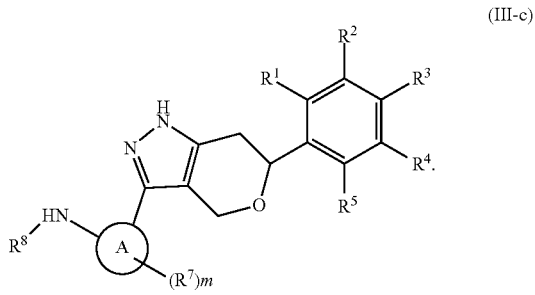

(III-c)

8. The compound of claim 1, or a stereoisomer, tautomer, or a pharmaceutically acceptable salt of any of the foregoing, wherein ≡≡≡ is a single bond.

9. The compound of claim 1, or a stereoisomer, tautomer, or a pharmaceutically acceptable salt of any of the foregoing, wherein ≡≡≡ is a double bond.

10. The compound of claim 1, or a stereoisomer, tautomer, or a pharmaceutically acceptable salt of any of the foregoing, wherein $L_1$ is —CR'R"—.

11. The compound of claim 1, or a stereoisomer, tautomer, or a pharmaceutically acceptable salt of any of the foregoing, wherein $L_1$ is —O— or —NR'"—.

12. The compound of claim 1, or a stereoisomer, tautomer, or a pharmaceutically acceptable salt of any of the foregoing, wherein $L_2$ is a bond.

13. The compound of claim 1, or a stereoisomer, tautomer, or a pharmaceutically acceptable salt of any of the foregoing, wherein $L_2$ is —CH$_2$—.

14. The compound of claim 1, or a stereoisomer, tautomer, or a pharmaceutically acceptable salt of any of the foregoing, wherein R' is H.

15. The compound of claim 1, or a stereoisomer, tautomer, or a pharmaceutically acceptable salt of any of the foregoing, wherein R' is $C_{1-6}$ alkyl.

16. The compound of claim 1, or a stereoisomer, tautomer, or a pharmaceutically acceptable salt of any of the foregoing, wherein R' is methyl.

17. The compound of claim 1, or a stereoisomer, tautomer, or a pharmaceutically acceptable salt of any of the foregoing, wherein R" is H.

18. The compound of claim 1, or a stereoisomer, tautomer, or a pharmaceutically acceptable salt of any of the foregoing, wherein R" is $C_{1-6}$ alkyl, $C_{1-6}$ haloalkyl, or halo.

19. The compound of claim 1, or a stereoisomer, tautomer, or a pharmaceutically acceptable salt of any of the foregoing, wherein $R^2$ is —OR$^{13}$ and $R^{13}$ is $C_{1-6}$ alkyl.

20. The compound of claim 1, or a stereoisomer, tautomer, or a pharmaceutically acceptable salt of any of the foregoing, wherein $R^2$ is —OCH$_3$ or —OCD$_3$.

21. The compound of claim 1, or a stereoisomer, tautomer, or a pharmaceutically acceptable salt of any of the foregoing, wherein $R^3$ is H.

22. The compound of claim 1, or a stereoisomer, tautomer, or a pharmaceutically acceptable salt of any of the foregoing, wherein $R^4$ is —OR$^{13}$ and $R^{13}$ is $C_{1-6}$ alkyl.

23. The compound of claim 1, or a stereoisomer, tautomer, or a pharmaceutically acceptable salt of any of the foregoing, wherein $R^4$ is —OCH$_3$ or —OCD$_3$.

24. The compound of claim 1, or a stereoisomer, tautomer, or a pharmaceutically acceptable salt of any of the foregoing, wherein $R^5$ is H.

25. The compound of claim 1, or a stereoisomer, tautomer, or a pharmaceutically acceptable salt of any of the foregoing, wherein $R^5$ is halo.

26. The compound of claim 1, or a stereoisomer, tautomer, or a pharmaceutically acceptable salt of any of the foregoing, wherein $R^1$ is H.

27. The compound of claim 1, or a stereoisomer, tautomer, or a pharmaceutically acceptable salt of any of the foregoing, wherein $R^1$ is halo.

28. The compound of claim 1, or a stereoisomer, tautomer, or a pharmaceutically acceptable salt of any of the foregoing, wherein $R^1$ and X are taken together with the carbons to which they are attached to form a 4- to 8-membered heterocyclyl.

29. The compound of claim 1, or a stereoisomer, tautomer, or a pharmaceutically acceptable salt of any of the foregoing, wherein A is a $C_6$ arylene, 5- to 6-membered heteroarylene, $C_{5-6}$ cycloalkylene, or 5- to 6-membered heterocyclylene.

30. The compound of claim 1, or a stereoisomer, tautomer, or a pharmaceutically acceptable salt of any of the foregoing, wherein A is

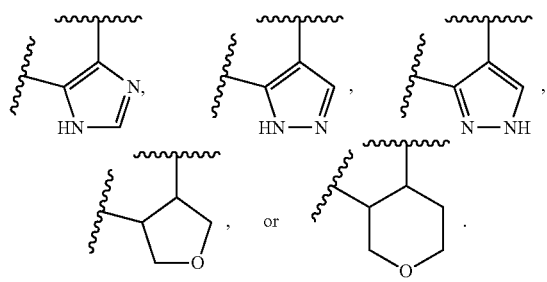

31. The compound of claim 1, or a stereoisomer, tautomer, or a pharmaceutically acceptable salt of any of the foregoing, wherein m is 0.

32. The compound of claim 1, or a stereoisomer, tautomer, or a pharmaceutically acceptable salt of any of the foregoing, wherein m is 1.

33. The compound of claim 1, or a stereoisomer, tautomer, or a pharmaceutically acceptable salt of any of the foregoing, wherein each $R^7$ is independently $C_{1-6}$ alkyl or $C_{1-6}$ haloalkyl.

34. The compound of claim 1, or a stereoisomer, tautomer, or a pharmaceutically acceptable salt of any of the foregoing, wherein each $R^7$ is independently —$CH_3$, —$CH_2CH_3$, —$CH(CH_3)_2$, —$CD_3$, or —$CH_2CF_3$.

35. The compound of claim 1, or a stereoisomer, tautomer, or a pharmaceutically acceptable salt of any of the foregoing, wherein $R^8$ is —$C(O)R^9$.

36. The compound of claim 1, or a stereoisomer, tautomer, or a pharmaceutically acceptable salt of any of the foregoing, wherein $R^8$ is —$S(O)_2R^9$.

37. The compound of claim 1, or a stereoisomer, tautomer, or a pharmaceutically acceptable salt of any of the foregoing, wherein $R^9$ is $C_{1-6}$ alkyl, $C_{2-6}$ alkenyl, or 3- to 10-membered heterocyclyl, each of which is optionally substituted with halo or —$C(O)OR^{9a}$, wherein $R^{9a}$ is $C_{1-6}$ alkyl.

38. The compound of claim 1, or a stereoisomer, tautomer, or a pharmaceutically acceptable salt of any of the foregoing, wherein $R^9$ is —$CH_3$, —$CH_2CH_3$,

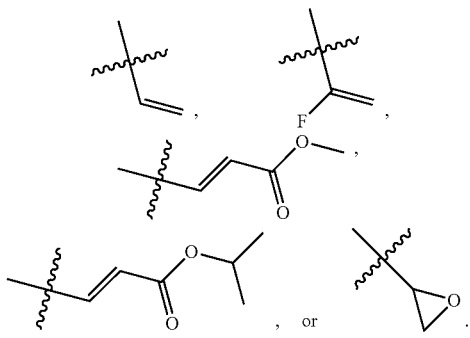

39. A compound selected from the group consisting of:

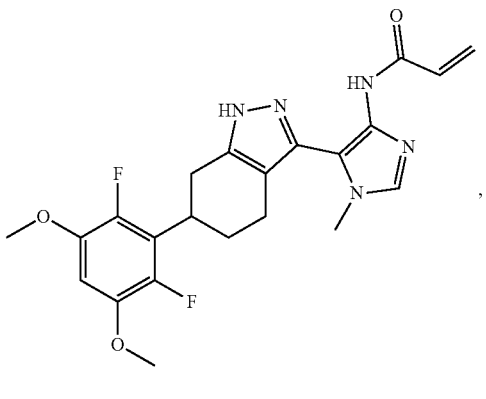

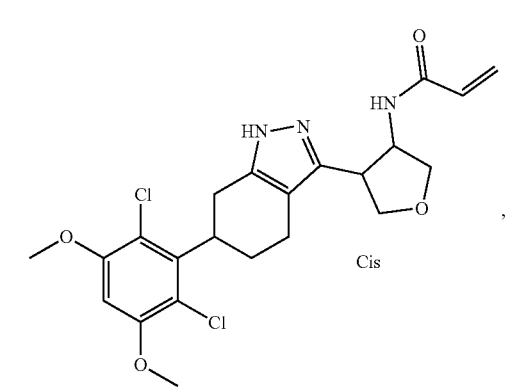

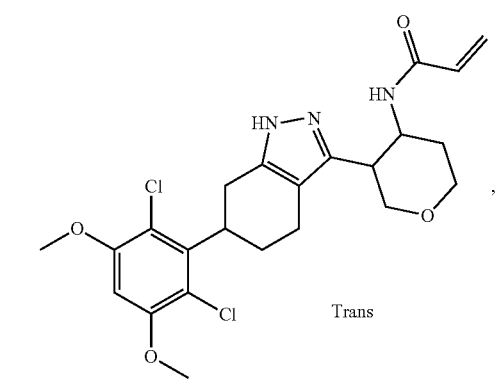

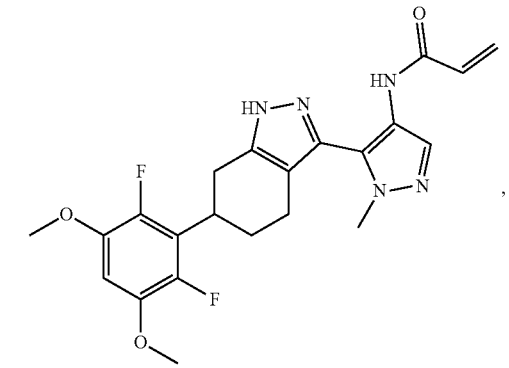

137
-continued
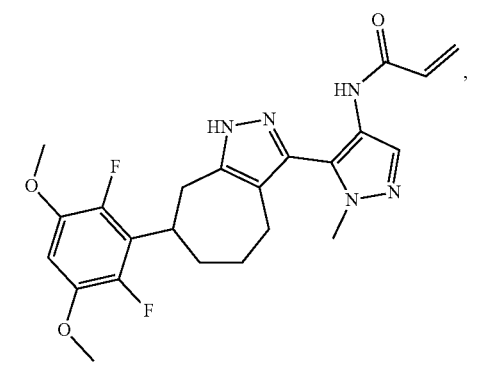
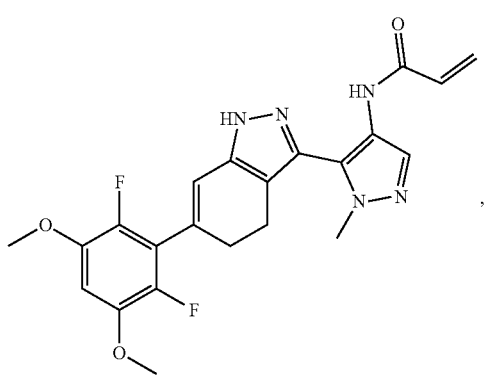
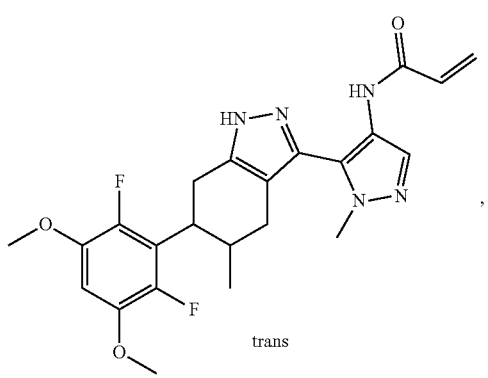
trans
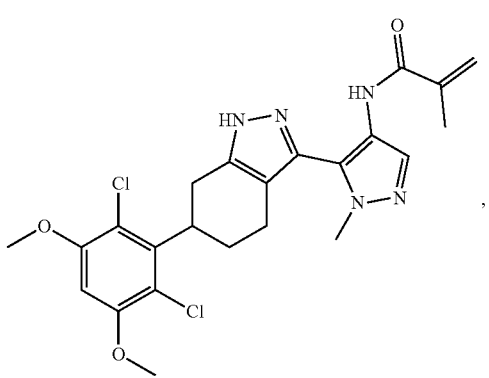
138
-continued
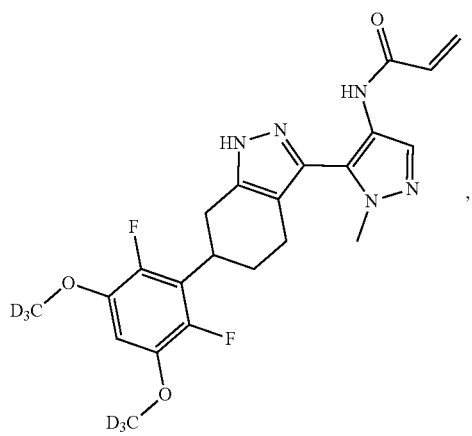
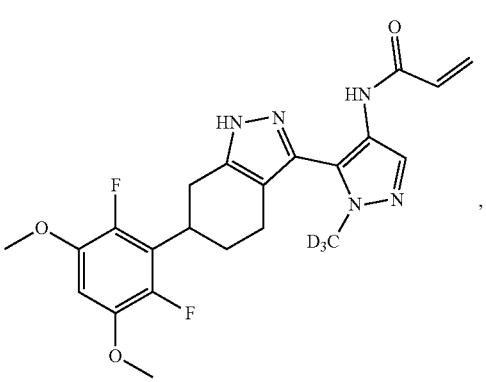
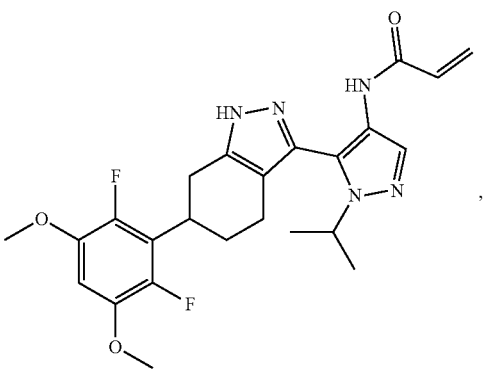
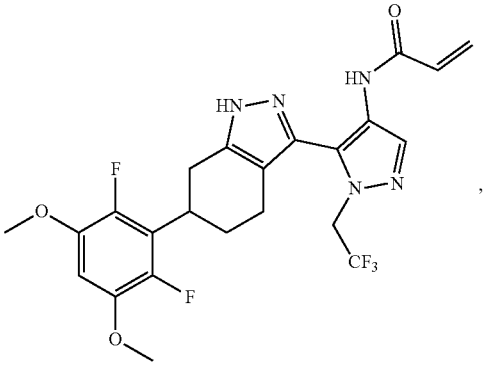

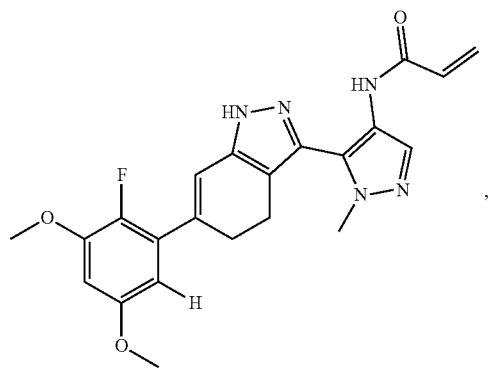
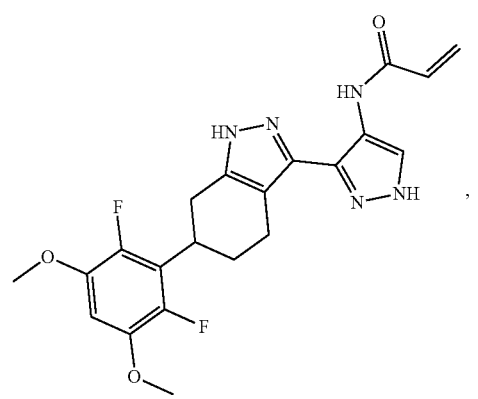
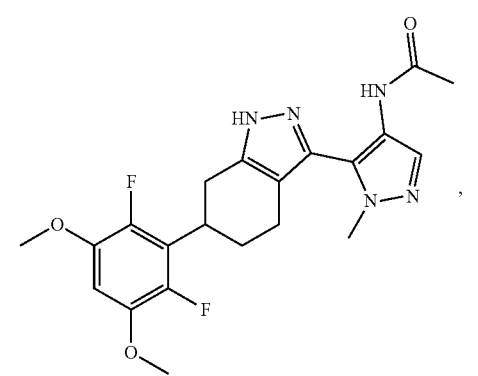
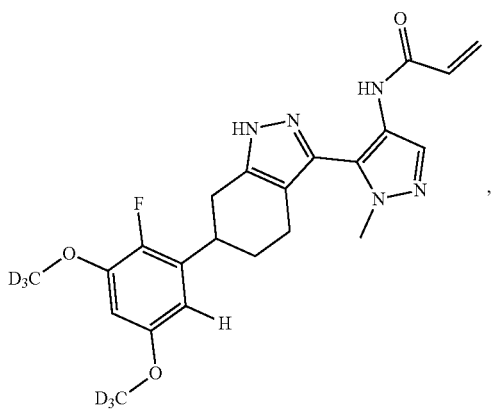
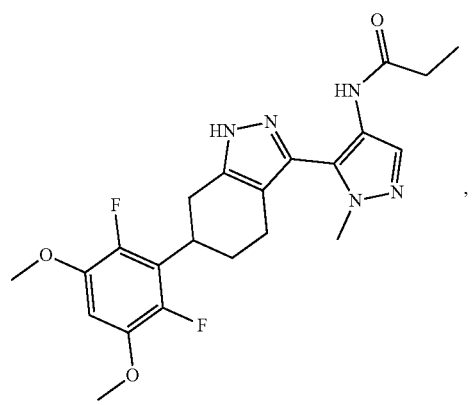
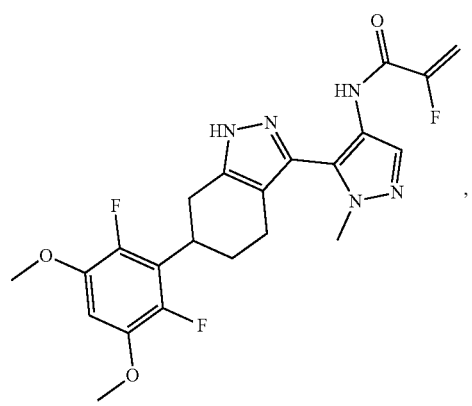
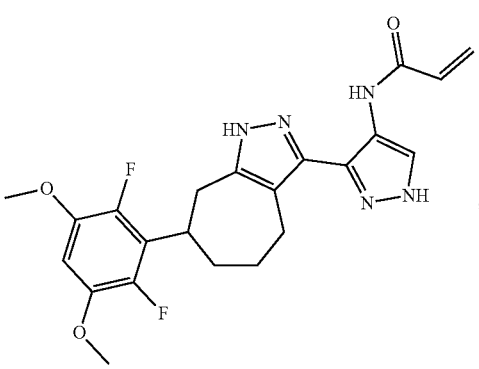
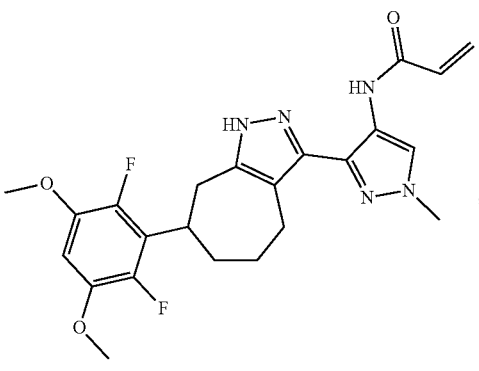

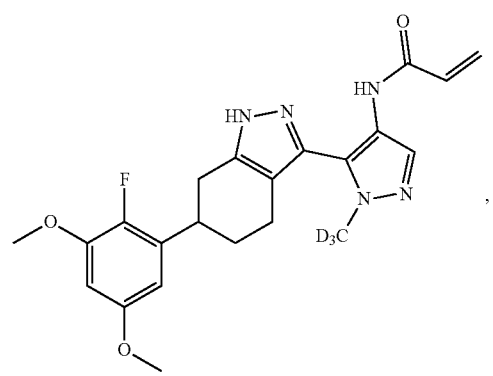
,
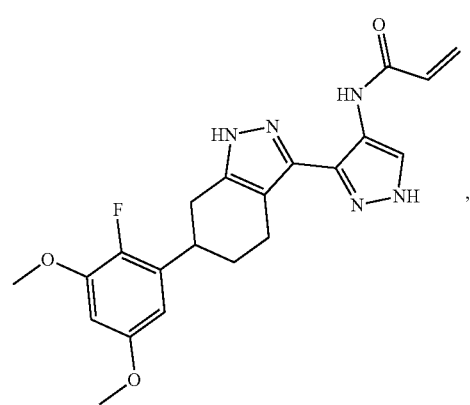
,
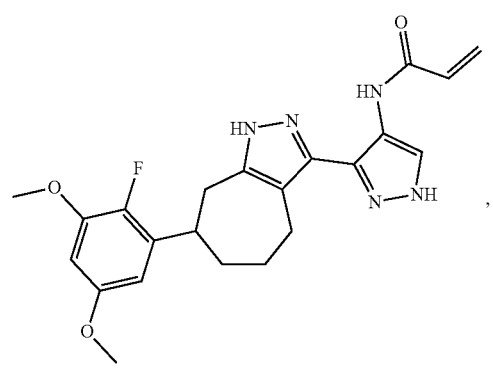
,
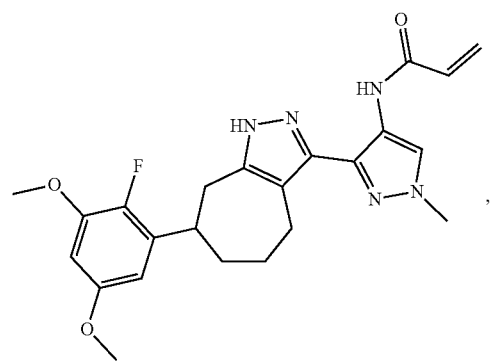
,
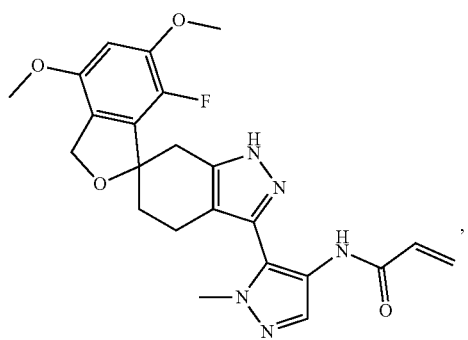
,
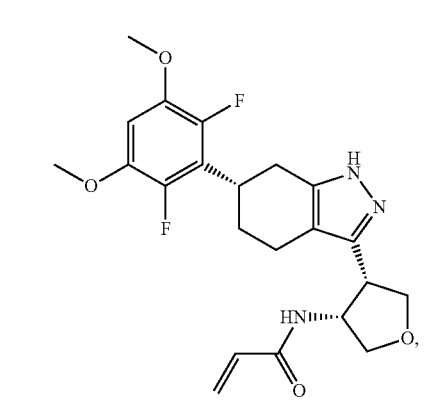
,
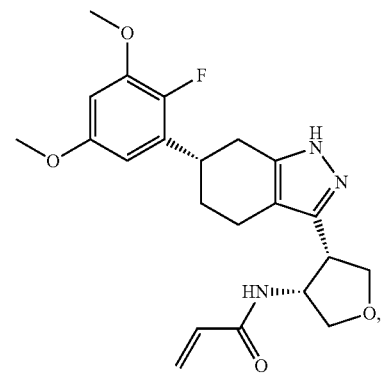
,
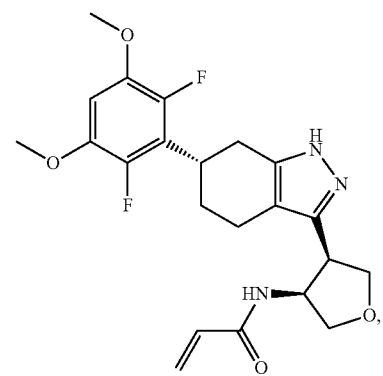
,

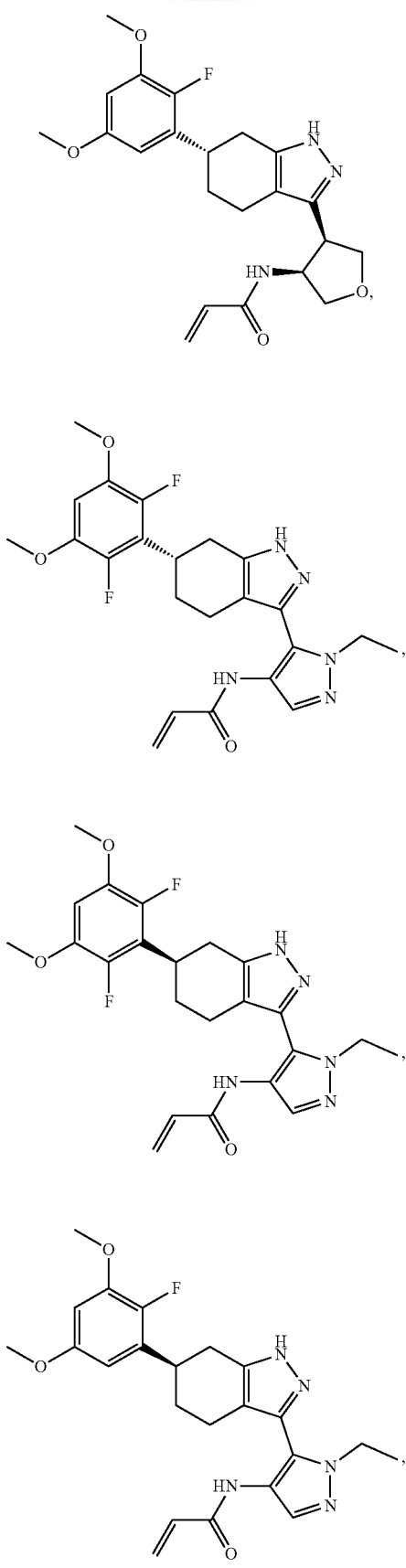
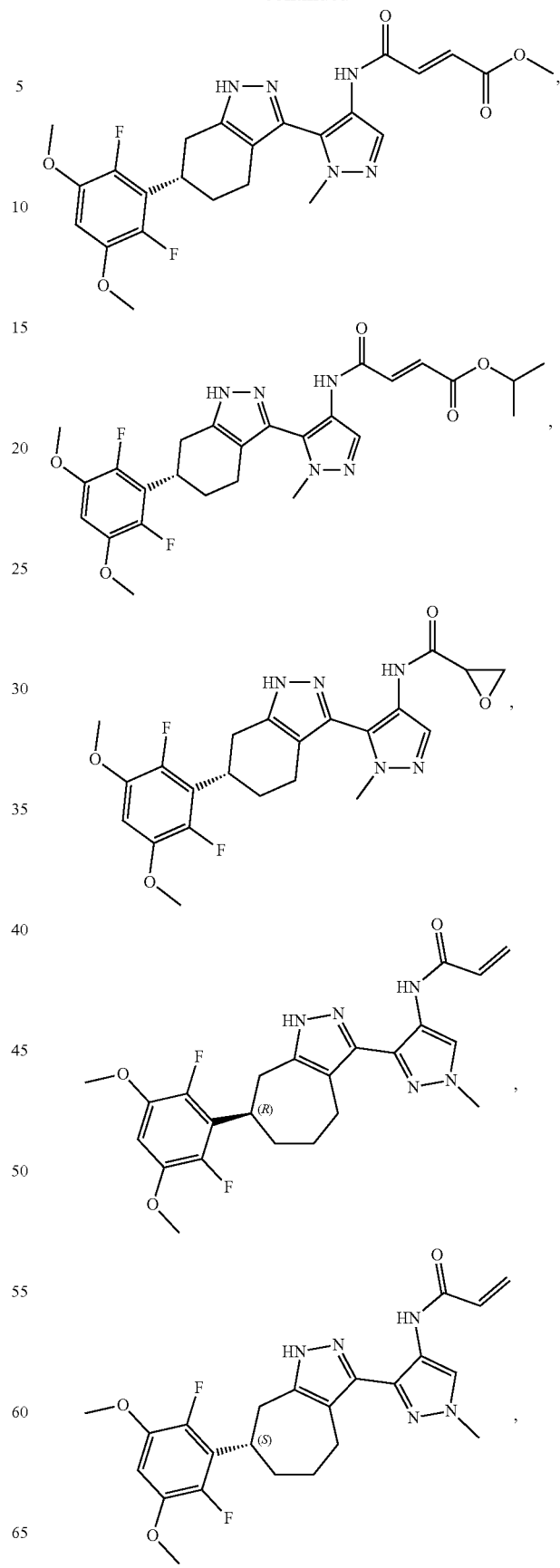

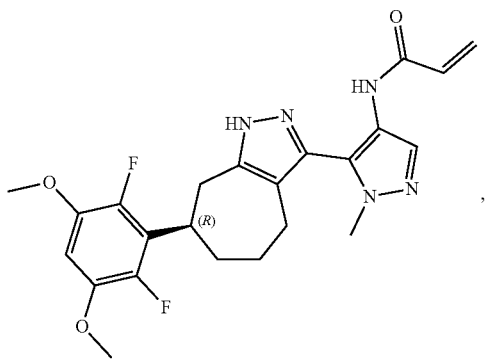

,

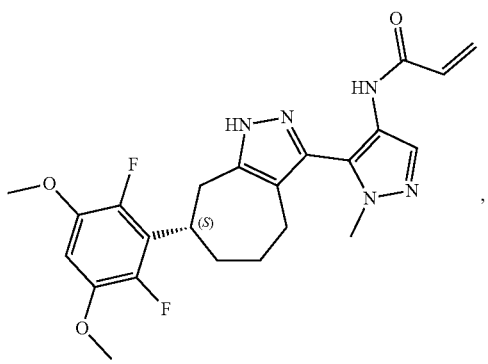

,

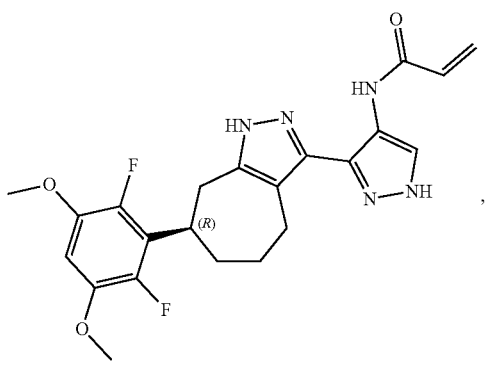

,

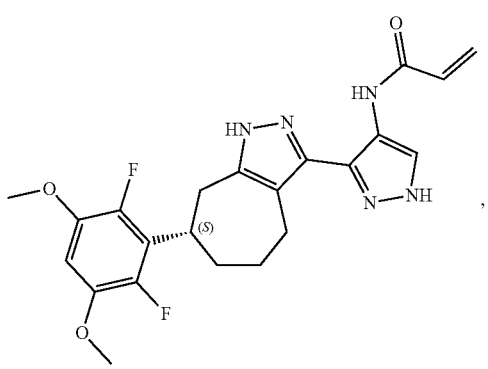

,

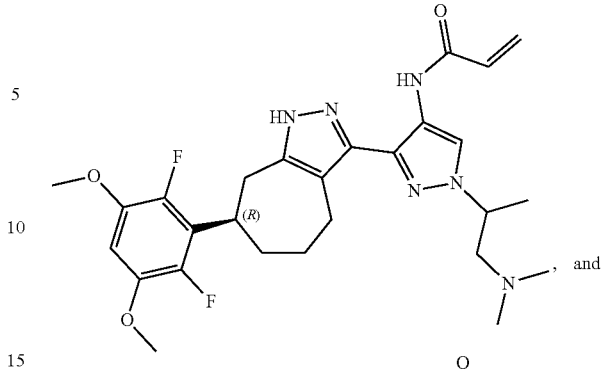

, and

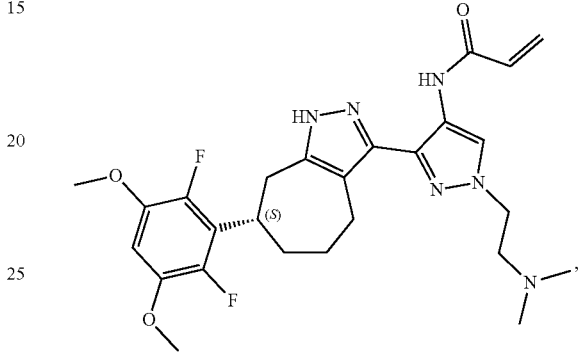

, or a stereoisomer, tautomer, or a pharmaceutically acceptable salt of any of the foregoing.

40. A pharmaceutical composition comprising at least one compound according to claim 1, or a stereoisomer, tautomer or a pharmaceutically acceptable salt of any of the foregoing, and a pharmaceutically acceptable carrier or excipient.

41. A kit comprising at least one compound according to claim 1, or a stereoisomer, tautomer or a pharmaceutically acceptable salt of any of the foregoing.

42. A method of treating a disease mediated by FGFR4 in an individual in need thereof, comprising administering to the individual a therapeutically effective amount of a compound according to claim 1, or a stereoisomer, tautomer or a pharmaceutically acceptable salt of any of the foregoing, wherein the disease is selected from the group consisting of bladder cancer, breast cancer, cervical cancer, colorectal cancer, cancer of the small intestine, colon cancer, rectal cancer, cancer of the anus, endometrial cancer, gastric cancer, head and neck cancer, kidney cancer, liver cancer, lung cancer, ovarian cancer, prostate cancer, testicular cancer, uterine cancer, esophageal cancer, gall bladder cancer, pancreatic cancer, stomach cancer, thyroid cancer, parathyroid cancer, skin cancer, brain cancer and rhabdomyosarcoma.

43. The method of claim 42, wherein the compound is administered orally.

44. The method of claim 42, wherein the disease is liver cancer.

45. A method of inhibiting FGFR4, comprising contacting FGFR4 with a compound according to claim 1, or a stereoisomer, tautomer or a pharmaceutically acceptable salt of any of the foregoing.

46. The method of claim 44, wherein the liver cancer is hepatocellular carcinoma.

47. The method of claim 45, wherein the compound, or a stereoisomer, tautomer or a pharmaceutically acceptable salt of any of the foregoing is selective for FGFR4 over FGFR1, FGFR2, and FGFR3.

48. The method of claim 1, wherein each $R^7$ is independently halo, —CN, —NO$_2$, C$_{1-6}$ alkyl, C$_{1-6}$ haloalkyl, C$_{2-6}$ alkenyl, C$_{2-6}$ alkynyl, C$_{3-8}$ cycloalkyl, —OR$^{13}$, or —NR$^a$R$^b$, wherein R$^a$ and R$^b$ are each independently H or C$_{1-6}$ alkyl optionally substituted by —NR$^c$R$^d$, wherein R$^c$ and R$^d$ are each independently H or C$_{1-6}$ alkyl.

\* \* \* \* \*